United States Patent
Okada et al.

(10) Patent No.: US 8,829,000 B2
(45) Date of Patent: Sep. 9, 2014

(54) SUBSTITUTED IMIDAZO[1,5-A]QUINOXALINES AS PHOSPHODIESTERASE 9 INHIBITORS

(75) Inventors: Makoto Okada, Inagi (JP); Shuichiro Sato, Komae (JP); Kenji Kawade, Kawasaki (JP); Kotaro Gotanda, Kawasaki (JP); Atsushi Shinbo, Niiza (JP); Youichi Nakano, Hachioji (JP); Hideo Kobayashi, Saitama (JP)

(73) Assignee: ASKA Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/617,683

(22) Filed: Sep. 14, 2012

(65) Prior Publication Data

US 2013/0225572 A1    Aug. 29, 2013

Related U.S. Application Data

(62) Division of application No. 12/448,212, filed as application No. PCT/JP2007/074363 on Dec. 12, 2007, now Pat. No. 8,299,080.

(30) Foreign Application Priority Data

Dec. 13, 2006    (JP) ................. 2006-336215

(51) Int. Cl.
*A61K 31/4985* (2006.01)
*C07D 487/04* (2006.01)
*C07D 487/14* (2006.01)

(52) U.S. Cl.
CPC ............ *C07D 487/14* (2013.01); *C07D 487/04* (2013.01)
USPC .......... 514/250; 544/346; 546/210; 546/268.1

(58) Field of Classification Search
CPC ........................... A61K 31/4985; C07D 487/04
USPC ................. 514/250; 544/346; 546/210, 268.1
See application file for complete search history.

(56) References Cited

U.S. PATENT DOCUMENTS

| | | | |
|---|---|---|---|
| 4,354,027 A | 10/1982 | Loev et al. | |
| 4,495,187 A | 1/1985 | Sarges | |
| 4,547,501 A | 10/1985 | Sarges | |
| 4,623,725 A | 11/1986 | Kadin et al. | |
| 5,055,465 A | 10/1991 | Davey | |
| 5,153,196 A | 10/1992 | McQuaid et al. | |
| 5,166,344 A | 11/1992 | Davey | |
| 5,196,421 A | 3/1993 | McQuaid et al. | |
| 5,504,085 A | 4/1996 | Jacobsen et al. | |
| 5,559,106 A | 9/1996 | Jacobsen et al. | |
| 5,683,998 A | 11/1997 | Shibayama et al. | |
| 5,723,463 A | 3/1998 | Höfgen et al. | |
| 5,741,785 A | 4/1998 | Jeppesen | |
| 6,001,832 A | 12/1999 | Nielsen | |
| 6,124,287 A | 9/2000 | Ceccarelli et al. | |
| 6,869,956 B2 | 3/2005 | Burke et al. | |
| 6,960,585 B2 | 11/2005 | Beaulieu et al. | |
| 6,967,204 B2 | 11/2005 | Fryburg et al. | |
| 2002/0072523 A1 | 6/2002 | Beaulieu et al. | |
| 2003/0022898 A1 | 1/2003 | Burke et al. | |
| 2003/0195205 A1 | 10/2003 | DeNinno et al. | |
| 2004/0023989 A1 | 2/2004 | Fryburg et al. | |
| 2005/0070557 A1 | 3/2005 | Fryburg et al. | |
| 2006/0106035 A1 | 5/2006 | Hendrix et al. | |
| 2007/0299079 A1 | 12/2007 | Norbert et al. | |
| 2008/0027064 A1 | 1/2008 | Hofgen et al. | |

FOREIGN PATENT DOCUMENTS

| | | |
|---|---|---|
| CA | 2158167 | 10/1994 |
| CA | 2296224 | 7/2000 |
| WO | 93/20077 | 10/1993 |

OTHER PUBLICATIONS

International Search Report dated Mar. 4, 2008 for International (PCT) Application No. PCT/JP2007/074363.
International Preliminary Report on Patentability (including the Written Opinion of the International Searching Authority) dated Jun. 25, 2009 for International (PCT) Application No. PCT/JP2007/074363.

(Continued)

*Primary Examiner* — Douglas M Willis
(74) *Attorney, Agent, or Firm* — Wenderoth, Lind & Ponack, L.L.P.

(57) ABSTRACT

The invention discloses quinoxaline derivatives or salts thereof having PDE9-inhibiting activity and being useful as treating agent of dysuria and the like, which are represented by the formula (I)

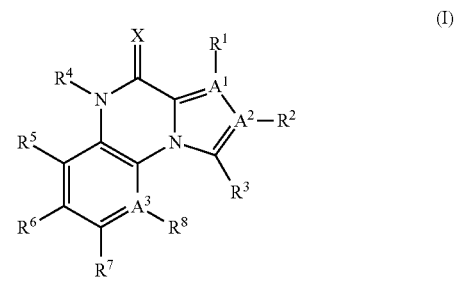

in the formula,
$R^1$ and $R^2$ each independently stands for hydrogen, halogen, alkyl, alkoxy, acyl, amino and the like,
$R^3$ stands for alkyl, aryl, saturated carbocyclic group, saturated heterocyclic group, acyl and the like,
$R^4$ stands for hydrogen, hydroxy, alkyl or amino,
$R^5$ and $R^8$ each independently stands for hydrogen, halogen, alkyl, alkenyl, alkoxy, cyano or nitro,
$R^6$ and $R^7$ each independently stands for hydrogen, halogen, alkyl, alkenyl, alkynyl, alkoxy, cyano, amino, carbocyclic group, heterocyclic group, $COR^9$ or $SO_2R^9$,
$R^9$ stands for hydrogen, hydroxy, alkyl, amino, pyrrolidin-1-yl, piperidin-1-yl, pyperazin-1-yl or the like,
X stands for S or O, and
$A^1$, $A^2$ and $A^3$ each independently stands for N or C.

16 Claims, No Drawings

(56) References Cited

OTHER PUBLICATIONS

Fisher et al., "Isolation and Characterization of PDE9A, a Novel Human cGMP-Specific Phosphodiesterase," The Journal of Biological Chemistry, vol. 273, No. 25, pp. 15559-15564 (1998).

Davey et al., "Novel Compounds Possessing Potent cAMP and cGMP Phosphodiesterase Inhibitory Activity. Synthesis and Cardiovascular Effects of a Series of Imidazo[1,2-a]quinoxalinones and Imidazo[1,5-a]quinoxalinones and Their Aza Analogues," Journal of Medicinal Chemistry, vol. 34, No. 9, pp. 2671-2677 (1991).

Colotta et al., "Synthesis of some Tricyclic Heteroaromatic Systems and their $A_1$ and $A_{2a}$ Adenosine Binding Activity," European Journal of Medicinal Chemistry, vol. 30, pp. 133-139 (1995).

Pompon et al., "On the Mechanism of Flavin Modification During Inactivation of Flavocytochrome $b_2$ from Baker's Yeast by Acetylenic Substrates," European Journal of Biochemistry, vol. 148, pp. 145-154 (1985).

Makino et al., "A Facile Synthesis of Novel Tricyclic Compounds, Tetrazoloquinoxalines and 1, 2, 4-Triazoloquinoxalines," Heterocycles, vol. 23, No. 8, pp. 2025-2034 (1985).

Polymeropoulos et al., "A Peptidic Binding Site Model for PDE 4 Inhibitors, Molecular Modeling and Prediction of Bioactivity," Proceedings of the European Symposium on Quantitative Structure-Activity Relationships: Molecular Modeling and Prediction of Bioactivity, 12th, Copenhagen, Denmark, Aug. 23-28, 1998, 2000, Meeting Date 1998, pp. 395-396.

Estrade et al., "Effect of cGMP-Specific Phosphodiesterase Inhibitor on Retinal Function," European Journal of Pharmacology, vol. 352, pp. 157-163 (1998).

Asano, K., "Studies on Chemotherapeutics, VII. Synthesis of Hydrazinoquinoxaline Derivatives," Yakugaku Zasshi, vol. 79, pp. 661-663 (1959).

Krishnan et al., "Reaction of 3-Hydrazino Quinoxalin-2-(1H)-One with Aromatic/Carboxylic Acids Using Diphenyl Phosphoryl Azide: Synthesis and Antiallergic Activity of s-Triazolo [4,3-a] Quinoxalin-4-Ones," Indian Journal of Heterocyclic Chemistry, vol. 3, pp. 227-232 (1994).

Kollenz, G., "Syntheses of Heterocyclic Compounds. CLXX. Reactions of Cyclic Oxalyl Compounds. X. Reaction of 2-Quinoxalinones with Polyphosphoric Acid," Justus Liebigs Annalen der Chemie, vol. 762, pp. 23-28 (1972).

Polymeropoulos et al., "A Peptidic Binding Site Model for PDE 4 Inhibitors," Quantitative Structure-Activity Relationships, vol. 18, No. 6, pp. 543-547 (1999).

Unciti-Broceta et al., "Regioselective One-Pot Synthesis of 9-Alkyl-6-chloropyridol[3,2-e][1,2,4]triazolo-[4,3-a]pyrazines. Reactivity of Aliphatic and Aromatic Hydrazides," Journal of Organic Chemistry, vol. 70, pp. 2878-2880 (2005).

Deleuze-Masquéfa et al., "Design and Synthesis of Novel Imidazo[1,2-a]quinoxalines as PDE4 Inhibitors," Bioorganic and Medicinal Chemistry, vol. 12, pp. 1129-1139 (2004).

Supplementary European Search Report issued Nov. 9, 2010 in corresponding European Application No. 07 85 9852.

G. W. Danswan et al., "Synthesis and Reactions of Some Novel Imidazobenzoxazines and Related Systems," Journal of the Chemical Society, Perkin Transactions 1, 1982, pp. 1049-1058.

I. R. Ager et al., "Synthesis and Oral Antiallergic Activity of Carboxylic Acids Derived from Imidazo[2,1-c][1,4]benzoxazines, Imidazo[1,2-a]quinolines, Imidazo[1,2-a]quinoxalines, Imidazo[1,2-a]quinoxalinones, Pyrrolo[1,2-a]quinoxalinones, Pyrrolo[2,3-a]quinoxalinones, and Imidazo[2,1-b]benzothiazoles," Journal of Medicinal Chemistry, vol. 31, No. 6, 1998, pp. 1098-1115.

V. A. Mamedov et al., "Fused Nitrogen-Containing Heterocycles: III. 4-Oxo-1-phenyl-4,5-dihydroimidazo[1,5-a]quinoxalines. A Retrosynthetic Approach," Russian Journal of Organic Chemistry, vol. 39, No. 1, 2003, pp. 125-130.

SUBSTITUTED IMIDAZO[1,5-A]QUINOXALINES AS PHOSPHODIESTERASE 9 INHIBITORS

This is a divisional of Ser. No. 12/448,212, filed Jun. 12, 2009 now U.S. Pat. No. 8,299,080, which is a U.S. national stage of International Application No. PCT/JP2007/074363 filed Dec. 12, 2007.

BACKGROUND OF THE INVENTION (1) Field of the Invention

This invention relates to novel quinoxaline derivatives and salts thereof, which exhibit phosphodiesterase type 9 (PDE9)-inhibiting activity and are useful as treating agent of dysuria and the like.

(2) Description of Related Art

Dysuria can be largely divided into emptying disorder due to inability to urinate with sufficient force at the time of emptying the bladder, and bladder-filling disorder due to inability to retain urine during the filling time. Presently, $\alpha_1$ blocker is frequently used for treating the emptying disorder and anticholine agent, for treating bladder-filling disorder. These drugs, however, have such defects as insufficient long-term therapeutic effect or reduction in quality of life (QOL) induced by side effect, and development of drugs having new activity mechanism different from the conventional approach, for example, drugs utilizing potassium channel opening activity, cyclic guanosine-3',5'-monophosphate (cGMP) degradation inhibiting activity, is in demand.

cGMP plays an important role in variegated cellular events such as smooth muscle relaxation, memory and learning function control, photoreaction of retina, cell proliferation, immunoreaction and the like. In normal cells, cGMP synthesis by nitrogen monoxide-(NO)-cGMP system and cGMP degradation by PDE system are maintained at balanced levels. Whereas, within the cells under various states of disorder, function of the NO-cGMP system lowers to render the cGMP synthesis level in the cells low, while the cGMP degradation level is unchanged. Hence, cGMP concentration in the affected cells becomes low. It is expected, therefore, prevention of cGMP degradation in the cells to redress the reduction in intracellular cGMP concentration would be useful for treating or preventing the diseases.

While there are many types of PDE, those which specifically hydrolyze cGMP are type 5 (PDE5), type 6 (PDE6) and type 9 (PDE9). Of these, PDE9 shows the least Km value (J. Biol. Chemistry, Vol. 273, No. 25, 15559-15564 (1998)), has high affinity to cGMP and is considered to participate in degradation of cGMP with particular significance.

Pyrazolopyrimidine derivatives as the compounds exhibiting PDE9-inhibiting activity are disclosed in PCT International Publications WO 03/037432 Pamphlet, WO 03/037899 Pamphlet and WO 2004/018474 Pamphlet, and it has been reported as to the derivatives, for example, that they are useful for treating insulin-resistant diseases or the circulatory system disorder, and for improving perception, learning and memory functions.

However, there exists no literature discussing relevancy of PDE9-inhibiting action to therapeutic efficacy on uropathy.

On the other hand, J. Med. Chem., 34, 2671-2677 (1991) discloses quinoxaline derivatives having PDE1-inhibiting activity and PDE4-inhibiting activity. However, this reference contains no description or suggestion that the derivatives have PDE9-inhibiting activity, or that PDE9-inhibiting activity is useful for treating dysuria or the like.

BRIEF SUMMARY OF THE INVENTION

The object of the present invention is to provide novel quinoxaline derivatives which have PDE9-inhibiting activity and are useful as treating agent of disorders including dysuria.

We have discovered, after ardent research activities, that inhibition of PDE9 is effective for treating dysuria such as overactive bladder syndrome, pollakiuria, urinary incontinence, dysuria in benign prostatic hyperplasia and various diseases relating to urinary tract such as urolithiasis. Based on this discovery, we have created novel quinoxaline derivatives having PDE9-inhibiting activity which are useful as treating agent of dysuria and the like, and come to complete the present invention.

DETAILED DESCRIPTION OF THE INVENTION

According to the present invention, therefore, quinoxaline derivatives represented by the formula (I)

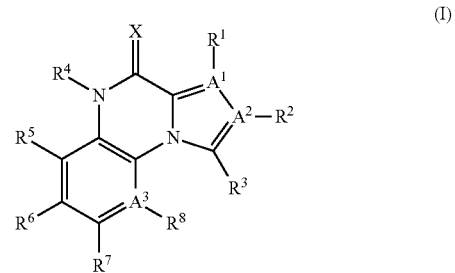

in the formula, $R^1$ and $R^2$ each independently stands for hydrogen; halogen; $C_{1-6}$ alkyl or $C_{1-6}$ alkoxy each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, $C_{1-6}$ alkanoyl, amino, amido, carbamoyl, oxo, carbocyclic group or heterocyclic group; acyl which is optionally substituted with hydroxy, $C_{1-6}$ alkyl, $C_{2-6}$ alkenyl, $C_{2-6}$ alkynyl, $C_{1-6}$ haloalkyl having 1-9 halogen atoms, $C_{1-6}$ alkoxy, $C_{1-6}$ haloalkoxy having 1-9 halogen atoms, amino, carbocyclic group or heterocyclic group; amino which is optionally substituted with 1-2 substituents selected from $C_{1-6}$ alkyl, $C_{2-6}$ alkenyl, $C_{2-6}$ alkynyl, alkanoyl, carbocyclic group and heterocyclic group; hydroxy; or pyrimidinyl which is optionally substituted with halogen, $C_{1-6}$ alkyl, $C_{1-6}$ alkoxy, $C_{1-6}$ haloalkoxy having 1-9 halogen atoms, nitro or amino, $R^3$ stands for $C_{1-9}$ alkyl, $C_{2-9}$ alkenyl or $C_{2-9}$ alkynyl which are optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (here the amino group may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic or heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); aryl, saturated carbocyclic group or saturated heterocyclic group each of which is optionally substituted with halogen, hydroxy, $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy may further be substituted with halogen, hydroxy, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, carbocyclic group or heterocyclic group, independently of each other), $C_{1-6}$ haloalkoxy having 1-9 halogen atoms, carboxy, $C_{1-6}$ alkoxycarbonyl, alkanoyl, amino, amido, carbamoyl, carbocyclic group or heterocyclic group; carboxy; $C_{1-6}$ alkoxycarbonyl (here the $C_{1-6}$ alkoxy moiety in the $C_{1-6}$ alkoxycarbonyl may further be substituted with hydroxy, halogen, $C_{1-6}$ alkoxy, $C_{1-6}$ haloalkoxy having 1-9 halogen atoms, carboxy, $C_{1-6}$ alkoxycarbonyl, amino, amido, carbamoyl, carbocyclic group or heterocyclic group); amido (here the amino moiety in the amido may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group); or carbamoyl (here the amino moiety in the carbamoyl may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), $R^4$ stands for hydrogen; hydroxy; $C_{1-6}$ alkyl which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl or oxo; or amino which is optionally substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group, $R^5$ and $R^8$ each independently stands for hydrogen; halogen; $C_{1-6}$ alkyl, $C_{2-6}$ alkenyl or $C_{1-6}$ alkoxy each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl or oxo; cyano; or nitro, $R^6$ and $R^7$ each independently stands for hydrogen; halogen; $C_{1-6}$ alkyl, $C_{2-6}$ alkenyl, $C_{2-6}$ alkynyl or $C_{1-6}$ alkoxy each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group or heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); cyano; amino which is optionally substituted with 1-2 substituents selected from $C_{1-6}$ alkyl, $C_{2-6}$ alkenyl, $C_{2-6}$ alkynyl (here the $C_{1-6}$ alkyl, $C_{2-6}$ alkenyl and $C_{2-6}$ alkynyl may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, $C_{1-6}$ alkanoyl, amino, amido, carbamoyl, oxo, carbocyclic group and heterocyclic group), alkanoyl, carbocyclic group and heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); carbocyclic group or heterocyclic group each of which is optionally substituted with hydroxy, halogen, $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, $C_{1-6}$ alkanoyl, amino, amido, carbamoyl, oxo, carbocyclic group or heterocyclic group), $C_{1-6}$ haloalkoxy having 1-9 halogen atoms, carboxy, $C_{1-6}$ alkoxycarbonyl, amino, amido or carbamoyl; $COR^9$; or $SO_2R^9$, $R^9$ stands for hydrogen; hydroxy; $C_{1-6}$ alkyl, $C_{2-6}$ alkenyl, $C_{2-6}$ alkynyl or $C_{1-6}$ alkoxy, each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, oxo, carbocyclic group or heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); amino which may be substituted with 1-2 substituents selected from $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, oxo, carbocyclic group or heterocyclic group), $C_{1-6}$ haloalkyl having 1-9 halogen atoms, alkanoyl, carbocyclic group and heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); or aziridin-1-yl, azetidin-1-yl, pyrrolidin-1-yl, piperidin-1-yl, piperazin-1-yl, morpholin-1-yl or pyrazol-1-yl, each of which may be substituted with 1-2 substituents selected from hydroxy, halogen, $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, oxo, carbocyclic group or heterocyclic group), $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group and heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl), X stands for S or O, $A^1$, $A^2$ and $A^3$ stand for N or C, independently of each other, with the proviso that $R^1$, $R^2$ and $R^8$ are respectively absent where $A^1$, $A^2$ and $A^3$ respectively stand for N, or salts thereof are provided.

In the present specification, "$C_{1-6}$", "$C_{1-9}$", "$C_{2-6}$", "$C_{2-9}$" and "$C_{5-7}$" signify that the carbon numbers of the group to which such a prefix is attached is within the given numerical range.

"$C_{1-6}$ alkyl" may be straight chain or branched, examples of which include methyl, ethyl, n-propyl, isopropyl, n-butyl, isobutyl, sec-butyl, tert-butyl, n-pentyl, n-hexyl and the like. Of these, methyl, ethyl, n-propyl, isopropyl and n-butyl are preferred. Also "$C_{1-9}$ alkyl" may be straight chain or branched, specific examples of which include, besides those exemplified as above $C_{1-6}$ alkyl groups, 1-ethyl-n-propyl, n-heptyl, n-octyl, n-nonyl, 2-ethyl-1,1-dimethyl-n-butyl, 1,2,3-trimethyl-n-butyl, 1,5-dimethyl-n-heptan-3-yl and the like. Of these, $C_{5-9}$ alkyl groups, in particular, 1-ethyl-n-propyl, are preferred. "$C_{2-6}$ alkyl" include those exemplified as to above $C_{1-6}$ alkyl excepting methyl, among which ethyl, n-propyl, isopropyl and n-butyl are preferred.

"$C_{2-6}$ alkenyl" contains one or more double bond(s) at optional position(s) and may be straight chain or branched, specific examples including vinyl, allyl, isopropenyl, 1-butenyl, 2-butenyl, 3-butenyl, 1,3-butadienyl, 2-methylallyl, 1-pentenyl, 1-hexenyl and the like, among which vinyl, allyl and isopropenyl are preferred. Also "$C_{2-9}$ alkenyl" contains one or more double bond(s) at optional position(s) and may be straight chain or branched, specific examples including, besides those exemplified as to above $C_{2-6}$ alkenyl, 1-heptenyl, 1-octenyl, 1-nonenyl and the like.

"$C_{2-6}$ alkynyl" contains one or more triple bond(s) at optional position(s) and may be straight chain or branched, specific examples including ethynyl, propynyl, 1-pentynyl and the like, ethynyl being preferred among these. Also "$C_{2-9}$ alkynyl" contains one or more triple bond(s) at optional position(s) and may be straight chain or branched, specific examples including, besides those exemplified as to above $C_{2-6}$ alkynyl, 1-heptynyl, 4-ethylheptan-5-ynyl and the like.

"$C_{1-6}$ alkoxy" refers to oxy (O) groups substituted with $C_{1-6}$ alkyl, examples of which include methoxy, ethoxy, n-propoxy, isopropoxy, n-butoxy, isobutyloxy, sec-butyloxy, tert-butoxy, n-pentyloxy, n-hexyloxy and the like. Of these, methoxy, ethoxy, n-propoxy, isopropoxy and n-butoxy are preferred.

"Acyl" refers to carbonyl (C=O) groups substituted with suitable groups. For example, $C_{1-6}$ alkylcarbonyl, amido, carbamoyl and the like can be named.

"$C_{3-8}$ cycloalkyl" includes cyclopropyl, cyclobutyl, cyclopentyl, cyclohexyl, cycloheptyl and cyclooctyl, among which cyclopentyl and cyclohexyl are preferred. Also "$C_{5-7}$ cycloalkyl" include cyclopentyl, cyclohexyl and cycloheptyl.

"halogen" includes fluorine, chlorine, bromine and iodine, fluorine, chlorine and bromine atoms being particularly preferred.

"$C_{1-6}$ haloalkyl having 1-9 halogen atoms" means $C_{1-6}$ alkyl following the earlier given definition, which are substituted with 1-9 same or different halogen atoms, examples of which include fluoromethyl, trifluoromethyl, 1,2-dichloroethyl, 1-chloro-2-bromoethyl, pentabromoethyl, heptafluoropropyl, 1-chloro-n-propyl, 2-bromo-2-methylethyl, 3-chloro-n-pentyl, 2-bromo-3-chloro-n-hexyl and the like. Of those, $C_{1-2}$ alkyl substituted with 1-5 same or different halogen atoms are preferred. Also "$C_{1-6}$ haloalkoxy having 1-9 halogen atoms" signifies oxy (O) groups substituted with above "$C_{1-6}$ haloalkyl having 1-9 halogen atoms".

The "saturated carbocyclic group" in the definition of $R^3$ in the formula (I) includes $C_{3-8}$ cycloalkyl, cyclopentyl and cyclohexyl being preferred among them. Also the "saturated heterocyclic group" in the definition of $R^3$ in the formula (I) means 5- to 7-membered saturated heterocyclic groups containing 1-3 hetero atoms selected from N, O and S, examples of which include pyrrolidinyl, furanyl, imidazolidinyl, pyrazolidinyl, oxathiolanyl, piperidinyl, piperazinyl, tetrahydropyranyl, morpholinyl, azepinyl, oxepinyl, diazepinyl and the like. Of these, pyrrolidinyl, piperidinyl and piperazinyl are preferred.

"Aryl" in the definition of $R^3$ in the formula (I) encompasses monocyclic or polycyclic aromatic carbocyclic groups and aromatic heterocyclic groups, here the aromatic carbocyclic groups including $C_{6-20}$ aromatic carbocyclic groups, specifically, phenyl, 1-indenyl, 1-naphthyl, 2-naphthyl, 2-anthoryl, 1-acenaphthenyl and the like. Of these, phenyl, 1-naphthyl and 2-naphthyl are preferred. Also the aromatic heterocyclic groups include monocyclic or polycyclic aromatic heterocyclic groups containing 1 or 2 hetero atoms selected from N, O and S, each one ring therein being 5- or 6-membered, examples of which include pyrrolyl, furyl, thienyl, imidazolyl, pyrazolyl, oxazolyl, isoxazolyl, thiazolyl, pyridyl, pyrazinyl, pyrimidinyl, pyridazinyl, indolyl, benzimidazolyl, benzoxazolyl, benzthiazolyl, quinolyl, isoquinolyl, quinazolyl and the like. Of these, monocyclic aromatic heterocyclic groups are preferred.

"Carbocyclic group" in the definitions of $R^1$-$R^4$, $R^6$, $R^7$ and $R^9$ in the formula (I) encompasses those saturated carbocyclic groups defined in the above and those aromatic carbocyclic groups belonging to the aryl as defined in the above, and "heterocyclic group" in the definitions of $R^1$-$R^4$, $R^6$, $R^7$ and $R^9$ in the formula (I) encompasses those saturated heterocyclic groups defined in the above and those aromatic heterocyclic groups belonging to the aryl as defined in the above.

A preferred group of compounds in the present invention are those of the formula (I) in which $A^1$ stands for C and $R^1$ stands for hydrogen.

Another preferred group of compounds in the present invention are those of the formula (I) in which $A^2$ stands for N.

A further different group of compounds preferred in the present invention are those of the formula (I) in which $A^3$ stands for C and $R^8$ stands for hydrogen.

Still another different group of compounds preferred in the present invention are those of the formula (I) in which $R^3$ stands for $C_{1-9}$ alkyl or $C_{2-9}$ alkenyl which are optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group or heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); or saturated carbocyclic group which is optionally substituted with halogen, hydroxy, $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy may further be substituted with halogen, hydroxy, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, carbocyclic group or heterocyclic group, independently of each other), $C_{1-6}$ haloalkoxy having 1-9 halogen atoms, carboxy, $C_{1-6}$ alkoxycarbonyl, alkanoyl, amino, amido, carbamoyl, carbocyclic group or heterocyclic group. In particular, the compounds of the formula (I) in which $R^3$ stands for $C_{1-9}$ alkyl or $C_{2-9}$ alkenyl each of which may be substituted with carboxy; or $C_{5-7}$ cycloalkyl, are preferred.

Another different group of compounds which are preferred in the present invention are those of the formula (I) in which $R^4$ is hydrogen; or $C_{1-6}$ alkyl which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl or oxo. In particular, the compounds of the formula (I) in which $R^4$ stands for hydrogen or $C_{1-6}$ alkyl are preferred.

A further different group of compounds which are preferred in the present invention are those of the formula (I) in which $A^3$ stands for C and $R^5$ and $R^8$ both stand for hydrogen.

Still another different group of compounds which are preferred in the present invention are those of the formula (I) in which $R^6$ is halogen; $C_{1-6}$ alkyl which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group or heterocyclic group (here the carbocyclic group and heterocyclic group may each be further substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); or $COR^9$, and $R^9$ stands for amino which may be substituted with 1-2 substituents selected from $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy 1 to may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, oxo, carbocyclic group or heterocyclic group), $C_{1-6}$ haloalkyl having 1-9 halogen atoms, alkanoyl, carbocyclic group and heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl) or aziridin-1-yl, azetidin-1-yl, pyrrolidin-1-yl, piperidin-1-yl, piperazin-1-yl, morpholin-1-yl or pyrazol-1-yl, each of which may be substituted with 1-2 substituents selected from hydroxy, halogen, $C_{1-6}$ alkyl, $C_{2-6}$ alkenyl, $C_{2-6}$ alkynyl, $C_{1-6}$ alkoxy (here the $C_{1-6}$ alkyl, $C_{2-6}$ alkenyl, $C_{2-6}$ alkynyl and $C_{1-6}$ alkoxy may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, oxo, carbocyclic group or heterocyclic group), $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group and heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl). In particular, the compounds of the formula (I) in which $R^6$ stands for halogen; $C_{1-6}$ alkyl which may be substituted with halogen; or $COR^9$, and $R^9$ stands for amino which may be substituted with 1 or 2 $C_{1-6}$ alkyl group(s) or piperazin-1-yl which may be substituted with $C_{1-6}$ alkyl (here the $C_{1-6}$ alkyl may further be substituted with hydroxy) are preferred.

A further different group of compounds preferred in the present invention are those of the formula (I) in which $R^7$ is halogen; or $C_{1-6}$ alkoxy which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (here the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group or heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl). Of these, the compounds of the formula (I) in which $R^7$ stands for halogen or $C_{1-6}$ alkoxy are particularly preferred.

Still another preferred group of compounds of the present invention are those of the formula (I) in which X stands for O.

As typical examples of the compounds of the formula (I) which are offered by the present invention, besides those shown in the later-appearing Examples, the following may be named:

1-cyclohexyl-N-methyl-4-oxo-N-trifluoromethyl-4,5-dihydroimi-dazo[1,5-a]quinoxaline-8-carboxamide,

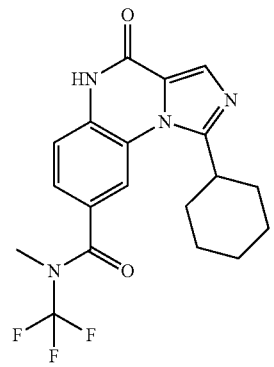 [SMILES: CN(C(=O)c1ccc2[nH]c(=O)c3cnc(C4CCCCC4)n3c2c1)C(F)(F)F]

1-cyclohexyl-4-oxo-N,N-bis(trifluoromethyl)-4,5-dihydro-imidazo[1,5-a]quinoxaline-8-carboxamide,

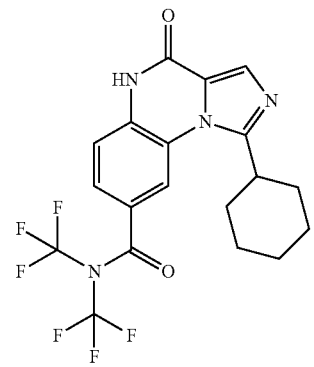 [SMILES: O=C(c1ccc2[nH]c(=O)c3cnc(C4CCCCC4)n3c2c1)N(C(F)(F)F)C(F)(F)F]

1-cyclohexyl-N-methyl-4-oxo-N-(2-propoxyethyl)-4,5-dihydro-imidazo[1,5-a]quinoxaline-8-carboxamide,

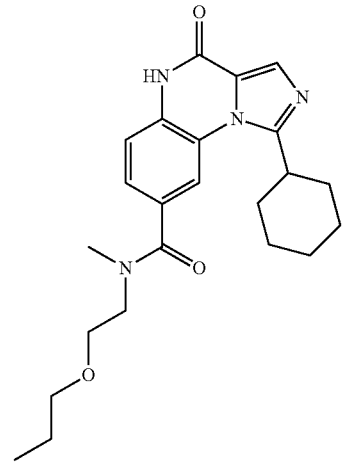 [SMILES: CCCOCCN(C)C(=O)c1ccc2[nH]c(=O)c3cnc(C4CCCCC4)n3c2c1]

1-cyclohexyl-N-(2-isopropoxyethyl)-N-methyl-4-oxo-4,5-dihydroimidazo[1,5-a]quinoxaline-8-carboxamide,

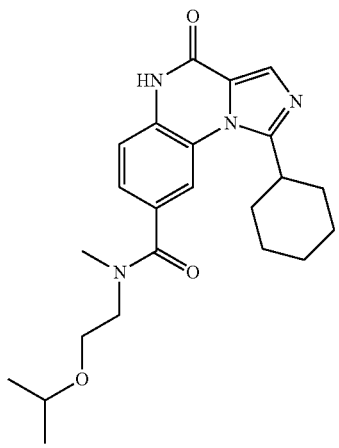 [SMILES: CC(C)OCCN(C)C(=O)c1ccc2[nH]c(=O)c3cnc(C4CCCCC4)n3c2c1]

1-cyclohexyl-N-(2-methoxyethyl)-4-oxo-N-trifluoromethyl-4,5-dihydroimidazo[1,5-a]quinoxaline-8-carboxamide,

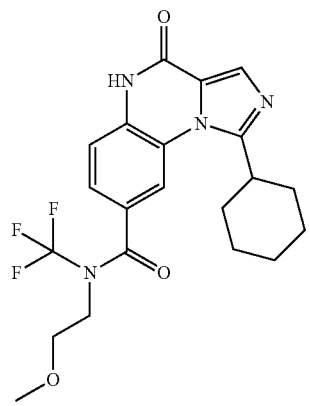 [SMILES: COCCN(C(=O)c1ccc2[nH]c(=O)c3cnc(C4CCCCC4)n3c2c1)C(F)(F)F]

1-cyclohexyl-N-(2-methoxyethyl)-3-methyl-4-oxo-N-trifluoromethyl-4,5-dihydroimidazo[1,5-a]quinoxaline-8-carboxamide,

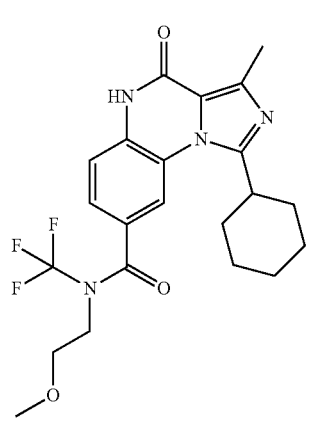 [SMILES: COCCN(C(=O)c1ccc2[nH]c(=O)c3c(C)nc(C4CCCCC4)n3c2c1)C(F)(F)F]

1-cyclohexyl-N-methyl-4-oxo-N-(2-trifluoromethoxyethyl)-4,5-dihydroimidazo[1,5-a]quinoxaline-8-carboxamide,

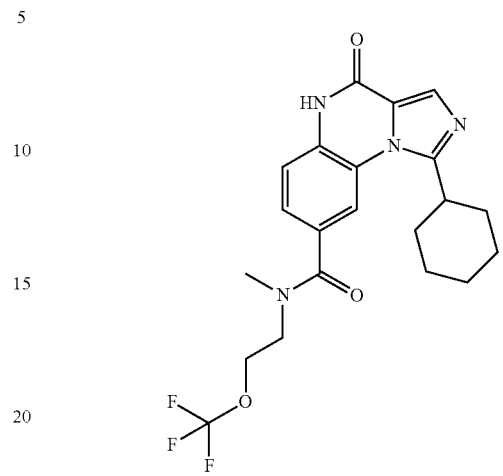

1-cyclohexyl-N,3-dimethyl-4-oxo-N-(2-trifluoromethoxyethyl)-4,5-dihydroimidazo[1,5-a]quinoxaline-8-carboxamide, 1-cyclohexyl-N-methyl-N-[4-(1-methylpiperidyl)]-4-oxo-4,5-dihydroimidazo[1,5-a]quinoxaline-8-carboxamide,

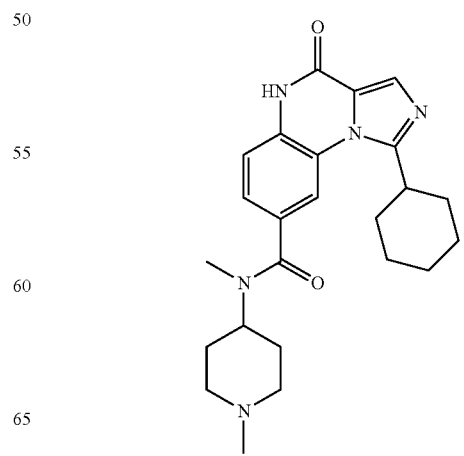

1-cyclohexyl-N-methyl-4-oxo-N-(2-pyridyl)-4,5-dihydroimidazo-[1,5-a]quinoxaline-8-carboxamide,

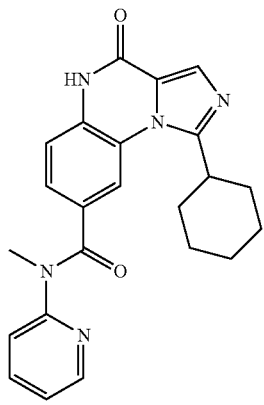 [SMILES: CN(C(=O)c1ccc2[nH]c(=O)c3cnc(C4CCCCC4)n3c2c1)c1ccccn1]

1-cyclohexyl-N-methyl-4-oxo-N-(3-pyridyl)-4,5-dihydroimidazo[1,5-a]quinoxaline-8-carboxamide,

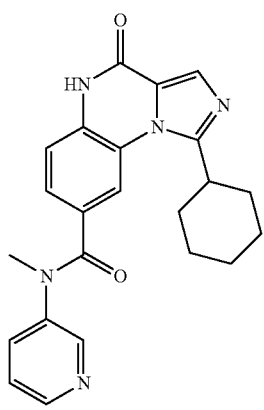 [SMILES: CN(C(=O)c1ccc2[nH]c(=O)c3cnc(C4CCCCC4)n3c2c1)c1cccnc1]

1-cyclohexyl-N-methyl-4-oxo-N-(4-pyridyl)-4,5-dihydroimidazo[1,5-a]quinoxaline-8-carboxamide,

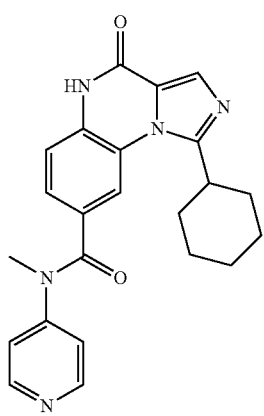 [SMILES: CN(C(=O)c1ccc2[nH]c(=O)c3cnc(C4CCCCC4)n3c2c1)c1ccncc1]

1-cyclohexyl-N,N-dimethyl-4-oxo-8-trifluoromethoxy-4,5-dihydroimidazo[1,5-a]quinoxaline-7-carboxamide,

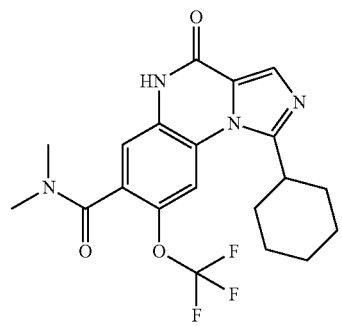 [SMILES: CN(C)C(=O)c1cc2[nH]c(=O)c3cnc(C4CCCCC4)n3c2cc1OC(F)(F)F]

1-(tetrahydropyran-4-yl)-8-trifluoromethylimidazo[1,5-a]-quinoxalin-4 (5H)-one, 8-acetyl-1-(tetrahydropyran-4-yl)imidazo[1,5-a]quinoxalin-4 (5H)-one, 8-chloro-N,N-dimethyl-4-oxo-1-(tetrahydropyran-4-yl)-4,5-dihydroimidazo[1,5-a]quinoxaline-7-carboxamide, 1-(morpholin-4-yl)-7-trifluoromethylimidazo[1,5-a]quinoxalin-4 (5H)-one,

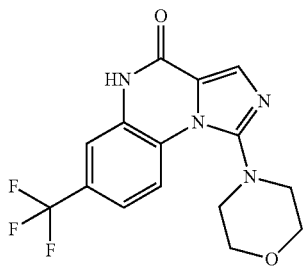

1-(morpholin-4-yl)-8-trifluoromethylimidazo[1,5-a]quinoxalin-4 (5H)-one,

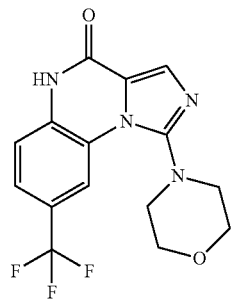 [SMILES: O=c1[nH]c2ccc(C(F)(F)F)cc2n2c(N3CCOCC3)ncc12]

8-acetyl-1-(morpholin-4-yl)imidazo[1,5-a]quinoxalin-4 (5H)-one,

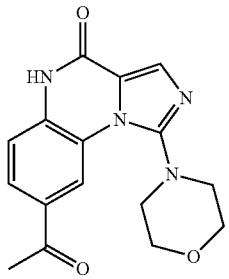 [SMILES: CC(=O)c1ccc2[nH]c(=O)c3cnc(N4CCOCC4)n3c2c1]

1-(pyrrolidin-1-yl)-7-trifluoromethylimidazo[1,5-a]quinoxalin-4 (5H)-one,

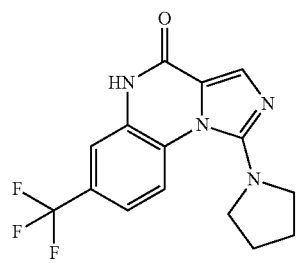 [SMILES: O=c1[nH]c2cc(C(F)(F)F)ccc2n2c(N3CCCC3)ncc12]

1-(pyrrolidin-1-yl)-8-trifluoromethylimidazo[1,5-a]quinoxalin-4 (5H)-one,

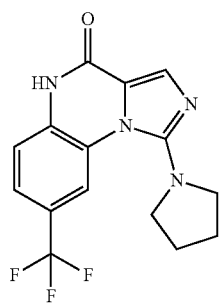 [SMILES: O=c1[nH]c2ccc(C(F)(F)F)cc2n2c(N3CCCC3)ncc12]

8-methoxy-N,N-dimethyl-4-oxo-1-(pyrrolidin-1-yl)-4,5-dihydroimidazo[1,5-a]quinoxaline-7-carboxamide,

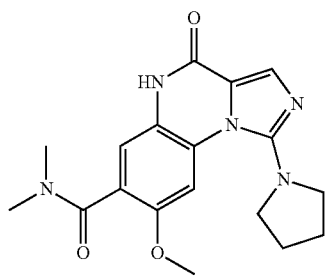 [SMILES: COc1cc2c(cc1C(=O)N(C)C)[nH]c(=O)c1cnc(N3CCCC3)n12]

8-methoxy-N,N,3-trimethyl-4-oxo-1-(pyrrolidin-1-yl)-4,5-dihydroimidazo[1,5-a]quinoxaline-7-carboxamide,

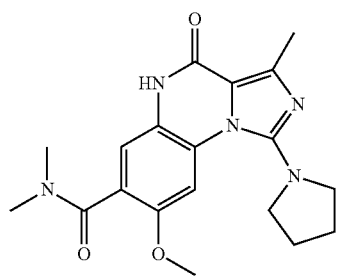 [SMILES: COc1cc2c(cc1C(=O)N(C)C)[nH]c(=O)c1c(C)nc(N3CCCC3)n12]

8-ethoxy-N,N-dimethyl-4-oxo-1-(pyrrolidin-1-yl)-4,5-dihydroimidazo[1,5-a]quinoxaline-7-carboxamide,

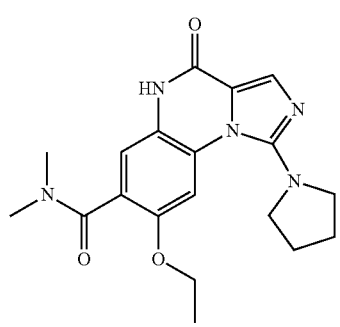 [SMILES: CCOc1cc2c(cc1C(=O)N(C)C)[nH]c(=O)c1cnc(N3CCCC3)n12]

8-chloro-N,N-dimethyl-4-oxo-1-(pyrrolidin-1-yl)-4,5-dihydroimidazo[1,5-a]quinoxaline-7-carboxamide,

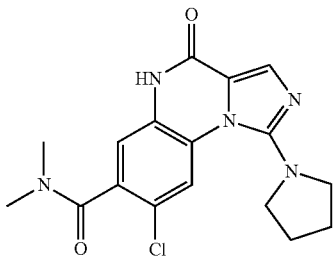 [SMILES: CN(C)C(=O)c1cc2[nH]c(=O)c3cnc(N4CCCC4)n3c2cc1Cl]

N,N-dimethyl-4-oxo-1-(pyrrolidin-1-yl)-4,5-dihydroimidazo[1,5-a]quinoxaline-8-carboxamide,

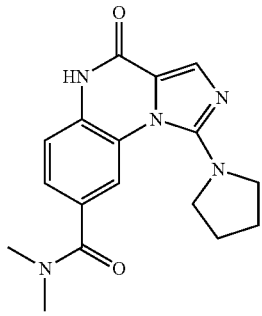 [SMILES: CN(C)C(=O)c1ccc2[nH]c(=O)c3cnc(N4CCCC4)n3c2c1]

N,N,3-trimethyl-4-oxo-1-(pyrrolidin-1-yl)-4,5-dihydroimidazo-[1,5-a]quinoxaline-8-carboxamide,

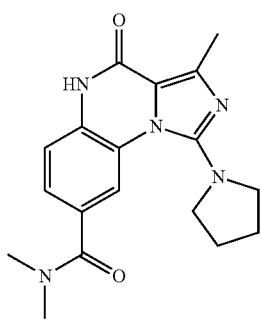 [SMILES: Cc1nc(N2CCCC2)n2c1c(=O)[nH]c1ccc(C(=O)N(C)C)cc12]

N-(2-methoxyethyl)-N-methyl-4-oxo-1-(pyrrolidin-1-yl)-4,5-dihydroimidazo[1,5-a]quinoxaline-8-carboxamide,

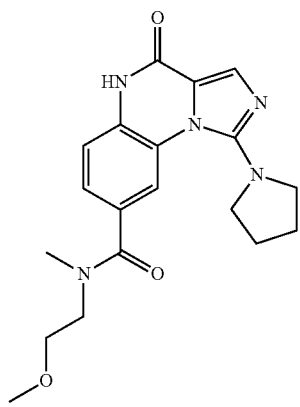 [SMILES: COCCN(C)C(=O)c1ccc2[nH]c(=O)c3cnc(N4CCCC4)n3c2c1]

N-(2-methoxyethyl)-N,3-dimethyl-4-oxo-1-(pyrrolidin-1-yl)-4,5-dihydroimidazo[1,5-a]quinoxaline-8-carboxamide,

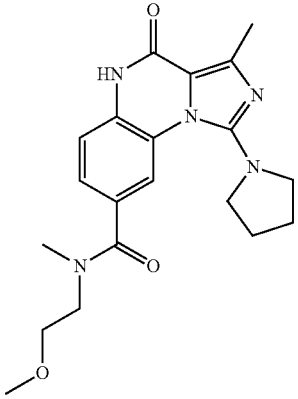 [SMILES: COCCN(C)C(=O)c1ccc2[nH]c(=O)c3c(C)nc(N4CCCC4)n3c2c1]

8-acetyl-1-(pyrrolidin-1-yl)imidazo[1,5-a]quinoxalin-4(5H)-one,

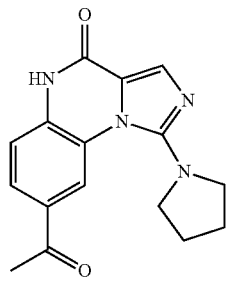 [SMILES: CC(=O)c1ccc2[nH]c(=O)c3cnc(N4CCCC4)n3c2c1]

7-methoxy-N,N-dimethyl-4-oxo-1-(pyrrolidin-1-yl)-4,5-dihydroimidazo[1,5-a]quinoxaline-8-carboxamide,

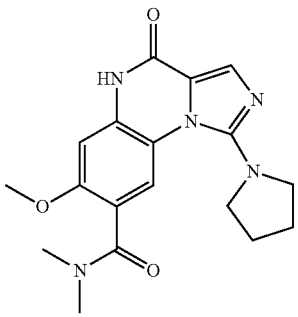 [SMILES: COc1cc2[nH]c(=O)c3cnc(N4CCCC4)n3c2cc1C(=O)N(C)C]

8-methanesulfonyl-1-(pyrrolidin-1-yl)imidazo[1,5-a]-quinoxalin-4(5H)-one,

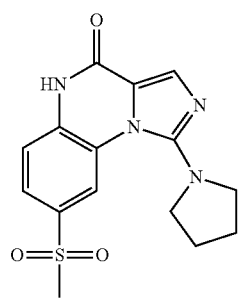 [SMILES: CS(=O)(=O)c1ccc2[nH]c(=O)c3cnc(N4CCCC4)n3c2c1]

1-(piperidin-1-yl)-7-trifluoromethylimidazo[1,5-a]quinoxa-
lin-4 (5H)-one,

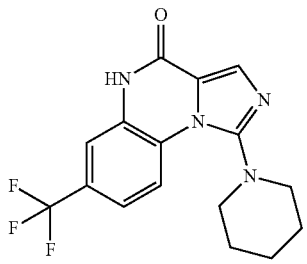 [SMILES: O=c1[nH]c2cc(C(F)(F)F)ccc2n2c(N3CCCCC3)ncc12]

1-(piperidin-1-yl)-8-trifluoromethylimidazo[1,5-a]quinoxa-
lin-4 (5H)-one,

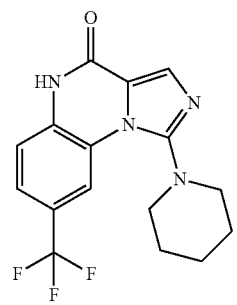

8-methoxy-N,N-dimethyl-4-oxo-1-(piperidin-1-yl)-4,5-di-
hydroimidazo[1,5-a]quinoxaline-7-carboxamide,

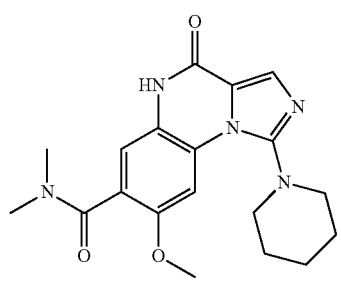 [SMILES: COc1cc2c(cc1C(=O)N(C)C)[nH]c(=O)c1cnc(N3CCCCC3)n12]

8-methoxy-N,N,3-trimethyl-4-oxo-1-(piperidin-1-yl)-4,5-
dihydroimidazo[1,5-a]quinoxaline-7-carboxamide,

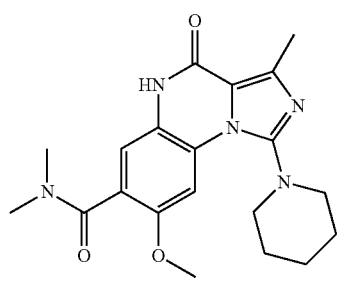 [SMILES: COc1cc2c(cc1C(=O)N(C)C)[nH]c(=O)c1c(C)nc(N3CCCCC3)n12]

8-ethoxy-N,N-dimethyl-4-oxo-1-(piperidin-1-yl)-4,5-dihy-
droimidazo[1,5-a]quinoxaline-7-carboxamide,

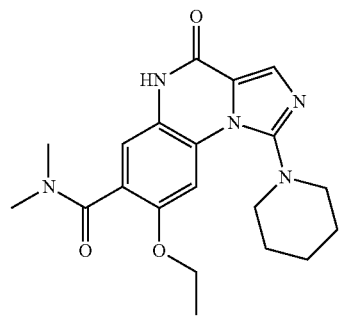 [SMILES: CCOc1cc2c(cc1C(=O)N(C)C)[nH]c(=O)c1cnc(N3CCCCC3)n12]

8-chloro-N,N-dimethyl-4-oxo-1-(piperidin-1-yl)-4,5-dihy-
droimidazo[1,5-a]quinoxaline-7-carboxamide,

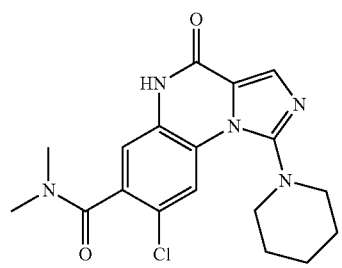 [SMILES: CN(C)C(=O)c1cc2[nH]c(=O)c3cnc(N4CCCCC4)n3c2cc1Cl]

N,N-dimethyl-4-oxo-1-(piperidin-1-yl)-4,5-dihydroimidazo
[1,5-a]quinoxaline-8-carboxamide,

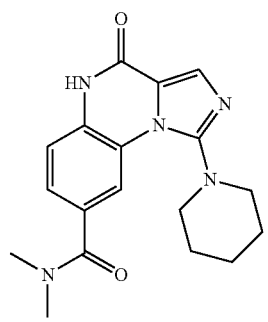

N,N,3-trimethyl-4-oxo-1-(piperidin-1-yl)-4,5-dihydroimi-
dazo-[1,5-a]quinoxaline-8-carboxamide,

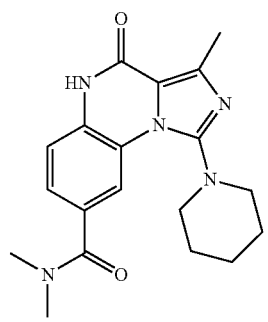 [SMILES: Cc1nc(N2CCCCC2)n2c1c(=O)[nH]c1ccc(C(=O)N(C)C)cc12]

N-(2-methoxyethyl)-N-methyl-4-oxo-1-(piperidin-1-yl)-4,
5-dihydroimidazo[1,5-a]quinoxaline-8-carboxamide,

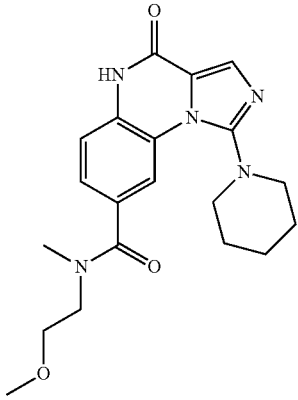

N-(2-methoxyethyl)-N,3-dimethyl-4-oxo-1-(piperidin-1-yl)-4,5-dihydroimidazo[1,5-a]quinoxaline-8-carboxamide,

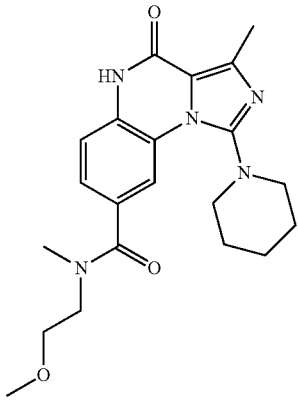

8-acetyl-1-(piperidin-1-yl)imidazo[1,5-a]quinoxalin-4 (5H)-one,

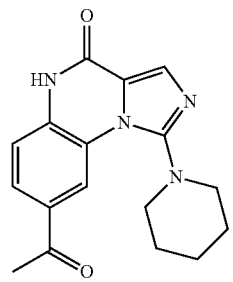

7-methoxy-N,N-dimethyl-4-oxo-1-(piperidin-1-yl)-4,5-dihydroimidazo[1,5-a]quinoxaline-8-carboxamide,

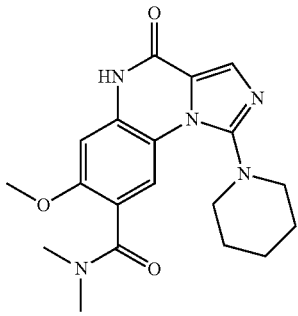

8-methanesulfonyl-1-(piperidin-1-yl)imidazo[1,5-a]quinoxalin-4 (5H)-one,

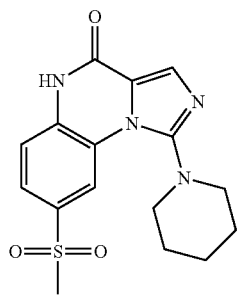 [SMILES: CS(=O)(=O)c1ccc2[nH]c(=O)c3cnc(N4CCCCC4)n3c2c1]

1-(azepin-1-yl)-7-trifluoromethylimidazo[1,5-a]quinoxalin-4 (5H)-one,

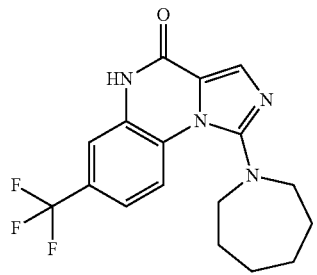 [SMILES: O=c1[nH]c2cc(C(F)(F)F)ccc2n2c(N3CCCCCC3)ncc12]

1-(azepin-1-yl)-8-trifluoromethylimidazo[1,5-a]quinoxalin-4 (5H)-one,

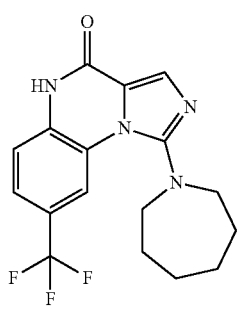 [SMILES: O=c1[nH]c2ccc(C(F)(F)F)cc2n2c(N3CCCCCC3)ncc12]

1-(azepin-1-yl)-8-methoxy-N,N-dimethyl-4-oxo-4,5-dihydroimidazo[1,5-a]quinoxaline-7-carboxamide,

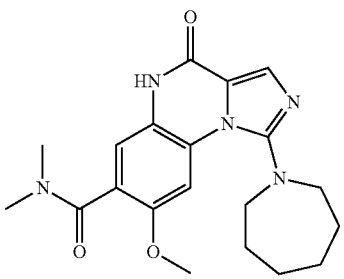 [SMILES: COc1cc2c(cc1C(=O)N(C)C)[nH]c(=O)c1cnc(N3CCCCCC3)n12]

21

1-(azepin-1-yl)-8-methoxy-N,N,3-trimethyl-4-oxo-4,5-di-
hydroimidazo[1,5-a]quinoxaline-7-carboxamide,

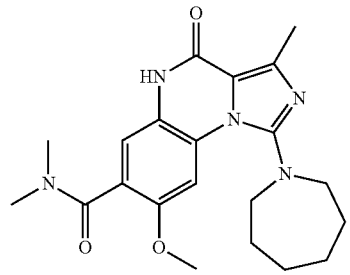 [SMILES: COc1cc2c(cc1C(=O)N(C)C)[nH]c(=O)c1c(C)nc(N3CCCCCC3)n12]

1-(azepin-1-yl)-8-ethoxy-N,N-dimethyl-4-oxo-4,5-dihy-
droimidazo[1,5-a]quinoxaline-7-carboxamide,

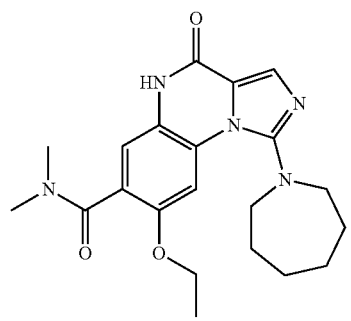 [SMILES: CCOc1cc2c(cc1C(=O)N(C)C)[nH]c(=O)c1cnc(N3CCCCCC3)n12]

1-(azepin-1-yl)-8-chloro-N,N-dimethyl-4-oxo-4,5-dihy-
droimidazo[1,5-a]quinoxaline-7-carboxamide,

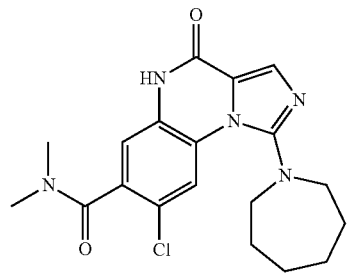 [SMILES: CN(C)C(=O)c1cc2[nH]c(=O)c3cnc(N4CCCCCC4)n3c2cc1Cl]

1-(azepin-1-yl)-N,N-dimethyl-4-oxo-4,5-dihydroimidazo[1,
5-a]-quinoxaline-8-carboxamide,

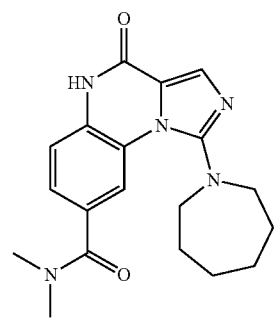 [SMILES: CN(C)C(=O)c1ccc2[nH]c(=O)c3cnc(N4CCCCCC4)n3c2c1]

22

1-(azepin-1-yl)-N,N,3-trimethyl-4-oxo-4,5-dihydroimi-
dazo-[1,5-a]quinoxaline-8-carboxamide,

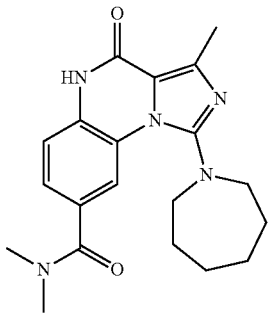 [SMILES: Cc1nc(N2CCCCCC2)n2c1c(=O)[nH]c1ccc(C(=O)N(C)C)cc12]

1-(azepin-1-yl)-N-(2-methoxyethyl)-N-methyl-4-oxo-4,5-
dihydroimidazo[1,5-a]quinoxaline-8-carboxamide,

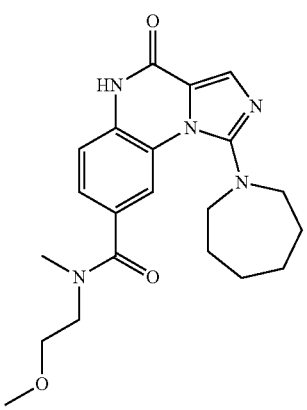 [SMILES: COCCN(C)C(=O)c1ccc2[nH]c(=O)c3cnc(N4CCCCCC4)n3c2c1]

1-(azepin-1-yl)-N-(2-methoxyethyl)-N,3-dimethyl-4-oxo-4,
5-dihydroimidazo[1,5-a]quinoxaline-8-carboxamide,

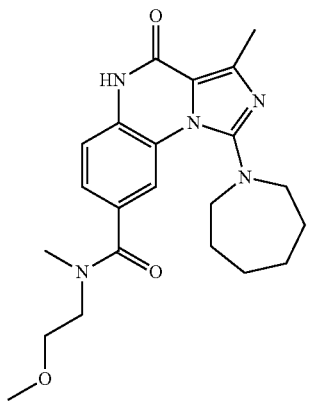 [SMILES: COCCN(C)C(=O)c1ccc2[nH]c(=O)c3c(C)nc(N4CCCCCC4)n3c2c1]

8-acetyl-1-(azepin-1-yl)imidazo[1,5-a]quinoxalin-4 (5H)-one,

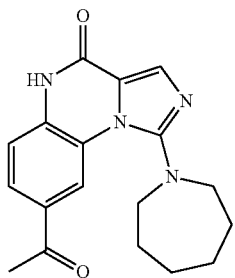 [SMILES: CC(=O)c1ccc2[nH]c(=O)c3cnc(N4CCCCCC4)n3c2c1]

1-(azepin-1-yl)-7-methoxy-N,N-dimethyl-4-oxo-4,5-dihydroimidazo[1,5-a]quinoxaline-8-carboxamide,

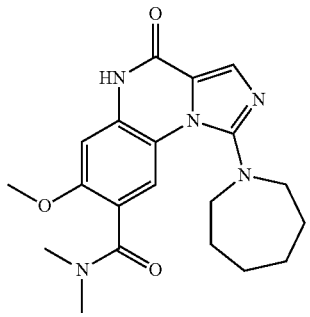 [SMILES: COc1cc2[nH]c(=O)c3cnc(N4CCCCCC4)n3c2cc1C(=O)N(C)C]

1-(azepin-1-yl)-8-methanesulfonylimidazo[1,5-a]quinoxalin-4 (5H)-one,

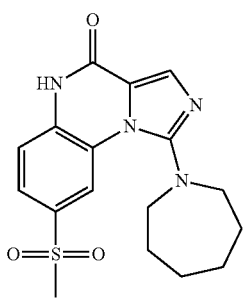 [SMILES: CS(=O)(=O)c1ccc2[nH]c(=O)c3cnc(N4CCCCCC4)n3c2c1]

1-cyclohexyl-7-methoxy-N,N-dimethyl-4-oxo-4,5-dihydroimidazo[1,5-a]quinoxaline-8-carboxamide,

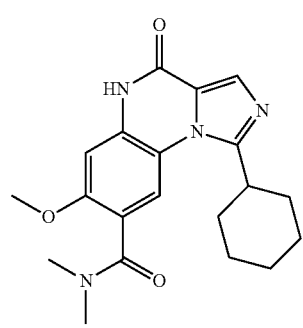 [SMILES: COc1cc2[nH]c(=O)c3cnc(C4CCCCC4)n3c2cc1C(=O)N(C)C]

1-cyclohexyl-8-methanesulfonylimidazo[1,5-a]quinoxalin-4 (5H)-one,

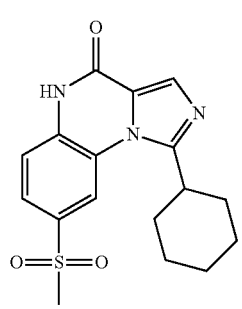 [SMILES: CS(=O)(=O)c1ccc2[nH]c(=O)c3cnc(C4CCCCC4)n3c2c1]

3-(7-chloro-4-oxo-4,5-dihydropyrrolo[1,2-a]quinoxalin-1-yl)-propanoic acid,

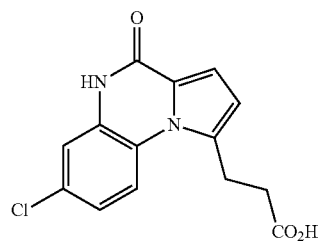 [SMILES: O=C(O)CCc1ccc2c(=O)[nH]c3cc(Cl)ccc3n12]

3-(7-chloro-2-methyl-4-oxo-4,5-dihydropyrrolo[1,2-a]-quinoxalin-1-yl)propanoic acid,

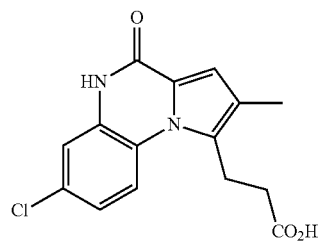 [SMILES: Cc1cc2c(=O)[nH]c3cc(Cl)ccc3n2c1CCC(=O)O]

3-(8-chloro-4-oxo-4,5-dihydropyrrolo[1,2-a]quinoxalin-1-yl)-propanoic acid,

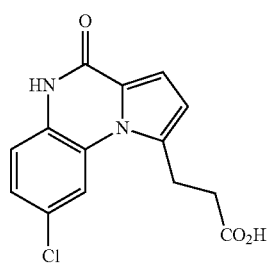 [SMILES: O=C(O)CCc1ccc2c(=O)[nH]c3ccc(Cl)cc3n12]

3-(8-chloro-2-methyl-4-oxo-4,5-dihydropyrrolo[1,2-a]-quinoxalin-1-yl)propanoic acid,

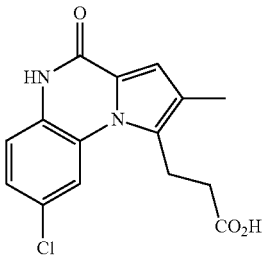 [SMILES: Cc1cc2c(=O)[nH]c3ccc(Cl)cc3n2c1CCC(=O)O]

3-(4-oxo-8-trifluoromethyl-4,5-dihydropyrrolo[1,2-a]-quinoxalin-1-yl)propanoic acid,

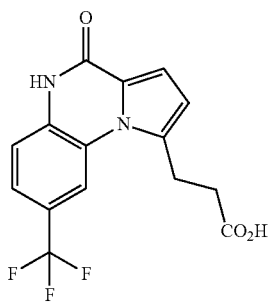 [SMILES: O=C(O)CCc1ccc2c(=O)[nH]c3ccc(C(F)(F)F)cc3n12]

3-(2-methyl-4-oxo-8-trifluoromethyl-4,5-dihydropyrrolo[1,2-a]-quinoxalin-1-yl)propanoic acid,

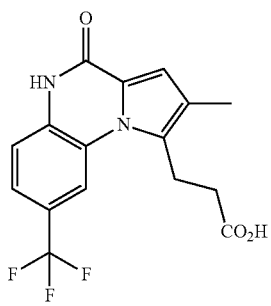

4-(4-oxo-7-trifluoromethyl-4,5-dihydropyrrolo[1,2-a]-quinoxalin-1-yl)butanoic acid,

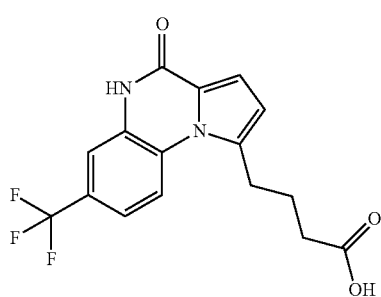 [SMILES: O=C(O)CCCc1ccc2c(=O)[nH]c3cc(C(F)(F)F)ccc3n12]

5-(4-oxo-7-trifluoromethyl-4,5-dihydropyrrolo[1,2-a]-quinoxalin-1-yl)pentanoic acid,

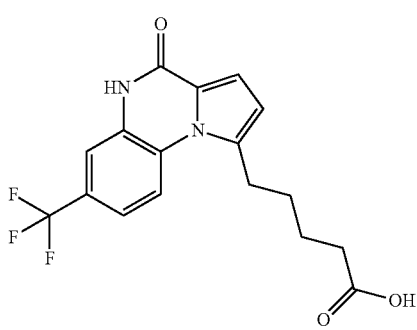 [SMILES: O=C(O)CCCCc1ccc2c(=O)[nH]c3cc(C(F)(F)F)ccc3n12]

3-(2-ethyl-4-oxo-7-trifluoromethyl-4,5-dihydropyrrolo[1,2-a]-quinoxalin-1-yl)propanoic acid,

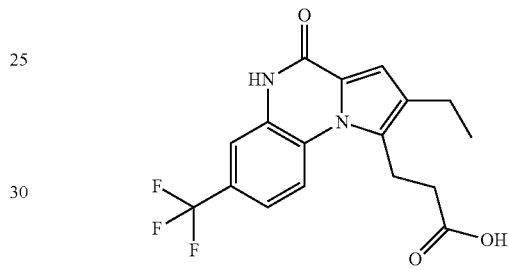

3-(2-ethyl-3-methyl-4-oxo-7-trifluoromethyl-4,5-dihydropyrrolo[1,2-a]quinoxalin-1-yl)propanoic acid,

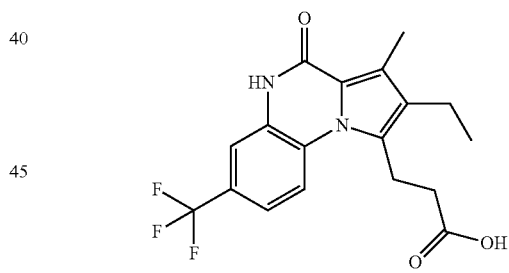

2-(4-oxo-7-trifluoromethyl-4,5-dihydropyrrolo[1,2-a]-quinoxalin-1-ylmethyl)butanoic acid,

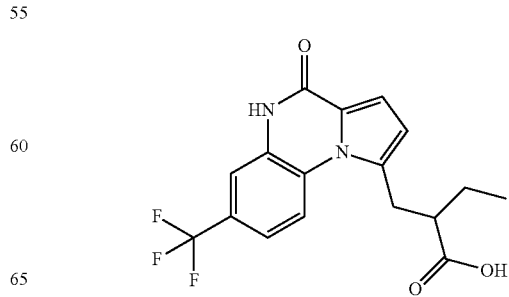

2,2-dimethyl-3-(4-oxo-7-trifluoromethyl-4,5-dihydropyr-rolo-[1,2-a]quinoxalin-1-yl)propanoic acid,

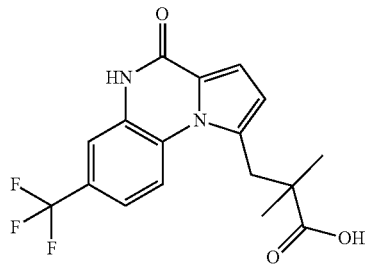 [SMILES: CC(C)(Cc1ccc2c(=O)[nH]c3cc(C(F)(F)F)ccc3n12)C(=O)O]

2-methyl-3-(2-methyl-4-oxo-7-trifluoromethyl-4,5-dihydro-pyrrolo[1,2-a]quinoxalin-1-yl)propanoic acid,

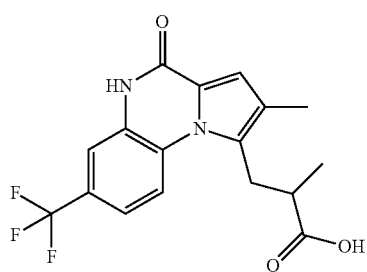 [SMILES: Cc1cc2c(=O)[nH]c3cc(C(F)(F)F)ccc3n2c1CC(C)C(=O)O]

2,2-dimethyl-3-(2-methyl-4-oxo-7-trifluoromethyl-4,5-di-hydro-pyrrolo[1,2-a]quinoxalin-1-yl)propanoic acid,

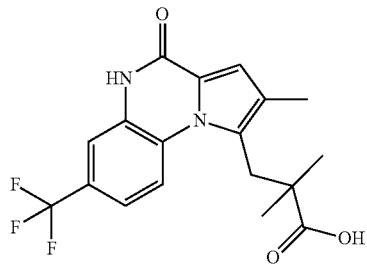 [SMILES: Cc1cc2c(=O)[nH]c3cc(C(F)(F)F)ccc3n2c1CC(C)(C)C(=O)O]

3-(7-methoxymethyl-4-oxo-4,5-dihydropyrrolo[1,2-a]-qui-noxalin-1-yl)propanoic acid,

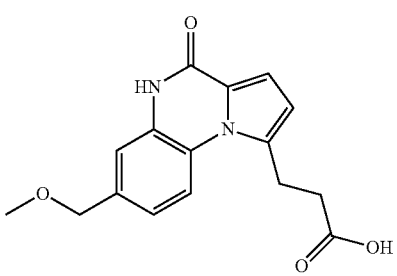

3-(7-ethoxymethyl-4-oxo-4,5-dihydropyrrolo[1,2-a]-qui-noxalin-1-yl)propanoic acid,

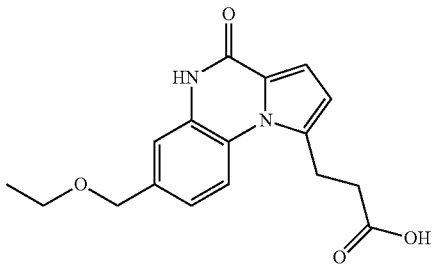

3-(4-oxo-7-propoxymethyl-4,5-dihydropyrrolo[1,2-a]qui-noxalin-1-yl)propanoic acid,

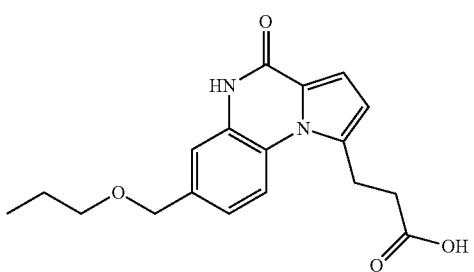 [SMILES: CCCOCc1ccc2c(c1)[nH]c(=O)c1ccc(CCC(=O)O)n12]

3-(7-butoxymethyl-4-oxo-4,5-dihydropyrrolo[1,2-a]qui-noxalin-1-yl)propanoic acid,

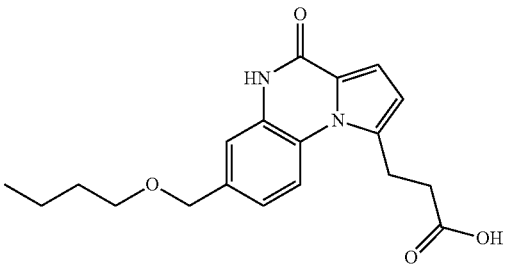 [SMILES: CCCCOCc1ccc2c(c1)[nH]c(=O)c1ccc(CCC(=O)O)n12]

3-(7-methoxymethyl-2-methyl-4-oxo-4,5-dihydropyrrolo[1,2-a]-quinoxalin-1-yl)propanoic acid,

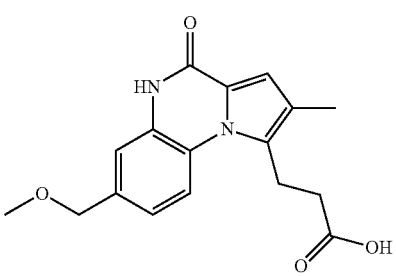 [SMILES: COCc1ccc2c(c1)[nH]c(=O)c1cc(C)c(CCC(=O)O)n12]

| 29 | 30 |
|---|---|
| 3-(7-ethoxymethyl-2-methyl-4-oxo-4,5-dihydropyrrolo[1,2-a]-quinoxalin-1-yl)propanoic acid, | 2-methyl-3-(7-ethoxymethyl-4-oxo-4,5-dihydropyrrolo[1,2-a]-quinoxalin-1-yl)propanoic acid, |

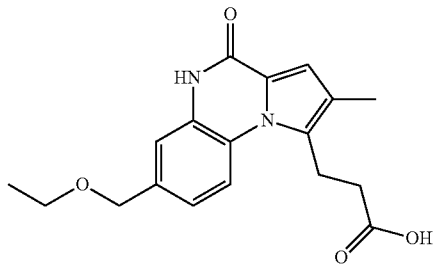 [SMILES: CCOCc1ccc2c(c1)[nH]c(=O)c1cc(C)c(CCC(=O)O)n12] 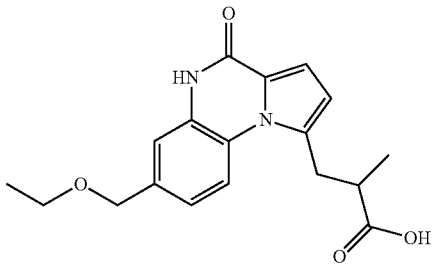

3-(2-methyl-4-oxo-7-propoxymethyl-4,5-dihydropyrrolo[1,2-a]-quinoxalin-1-yl)propanoic acid, 2-methyl-3-(4-oxo-7-propoxymethyl-4,5-dihydropyrrolo[1,2-a]-quinoxalin-1-yl)propanoic acid,

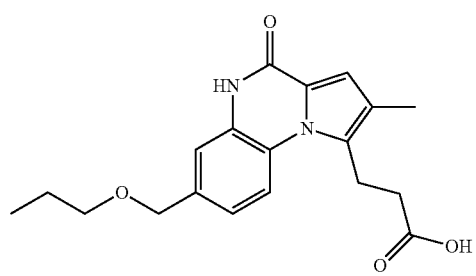 [SMILES: CCCOCc1ccc2c(c1)[nH]c(=O)c1cc(C)c(CCC(=O)O)n12] 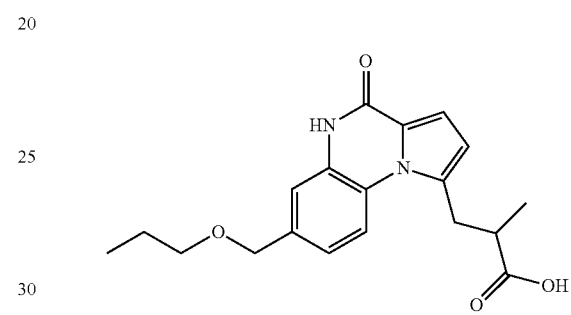

3-(7-butoxymethyl-2-methyl-4-oxo-4,5-dihydropyrrolo[1,2-a]-quinoxalin-1-yl)propanoic acid, 2-methyl-3-(7-butoxymethyl-4-oxo-4,5-dihydropyrrolo[1,2-a]-quinoxalin-1-yl)propanoic acid,

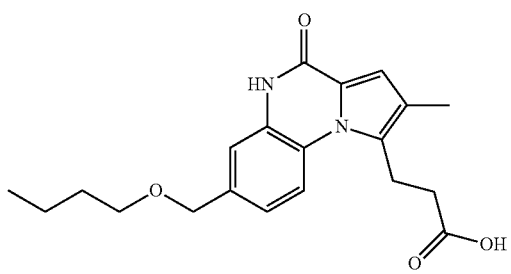 [SMILES: CCCCOCc1ccc2c(c1)[nH]c(=O)c1cc(C)c(CCC(=O)O)n12] 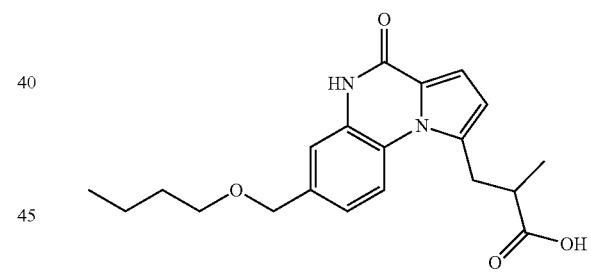

2-methyl-3-(7-methoxymethyl-4-oxo-4,5-dihydropyrrolo[1,2-a]-quinoxalin-1-yl)propanoic acid, 1-cyclohexyl-4-oxo-4,5-dihydro[1,2,4]triazolo[4,3-a]-quinoxaline-8-carboxyic acid,

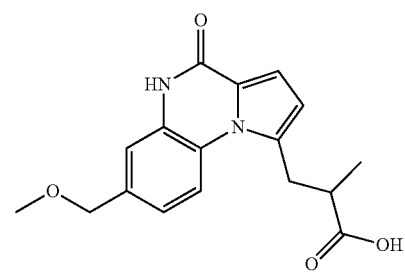 [SMILES: COCc1ccc2c(c1)[nH]c(=O)c1ccc(CC(C)C(=O)O)n12] 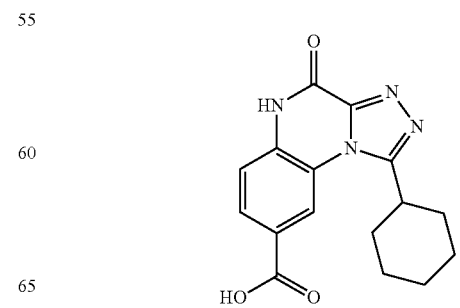

ethyl 1-cyclohexyl-4-oxo-4,5-dihydro[1,2,4]triazolo[4,3-a]-quinoxaline-8-carboxyate,

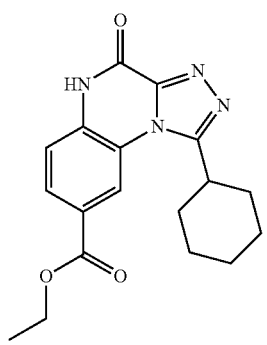 [SMILES: CCOC(=O)c1ccc2[nH]c(=O)c3nnc(C4CCCCC4)n3c2c1]

1-cyclohexyl-8-methoxy-N,N-dimethyl-4-oxo-4,5-dihydro-[1,2,4]triazolo[4,3-a]quinoxaline-7-carboxamide,

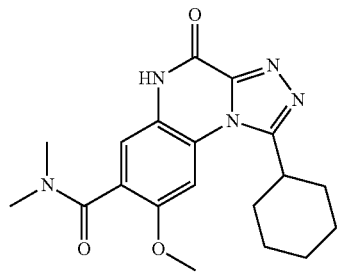 [SMILES: COc1cc2c(cc1C(=O)N(C)C)[nH]c(=O)c1nnc(C3CCCCC3)n12]

1-cyclohexyl-8-ethoxy-N,N-dimethyl-4-oxo-4,5-dihydro-[1,2,4]triazolo[4,3-a]quinoxaline-7-carboxamide,

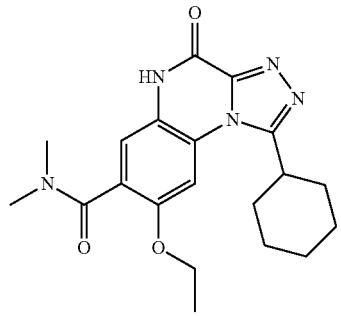 [SMILES: CCOc1cc2c(cc1C(=O)N(C)C)[nH]c(=O)c1nnc(C3CCCCC3)n12]

8-chloro-1-cyclohexyl-N,N-dimethyl-4-oxo-4,5-dihydro[1,2,4]-triazolo[4,3-a]quinoxaline-7-carboxamide,

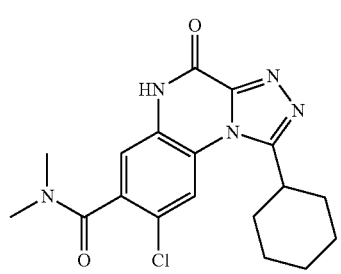

8-chloro-1-cyclohexyl-N-(2-methoxyethyl)-N-methyl-4-oxo-4,5-dihydro[1,2,4]triazolo[4,3-a]quinoxaline-7-carboxamide,

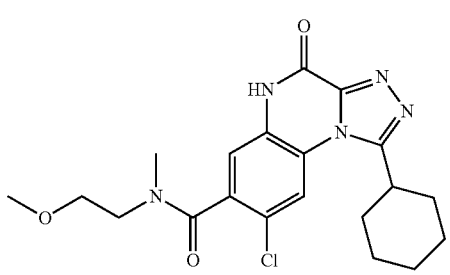 [SMILES: COCCN(C)C(=O)c1cc2[nH]c(=O)c3nnc(C4CCCCC4)n3c2cc1Cl]

1-cyclohexyl-N-methyl-4-oxo-4,5-dihydro[1,2,4]triazolo[4,3-a]-quinoxaline-8-carboxamide,

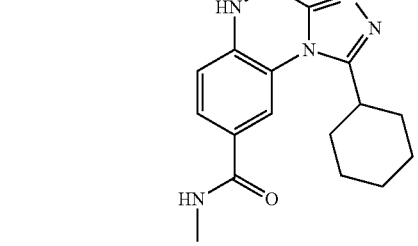

1-cyclohexyl-N,N-dimethyl-4-oxo-4,5-dihydro[1,2,4]triazolo-[4,3-a]quinoxaline-8-carboxamide,

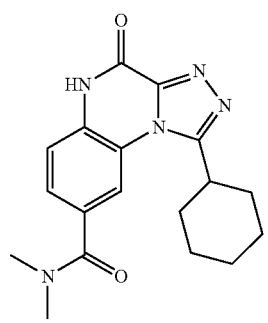 [SMILES: CN(C)C(=O)c1ccc2[nH]c(=O)c3nnc(C4CCCCC4)n3c2c1]

1-cyclohexyl-N-ethyl-N-methyl-4-oxo-4,5-dihydro[1,2,4]-triazolo[4,3-a]quinoxaline-8-carboxamide,

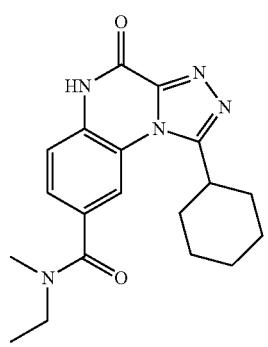 [SMILES: CCN(C)C(=O)c1ccc2[nH]c(=O)c3nnc(C4CCCCC4)n3c2c1]

1-cyclohexyl-N-(2-methoxyethyl)-4-oxo-4,5-dihydro[1,2,4]-triazolo[4,3-a]quinoxaline-8-carboxamide,

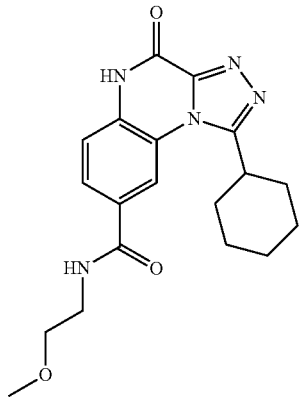 [SMILES: COCCNC(=O)c1ccc2[nH]c(=O)c3nnc(C4CCCCC4)n3c2c1]

1-cyclohexyl-N-(2-methoxyethyl)-N-methyl-4-oxo-4,5-dihydro-[1,2,4]triazolo[4,3-a]quinoxaline-8-carboxamide,

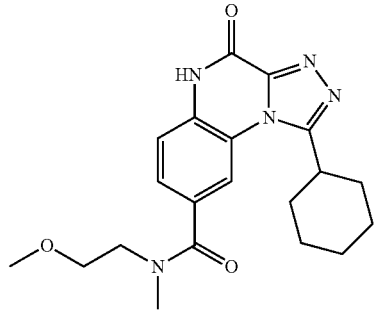 [SMILES: COCCN(C)C(=O)c1ccc2[nH]c(=O)c3nnc(C4CCCCC4)n3c2c1]

1-(1-cyclohexyl-4-oxo-4,5-dihydro[1,2,4]triazolo[4,3-a]-quinoxalin-8-yl)carbonyl-4-methylpiperazine,

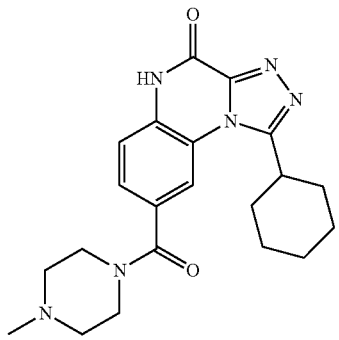 [SMILES: CN1CCN(C(=O)c2ccc3[nH]c(=O)c4nnc(C5CCCCC5)n4c3c2)CC1]

1-(1-cyclohexyl-4-oxo-4,5-dihydro[1,2,4]triazolo[4,3-a]-quinoxalin-8-yl)carbonyl-4-(2-hydroxyethyl)piperidine,

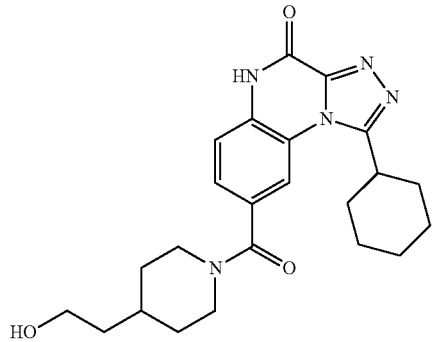 [SMILES: O=C(c1ccc2[nH]c(=O)c3nnc(C4CCCCC4)n3c2c1)N1CCC(CCO)CC1]

and the like.

Those compounds of the formula (I) in the present invention may be present in the form of their salts, depending on the kind of the substituent(s). As the salts, for example, alkali metal salts such as sodium salt, potassium salt, lithium salt and the like; alkaline earth metal salts such as calcium salt, magnesium salt and the like; salts with organic bases such as triethylamine, dicyclohexylamine, pyrrolidine, morpholine, pyridine and the like; ammonium salts; salts with inorganic acids such as hydrochloric acid, hydrobromic acid, sulfuric acid, nitric acid, phosphoric acid and the like; and salts with organic acids such as acetic acid, oxalic acid, citric acid, lactic acid, tartaric acid, p-toluenesulfonic acid and the like. Of these salts, pharmaceutically acceptable salts are particularly preferred.

According to the present invention, those compounds of the formula (I) can be prepared, depending on the kind(s) of the $A^1$ and/or $A^2$, for example by the following methods (a)-(c). For the particulars such as the reaction conditions, later-appearing Examples should be referred to.

Method (a): Preparation of the Compounds of the Formula (I) Having Imidazoquinoxaline Skeleton The compounds of the formula (I) in which $A^1$ stands for C and $A^2$ stands for N, i.e., imidazoquinoxaline derivatives of the following formula,

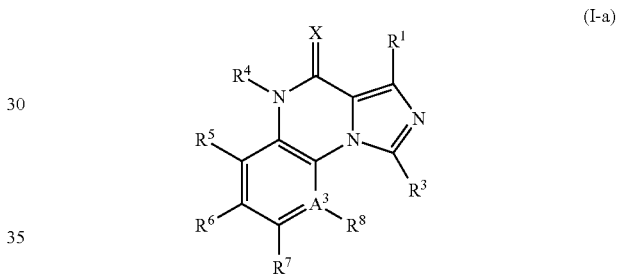

(I-a)

in which $R^1$, $R^3$-$R^8$, $A^3$ and X have the previously defined significations, can be prepared by, for example, reacting the compounds of the formula,

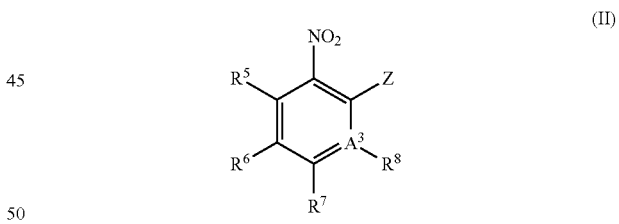

(II)

in which $R^5$-$R^8$ and $A^3$ have the previously defined significations, and Z stands for halogen, with imidazole compounds of the formula,

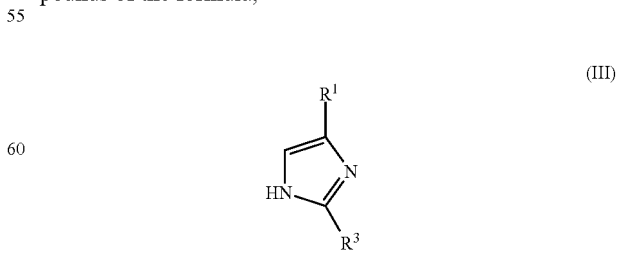

(III)

in which $R^1$ and $R^3$ have the previously defined significations, to obtain the compounds of the formula,

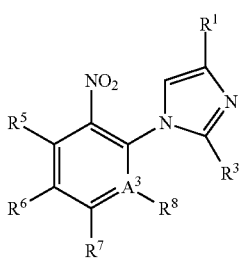

(IV)

in which $R^1$, $R^3$, $R^5$-$R^8$ and $A^3$ have the previously defined significations, reducing the nitro groups in the resultant compounds of the formula (IV) to amino groups, isolating the products where necessary, thereafter subjecting them to the ring closure reaction using carbonyldiimidazole, and, where necessary, further introducing thereinto $R^4$ other than hydrogen.

Method (b): Preparation of the Compounds of the Formula (I) Having Triazoloquinoxaline Skeleton The compounds of the formula (I) in which $A^1$ and $A^2$ both represent N, i.e., the triazoloquinoxaline derivatives of the following formula,

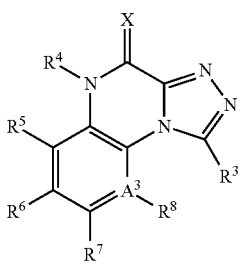

(I-b)

in which $R^3$-$R^8$, $A^3$ and X have the previously defined significations, can be prepared by, for example, treating the quinoxaline compounds of the formula,

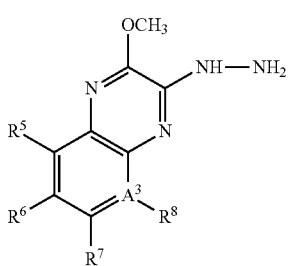

(V)

in which $R^5$-$R^8$ and $A^3$ have the previously defined significations, with $R^3$—C(OCH$_3$)$_3$ to obtain the compounds having triazoloquinoxaline skeleton of the formula,

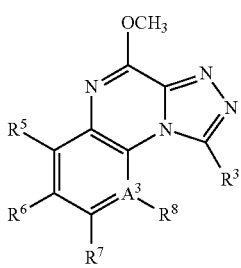

(VI)

in which $R^3$, $R^5$-$R^8$ and $A^3$ have the previously defined significations, then hydrolyzing the methoxy groups in the resultant compounds of the formula (VI) to change them to those of amide structures, and further introducing threeinto, where necessary, $R^4$ other than hydrogen.

Method (c): Preparation of the Compounds of the Formula (I) Having Pyrroloquinoxaline Skeleton The compounds of the formula (I) in which $A^1$ and $A^2$ stand for C, i.e., pyrroloquinoxaline derivatives of the following formula,

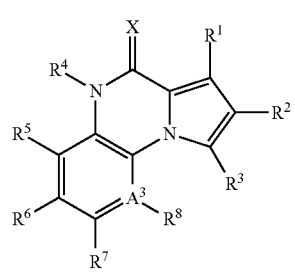

(I-c)

in which $R^1$-$R^8$, $A^3$ and X have the previously defined significations, can be prepared by reacting, for example, the compounds of the formula,

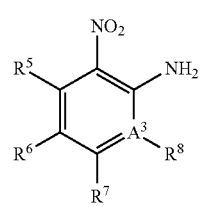

(VII)

in which $R^5$-$R^8$ and $A^3$ have the previously defined significations, with the compounds of the formula,

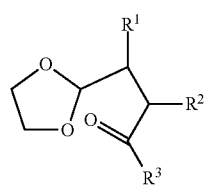

(VIII)

in which $R^1$-$R^3$ have the previously defined significations, to obtain the compounds having pyrrole rings of the formula,

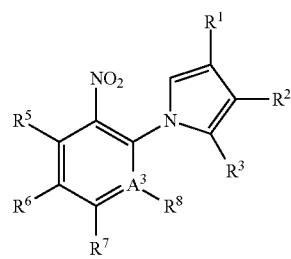

(IX)

in which $R^1$-$R^3$, $R^5$-$R^8$ and $A^3$ have the previously defined significations, reducing the nitro groups in the resultant compounds of the formula (IX) to amino groups, isolating the products where necessary, thereafter subjecting them to ring closure reaction using carbonyldiimidazole, and further introducing thereinto, where necessary, $R^4$ other than hydrogen.

Thus the compounds of the formulae (I-a), (I-b) and (I-c) of the present invention, i.e., the compounds of the formula (I), can be prepared.

The reaction of a compound of the formula (II) with an imidazole compound of the formula (III) in the above method (a) can be generally carried out in an inert solvent, for example, amides such as N,N-dimethylformamide, N,N-dimethylacetamide and the like; alcohols such as methanol, ethanol, isopropanol and the like; or ethers such as tetrahydrofuran, dioxane and the like; in the presence of alkalies such as sodium hydroxide, potassium hydroxide, potassium carbonate and the like, at temperatures within a range of from room temperature to refluxing temperature of the reaction mixture, preferably 50-120° C.

The use ratio of the imidazole compound of the formula (III) to the compound of formula (II) is not particularly limited, but it is generally convenient to use at least 1 mol, preferably within a range of 1.05-5 mols, inter alia, 1.2-2 mols, of the imidazole compound of the formula (III) per mol of the compound of the formula (II). Also the alkalies can be used within a range of about 0.2-about 10 mols, per mol of the compound of the formula (II).

The reduction of nitro in the resulting compound of the formula (IV) to amino can be carried out following the per se known means, for example, in amides such as N,N-dimethylformamide, N,N-dimethylacetamide and the like; or alcohols such as methanol, ethanol, isopropanol and the like; in the presence of a catalyst such as palladium-carbon or the like; in hydrogen atmosphere at 0-80° C., preferably room temperature –50° C.

The use ratio of the catalyst to the compound of the formula (IV) is not particularly limited, while generally the catalyst can be used within a range of about 0.01-1 mol, per mol of the compound of the formula (IV). The subsequent ring closure reaction using carbonyldiimidazole can be carried out following per se known method, for example, in hydrocarbons such as benzene, toluene, xylene and the like; or ethers such as tetrahydrofuran, dioxane and the like, at temperatures within a range of from room temperature to the 1 to refluxing temperature of the reaction mixture, preferably from room temperature to 80° C. The use ratio of carbonyldiimidazole in that occasion is not particularly limited, while generally it is convenient to use at least 1 mol, preferably within a range of 1.1-5 mols, inter alia, 1.2-2 mols of carbonyldiimidazole, per mol of the nitro compound of formula (IV) in the preceding reaction.

The reaction of a compound of the formula (V) with $R^3$—C(OCH$_3$)$_3$ in the method (b) can be carried out generally in the absence of solvent, by heating a mixture of the two at temperatures ranging from room temperature to 150° C., preferably 50-120° C.

The use ratio of $R^3$—C(OCH$_3$)$_3$ to the compound of the formula (V) is not particularly limited, while it is generally convenient to use at least 1 mol, preferably within a range of 1.05-50 mols, inter alia, 1.2-10 mols, of $R^3$—C(OCH$_3$)$_3$ per mol of the compound of formula (V).

Hydrolysis of methoxy in the resulting compound of formula (V) can be carried out following per se known method, for example, in amides such as N,N-dimethylformamide, N,N-dimethylacetamide and the like; or alcohols such as methanol, ethanol, isopropanol and the like; in the presence of an acid catalyst such as hydrochloric acid, para-toluenesulfonic acid and the like, at temperatures ranging from 0° C. to the refluxing temperature of the reaction mixture, preferably from room temperature to 100° C.

The reaction of a compound of formula (VII) with a compound of formula (VIII) in the method (c) can be carried out, generally in inert solvents, for example, amides such as N,N-dimethylformamide, N,N-dimethylacetamide and the like; alcohols such as methanol, ethanol, isopropanol and the like; ethers such as tetrahydrofuran, dioxane and the like; or hydrocarbons such as benzene, toluene, xylene and the like; in the presence of an acid catalyst such as hydrochloric acid, acetic acid, para-toluenesulfonic acid and the like, at temperatures ranging from room temperature to the refluxing temperature of the reaction mixture, preferably 50-120° C.

The use ratio of the compound of formula (VIII) to the compound of formula (VII) is not particularly limited, while it is generally convenient to use at least 1 mol, preferably within a range of 1.05-5 mols, inter alia, 1.2-2 mols, of the compound of formula (VIII) per mol of the compound of formula (VII).

Reduction of nitro in the resulting compound of formula (IX) to amino and the subsequent ring closure reaction using carbonyldiimidazole can be carried out similarly to the reduction of nitro in the compound of formula (IV) to amino and the subsequent ring closure reaction using carbonyldiimidazole.

Furthermore, introduction of $R^4$ other than hydrogen into the compounds of the formulae (I-a), (I-b) and (I-c) in which $R^4$ is hydrogen can be carried out by per se known means, for example, by N-alkylation reaction using a halogen-substituted compounds and alkalies.

In the reactions of methods (a)-(c), those compounds of the formulae (II), (III), (V), (VII) and (VIII) which are used as the starting materials are commercially available or, even when they are novel compounds, can be easily synthesized from known compounds or easily synthesized by referring to the later-appearing Production Examples.

The compounds of formula (I) of the present invention which are produced by the methods (a)-(c) can be isolated from the reaction mixtures and purified by per se known means, for example, recrystallization, column chromatography, thin layer chromatography and the like.

Those quinoxaline derivatives represented by the formula (I) or salts thereof offered by the present invention exhibit potent PDE9-inhibiting activity, and are useful for therapeutic and treating agents of diseases associated with degradation of cGMP by PDE9, for example, overactive bladder syndrome, pollakiuria, urinary incontinence, dysuria in benign prostatic hyperplasia, neurogenic bladder, interstitial cystitis, urolithiasis, benign prostatic hyperplasia, erectile dysfunction, cognitive impairment, neuropathy, Alzheimer's disease, pulmonary hypertension, chronic obstructive pulmonary disease, ischemic heart disease, hypertension, angina, myocardial infarction, arteriosclerosis, thrombosis, embolism, type 1 diabetes and type 2 diabetes.

Among the quinoxaline derivatives represented by the formula (I) or salts thereof that are offered by the present invention, those which exhibit slight PDE5-inhibiting activity in addition to their PDE9-inhibiting activity are expected to achieve also the functional effects based on the PDE5-inhibiting activity.

PDE9-inhibiting activity and PDE5-inhibiting activity of the compounds of the formula (I) of the present invention and their salts are demonstrated by the following experiments.
(1) Measurement of PDE9-Inhibiting Activity:
1) Preparation of Human Recombinant PDE9 Protein Based on the base sequence of hsPDE9A1 registered with GenBank database (accession No.: AF048837), hsPDE9A1 fragment was amplified by polymerase chain reaction under the following conditions, using the following sequence (Amasham Pharmacia Biotech) as the primer and Human Prostate MATCHMAKER cDNA library (CLONTECH) as the template DNA, with Pfu Turbo DNA polymerase (STRATAGENE):

hPDE9-5A primer:
(SEQ ID NO: 1)
CCTAGCTAGCCACCATGGGATCCGGCTCCTCC hPDE9-3A primer:
(SEQ ID NO: 2)
TTTTCCTTTTGCGGCCGCTTATTAGGCACAGTCTCCTTCACTG PCR condition: [95° C., 5 min]×1 cycle, [(95° C., 1 min), (58° C., 2 min), (72° C., 3 min)]×25 cycles, [72° C., 10 min]×1 cycle Thus obtained hsPDE9A1 fragment was given a restricted enzymatic treatment with NheI and NotI, and thereafter inserted into pcDNA 3.1 (+) expression vector (Invitrogen) to let it serve as a human PDE9 expression vector.

Human PDE9 expression vector-transformed *Escherichia coli* was mass incubated to produce a large amount of human PDE9 expression vector, which was transiently transfected into COS-1 cells, with LIPOFECTAMINE 2000 Reagent (GIBCO). The cells were homogenized in ice-cooled buffer A (40 mmol/L Tris-HCl, pH7.5, 15 mmol/L benzamidine, 15 mmol/L 2-mercaptoethanol, 1 μg/mL Pepstatin A, 1 μg/mL Leupeptin, 5 mmol/L EDTA) and centrifuged at 4° C., 14,000×g for 10 minutes. The supernatant was isolated to provide human recombinant PDE9 protein solution.

2) Measurement of PDE9-Inhibiting Activity

To 150 μL of buffer B (70 mmol/L Tris-HCl, pH7.5, 16.7 mmol/L MgCl$_2$, 33.3 nmol/L [$^3$H]-cGMP) solution containing [$^3$H]-cGMP (specific activity=244.2 GBq/mmol) at a concentration of 33.3 nmol/L, 50 μL of a solution of the compound to be evaluated (formed by dissolving the compound in DMSO and diluting it with distilled water to DMSO concentration of 5%) and 50 μL of the PDE9 protein solution as prepared in the above, as diluted with buffer C (40 mmol/L Tris-HCl, pH7.5, 15 mmol/L benzamidine, 15 mmol/L 2-mercaptoethanol, 1 μg/mL Pepstatin A, 1 μg/mL Leupeptin) by 1,500×, were added under cooling with ice. This mixed solution was incubated at 30° C. for 30 minutes and the enzymatic reaction of PDE9 was terminated by heating the system in boiling water for 90 seconds. Returning the system to room temperature, 50 μL of Snake venom (SIGMA: 1 mg/mL) was added, followed by 10 minutes' incubation at 30° C., to convert the [$^3$H]-5'-GMP produced in the previous reaction to [$^3$H]-guanosine. This reaction solution was passed through a column filled with 1 mL of 0.5 mol/L hydrochloric acid-activated cation-exchange resin (Bio-Rad AG50W—X4 resin, mesh size 200-400) and removed of the unreacted substrate ([$^3$H]-cGMP) by elution with 12 mL of distilled water. Thereafter [$^3$H]-guanosine was eluted with 3 mL of 3 mol/L aqueous ammonia and its radiation activity was measured with liquid scintillation counter.

PDE9 inhibition of the tested compound can be calculated by the following formula:

$$\left[\left(1 - \frac{\text{radiation activity where a test compound is used}}{\text{radiation activity in control test}}\right) \times 100\right].$$

From the percent inhibition at various concentration levels of each tested compound, its IC$_{50}$ value against PDE9 can be determined. The results are shown in Table A given later.

(2) Measurement of PDE5-Inhibiting Activity:
1) Preparation of Human Recombinant PDE5 Protein Based on the base sequence of hsPDE5A1 registered with GenBank database (accession No.: NM-001083), hsPDE5A1 fragment was amplified by polymerase chain reaction (PCR) under the following conditions, using the following sequence (SIGMA GENOSYS) as the primer and Human Prostate MATCHMAKER cDNA library (CLONTECH) as the template DNA, with KDD plus DNA polymerase (TOYOBO):

(SEQ ID NO: 3)
hPDE5-5' E primer: CGGAATTCCAACCATGGAGCGGGC (SEQ ID NO: 4)
hPDE5-3' primer: GCTCTAGATCAGTTCCGCTTGGCCTGG PCR condition: [94° C., 2 min]×1 cycle, [(94° C., 30 sec), (65° C., 30 sec), (68° C., 3 min)]×25 cycles, [68° C., 6 min]×1 cycle Thus obtained hsPDE5A1 fragment was given a restricted enzymatic treatment with XBaI and EcoRI, and thereafter inserted into pcDNA 3.1 (+) expression vector (Invitrogen) to let it serve as a human PDE5 expression vector.

Human PDE5 expression vector-transformed *Escherichia coli* was mass incubated to produce a large amount of human PDE5 expression vector, which was transiently transfected into COS-1 cells, with LIPOFECTAMINE 2000 Reagent (GIBCO). The cells were homogenized in ice-cooled buffer A and centrifuged at 4° C., 14,000×g for 10 minutes. The supernatant was isolated to provide human recombinant PDE5 protein solution.

2) Measurement of PDE5-Inhibiting Activity

By a method similar to the measurement of PDE9-inhibiting activity, PDE5-inhibiting activity of each of the test compounds was measured, percent inhibition was calculated and IC$_{50}$ value against PDE5 was determined. The results are shown in the following Table A, concurrently with the compounds' inhibiting activity against PDE9. In the following Table A and later-appearing Table B, the compound of Referential Example 1 is the sole compound whose pharmacological activity is disclosed in PCT International Publication WO 03/37432 Pamphlet.

TABLE A

| Compound | Structural Formula | Inhibiting Activity (IC$_{50}$ value) | |
|---|---|---|---|
| | | PDE9 | PDE5 |
| Example 6 | 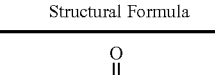 | 10 | 1,259 |

TABLE A-continued

| Compound | Structural Formula | Inhibiting Activity (IC$_{50}$value) | |
|---|---|---|---|
| | | PDE9 | PDE5 |
| Example 9 | | 42 | >10,000 |
| Example 70 | | 1.2 | >10,000 |
| Example 82 | | 3.4 | >10,000 |
| Example 85 | | 3.0 | >10,000 |
| Example 86 | | 8.0 | 7,544 |

TABLE A-continued

| Compound | Structural Formula | Inhibiting Activity (IC$_{50}$ value) | |
|---|---|---|---|
| | | PDE9 | PDE5 |
| Example 180 | | 3.0 | 2,814 |
| Example 185 | | 2.0 | >10,000 |
| Example 187 | | 2.0 | 6,371 |
| Example 189 | | 8.0 | 4,561 |
| Referential Example 1 | | 8.0 | 1,337 |

(3) Investigation of PDE9-Inhibiting Activity on Dysuria Pathological Model

Three-four weeks old Hartley female guinea pigs (Japan SLC, Inc.) were given celiotomy under anesthesia with pentobarbital (30 mg/kg i.p.) and in their urethra to the peripheral side by 1-2 mm from the bladder neck, each a polyethylene tube of 1.4 mm in width and 2.0 mm in inner diameter was placed. After closing the wound, the guinea pigs were bred for at least 3 weeks to produce partial urethra obstruction model in guinea pigs in which occurrence of intravesical pressure rise (uninhibited contraction) not accompanied by micturition and residual urine were observed.

The model was catheterized under anesthesia with urethane (1 g/kg i.p.) at the apex of urinary bladder and right jugular vein for cystometrography and intravenous administration, respectively. The other end of the bladder catheter was connected to a pressure transducer and infusion pump via a three way stop-cock, and physiological saline was continuously infused into the bladder through the infusion pump at a rate of 0.4 mL/min. to induce micturition reflex. Immediately after the micturition reflex was induced, infusion of physiological saline into the bladder was stopped. The intravesical pressure at the time the micturition reflex was induced was measured with the pressure transducer, and the obtained cystometrogram was recorded with pen recorder. The urine voided was collected with disposable type weighing dish and its weight was measured. Further the physiological saline remained in the bladder was sucked with syringe via the bladder catheter and the residual urine volume was measured. The operations of suspending the infusion of physiological saline upon induction of micturition reflex, and about 1 minute thereafter resuming the infusion of physiological saline to induce micturition reflex were repeated plural times (generally 4 times) to stabilize the micturition reflex.

After stabilizing the micturition reflex, a compound solution (prepared by dissolving the compound or methanesulfonic acid salt thereof in DMSO and diluting it with physiological saline or distilled water) or physiological saline was administered into the vein at a volume of 10 mL/kg over 4 minutes, and simultaneously the above-described micturition reflex operations were repeated until 30 minutes passed after initiation of the administration, while measuring the intravesical pressure and the volumes of micturition and residual urine. Also the frequency of uninhibited contraction occurrence during the above-described operations was recorded. The average values of the frequency of uninhibited contraction occurrence and the volume of residual urine in the experiment using several guinea pigs are shown in the following Table B.

As demonstrated in above Table B, the compounds used in the treating agent of the present invention also exhibited significant effect of reducing residual urine volume.

Thus the quinoxaline derivatives represented by the formula (I) of this invention or salts thereof can be administered as PDE9 inhibitor or PDE9 inhibitor concurrently exhibiting slight PDE5-inhibiting activity, for therapy or treatment of PDE9-associated diseases of human and other mammals, orally or parenterally (e.g., intramuscular injection, intravenous injection, rectal administration, percutaneous administration and the like). When PDE5 is inhibited, urethra relaxation is induced, and hence the compounds of the present invention are expected to also act to reduce residual urine volume, when they have the slight PDE5-inhibiting activity concurrently.

The drugs of the present invention can be formulated, together with non-toxic excipients, any of the preparation forms such as solid (e.g., tablet, hard capsule, soft capsule, granule, powder, fine granule, pill, troche and the like); semi-solid (e.g., suppository, ointment and the like); or liquid (e.g., injection, emulsion, suspension, lotion, spray and the like). As non-toxic excipients useful for such formulations, for example, starch, gelatin, glucose, lactose, fructose, maltose, magnesium carbonate, talc, magnesium stearate, methyl cellulose, carboxymethyl cellulose or salts thereof, gum Arabic, polyethylene glycol, p-hydroxybenzoic acid alkyl ester, syrup, ethanol, propylene glycol, vaseline, Carbowax, glycerin, sodium chloride, sodium sulfite, sodium phosphate, citric acid and the like can be named. These drugs may also contain other therapeutically useful drugs.

Content of the compounds of the formula (I) in these drugs differs depending on such factors as the preparation form and administration route, while generally the compounds can be contained at a concentration of 0.1-50 wt % in solid and semi-solid forms, and of 0.05-10 wt %, in liquid form.

Doses of the compounds of the formula (I) are variable over broad ranges according to the kind of warm-blooded animals including human to be treated, kind of involved disease, administration route, seriousness of symptoms, doctor's diagnosis and so on. Whereas, generally they can be each within a range of 0.01-5 mg/kg, preferably 0.02-2 mg/kg, per

TABLE B

| Compound | Dose (i.v., mg/kg) | Frequency of occurrence of uninhibited contraction (times/min) | | | Residual urine volume (mL) | | |
|---|---|---|---|---|---|---|---|
| | | before administration | after administration | quantitative change | before administration | after administration | quantitative change |
| Physiological saline | — | 1.25 | 1.49 | +0.24 | 1.25 | 1.10 | −0.15 |
| Example 6 (methanesulfonic acid salt) | 0.1 | 1.20 | 1.82 | +0.62 | 0.25 | 0.13 | −0.12 |
| | 1 | 1.20 | 1.97 | +0.77 | 0.25 | 0.47 | 0.22 |
| | 3 | 1.20 | 0.68 | −0.52 | 0.25 | 0.21 | −0.04 |
| Example 9 (methanesulfonic acid salt) | 0.3 | 2.09 | 1.45 | −0.64 | 0.43 | 0.11 | −0.32 |
| | 3 | 2.09 | 0.99 | −1.10 | 0.43 | 0.63 | +0.20 |
| | 10 | 0.57 | 0.00 | −0.57 | 0.37 | 0.03 | −0.34 |
| Referential Example 1 | 0.1 | 1.36 | 0.91 | −0.45 | 0.88 | 1.18 | +0.30 |
| | 1 | 1.36 | 1.03 | −0.33 | 0.88 | 1.02 | +0.14 |
| | 3 | 1.60 | 1.09 | −0.51 | 0.95 | 1.00 | +0.05 |

EXAMPLES

Hereinafter the present invention is more specifically explained, referring to Examples, Production Examples and Formulation Example.

Example 1

N,N-dimethyl-4-oxo-1-m-tolyl-4,5-dihydroimidazo[1,5-a]-quinoxaline-7-carboxamide

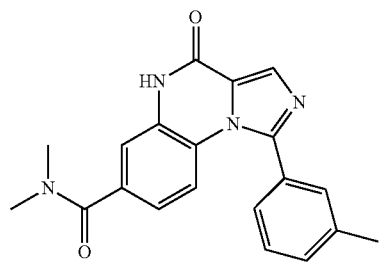

4-Fluoro-N,N-dimethyl-3-nitrobenzamide 1.21 g, 2-m-tolyl-1H-imidazole 600 mg, potassium carbonate 524 mg and N,N-dimethylacetamide 20 mL were mixed and stirred in nitrogen atmosphere for 12 hours at 100° C. After cooling off, the reaction liquid was diluted with ethyl acetate, and water was added to effect phase separation. The organic layer was washed with saturated brine, dried over anhydrous sodium sulfate, and from which the solvent was distilled off. Thus obtained crude product was dissolved in acetic acid 10 mL and water 10 mL, and to the solution 85% sodium hyposulfite 2.65 g was added, followed by 2 hours' heating under reflux. The reaction liquid was cooled with ice and neutralized with saturated sodium hydrogencarbonate solution, which was then extracted with ethyl acetate. The extract was washed with saturated brine and dried over anhydrous sodium sulfate. Distilling the solvent off, the resulting compound was mixed with 1,1'-carbonyldiimidazole 924 mg and 1,2-dichlorobenzene 30 mL, followed by heating under reflux for 10 hours in nitrogen, atmosphere. The reaction liquid was filtered to remove the insoluble matter, and then the solvent was distilled off. Purifying the product on silica gel column chromatography (chloroform:methanol=10:1) and P-TLC (chloroform:methanol=20:1) by the order stated, 112 mg of the title compound was obtained.

$^1$H-NMR (DMSO-$d_6$, δ): 2.41 (3H, s), 2.89 (3H, br s), 2.96 (3H, br s), 6.97 (1H, dd, J=1.9, 8.8 Hz), 7.13 (1H, d, J=8.8 Hz), 7.34 (1H, d, J=1.9 Hz), 7.4-7.6 (4H, m), 7.96 (1H, s), 11.55 (1H, s).

MS (m/z): 346 (M$^+$).

Example 2

N,N-dimethyl-4-oxo-1-p-tolyl-4,5-dihydroimidazo[1,5-a]-quinoxaline-7-carboxamide

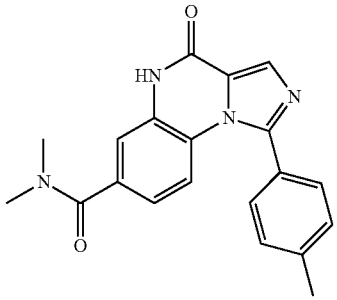 [SMILES: Cc1ccc(-c2ncc3c(=O)[nH]c4cc(C(=O)N(C)C)ccc4n23)cc1]

Procedures similar to Example 1 were conducted to provide the title compound.

$^1$H-NMR (DMSO-$d_6$, δ): 2.45 (3H, s), 2.89 (3H, br s), 2.96 (3H, br s), 6.98 (1H, dd, J=1.5, 8.5 Hz), 7.18 (1H, d, J=8.5 Hz), 7.34 (1H, d, J=1.5 Hz), 7.42 (2H, d, J=8.1 Hz), 7.56 (2H, d, J=8.1 Hz), 7.97 (1H, s), 11.54 (1H, s).

MS (m/z): 346 (M$^+$).

Example 3

7-Chloro-1-[3-(2-methyl)pyridyl]imidazo[1,5-a]quinoxalin-4(5H)-one

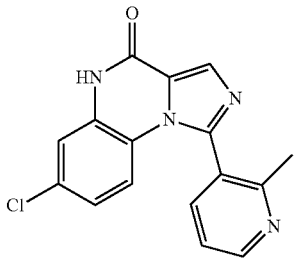 [SMILES: Cc1ncccc1-c1ncc2c(=O)[nH]c3cc(Cl)ccc3n12]

The title compound was obtained from 3-(1H-imidazol-2-yl)-2-methylpyridine as synthesized in Production Example 1, by the operations similar to Example 1.

$^1$H-NMR (DMSO-$d_6$, δ): 2.23 (3H, s), 6.76 (1H, d, J=9.2 Hz), 7.04 (1H, dd, J=2.4, 9.1 Hz), 7.36 (1H, d, J=2.3 Hz), 7.48 (1H, dd, J=5.0, 7.7 Hz), 7.94 (1H, dd, J=1.6, 7.7 Hz), 8.05 (1H, s), 8.74 (1H, dd, J=1.7, 4.8 Hz), 11.63 (1H, s).

MS (m/z): 309 (M$^+$−1).

Example 4

N,N-dimethyl-4-oxo-1-(3-thienyl)-4,5-dihydroimidazo[1,5-a]quinoxaline-7-carboxamide

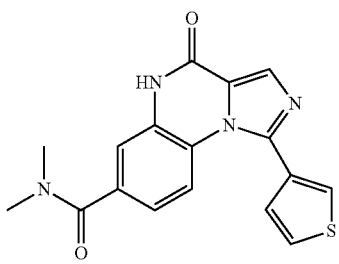 [SMILES: CN(C)C(=O)c1ccc2c(c1)[nH]c(=O)c1cnc(-c3ccsc3)n12]

3-Amino-N,N-dimethyl-4-[2-(3-thienyl)-1H-imidazol-1-yl]-benzamide, which was synthesized in Production Example 4, 759 mg, 1,1'-carbonyldiimidazole 591 mg and 1,2-dichlorobenzene 13 mL were mixed and heated under reflux for 4 hours in nitrogen atmosphere. The reaction liquid was allowed to cool off and from which the solvent was distilled off, followed by purification on silica gel column chromatography. The product was further purified by heat-suspension in 10 mL of acetone to provide 461 mg of the title compound.

$^1$H-NMR (DMSO-d$_6$, δ): 2.8-3.1 (6H, m), 7.04 (1H, dd, J=2.0, 8.5 Hz), 7.19 (1H, d, J=8.9 Hz), 7.34 (1H, d, J=1.5 Hz), 7.41 (1H, dd, J=1.2, 5.0 Hz), 7.85 (1H, dd, J=2.9, 4.8 Hz), 7.97 (1H, s), 8.04 (1H, dd, J=1.2, 3.1 Hz), 11.56 (1H, br s).

MS (m/z): 338 (M$^+$).

Example 5

1-(3-Chlorophenyl)-N,N-dimethyl-4-oxo-4,5-dihydroimidazo-[1,5-a]quinoxaline-7-carboxamide

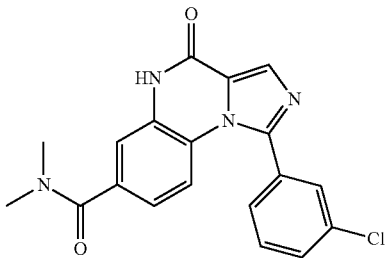 [SMILES: CN(C)C(=O)c1ccc2c(c1)[nH]c(=O)c1cnc(-c3cccc(Cl)c3)n12]

The title compound was obtained from 3-amino-4-[2-(3-chlorophenyl)-1H-imidazol-1-yl]-N,N-dimethylbenzamide as synthesized in Production Example 6, by the operations similar to Example 4.

$^1$H-NMR (DMSO-d$_6$, δ): 2.8-3.1 (6H, m), 7.03 (1H, dd, J=1.8, 8.7 Hz), 7.11 (1H, d, J=8.9 Hz), 7.35 (1H, d, J=1.9 Hz), 7.6-7.8 (3H, m), 7.79 (1H, d, J=1.5 Hz), 8.00 (1H, s), 11.60 (1H, br s).

MS (m/z): 368 (M$^+$+2), 366 (M$^+$).

Example 6

7-Chloro-1-isopropyl-4-oxo-4,5-dihydroimidazo[1,5-a]-quinoxaline

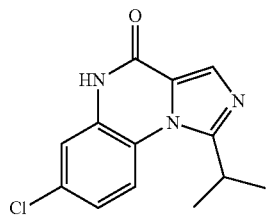 [SMILES: CC(C)c1ncc2c(=O)[nH]c3cc(Cl)ccc3n12]

The title compound was obtained from 5-chloro-2-(2-isopropyl-1H-imidazol-1-yl)aniline as synthesized in Production Example 8, by the operations similar to Example 4.

$^1$H-NMR (DMSO-d$_6$, δ): 1.39 (6H, d, J=6.6 Hz), 3.7-3.9 (1H, m), 7.28 (1H, dd, J=2.7, 8.9 Hz), 7.35 (1H, d, J=2.3 Hz), 7.79 (1H, s), 8.05 (1H, d, J=8.9 Hz), 11.44 (1H, br s).

MS (m/z): 263 (M$^+$+2), 261 (M$^+$).

Example 7

Ethyl 1-isopropyl-4-oxo-4,5-dihydroimidazo[1,5-a]quinoxaline-7-carboxyate

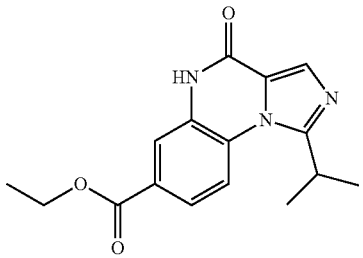 [SMILES: CCOC(=O)c1ccc2c(c1)[nH]c(=O)c1cnc(C(C)C)n12]

The title compound was obtained from ethyl 3-amino-4-(2-isopropyl-1H-imidazol-1-yl)benzoate as synthesized in Production Example 10, by the operations similar to Example 4.

$^1$H-NMR (DMSO-d$_6$, δ): 1.35 (3H, t, J=7.1 Hz), 1.41 (6H, d, J=6.9 Hz), 3.7-3.9 (1H, m), 4.36 (2H, q, J=7.1 Hz), 7.7-7.9 (2H, m), 7.96 (1H, d, J=1.9 Hz), 8.17 (1H, d, J=8.9 Hz), 11.49 (1H, br s).

MS (m/z): 299 (M$^+$).

Example 8

1-Isopropyl-4-oxo-4,5-dihydroimidazo[1,5-a]quinoxaline-7-carboxyic acid

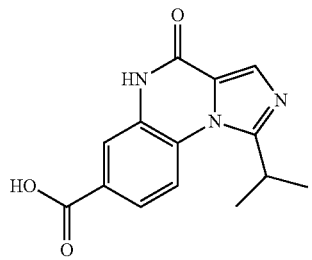 [SMILES: CC(C)c1ncc2c(=O)[nH]c3cc(C(=O)O)ccc3n12]

A mixture of ethyl 1-isopropyl-4-oxo-4,5-dihydroimidazo[1,5-a]-quinoxaline-7-carboxyate as obtained in above Example 7, 2.15 g, ethanol 10 mL and 1N aqueous sodium hydroxide solution 21.7 mL was heated under reflux for an hour in nitrogen atmosphere. The reaction liquid was poured in ice water, and its pH was adjusted to 3 with diluted hydrochloric acid. The precipitated crystals were recovered by filtration, washed with water, and dried by heating under reduced pressure to provide 1.02 g of the title compound.

$^1$H-NMR (DMSO-d$_6$, δ): 1.41 (6H, d, J=6.6 Hz), 3.7-3.9 (1H, m), 7.7-7.9 (2H, m), 7.94 (1H, d, J=1.9 Hz), 8.15 (1H, d, J=8.9 Hz), 11.50 (1H, br s), 13.20 (1H, br s).

MS (m/z): 271 (M$^+$).

Example 9

1-Isopropyl-N,N-dimethyl-4-oxo-4,5-dihydroimidazo[1,5-a]-quinoxaline-7-carboxamide

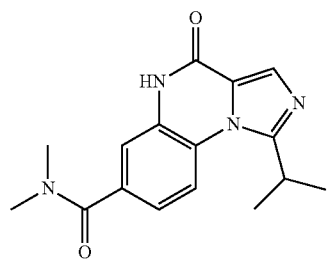 [SMILES: CC(C)c1ncc2c(=O)[nH]c3cc(C(=O)N(C)C)ccc3n12]

A mixture of 1-isopropyl-4-oxo-4,5-dihydroimidazo[1,5-a]-quinoxaline-7-carboxyic acid as synthesized in above Example 8, 271 mg, dimethylamine hydrochloride 90 mg, 1-hydroxybenzotriazole 230 mg, 4-dimethylaminopyridine 24 mg, pyridine 6.8 mL and 1-ethyl-3-(3-dimethylaminopropyl) carbodiimide hydrochloride 288 mg was stirred for 18.5 hours in nitrogen atmosphere. After distilling the solvent off, 25 mL of water was added to the residue and heated under reflux. Cooling the reaction liquid off, the precipitated crystals were recovered by filtration and washed successively with water, hexane and then with diethyl ether. Drying the crystals by heating under reduced pressure, 235 mg of the title compound was obtained.

$^1$H-NMR (DMSO-d$_6$, δ): 1.42 (6H, d, J=6.6 Hz), 2.8-3.1 (6H, m), 3.7-3.9 (1H, m), 7.29 (1H, dd, J=1.9, 8.5 Hz), 7.35 (1H, d, J=1.5 Hz), 7.80 (1H, s), 8.08 (1H, d, J=8.5 Hz), 11.44 (1H, br s).

MS (m/z): 298 (M$^+$).

Example 10

1-(1-Ethylpropyl)-N,N-dimethyl-4-oxo-4,5-dihydroimidazo-[1,5-a]quinoxaline-7-carboxamide

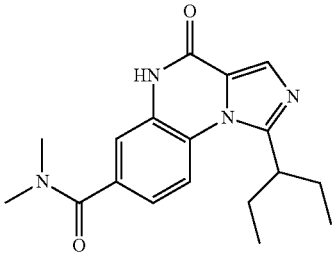 [SMILES: CCC(CC)c1ncc2c(=O)[nH]c3cc(C(=O)N(C)C)ccc3n12]

The title compound was obtained from 3-amino-4-[2-(1-ethylpropyl)-1H-imidazol-1-yl]-N,N-dimethylbenzamide as synthesized in Production Example 12, by the operations similar to Example 4.

$^1$H-NMR (DMSO-d$_6$, δ): 0.86 (6H, t, J=7.3 Hz), 1.7-1.9 (2H, m), 1.9-2.1 (2H, m), 2.9-3.1 (6H, m), 3.4-3.6 (1H, m), 7.29 (1H, dd, J=1.4, 8.7 Hz), 7.36 (1H, d, J=1.5 Hz), 7.85 (1H, s), 8.10 (1H, d, J=8.9 Hz), 11.44 (1H, br s).

MS (m/z): 326 (M$^+$).

Example 11

8-Chloro-1-(1-ethylpropyl)-N,N-dimethyl-4-oxo-4,5-dihydroimidazo[1,5-a]quinoxaline-7-carboxamide

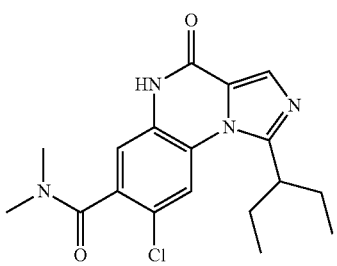 [SMILES: CCC(CC)c1ncc2c(=O)[nH]c3cc(C(=O)N(C)C)c(Cl)cc3n12]

The title compound was obtained from 5-amino-2-chloro-4-[2-(1-ethylpropyl)-1H-imidazol-1-yl]-N,N-dimethylbenzamide as synthesized in Production Example 14, by the operations similar to Example 4.

$^1$H-NMR (DMSO-d$_6$, δ): 0.91 (6H, t, J=7.5 Hz), 1.6-1.9 (2H, m), 1.9-2.1 (2H, m), 2.84 (3H, s), 3.03 (3H, s), 3.4-3.6 (1H, m), 7.22 (1H, s), 7.86 (1H, s), 7.98 (1H, s), 11.57 (1H, br s).

MS (m/z): 362 (M$^+$+2), 360 (M$^+$).

Example 12

Ethyl-1-(1-ethylpropyl)-4-oxo-4,5-dihydroimidazo[1,5-a]-quinoxaline-7-carboxyate

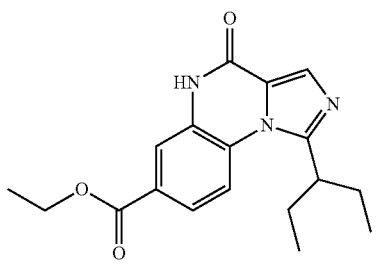 [SMILES: CCOC(=O)c1ccc2c(c1)[nH]c(=O)c1cnc(C(CC)CC)n12]

The title compound was obtained from ethyl 3-amino-4-[2-(1-ethylpropyl)-1H-imidazol-1-yl]benzoate as synthesized in Production Example 16, by the operations similar to Example 4.

$^1$H-NMR (DMSO-d$_6$, δ): 0.87 (6H, t, J=7.5 Hz), 1.35 (3H, t, J=7.1 Hz), 1.7-1.9 (2H, m), 1.9-2.1 (2H, m), 3.4-3.6 (1H, m), 4.36 (2H, q, J=7.1 Hz), 7.82 (1H, dd, J=1.9, 8.9 Hz), 7.87 (1H, s), 7.97 (1H, d, J=1.9 Hz), 8.19 (1H, d, J=8.9 Hz), 11.50 (1H, br s).

MS (m/z): 327 (M$^+$).

Example 13

1-(1-Ethylpropyl)-4-oxo-4,5-dihydroimidazo[1,5-a]-quinoxaline-7-carboxyic acid

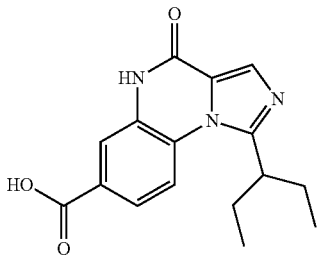 [SMILES: CCC(CC)c1ncc2c(=O)[nH]c3cc(C(=O)O)ccc3n12]

The title compound was obtained from ethyl 1-(1-ethylpropyl)-4-oxo-4,5-dihydroimidazo[1,5-a]quinoxaline-7-carboxyate as synthesized in above Example 12, by the operations similar to Example 8.

$^1$H-NMR (DMSO-d$_6$, δ): 0.87 (6H, t, J=7.3 Hz), 1.7-1.9 (2H, m), 1.9-2.1 (2H, m), 3.5-3.7 (1H, m), 7.81 (1H, dd, J=1.9, 8.9 Hz), 7.86 (1H, s), 7.95 (1H, d, J=1.9 Hz), 8.18 (1H, d, J=8.9 Hz), 11.51 (1H, br s), 13.20 (1H, br s).

MS (m/z): 299 (M$^+$).

Example 14

1-(1-Ethylpropyl)-4-oxo-4,5-dihydroimidazo[1,5-a]quinoxaline-7-carboxamide

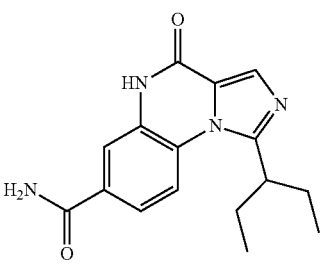 [SMILES: CCC(CC)c1ncc2c(=O)[nH]c3cc(C(N)=O)ccc3n12]

1-(1-Ethylpropyl)-4-oxo-4,5-dihydroimidazo[1,5-a]quinoxaline-7-carboxyic acid as synthesized in above Example 13, 300 mg was dissolved in 10 mL of N,N-dimethylformamide, and to the solution 1,1'-carbonyldiimidazole 275 mg was added little by little in nitrogen atmosphere. After another hour's stirring, ammonia gas was injected into the reaction liquid for 30 minutes, followed by an hour's stirring. Water 30 mL was added and the formed precipitate was recovered by filtration. The crystals were washed with water and dried by heating under reduced pressure to provide 250 mg of the title compound.

$^1$H-NMR (DMSO-d$_6$, δ): 0.87 (6H, t, J=7.3 Hz), 1.7-1.9 (2H, m), 1.9-2.1 (2H, m), 3.57 (1H, quin, J=6.2 Hz), 7.48 (1H, s), 7.72 (1H, dd, J=1.9, 8.9 Hz), 7.84 (1H, d, J=1.9 Hz), 7.85 (1H, s), 8.08 (1H, s), 8.10 (1H, d, J=8.9 Hz), 11.47 (1H, s).

MS (m/z): 298 (M$^+$).

Example 15

Ethyl 8-chloro-1-(1-ethylpropyl)-4-oxo-4,5-dihydroimidazo-[1,5-a]quinoxaline-7-carboxylate

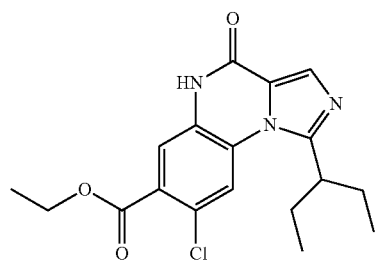 [SMILES: CCOC(=O)c1cc2[nH]c(=O)c3cnc(C(CC)CC)n3c2cc1Cl]

The title compound was obtained from ethyl 5-amino-2-chloro-4-[2-(1-ethylpropyl)-1H-imidazol-1-yl]benzoate as synthesized in Production Example 18, by the operations similar to Example 4.

$^1$H-NMR (DMSO-d$_6$, δ): 0.91 (6H, t, J=7.3 Hz), 1.35 (3H, t, J=7.1 Hz), 1.6-1.9 (2H, m), 1.9-2.1 (2H, m), 3.42 (1H, quin, J=6.2 Hz), 4.36 (2H, q, J=7.3 Hz), 7.83 (1H, s), 7.87 (1H, s), 8.00 (1H, s), 11.56 (1H, s).

MS (m/z): 361 (M$^+$).

Example 16

8-Chloro-1-(1-ethylpropyl)-4-oxo-4,5-dihydroimidazo[1,5-a]-quinoxaline-7-carboxyic acid

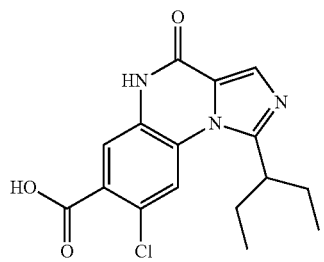 [SMILES: CCC(CC)c1ncc2c(=O)[nH]c3cc(C(=O)O)c(Cl)cc3n12]

The title compound was obtained from ethyl 8-chloro-1-(1-ethylpropyl)-4-oxo-4,5-dihydroimidazo[1,5-a]quinoxaline-7-carboxyate as synthesized in above Example 15, by the operations similar to Example 8.

$^1$H-NMR (DMSO-d$_6$, δ): 0.91 (6H, t, J=7.3 Hz), 1.6-1.9 (2H, m), 1.9-2.1 (2H, m), 3.42 (1H, quin, J=6.2 Hz), 7.82 (1H, s), 7.87 (1H, s), 7.98 (1H, s), 11.56 (1H, s), 13.75 (1H, br s).

MS (m/z): 333 (M$^+$).

Example 17

8-Chloro-N-ethyl-1-(1-ethylpropyl)-N-methyl-4-oxo-4,5-dihydroimidazo[1,5-a]quinoxaline-7-carboxamide

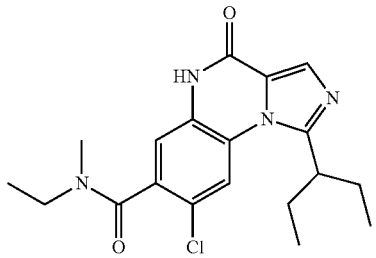 [SMILES: CCC(CC)c1ncc2c(=O)[nH]c3cc(C(=O)N(C)CC)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.91 (6H, t, J=7.3 Hz), 1.06 (1.5H, t, J=7.1 Hz), 1.16 (1.5H, t, J=7.1 Hz), 1.7-1.9 (2H, m), 1.9-2.1 (2H, m), 2.81 (1.5H, s), 3.01 (1.5H, s), 3.16 (1H, q, J=7.1 Hz), 3.4-3.6 (2H, m), 7.21 (0.5H, s), 7.22 (0.5H, s), 7.86 (1H, s), 7.98 (1H, s), 11.53 (1H, s).

MS (m/z): 374 (M$^+$).

Example 18

8-Chloro-1-(1-ethylpropyl)-N-methyl-4-oxo-N-propyl-4,5-dihydroimidazo[1,5-a]quinoxaline-7-carboxamide

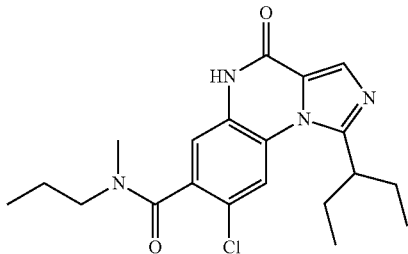 [SMILES: CCCN(C)C(=O)c1cc2[nH]c(=O)c3cnc(C(CC)CC)n3c2cc1Cl]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.73 (1.5H, t, J=7.3 Hz), 0.8-1.0 (7.5H, m), 1.4-1.9 (4H, m), 1.9-2.1 (2H, m), 2.81 (1.5H, s), 3.00 (1.5H, s), 3.0-3.2 (1H, m), 3.4-3.5 (2H, m), 7.22 (0.5H, s), 7.23 (0.5H, s), 7.86 (1H, s), 7.98 (0.5H, s), 7.99 (0.5H, s), 11.52 (1H, s).

MS (m/z): 388 (M$^+$).

Example 19

1-{[8-Chloro-1-(1-ethylpropyl)-4-oxo-4,5-dihydroimidazo-[1,5-a]quinoxalin-7-yl]carbonyl}piperidine

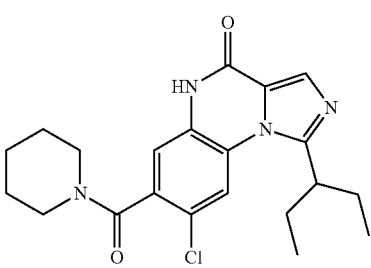 [SMILES: CCC(CC)c1ncc2c(=O)[nH]c3cc(C(=O)N4CCCCC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.90 (6H, t, J=7.3 Hz), 1.3-1.7 (6H, m), 1.7-1.9 (2H, m), 1.9-2.1 (2H, m), 3.1-3.3 (2H, m), 3.45 (1H, quin, J=6.2 Hz), 3.5-3.8 (2H, m), 7.21 (1H, s), 7.86 (1H, s), 7.98 (1H, s), 11.52 (1H, s).

MS (m/z): 400 (M$^+$).

Example 20

8-Chloro-1-(1-ethylpropyl)-N-(2-methoxyethyl)-N-methyl-4-oxo-4,5-dihydroimidazo[1,5-a]quinoxaline-7-carboxamide

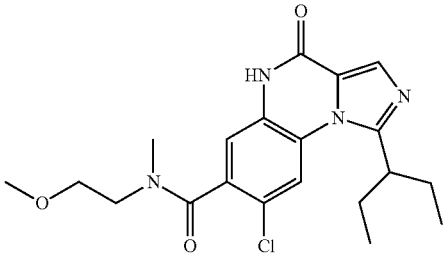 [SMILES: CCC(CC)c1ncc2c(=O)[nH]c3cc(C(=O)N(C)CCOC)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.91 (6H, t, J=7.3 Hz), 1.6-1.9 (2H, m), 1.9-2.1 (2H, m), 2.87 (1.5H, s), 3.03 (1.5H, s), 3.20 (1.5H, s), 3.32 (1.5H, s), 3.3-3.7 (5H, m), 7.22 (0.5H, s), 7.25 (0.5H, s), 7.856 (0.5H, s), 7.863 (0.5H, s), 7.96 (0.5H, s), 7.99 (0.5H, s), 11.53 (0.5H, s), 11.57 (0.5H, s).

MS (m/z): 404 (M$^+$).

Example 21

1-{[8-Chloro-1-(1-ethylpropyl)-4-oxo-4,5-dihydroimidazo-[1,5-a]quinoxalin-7-yl]carbonyl}-4-hydroxypiperidine

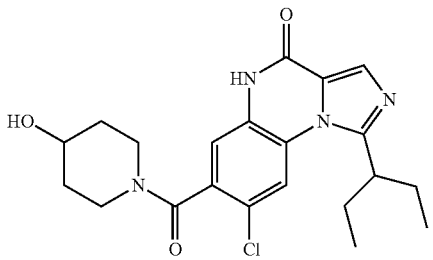 [SMILES: CCC(CC)c1ncc2c(=O)[nH]c3cc(C(=O)N4CCC(O)CC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-d$_6$, δ): 0.90 (6H, t, J=7.3 Hz), 1.2-1.5 (2H, m), 1.6-2.1 (6H, m), 3.0-3.2 (1H, m), 3.2-3.5 (3H, m), 3.78 (1H, br s), 3.9-4.1 (1H, m), 4.7-4.8 (1H, m), 7.20 (0.5H, s), 7.25 (0.5H, s), 7.86 (1H, s), 7.98 (0.5H, s), 7.99 (0.5H, s), 11.50 (0.5H, s), 11.53 (0.5H, s).

MS (m/z): 416 (M$^+$).

Example 22

1-{[8-Chloro-1-(1-ethylpropyl)-4-oxo-4,5-dihydroimidazo-[1,5-a]quinoxalin-7-yl]carbonyl}pyrrolidine

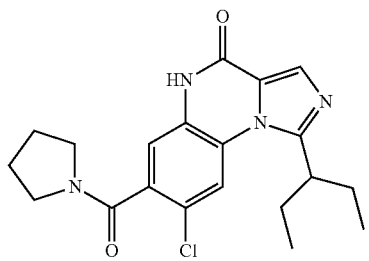 [SMILES: CCC(CC)c1ncc2c(=O)[nH]c3cc(C(=O)N4CCCC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-d$_6$, δ): 0.91 (6H, t, J=7.3 Hz), 1.7-2.1 (8H, m), 3.17 (2H, t, J=6.6 Hz), 3.4-3.6 (3H, m), 7.25 (1H, s), 7.86 (1H, s), 7.99 (1H, s), 11.56 (1H, s).

MS (m/z): 386 (M$^+$).

Example 23

1-{[8-Chloro-1-(1-ethylpropyl)-4-oxo-4,5-dihydroimidazo-[1,5-a]quinoxalin-7-yl]carbonyl}-4-methylpiperazine

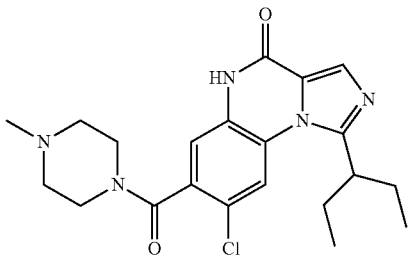 [SMILES: CCC(CC)c1ncc2c(=O)[nH]c3cc(C(=O)N4CCN(C)CC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-d$_6$, δ): 0.90 (6H, t, J=7.3 Hz), 1.6-2.1 (4H, m), 2.21 (3H, s), 2.2-2.5 (4H, m), 3.1-3.3 (2H, m), 3.44 (1H, quin, J=6.4 Hz), 3.5-3.8 (2H, m), 7.23 (1H, s), 7.86 (1H, s), 7.98 (1H, s), 11.53 (1H, s).

MS (m/z): 415 (M$^+$).

Example 24

N-butyl-8-chloro-1-(1-ethylpropyl)-N-methyl-4-oxo-4,5-dihydroimidazo[1,5-a]quinoxaline-7-carboxamide

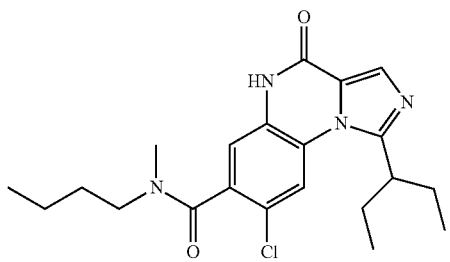 [SMILES: CCCCN(C)C(=O)c1cc2[nH]c(=O)c3cnc(C(CC)CC)n3c2cc1Cl]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-d$_6$, δ): 0.76 (1.3H, t, J=7.3 Hz), 0.90 (6H, t, J=7.3 Hz), 0.95 (1.7H, t, J=7.3 Hz), 1.0-1.7 (4H, m), 1.7-1.9 (2H, m), 1.9-2.1 (2H, m), 2.81 (1.7H, s), 3.00 (1.3H, s), 3.0-3.2 (1.2H, m), 3.4-3.5 (1.8H, m), 7.22 (0.6H, s), 7.23 (0.4H, s), 7.86 (1H, s), 7.98 (1H, s), 11.51 (0.6H, s), 11.53 (0.4H, s).

MS (m/z): 402 (M$^+$).

Example 25

1-{[8-Chloro-1-(1-ethylpropyl)-4-oxo-4,5-dihydroimidazo[1,5-a]-quinoxalin-7-yl]carbonyl}-4-(2-hydroxyethyl)piperidine

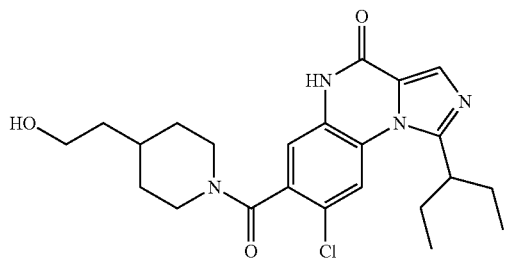 [SMILES: CCC(CC)c1ncc2c(=O)[nH]c3cc(C(=O)N4CCC(CCO)CC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.90 (6H, t, J=7.3 Hz), 1.0-2.0 (13H, m), 2.7-3.1 (2H, m), 3.2-3.5 (2H, m), 4.3-4.6 (2H, m), 7.16 (0.5H, s), 7.26 (0.5H, s), 7.86 (1H, s), 7.97 (0.5H, s), 7.98 (0.5H, s), 11.47 (0.5H, s), 11.55 (0.5H, s).

MS (m/z): 443 (M$^+$–1).

Example 26

8-Chloro-N,N-diethyl-1-(1-ethylpropyl)-4-oxo-4,5-dihydroimidazo[1,5-a]quinoxaline-7-carboxamide

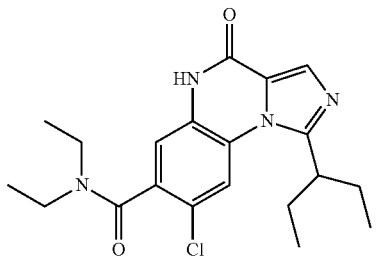 [SMILES: CCC(CC)c1ncc2c(=O)[nH]c3cc(C(=O)N(CC)CC)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.91 (6H, t, J=7.3 Hz), 1.03 (3H, t, J=7.0 Hz), 1.18 (3H, t, J=7.0 Hz), 1.6-1.9 (2H, m), 1.9-2.1 (2H, m), 3.0-3.7 (5H, m), 7.23 (1H, s), 7.86 (1H, s), 7.99 (1H, s), 11.49 (1H, s).

MS (m/z): 388 (M$^+$).

Example 27

1-Acetyl-4-{[8-chloro-1-(1-ethylpropyl)-4-oxo-4,5-dihydro-imidazo[1,5-a]quinoxalin-7-yl]carbonyl}piperazine

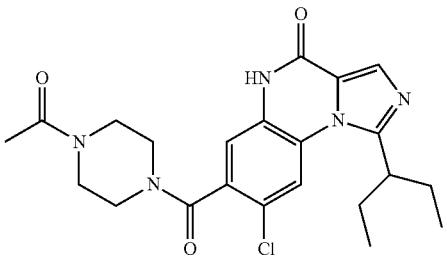 [SMILES: CCC(CC)c1ncc2c(=O)[nH]c3cc(C(=O)N4CCN(C(C)=O)CC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.90 (6H, t, J=7.3 Hz), 1.7-1.9 (2H, m), 1.9-2.1 (5H, m), 3.1-3.8 (9H, m), 7.26 (1H, br s), 7.87 (1H, s), 7.99 (1H, s), 11.58 (1H, s).

MS (m/z): 443 (M$^+$).

Example 28

8-Chloro-1-(1-ethylpropyl)-N-(2-hydroxyethyl)-N-methyl-4-oxo-4,5-dihydroimidazo[1,5-a]quinoxaline-7-carboxamide

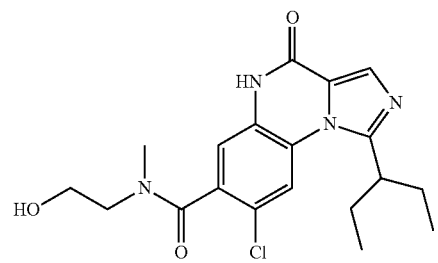 [SMILES: CCC(CC)c1ncc2c(=O)[nH]c3cc(C(=O)N(C)CCO)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.91 (6H, t, J=7.3 Hz), 1.6-1.9 (2H, m), 1.9-2.1 (2H, m), 2.88 (1.3H, s), 3.04 (1.7H, s), 3.1-3.3 (1.1H, m), 3.4-3.7 (3.9H, m), 4.71 (0.6H, t, J=5.4 Hz), 4.81 (0.4H, t, J=5.4 Hz), 7.23 (0.4H, s), 7.27 (0.6H, s), 7.86 (1H, s), 7.96 (0.6H, s), 7.99 (0.4H, s), 11.55 (0.4H, s), 11.57 (0.6H, s).

MS (m/z): 390 (M$^+$).

Example 29

4-{[8-Chloro-1-(1-ethylpropyl)-4-oxo-4,5-dihydroimidazo[1,5-a]-quinoxalin-7-yl]carbonyl}morpholine

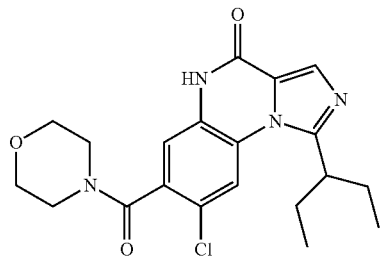 [SMILES: CCC(CC)c1ncc2c(=O)[nH]c3cc(C(=O)N4CCOCC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.90 (6H, t, J=7.3 Hz), 1.7-1.9 (2H, m), 1.9-2.1 (2H, m), 3.2-3.3 (2H, m), 3.4-3.5 (1H, m), 3.5-3.6 (2H, m), 3.67 (4H, br s), 7.25 (1H, s), 7.87 (1H, s), 7.99 (1H, s), 11.57 (1H, s).

MS (m/z): 402 (M$^+$).

Example 30

1-{[8-Chloro-1-(1-ethylpropyl)-4-oxo-4,5-dihydroimidazo[1,5-a]-quinoxalin-7-yl]carbonyl}-4-(2-hydroxyethyl)piperazine

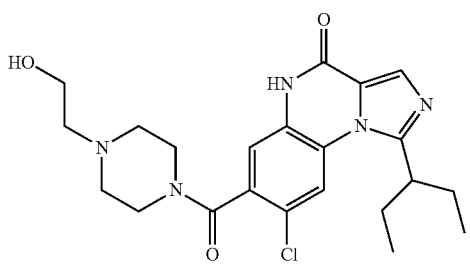 [SMILES: CCC(CC)c1ncc2c(=O)[nH]c3cc(C(=O)N4CCN(CCO)CC4)c(Cl)cc3n12]

The title compound was obtained from 8-chloro-1-(1-ethylpropyl)-4-oxo-4,5-dihydroimidazo[1,5-a]quinoxaline-7-carboxyic acid as synthesized in above Example 16, by the operations similar to Example 9.

$^1$H-NMR (DMSO-$d_6$, δ): 0.90 (6H, t, J=7.3 Hz), 1.6-1.9 (2H, m), 1.9-2.1 (2H, m), 2.3-2.5 (4H, m), 3.1-3.2 (2H, m), 3.4-3.6 (5H, m), 3.6-3.7 (2H, m), 4.42 (1H, t, J=5.4 Hz), 7.23 (1H, s), 7.86 (1H, s), 7.98 (1H, s), 11.53 (1H, s).

MS (m/z): 445 (M$^+$).

Example 31

Methyl 1-(1-ethylpropyl)-8-methoxy-4-oxo-4,5-dihydro-imidazo[1,5-a]quinoxaline-7-carboxyate

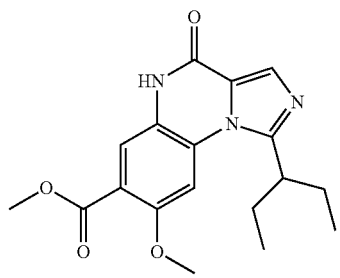 [SMILES: CCC(CC)c1ncc2c(=O)[nH]c3cc(C(=O)OC)c(OC)cc3n12]

The title compound was obtained from methyl 5-amino-4-[2-(1-ethylpropyl)-1H-imidazol-1-yl]-2-methoxybenzoate as synthesized in Production Example 20, by the operations similar to Example 4.

$^1$H-NMR (DMSO-$d_6$, δ): 0.90 (6H, t, J=7.3 Hz), 1.80 (2H, sep, J=7.0 Hz), 2.02 (2H, sep, J=7.2 Hz), 3.53 (1H, quin, J=6.2 Hz), 3.83 (3H, s), 3.95 (3H, s), 7.58 (1H, s), 7.73 (1H, s), 7.85 (1H, s), 11.33 (1H, s).

MS (m/z): 343 (M$^+$).

Example 32

1-(1-Ethylpropyl)-8-methoxy-4-oxo-4,5-dihydroimidazo[1,5-a]-quinoxaline-7-carboxyic acid

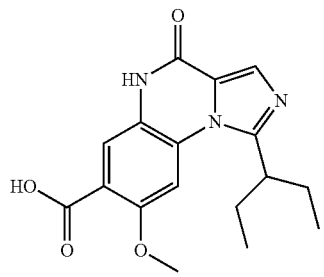 [SMILES: CCC(CC)c1ncc2c(=O)[nH]c3cc(C(=O)O)c(OC)cc3n12]

The title compound was obtained from methyl 1-(1-ethylpropyl)-8-methoxy-4-oxo-4,5-dihydroimidazo[1,5-a]-quinoxaline-7-carboxyate as synthesized in above Example 31, by the operations similar to Example 8.

$^1$H-NMR (DMSO-$d_6$, δ): 0.90 (6H, t, J=7.3 Hz), 1.80 (2H, sep, J=6.8 Hz), 2.02 (2H, sep, J=6.9 Hz), 3.53 (1H, quin, J=6.2 Hz), 3.94 (3H, s), 7.56 (1H, s), 7.73 (1H, s), 7.84 (1H, s), 11.32 (1H, s), 12.90 (1H, br s).

MS (m/z): 329 (M$^+$).

Example 33

1-(1-Ethylpropyl)-8-methoxy-N,N-dimethyl-4-oxo-4,5-dihydroimidazo[1,5-a]quinoxaline-7-carboxamide

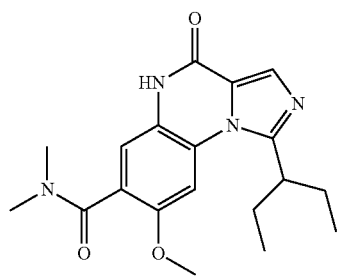 [SMILES: CCC(CC)c1ncc2c(=O)[nH]c3cc(C(=O)N(C)C)c(OC)cc3n12]

1-(1-Ethylpropyl)-8-methoxy-4-oxo-4,5-dihydroimidazo[1,5-a]-quinoxaline-7-carboxyic acid as synthesized in above Example 32, 329 mg, N,N-diimethylformamide 5 mL and 1,1'-carbonyldiimidazole 275 mg were mixed and stirred for an hour at room temperature in nitrogen atmosphere. Dimethylamine hydrochloride 816 mg was added, followed by 5.5 hours' stirring. The reaction mixture was diluted with water, extracted with ethyl acetate and washed with saturated saline. The extract was dried over anhydrous sodium sulfate, and from which the solvent was distilled off. To the residue tert-butyl methyl ether was added, heated under stirring, and the precipitate was recovered by filtration, followed by washing with tert-butyl methyl ether. The product was dried in flowing air (40° C.) to provide 223 mg of the title compound.

$^1$H-NMR (DMSO-$d_6$, δ): 0.91 (6H, t, J=7.3 Hz), 1.7-1.9 (2H, m), 1.9-2.1 (2H, m), 2.81 (3H, s), 2.99 (3H, s), 3.4-3.6 (1H, m), 3.93 (3H, s), 7.14 (1H, s), 7.54 (1H, s), 7.83 (1H, s), 11.32 (1H, s).

MS (m/z): 356 (M$^+$).

Example 34

N-ethyl-1-(1-ethylpropyl)-8-methoxy-N-methyl-4-oxo-4,5-dihydroimidazo[1,5-a]quinoxaline-7-carboxamide

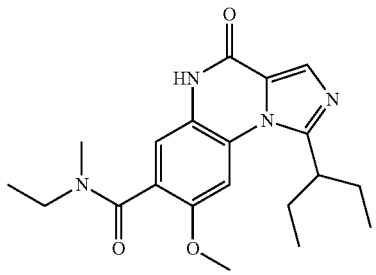 [SMILES: CCC(CC)c1ncc2c(=O)[nH]c3cc(C(=O)N(C)CC)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in Example 32, by the operations similar to Example 33.

$^1$H-NMR (DMSO-$d_6$, δ): 0.91 (6H, t, J=7.3 Hz), 1.02 (1.5H, t, J=7.0 Hz), 1.13 (1.5H, t, J=7.0 Hz), 1.7-1.9 (2H, m), 1.9-2.1 (2H, m), 2.78 (1.5H, s), 2.96 (1.5H, s), 3.13 (1H, q, J=7.0 Hz), 3.47 (1H, q, J=7.0 Hz), 3.54 (1H, quin, J=6.6 Hz), 3.91 (1.5H, s), 3.93 (1.5H, s), 7.12 (0.5H, s), 7.13 (0.5H, s), 7.53 (1H, s), 7.83 (1H, s), 11.28 (0.5H, s), 11.29 (0.5H, s).

MS (m/z): 370 (M$^+$).

Example 35

N,N-diethyl-1-(1-ethylpropyl)-8-methoxy-4-oxo-4,5-dihydroimidazo[1,5-a]quinoxaline-7-carboxamide

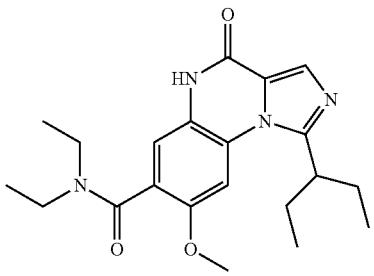 [SMILES: CCC(CC)c1ncc2c(=O)[nH]c3cc(C(=O)N(CC)CC)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.91 (6H, t, J=7.3 Hz), 1.01 (3H, t, J=6.9 Hz), 1.15 (3H, t, J=7.0 Hz), 1.7-1.9 (2H, m), 1.9-2.1 (2H, m), 3.12 (2H, q, J=7.0 Hz), 3.3-3.6 (3H, m), 3.91 (3H, s), 7.12 (1H, s), 7.53 (1H, s), 7.83 (1H, s), 11.25 (1H, s).

MS (m/z): 384 (M$^+$).

Example 36

1-(1-Ethylpropyl)-8-methoxy-N-(2-methoxyethyl)-N-methyl-4-oxo-4,5-dihydroimidazo[1,5-a]quinoxaline-7-carboxamide

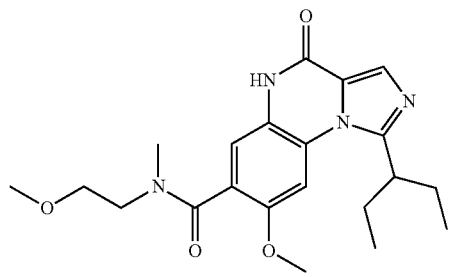 [SMILES: CCC(CC)c1ncc2c(=O)[nH]c3cc(C(=O)N(C)CCOC)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.91 (6H, t, J=7.3 Hz), 1.7-1.9 (2H, m), 1.9-2.1 (2H, m), 2.83 (1.5H, s), 3.00 (1.5H, s), 3.17 (1.5H, s), 3.32 (1.5H, s), 3.4-3.7 (5H, m), 3.92 (1.5H, s), 3.93 (1.5H, s), 7.14 (1H, s), 7.51 (0.5H, s), 7.53 (0.5H, s), 7.83 (0.5H, s), 7.84 (0.5H, s), 11.30 (0.5H, s), 11.33 (0.5H, s).

MS (m/z): 400 (M$^+$).

Example 37

1-{[1-(1-ethylpropyl)-8-methoxy-4-oxo-4,5-dihydroimidazo-[1,5-a]quinoxalin-7-yl]carbonyl}pyrrolidine

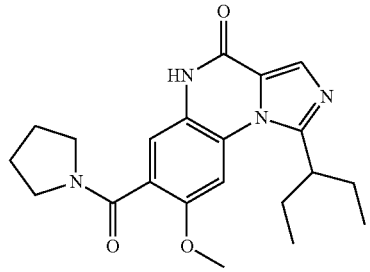 [SMILES: CCC(CC)c1ncc2c(=O)[nH]c3cc(C(=O)N4CCCC4)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.91 (6H, t, J=7.3 Hz), 1.7-2.0 (6H, m), 1.9-2.1 (2H, m), 3.18 (2H, t, J=6.6 Hz), 3.46 (2H, t, J=6.9 Hz), 3.54 (1H, quin, J=6.6 Hz), 3.93 (3H, s), 7.17 (1H, s), 7.54 (1H, s), 7.83 (1H, s), 11.32 (1H, s).

MS (m/z): 382 (M$^+$).

Example 38

1-{[1-(1-ethylpropyl)-8-methoxy-4-oxo-4,5-dihydroimidazo-[1,5-a]quinoxalin-7-yl]carbonyl}piperidine

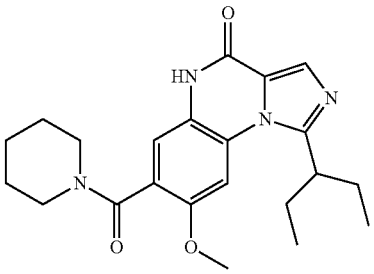 [SMILES: CCC(CC)c1ncc2c(=O)[nH]c3cc(C(=O)N4CCCCC4)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.91 (6H, t, J=7.3 Hz), 1.3-1.7 (6H, m), 1.7-1.9 (2H, m), 1.9-2.1 (2H, m), 3.1-3.2 (2H, m), 3.5-3.7 (3H, m), 3.92 (3H, s), 7.14 (1H, s), 7.53 (1H, s), 7.83 (1H, s), 11.28 (1H, s).

MS (m/z): 396 (M$^+$).

Example 39

1-{[1-(1-ethylpropyl)-8-methoxy-4-oxo-4,5-dihydroimidazo-[1,5-a]quinoxalin-7-yl]carbonyl}-4-methylpiperazine

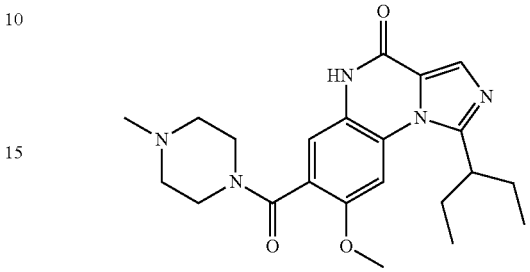

The title compound was obtained from 1-(1-ethylpropyl)-8-methoxy-4-oxo-4,5-dihydroimidazol[1,5-a]quinoxaline-7-carboxyic acid as synthesized in above Example 32, by the operations similar to Example 33.

$^1$H-NMR (DMSO-$d_6$, δ): 0.90 (6H, t, J=7.3 Hz), 1.7-1.9 (2H, m), 1.9-2.1 (2H, m), 2.20 (3H, s), 2.2-2.5 (4H, m), 3.1-3.3 (2H, m), 3.4-3.7 (3H, m), 3.93 (3H, s), 7.16 (1H, s), 7.53 (1H, s), 7.83 (1H, s), 11.29 (1H, s).

MS (m/z): 411 (M$^+$).

Example 40

4-{[1-(1-Ethylpropyl)-8-methoxy-4-oxo-4,5-dihydroimidazo-[1,5-a]quinoxalin-7-yl]carbonyl}morpholine

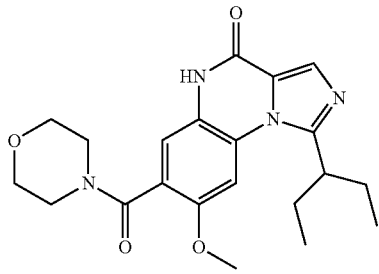 [SMILES: CCC(CC)c1ncc2c(=O)[nH]c3cc(C(=O)N4CCOCC4)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.90 (6H, t, J=7.3 Hz), 1.7-1.9 (2H, m), 1.9-2.1 (2H, m), 3.1-3.3 (2H, m), 3.4-3.6 (3H, m), 3.65 (4H, br s), 3.94 (3H, s), 7.18 (1H, s), 7.53 (1H, s), 7.84 (1H, s), 11.32 (1H, s).

MS (m/z): 398 (M$^+$).

Example 41

1-(1-Ethylpropyl)-8-methoxy-N-methyl-4-oxo-N-propyl-4,5-dihydroimidazo[1,5-a]quinoxaline-7-carboxamide

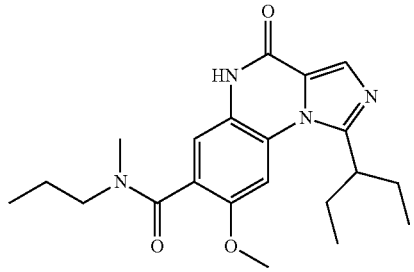 [SMILES: CCCN(C)C(=O)c1cc2[nH]c(=O)c3cnc(C(CC)CC)n3c2cc1OC]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.70 (1.5H, t, J=7.3 Hz), 0.91 (6H, t, J=7.3 Hz), 0.92 (1.5H, t, J=7.3 Hz), 1.4-1.7 (2H, m), 1.7-1.9 (2H, m), 1.9-2.1 (2H, m), 2.77 (1.5H, s), 2.96 (1.5H, s), 3.06 (1H, t, J=7.0 Hz), 3.3-3.6 (2H, m), 3.91 (1.5H, s), 3.93 (1.5H, s), 7.13 (0.5H, s), 7.14 (0.5H, s), 7.53 (1H, s), 7.83 (1H, s), 11.27 (1H, s).

MS (m/z): 384 (M$^+$).

Example 42

1-(1-Ethylpropyl)-8-methoxy-N-methyl-4-oxo-N-[2-(2-pyridyl)-ethyl]-4,5-dihydroimidazo[1,5-a]quinoxaline-7-carboxamide

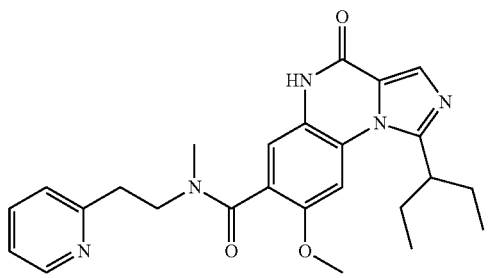 [SMILES: CCC(CC)c1ncc2c(=O)[nH]c3cc(C(=O)N(C)CCc4ccccn4)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.91 (6H, t, J=7.3 Hz), 1.7-1.9 (2H, m), 1.9-2.1 (2H, m), 2.71 (1.5H, s), 2.8-3.0 (1H, m), 2.98 (1.5H, s), 3.0-3.1 (1H, m), 3.4-3.6 (2H, m), 3.7-3.9 (1H, m), 3.90 (1.5H, s), 3.91 (1.5H, s), 6.88 (0.5H, s), 7.10 (0.5H, s), 7.1-7.2 (1H, m), 7.2-7.3 (0.5H, m), 7.34 (0.5H, d, J=7.7 Hz), 7.51 (0.5H, s), 7.52 (0.5H, s), 7.64 (0.5H, dt, J=2.0, 7.7 Hz), 7.76 (0.5H, dt, J=2.0, 7.7 Hz), 7.83 (0.5H, s), 7.84 (0.5H, s), 8.3-8.4 (0.5H, m), 8.5-8.6 (0.5H, m).

MS (m/z): 447 (M$^+$).

Example 43

N-cyclohexyl-1-(1-ethylpropyl)-8-methoxy-N-methyl-4-oxo-4,5-dihydroimidazo[1,5-a]quinoxaline-7-carboxamide

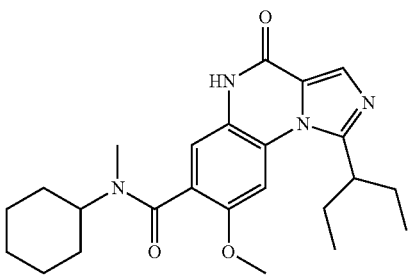 [SMILES: CCC(CC)c1ncc2c(=O)[nH]c3cc(C(=O)N(C)C4CCCCC4)c(OC)cc3n12]

The title compound was obtained from 1-(1-ethylpropyl)-8-methoxy-4-oxo-4,5-dihydroimidazo[1,5-a]quinoxaline-7-carboxyic acid as synthesized in above Example 32, by the operations similar to Example 33.

$^1$H-NMR (DMSO-$d_6$, δ): 0.8-1.2 (8H, m), 1.3-2.2 (12H, m), 2.66 (1.5H, s), 2.87 (1.5H, s), 3.1-3.3 (0.5H, m), 3.5-3.6 (1H, m), 3.91 (3H, br s), 4.3-4.4 (0.5H, m), 7.11 (0.5H, s), 7.12 (0.5H, s), 7.53 (0.5H, s), 7.54 (0.5H, s), 7.84 (1H, br s), 11.27 (1H, s).

MS (m/z): 424 (M$^+$).

Example 44

Ethyl 1-(1-ethylpropyl)-4-oxo-4,5-dihydroimidazo[1,5-a]-quinoxaline-8-carboxyate

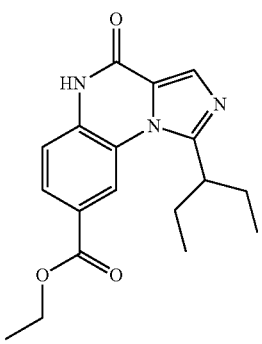 [SMILES: CCOC(=O)c1ccc2[nH]c(=O)c3cnc(C(CC)CC)n3c2c1]

The title compound was obtained from ethyl 4-amino-3-[2-(1-ethylpropyl)-1H-imidazol-1-yl]benzoate as synthesized in Production Example 22, by the operations similar to Example 4.

$^1$H-NMR (DMSO-$d_6$, δ): 0.97 (6H, t, J=7.4 Hz), 1.36 (3H, t, J=7.3 Hz), 1.79 (2H, sep, J=6.9 Hz), 2.01 (2H, sep, J=6.9 Hz), 3.2-3.4 (1H, m), 4.36 (2H, q, J=7.0 Hz), 7.43 (1H, d, J=8.5 Hz), 7.88 (1H, s), 7.95 (1H, dd, J=1.6, 8.5 Hz), 8.54 (1H, d, J=1.6 Hz), 11.71 (1H, s).

MS (m/z): 327 (M$^+$).

Example 45

1-(1-Ethylpropyl)-4-oxo-4,5-dihydroimidazo[1,5-a]quinoxaline-8-carboxyic acid

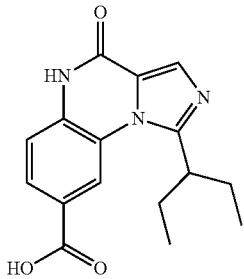

The title compound was obtained from ethyl 1-(1-ethylpropyl)-4-oxo-4,5-dihydroimidazo[1,5-a]quinoxaline-8-carboxyate as synthesized in above Example 44, by the operations similar to Example 8.

$^1$H-NMR (DMSO-$d_6$, δ): 0.95 (6H, t, J=7.3 Hz), 1.79 (2H, sep, J=7.3 Hz), 2.00 (2H, sep, J=7.0 Hz), 3.2-3.4 (1H, m), 7.42 (1H, d, J=8.5 Hz), 7.87 (1H, s), 7.94 (1H, dd, J=1.2, 8.5 Hz), 8.56 (1H, d, J=1.2 Hz), 11.68 (1H, s), 13.14 (1H, br s).

MS (m/z): 299 (M$^+$).

Example 46

1-(1-Ethylpropyl)-N,N-dimethyl-4-oxo-4,5-dihydroimidazo-[1,5-a]quinoxaline-8-carboxamide

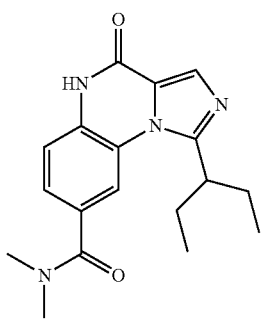 [SMILES: CCC(CC)c1ncc2c(=O)[nH]c3ccc(C(=O)N(C)C)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.88 (6H, t, J=7.3 Hz), 1.76 (2H, sep, J=7.3 Hz), 1.98 (2H, sep, J=7.3 Hz), 3.01 (6H, s), 3.42 (1H, quin, J=6.2 Hz), 7.37 (1H, d, J=8.5 Hz), 7.48 (1H, dd, J=1.2, 8.5 Hz), 7.86 (1H, s), 8.03 (1H, d, J=1.2 Hz), 11.53 (1H, s).

MS (m/z): 326 (M$^+$).

Example 47

4-{[1-(1-Ethylpropyl)-4-oxo-4,5-dihydroimidazo[1,5-a]-quinoxalin-8-yl]carbonyl}morpholine

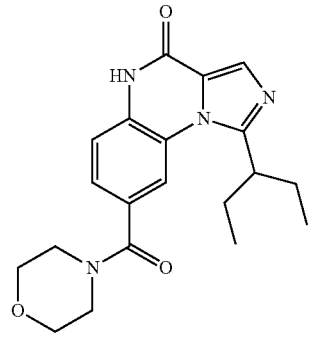 [SMILES: CCC(CC)c1ncc2c(=O)[nH]c3ccc(C(=O)N4CCOCC4)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.89 (6H, t, J=7.3 Hz), 1.77 (2H, sep, J=7.3 Hz), 1.98 (2H, sep, J=7.0 Hz), 3.43 (1H, quin, J=6.2 Hz), 3.55 (4H, br s), 3.63 (4H, br s), 7.39 (1H, d, J=8.1 Hz), 7.46 (1H, dd, J=1.5, 8.5 Hz), 7.86 (1H, s), 8.02 (1H, br s), 11.55 (1H, s).

MS (m/z): 368 (M$^+$).

Example 48

1-{[1-(1-Ethylpropyl)-4-oxo-4,5-dihydroimidazo[1,5-a]-quinoxalin-8-yl]carbonyl}-4-methylpiperazine

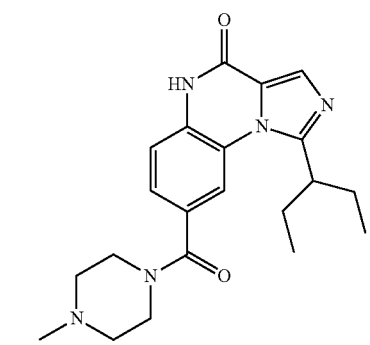 [SMILES: CCC(CC)c1ncc2c(=O)[nH]c3ccc(C(=O)N4CCN(C)CC4)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.89 (6H, t, J=7.3 Hz), 1.77 (2H, sep, J=7.3 Hz), 1.98 (2H, sep, J=7.3 Hz), 2.21 (3H, s), 2.34 (4H, br s), 3.41 (1H, quin, J=6.2 Hz), 3.53 (4H, br s), 7.38 (1H, d, J=8.5 Hz), 7.44 (1H, dd, J=1.5, 8.5 Hz), 7.85 (1H, s), 7.98 (1H, d, J=1.5 Hz), 11.53 (1H, br s).

MS (m/z): 381 (M$^+$).

Example 49

1-(1-Ethylpropyl)-N-(2-mehtoxyethyl)-N-methyl-4-oxo-4,5-dihydroimidazo[1,5-a]quinoxaline-8-carboxamide

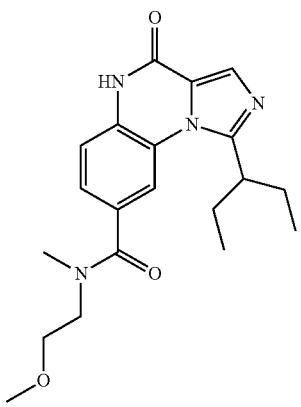 [SMILES: CCC(CC)c1ncc2c(=O)[nH]c3ccc(C(=O)N(C)CCOC)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.88 (6H, t, J=7.3 Hz), 1.76 (2H, sep, J=7.3 Hz), 1.98 (2H, sep, J=7.3 Hz), 3.02 (3H, s), 3.1-3.7 (8H, m), 7.37 (1H, d, J=8.1 Hz), 7.45 (1H, d, J=8.1 Hz), 7.86 (1H, s), 7.97 (1H, s), 11.52 (1H, s).

MS (m/z): 370 (M$^+$).

Example 50

1-{[1-(1-Ethylpropyl)-4-oxo-4,5-dihydroimidazo[1,5-a]-quinoxalin-8-yl]carbonyl}piperidine

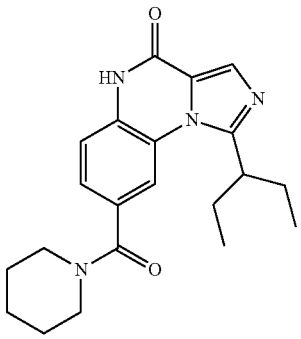 [SMILES: CCC(CC)c1ncc2c(=O)[nH]c3ccc(C(=O)N4CCCCC4)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.88 (6H, t, J=7.2 Hz), 1.4-1.7 (6H, m), 1.77 (2H, sep, J=7.2 Hz), 1.98 (2H, sep, J=7.2 Hz), 3.40 (1H, quin, J=6.3 Hz), 3.49 (4H, br s), 7.38 (1H, d, J=8.2 Hz), 7.42 (1H, dd, J=1.4, 8.2 Hz), 7.85 (1H, s), 7.97 (1H, d, J=1.0 Hz), 11.53 (1H, s).

MS (m/z): 366 (M$^+$).

Example 51

1-{[1-(1-Ethylpropyl)-4-oxo-4,5-dihydroimidazo[1,5-a]-quinoxalin-8-yl]carbonyl}pyrrolidine

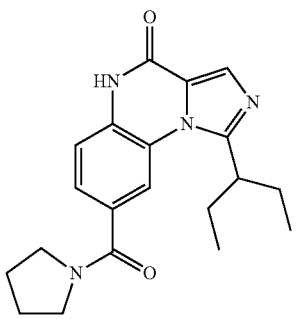 [SMILES: CCC(CC)c1ncc2c(=O)[nH]c3ccc(C(=O)N4CCCC4)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.89 (6H, t, J=7.3 Hz), 1.77 (2H, sep, J=7.3 Hz), 1.87 (4H, br s), 1.98 (2H, sep, J=7.3 Hz), 3.41 (1H, quin, J=6.2 Hz), 3.52 (4H, t, J=6.6 Hz), 7.37 (1H, d, J=8.1 Hz), 7.62 (1H, dd, J=1.2, 8.1 Hz), 7.86 (1H, s), 8.12 (1H, d, J=1.2 Hz), 11.54 (1H, s).

MS (m/z): 352 (M$^+$).

Example 52

N,N-diethyl-1-(1-ethylpropyl)-4-oxo-4,5-dihydroimidazo[1,5-a]-quinoxaline-8-carboxamide

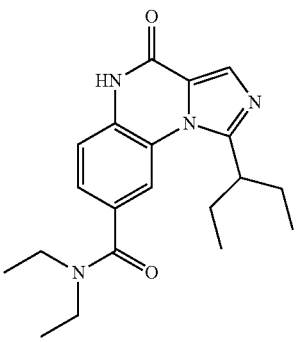 [SMILES: CCC(CC)c1ncc2c(=O)[nH]c3ccc(C(=O)N(CC)CC)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.89 (6H, t, J=7.3 Hz), 1.13 (6H, t, J=6.6 Hz), 1.76 (2H, sep, J=7.0 Hz), 1.97 (2H, sep, J=7.0 Hz), 3.2-3.5 (5H, m), 7.3-7.4 (2H, m), 7.85 (1H, s), 7.91 (1H, br s), 11.52 (1H, s).

MS (m/z): 354 (M$^+$).

Example 53

N-ethyl-1-(1-ethylpropyl)-N-methyl-4-oxo-4,5-dihydroimidazo-[1,5-a]quinoxaline-8-carboxamide

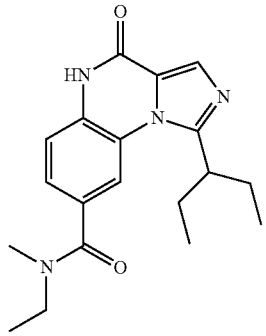 [SMILES: CCC(CC)c1ncc2c(=O)[nH]c3ccc(C(=O)N(C)CC)cc3n12]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.88 (6H, t, J=7.3 Hz), 1.14 (3H, t, J=7.0 Hz), 1.76 (2H, sep, J=7.3 Hz), 1.97 (2H, sep, J=7.3 Hz), 2.98 (3H, s), 3.3-3.5 (3H, m), 7.37 (1H, d, J=8.5 Hz), 7.44 (1H, d, J=8.1 Hz), 7.85 (1H, s), 7.97 (1H, d, J=1.2 Hz), 11.53 (1H, s).

MS (m/z): 340 (M$^+$).

Example 54

1-(1-Ethylpropyl)-4-oxo-N-propyl-4,5-dihydroimidazo[1,5-a]-quinoxaline-8-carboxamide

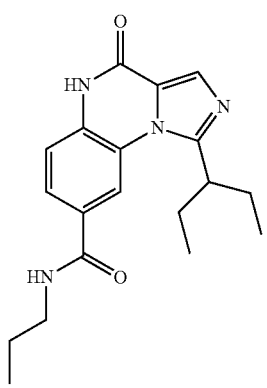 [SMILES: CCCNC(=O)c1ccc2[nH]c(=O)c3cnc(C(CC)CC)n3c2c1]

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.91 (3H, t, J=7.2 Hz), 0.94 (6H, t, J=7.2 Hz), 1.57 (2H, sex, J=7.2 Hz), 1.77 (2H, sep, J=7.0 Hz), 1.99 (2H, sep, J=7.2 Hz), 3.2-3.4 (2H, m), 3.45 (1H, quin, J=6.3 Hz), 7.36 (1H, d, J=8.8 Hz), 7.86 (1H, s), 7.88 (1H, d, J=8.1 Hz), 8.49 (1H, s), 8.58 (1H, t, J=5.7 Hz), 11.56 (1H, s).

MS (m/z): 340 (M$^+$).

Example 55

1-{[1-(1-Ethylpropyl)-4-oxo-4,5-dihydroimidazo[1,5-a]-quinoxalin-8-yl]carbonyl}-4-(2-hydroxyethyl)piperidine

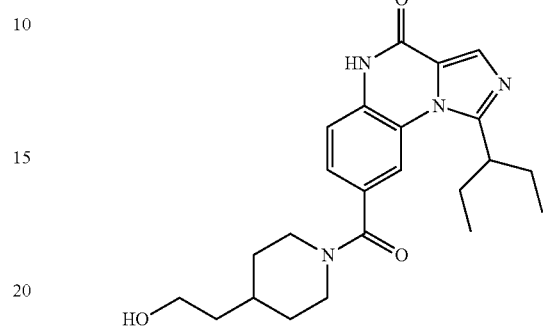

The title compound was obtained from 1-(1-ethylpropyl)-4-oxo-4,5-dihydroimidazo[1,5-a]quinoxaline-8-carboxyic acid as synthesized in above Example 45, by the operations similar to Example 33.

$^1$H-NMR (DMSO-$d_6$, δ): 0.88 (6H, t, J=7.3 Hz), 1.0-1.2 (2H, m), 1.40 (2H, q, J=6.2 Hz), 1.6-1.9 (6H, m), 1.97 (2H, sep, J=7.0 Hz), 2.7-3.1 (2H, m), 3.3-3.5 (4H, m), 4.37 (1H, t, J=5.0 Hz), 7.3-7.5 (2H, m), 7.85 (1H, s), 7.96 (1H, s), 11.54 (1H, s).

MS (m/z): 410 (M$^+$).

Example 56

1-Cyclohexyl-N,N-dimethyl-4-oxo-4,5-dihydroimidazo[1,5-a]-quinoxaline-7-carboxamide

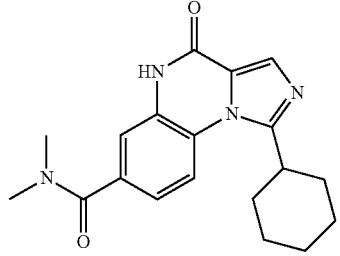 [SMILES: CN(C)C(=O)c1ccc2c(c1)[nH]c(=O)c1cnc(C3CCCCC3)n12]

The title compound was obtained from 3-amino-4-(2-cyclohexyl-1H-imidazol-1-yl)-N,N-dimethylbenzamide as synthesized in Production Example 24, by the operations similar to Example 4.

$^1$H-NMR (DMSO-$d_6$, δ): 1.2-1.4 (1H, m), 1.4-2.0 (7H, m), 2.08 (2H, br d, J=10.4 Hz), 2.9-3.2 (6H, m), 3.4-3.6 (1H, m), 7.3-7.5 (2H, m), 7.79 (1H, s), 7.97 (1H, d, J=8.5 Hz), 11.44 (1H, br s).

MS (m/z): 338 (M$^+$).

Example 57

Ethyl 1-cyclohexyl-4-oxo-4,5-dihydroimidazo[1,5-a]-quinoxaline-7-carboxyate

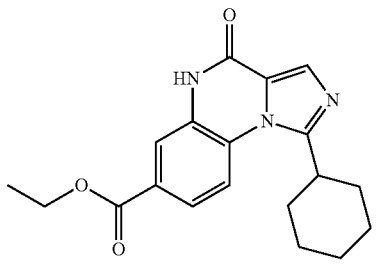 [SMILES: CCOC(=O)c1ccc2c(c1)[nH]c(=O)c1cnc(C3CCCCC3)n12]

The title compound was obtained from ethyl 3-amino-4-(2-cyclohexyl-1H-imidazol-1-yl)benzoate as synthesized in Production Example 26, by the operations similar to Example 4.

$^1$H-NMR (DMSO-d$_6$, δ): 1.2-1.5 (1H, m), 1.35 (3H, t, J=7.1 Hz), 1.4-1.9 (7H, m), 2.07 (2H, br d, J=12.3 Hz), 3.4-3.6 (1H, m), 4.35 (2H, q, J=7.1 Hz), 7.81 (1H, s), 7.85 (1H, dd, J=1.9, 8.9 Hz), 7.95 (1H, d, J=1.9 Hz), 8.05 (1H, d, J=8.9 Hz), 11.48 (1H, br s).

MS (m/z): 339 (M$^+$).

Example 58

1-Cyclohexyl-4-oxo-4,5-dihydroimidazo[1,5-a]quinoxaline-7-carboxyic acid

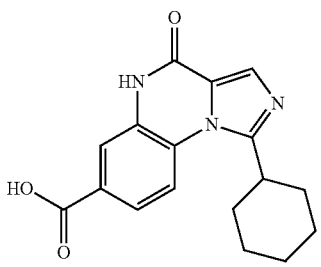 [SMILES: O=C(O)c1ccc2c(c1)[nH]c(=O)c1cnc(C3CCCCC3)n12]

Ethyl 1-cyclohexyl-4-oxo-4,5-dihydroimidazo[1,5-a]-quinoxaline-7-carboxyate as synthesized in the above Example 57, 3.33 g, ethanol 14 mL and 1N aqueous sodium hydroxide solution 29.4 mL were mixed, and heated under reflux for an hour in nitrogen atmosphere. The reaction liquid was allowed to cool off, and its pH was adjusted to 7 by addition of diluted hydrochloric acid. The precipitated crystals were recovered by filtration, washed with water and dried by heating under reduced pressure to provide 2.96 g of the title compound.

$^1$H-NMR (DMSO-d$_6$, δ): 1.2-1.4 (1H, m), 1.4-1.9 (7H, m), 2.08 (2H, br d, J=12.7 Hz), 3.3-3.6 (1H, m), 7.7-7.9 (2H, m), 7.8-8.0 (2H, m), 11.36 (1H, br s).

MS (m/z): 311 (M$^+$).

Example 59

1-[(1-Cyclohexyl-4-oxo-4,5-dihydroimidazo[1,5-a]quinoxalin-7-yl)carbonyl]-4-methylpiperazine

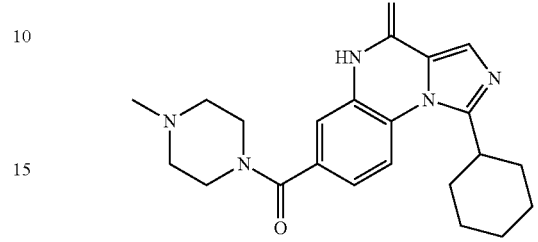

1-Cyclohexyl-4-oxo-4,5-dihydroimidazo[1,5-a]quinoxaline-7-carboxyic acid as synthesized in above Example 58, 218 mg, N-methylpiperazine 85 µL, 1-hydroxybenzotriazole monohydrate 161 mg, 4-dimethylaminopyridine 17 mg, pyridine 4.8 mL and 1-(3-dimethylaminopropyl)-3-ethylcarbodiimide hydrochloride 202 mg were mixed and stirred overnight under nitrogen atmosphere. After distilling the solvent off, ethyl acetate, tetrahydrofuran and saturated aqueous sodium hydrogencarbonate solution were added, and the organic layer was separated. The organic layer was washed with water and dried over magnesium sulfate. After distilling the solvent off, 67 mg of the title compound was obtained upon recrystallization from diethyl ether.

$^1$H-NMR (DMSO-d$_6$, δ): 1.2-1.4 (1H, m), 1.4-1.9 (7H, m), 2.07 (2H, br d, J=12.0 Hz), 2.21 (3H, s), 2.2-2.5 (4H, m), 3.1-3.8 (5H, m), 7.31 (1H, dd, J=1.7, 8.7 Hz), 7.35 (1H, d, J=1.9 Hz), 7.80 (1H, s), 7.98 (1H, d, J=8.5 Hz), 11.44 (1H, br s).

MS (m/z): 393 (M$^+$).

Example 60

1-[(1-Cyclohexyl-4-oxo-4,5-dihydroimidazo[1,5-a]quinoxalin-7-yl)carbonyl]pyrrolidine

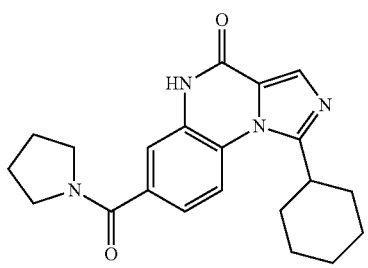 [SMILES: O=C(c1ccc2c(c1)[nH]c(=O)c1cnc(C3CCCCC3)n12)N1CCCC1]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.2-1.4 (1H, m), 1.4-2.0 (11H, m), 2.08 (2H, br d, J=12.0 Hz), 3.3-3.6 (5H, m), 7.45 (1H, dd, J=1.9, 8.9 Hz), 7.49 (1H, d, J=1.9 Hz), 7.80 (1H, s), 7.97 (1H, d, J=8.9 Hz), 11.42 (1H, br s).

MS (m/z): 364 (M$^+$).

Example 61

1-[(1-Cyclohexyl-4-oxo-4,5-dihydroimidazo[1,5-a]quinoxalin-7-yl)carbonyl]piperidine

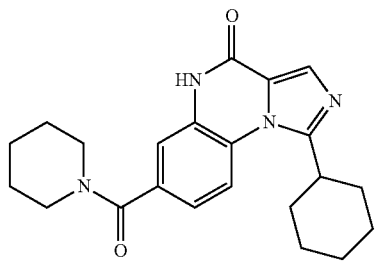 [SMILES: O=C(c1ccc2c(c1)[nH]c(=O)c1cnc(C3CCCCC3)n12)N1CCCCC1]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.2-1.4 (1H, m), 1.4-1.9 (13H, m), 2.08 (2H, br d, J=11.2 Hz), 3.2-3.8 (5H, m), 7.29 (1H, dd, J=1.9, 8.5 Hz), 7.33 (1H, d, J=1.9 Hz), 7.79 (1H, s), 7.98 (1H, d, J=8.9 Hz), 11.43 (1H, br s).

MS (m/z): 378 (M$^+$).

Example 62

4-[(1-Cyclohexyl-4-oxo-4,5-dihydroimidazo[1,5-a]quinoxalin-7-yl)carbonyl]morpholine

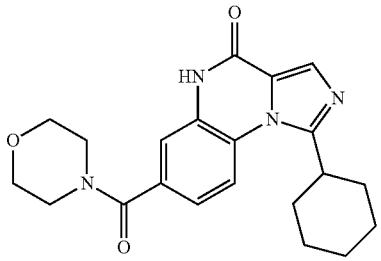 [SMILES: O=C(c1ccc2c(c1)[nH]c(=O)c1cnc(C3CCCCC3)n12)N1CCOCC1]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.2-1.4 (1H, m), 1.4-1.9 (7H, m), 2.08 (2H, br d, J=11.6 Hz), 3.3-3.8 (9H, m), 7.33 (1H, dd, J=1.9, 8.9 Hz), 7.37 (1H, d, J=1.9 Hz), 7.80 (1H, s), 7.98 (1H, d, J=8.9 Hz), 11.45 (1H, br s).

MS (m/z): 380 (M$^+$).

Example 63

1-Cyclohexyl-N-ethyl-N-methyl-4-oxo-4,5-dihydroimidazo-[1,5-a]quinoxaline-7-carboxamide

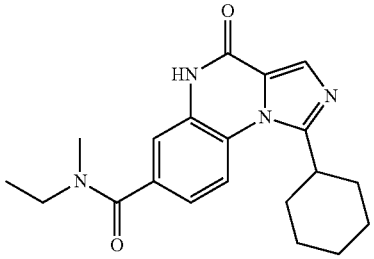 [SMILES: CCN(C)C(=O)c1ccc2c(c1)[nH]c(=O)c1cnc(C3CCCCC3)n12]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.13 (3H, br s), 1.2-1.4 (1H, m), 1.4-1.9 (7H, m), 2.08 (2H, br d, J=12.7 Hz), 2.95 (3H, br s), 3.2-3.4 (1H, m), 3.4-3.6 (2H, m), 7.2-7.4 (2H, m), 7.80 (1H, s), 7.98 (1H, d, J=8.5 Hz), 11.44 (1H, br s).

MS (m/z): 352 (M$^+$).

Example 64

1-Cyclohexyl-N-(2-hydroxyethyl)-N-methyl-4-oxo-4,5-dihydroimidazo[1,5-a]quinoxaline-7-carboxamide

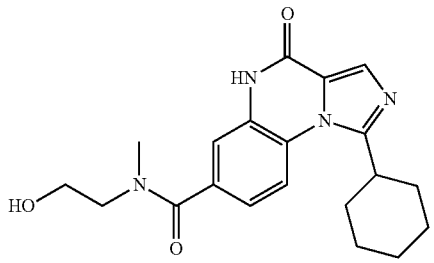 [SMILES: CN(CCO)C(=O)c1ccc2c(c1)[nH]c(=O)c1cnc(C3CCCCC3)n12]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.2-1.4 (1H, m), 1.4-1.9 (7H, m), 2.08 (2H, br d, J=12.3 Hz), 3.00 (3H, s), 3.2-3.4 (1H, m), 3.4-3.8 (4H, m), 4.77 (1H, br s), 7.2-7.5 (2H, m), 7.79 (1H, s), 7.96 (1H, d, J=8.5 Hz), 11.43 (1H, br s).

MS (m/z): 368 (M$^+$).

Example 65

1-Cyclohexyl-N-(2-methoxyethyl)-N-methyl-4-oxo-4,5-dihydroimidazo[1,5-a]quinoxaline-7-carboxamide

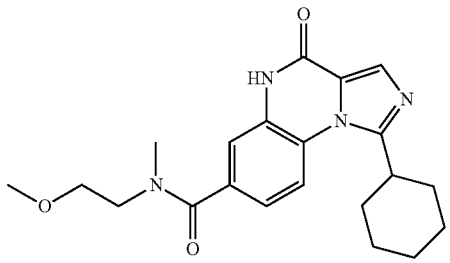 [SMILES: COCCN(C)C(=O)c1ccc2c(c1)[nH]c(=O)c1cnc(C3CCCCC3)n12]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.2-1.4 (1H, m), 1.4-1.9 (7H, m), 2.08 (2H, br d, J=13.1 Hz), 2.99 (3H, s), 3.1-3.8 (8H, m), 7.2-7.4 (2H, m), 7.79 (1H, s), 7.97 (1H, d, J=8.5 Hz), 11.43 (1H, br s).

MS (m/z): 382 (M$^+$).

Example 66

1-Cyclohexyl-N,N-diethyl-4-oxo-4,5-dihydroimidazo[1,5-a]-quinoxaline-7-carboxamide

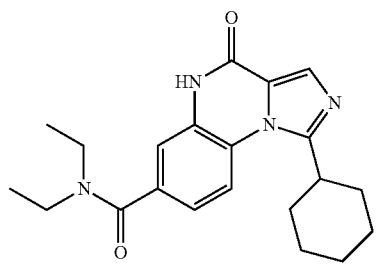 [SMILES: CCN(CC)C(=O)c1ccc2c(c1)[nH]c(=O)c1cnc(C3CCCCC3)n12]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 1.13 (6H, br s), 1.2-1.4 (1H, m), 1.4-1.9 (7H, m), 2.08 (2H, br d, J=11.9 Hz), 3.1-3.6 (5H, m), 7.27 (1H, dd, J=1.9, 8.9 Hz), 7.31 (1H, d, J=1.5 Hz), 7.79 (1H, s), 7.98 (1H, d, J=8.9 Hz), 11.42 (1H, br s).

MS (m/z): 366 (M$^+$).

Example 67

1-Cyclohexyl-N-methyl-4-oxo-N-propyl-4,5-dihydroimidazo-[1,5-a]quinoxaline-7-carboxamide

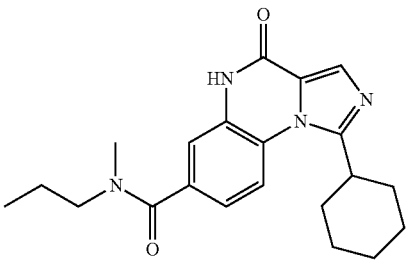 [SMILES: CCCN(C)C(=O)c1ccc2c(c1)[nH]c(=O)c1cnc(C3CCCCC3)n12]

The title compound was obtained from 1-cyclohexyl-4-oxo-4,5-dihydroimidazo[1,5-a]quinoxaline-7-carboxyic acid as synthesized in above Example 58, by the operations similar to Example 59.

$^1$H-NMR (DMSO-d$_6$, δ): 0.6-1.0 (3H, m), 1.2-1.4 (1H, m), 1.4-1.9 (9H, m), 2.08 (2H, br d, J=12.7 Hz), 2.95 (3H, br s), 3.1-3.3 (1H, m), 3.3-3.6 (2H, m), 7.31 (2H, br s), 7.80 (1H, s), 7.98 (1H, d, J=8.9 Hz), 11.41 (1H, br s).

MS (m/z): 366 (M$^+$).

Example 68

Methyl 1-cyclohexyl-8-methoxy-4-oxo-4,5-dihydroimidazo-[1,5-a]quinoxaline-7-carboxyate

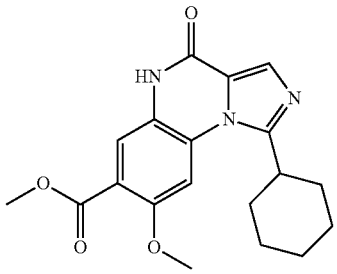 [SMILES: COC(=O)c1cc2[nH]c(=O)c3cnc(C4CCCCC4)n3c2cc1OC]

The title compound was obtained from methyl 5-amino-4-(2-cyclohexyl-1H-imidazol-1-yl)-2-methoxybenzoate as synthesized in Production Example 28, by the operations similar to Example 4.

$^1$H-NMR (DMSO-d$_6$, δ): 1.2-1.4 (1H, m), 1.4-1.6 (2H, m), 1.6-1.9 (3H, m), 1.87 (2H, br d, J=12.7 Hz), 2.16 (2H, br d, J=12.3 Hz), 3.4-3.6 (1H, m), 3.83 (3H, s), 3.96 (3H, s), 7.55 (1H, s), 7.73 (1H, s), 7.79 (1H, s), 11.31 (1H, br s).

MS (m/z): 355 (M$^+$).

Example 69

1-Cyclohexyl-8-methoxy-4-oxo-4,5-dihydroimidazo[1,5-a]-quinoxaline-7-carboxyic acid

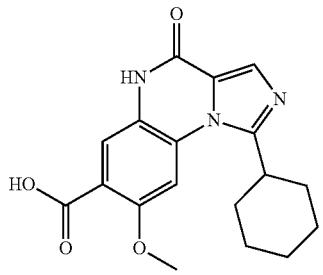 [SMILES: COc1cc2c(cc1C(=O)O)[nH]c(=O)c1cnc(C3CCCCC3)n12]

The title compound was obtained from methyl 1-cyclohexyl-8-methoxy-4-oxo-4,5-dihydroimidazo[1,5-a]quinoxaline-7-carboxyate as synthesized in above Example 68, by the operations similar to Example 8.

$^1$H-NMR (DMSO-d$_6$, δ): 1.2-1.4 (1H, m), 1.4-1.6 (2H, m), 1.6-1.9 (3H, m), 1.87 (2H, br d, J=12.7 Hz), 2.16 (2H, br d, J=12.7 Hz), 3.4-3.6 (1H, m), 3.96 (3H, s), 7.54 (1H, s), 7.72 (1H, s), 7.79 (1H, s), 11.30 (1H, br s), 12.88 (1H, br s).

MS (m/z): 341 (M$^+$).

Example 70

1-Cyclohexyl-8-methoxy-N,N-dimethyl-4-oxo-4,5-dihydroimidazo[1,5-a]quinoxaline-7-carboxamide

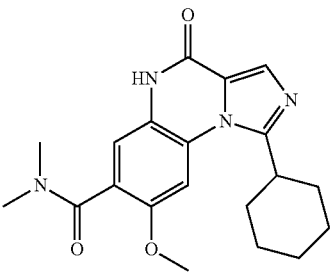

The title compound was obtained from 1-cyclohexyl-8-methoxy-4-oxo-4,5-dihydroimidazo[1,5-a]quinoxaline-7-carboxyic acid as synthesized in above Example 69, in the manner similar to Example 9.

$^1$H-NMR (DMSO-d$_6$, δ): 1.2-1.4 (1H, m), 1.4-1.6 (2H, m), 1.6-2.0 (5H, m), 2.17 (2H, br d, J=12.7 Hz), 2.80 (3H, s), 2.99 (3H, s), 3.4-3.6 (1H, m), 3.94 (3H, s), 7.13 (1H, s), 7.51 (1H, s), 7.78 (1H, s), 11.31 (1H, br s).

MS (m/z): 368 (M$^+$).

Example 71

1-Cyclohexyl-N-ethyl-8-methoxy-N-methyl-4-oxo-4,5-dihydroimidazo[1,5-a]quinoxaline-7-carboxamide

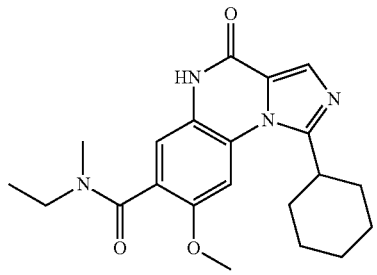 [SMILES: CCN(C)C(=O)c1cc2[nH]c(=O)c3cnc(C4CCCCC4)n3c2cc1OC]

The title compound was obtained from 1-cyclohexyl-8-methoxy-4-oxo-4,5-dihydroimidazo[1,5-a]quinoxaline-7-carboxyic acid as synthesized in above Example 69, by the operations similar to Example 59.

$^1$H-NMR (DMSO-d$_6$, δ): 1.02 (1.6H, t, J=6.9 Hz), 1.13 (1.4H, t, J=7.1 Hz), 1.2-1.4 (1H, m), 1.4-1.6 (2H, m), 1.6-1.9 (3H, m), 1.87 (2H, br d, J=12.7 Hz), 2.17 (2H, br d, J=12.7 Hz), 2.78 (1.4H, s), 2.96 (1.6H, s), 3.0-3.2 (1H, m), 3.4-3.6 (2H, m), 3.92 (1.6H, s), 3.94 (1.4H, s), 7.11 (0.5H, s), 7.12 (0.5H, s), 7.51 (1H, s), 7.78 (1H, s), 11.27 (0.5H, br s), 11.28 (0.5H, br s).

MS (m/z): 382 (M$^+$).

Example 72

1-Cyclohexyl-8-methoxy-N-(2-methoxyethyl)-N-methyl-4-oxo-4,5-dihydroimidazo[1,5-a]quinoxaline-7-carboxamide

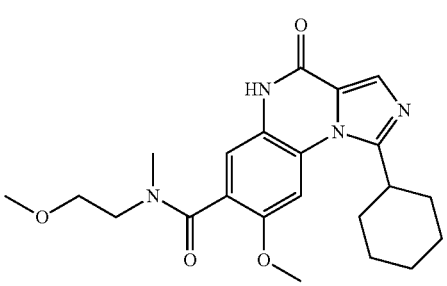 [SMILES: COCCN(C)C(=O)c1cc2[nH]c(=O)c3cnc(C4CCCCC4)n3c2cc1OC]

The title compound was obtained from 1-cyclohexyl-8-methoxy-4-oxo-4,5-dihydroimidazo[1,5-a]quinoxaline-7-carboxyic acid as synthesized in above Example 69, by the operations similar to Example 59.

$^1$H-NMR (DMSO-d$_6$, δ): 1.2-1.4 (1H, m), 1.4-1.6 (2H, m), 1.6-1.9 (3H, m), 1.87 (2H, br d, J=12.7 Hz), 2.17 (2H, br d, J=12.7 Hz), 2.83 (1.5H, s), 3.00 (1.5H, s), 3.1-3.8 (8H, m), 3.92 (1.6H, s), 3.94 (1.4H, s), 7.13 (1H, s), 7.50 (0.5H, s), 7.52 (0.5H, s), 7.77 (0.5H, s), 7.78 (0.5H, s), 11.27 (0.5H, br s), 11.30 (0.5H, br s).

MS (m/z): 412 (M$^+$).

Example 73

1-[(1-Cyclohexyl-8-methoxy-4-oxo-4,5-dihydroimidazo[1,5-a]-quinoxalin-7-yl)carbonyl]pyrrolidine

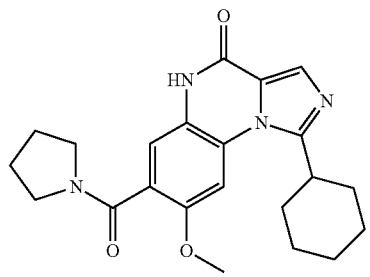 [SMILES: COc1cc2c(cc1C(=O)N1CCCC1)[nH]c(=O)c1cnc(C3CCCCC3)n12]

The title compound was obtained from 1-cyclohexyl-8-methoxy-4-oxo-4,5-dihydroimidazo[1,5-a]quinoxaline-7-carboxyic acid as synthesized in above Example 69, by the operations similar to Example 59.

$^1$H-NMR (DMSO-d$_6$, δ): 1.2-1.4 (1H, m), 1.4-1.6 (2H, m), 1.6-2.0 (9H, m), 2.17 (2H, br d, J=12.7 Hz), 3.1-3.3 (2H, m), 3.4-3.6 (3H, m), 3.95 (3H, s), 7.16 (1H, s), 7.52 (1H, s), 7.78 (1H, s), 11.31 (1H, br s).

MS (m/z): 394 (M$^+$).

Example 74

1-Cyclohexyl-N,N-diethyl-8-mehtoxy-4-oxo-4,5-dihydro-imidazo[1,5-a]quinoxaline-7-carboxamide

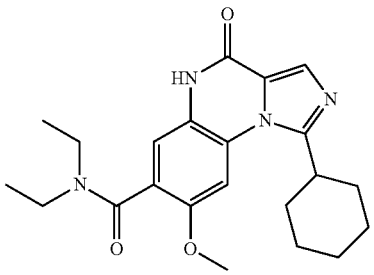 [SMILES: CCN(CC)C(=O)c1cc2[nH]c(=O)c3cnc(C4CCCCC4)n3c2cc1OC]

The title compound was obtained from 1-cyclohexyl-8-methoxy-4-oxo-4,5-dihydroimidazo[1,5-a]quinoxaline-7-carboxyic acid as synthesized in above Example 69, by the operations similar to Example 59.

$^1$H-NMR (DMSO-d$_6$, δ): 1.00 (3H, t, J=7.1 Hz), 1.15 (3H, t, J=7.1 Hz), 1.2-1.4 (1H, m), 1.4-1.6 (2H, m), 1.6-1.9 (3H, m), 1.87 (2H, br d, J=12.7 Hz), 2.17 (2H, br d, J=13.1 Hz), 3.0-3.2 (2H, m), 3.3-3.6 (3H, m), 3.92 (3H, s), 7.11 (1H, s), 7.51 (1H, s), 7.78 (1H, s), 11.24 (1H, br s).

MS (m/z): 396 (M$^+$).

Example 75

1-Cyclohexyl-8-methoxy-N-methyl-4-oxo-N-propyl-4,5-dihydroimidazo[1,5-a]quinoxaline-7-carboxamide

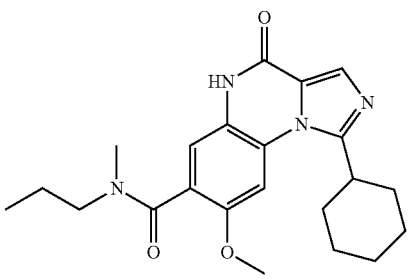 [SMILES: CCCN(C)C(=O)c1cc2[nH]c(=O)c3cnc(C4CCCCC4)n3c2cc1OC]

The title compound was obtained from 1-cyclohexyl-8-methoxy-4-oxo-4,5-dihydroimidazo[1,5-a]quinoxaline-7-carboxyic acid as synthesized in above Example 69, by the operations similar to Example 59.

$^1$H-NMR (DMSO-d$_6$, δ): 0.70 (1.3H, t, J=7.3 Hz), 0.92 (1.7H, t, J=7.5 Hz), 1.2-1.4 (1H, m), 1.4-1.9 (7H, m), 1.87 (2H, br d, J=12.7 Hz), 2.17 (2H, br d, J=12.7 Hz), 2.77 (1.6H, s), 2.96 (1.4H, s), 3.0-3.1 (1H, m), 3.2-3.6 (2H, m), 3.92 (1.4H, s), 3.94 (1.6H, s), 7.12 (0.5H, s), 7.13 (0.5H, s), 7.51 (1H, s), 7.78 (1H, s), 11.27 (1H, br s).

MS (m/z): 396 (M$^+$).

Example 76

1-[(1-Cyclohexyl-8-methoxy-4-oxo-4,5-dihydroimidazo[1,5-a]-quinoxalin-7-yl)carbonyl]piperidine

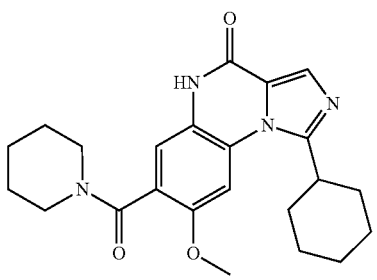 [SMILES: COc1cc2c(cc1C(=O)N1CCCCC1)[nH]c(=O)c1cnc(C3CCCCC3)n12]

The title compound was obtained from 1-cyclohexyl-8-methoxy-4-oxo-4,5-dihydroimidazo[1,5-a]quinoxaline-7-carboxyic acid as synthesized in above Example 69, by the operations similar to Example 59.

$^1$H-NMR (DMSO-d$_6$, δ): 1.2-1.9 (12H, m), 1.87 (2H, br d, J=12.7 Hz), 2.17 (2H, br d, J=12.3 Hz), 3.0-3.2 (2H, m), 3.4-3.7 (3H, m), 3.93 (3H, s), 7.13 (1H, s), 7.50 (1H, s), 7.77 (1H, s), 11.27 (1H, br s).

MS (m/z): 408 (M$^+$).

Example 77

Methyl 1-cyclohexyl-8-methoxy-3-methyl-4-oxo-4,5-dihydroimidazo[1,5-a]quinoxaline-7-carboxyate

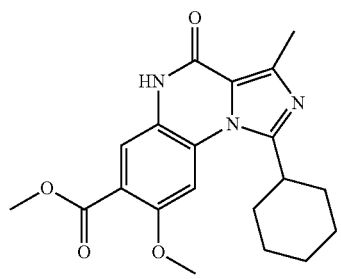 [SMILES: COC(=O)c1cc2[nH]c(=O)c3c(C)nc(C4CCCCC4)n3c2cc1OC]

The title compound was obtained from methyl 5-amino-4-(2-cyclohexyl-4-methyl-1H-imidazol-1-yl)-2-methoxybenzoate as synthesized in Production Example 30, by the operations similar to Example 4.

$^1$H-NMR (DMSO-d$_6$, δ): 1.2-1.4 (1H, m), 1.4-1.6 (2H, m), 1.6-1.8 (3H, m), 1.86 (2H, br d, J=12.3 Hz), 2.13 (2H, br d, J=13.5 Hz), 2.53 (3H, s), 3.4-3.6 (1H, m), 3.82 (3H, s), 3.95 (3H, s), 7.48 (1H, s), 7.66 (1H, s), 11.09 (1H, br s).

MS (m/z): 369 (M$^+$).

Example 78

1-Cyclohexyl-8-methoxy-3-methyl-4-oxo-4,5-dihydroimidazo-[1,5-a]quinoxaline-7-carboxyic acid

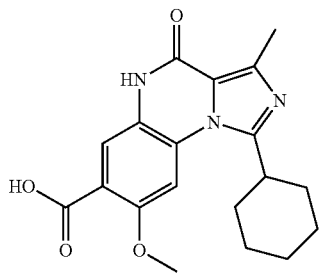 [SMILES: COc1cc2c(cc1C(=O)O)[nH]c(=O)c1c(C)nc(C3CCCCC3)n12]

The title compound was obtained from methyl 1-cyclohexyl-8-methoxy-3-methyl-4-oxo-4,5-dihydroimidazo[1,5-a]quinoxaline-7-carboxyate as synthesized in above Example 77, by the operations similar to Example 58.

$^1$H-NMR (DMSO-d$_6$, δ): 1.2-1.4 (1H, m), 1.4-1.6 (2H, m), 1.6-1.8 (3H, m), 1.86 (2H, br d, J=13.1 Hz), 2.13 (2H, br d, J=12.7 Hz), 2.54 (3H, s), 3.4-3.6 (1H, m), 3.94 (3H, s), 7.46 (1H, s), 7.66 (1H, s), 11.07 (1H, br s), 12.81 (1H, br s).

MS (m/z): 355 (M$^+$).

Example 79

1-Cyclohexyl-8-methoxy-N,N,3-trimethyl-4-oxo-4,5-dihydroimidazo[1,5-a]quinoxaline-7-carboxamide

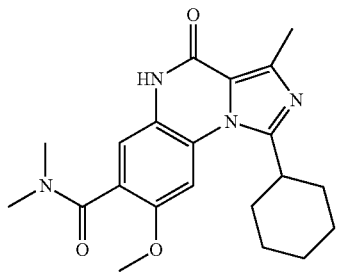 [SMILES: COc1cc2c(cc1C(=O)N(C)C)[nH]c(=O)c1c(C)nc(C3CCCCC3)n12]

The title compound was obtained from 1-cyclohexyl-8-methoxy-3-methyl-4-oxo-4,5-dihydroimidazo[1,5-a]quinoxaline-7-carboxyic acid as synthesized in above Example 78, by the operations similar to Example 59.

$^1$H-NMR (DMSO-d$_6$, δ): 1.2-1.4 (1H, m), 1.4-1.6 (2H, m), 1.6-1.9 (3H, m), 1.88 (2H, br d, J=13.1 Hz), 2.17 (2H, br d, J=12.3 Hz), 2.62 (3H, s), 2.80 (3H, s), 2.99 (3H, s), 3.5-3.7 (1H, m), 3.94 (3H, s), 7.14 (1H, s), 7.44 (1H, s), 11.42 (1H, br s).

MS (m/z): 382 (M$^+$).

Example 80

Ethyl 1-cyclohexyl-8-ethoxy-4-oxo-4,5-dihydroimidazo-[1,5-a]quinoxaline-7-carboxyate

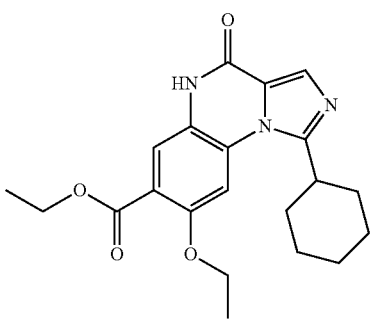 [SMILES: CCOC(=O)c1cc2[nH]c(=O)c3cnc(C4CCCCC4)n3c2cc1OCC]

The title compound was obtained from ethyl 5-amino-4-(2-cyclohexyl-1H-imidazol-1-yl)-2-ethoxybenzoate as synthesized in Production Example 34, in the manner similar to Example 4.

$^1$H-NMR (DMSO-d$_6$, δ): 1.2-1.6 (3H, m), 1.32 (3H, t, J=7.1 Hz), 1.41 (3H, t, J=6.9 Hz), 1.6-1.9 (3H, m), 1.87 (2H, br d, J=13.1 Hz), 2.14 (2H, br d, J=12.3 Hz), 3.4-3.6 (1H, m), 4.21 (2H, q, J=6.9 Hz), 4.30 (2H, q, J=7.1 Hz), 7.52 (1H, s), 7.70 (1H, s), 7.78 (1H, s), 11.29 (1H, br s).

MS (m/z): 383 (M$^+$).

Example 81

1-Cyclohexyl-8-ethoxy-4-oxo-4,5-dihydroimidazo[1,5-a]-quinoxaline-7-carboxyic acid

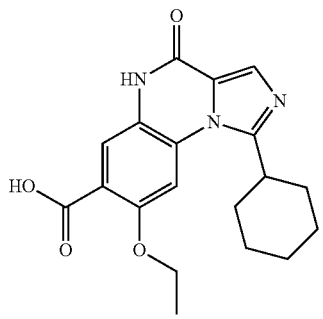 [SMILES: CCOc1cc2c(cc1C(=O)O)[nH]c(=O)c1cnc(C3CCCCC3)n12]

The title compound was obtained from ethyl 1-cyclohexyl-8-ethoxy-4-oxo-4,5-dihydroimidazo[1,5-a]quinoxaline-7-carboxyate as synthesized in above Example 80, in the manner similar to Example 58.

$^1$H-NMR (DMSO-d$_6$, δ): 1.2-1.6 (3H, m), 1.40 (3H, t, J=6.9 Hz), 1.6-1.9 (3H, m), 1.87 (2H, br d, J=13.1 Hz), 2.14 (2H, br d, J=13.1 Hz), 3.3-3.6 (1H, m), 4.20 (2H, q, J=6.9 Hz), 7.50 (1H, s), 7.67 (1H, s), 7.77 (1H, s), 11.33 (1H, br s).

MS (m/z): 355 (M$^+$).

Example 82

1-Cyclohexyl-8-ethoxy-N,N-dimethyl-4-oxo-4,5-dihydroimidazo[1,5-a]quinoxaline-7-carboxamide

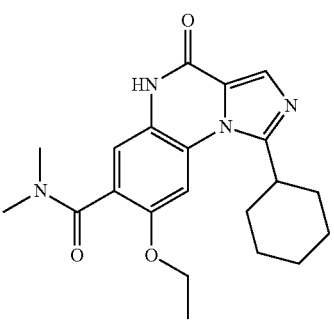 [SMILES: CCOc1cc2c(cc1C(=O)N(C)C)[nH]c(=O)c1cnc(C3CCCCC3)n12]

The title compound was obtained from 1-cyclohexyl-8-ethoxy-4-oxo-4,5-dihydroimidazo[1,5-a]quinoxaline-7-carboxyic acid as synthesized in above Example 81, in the manner similar to Example 59.

$^1$H-NMR (DMSO-d$_6$, δ): 1.2-1.6 (3H, m), 1.38 (3H, t, J=6.9 Hz), 1.6-1.9 (3H, m), 1.87 (2H, br d, J=13.1 Hz), 2.15 (2H, br d, J=12.0 Hz), 2.82 (3H, s), 3.00 (3H, s), 3.4-3.6 (1H, m), 4.21 (2H, q, J=6.8 Hz), 7.14 (1H, s), 7.48 (1H, s), 7.77 (1H, s), 11.30 (1H, br s).

MS (m/z): 382 (M$^+$).

Example 83

Ethyl 8-chloro-1-cyclohexyl-4-oxo-4,5-dihydroimidazo-[1,5-a]quinoxaline-7-carboxyate

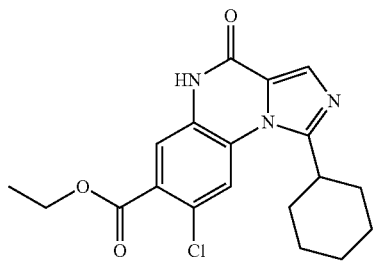 [SMILES: CCOC(=O)c1cc2[nH]c(=O)c3cnc(C4CCCCC4)n3c2cc1Cl]

The title compound was obtained from ethyl 5-amino-2-chloro-4-(2-cyclohexyl-1H-imidazol-1-yl)benzoate as synthesized in Production Example 36, in the manner similar to Example 4.

$^1$H-NMR (DMSO-d$_6$, δ): 1.2-1.9 (6H, m), 1.35 (3H, t, J=7.1 Hz), 1.87 (2H, br d, J=12.7 Hz), 2.09 (2H, br d, J=11.9 Hz), 3.3-3.5 (1H, m), 4.37 (2H, q, J=7.2 Hz), 7.82 (2H, s), 7.92 (1H, s), 11.55 (1H, br s).

MS (m/z): 375 (M$^+$+2), 373 (M$^+$).

Example 84

8-Chloro-1-cyclohexyl-4-oxo-4,5-dihydroimidazo[1,5-a]-quinoxaline-7-carboxyic acid

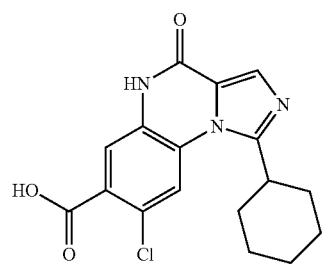 [SMILES: O=C(O)c1cc2[nH]c(=O)c3cnc(C4CCCCC4)n3c2cc1Cl]

The title compound was obtained from ethyl 8-chloro-1-cyclohexyl-4-oxo-4,5-dihydroimidazo[1,5-a]quinoxaline-7-carboxyate as synthesized in above Example 83, in the manner similar to Example 58.

$^1$H-NMR (DMSO-d$_6$, δ): 1.2-1.4 (1H, m), 1.4-1.9 (5H, m), 1.87 (2H, br d, J=12.7 Hz), 2.09 (2H, br d, J=11.6 Hz), 3.3-3.5 (1H, m), 7.82 (1H, s), 7.82 (1H, s), 7.90 (1H, s), 11.55 (1H, br s).

MS (m/z): 347 (M$^+$+2), 345 (M$^+$).

Example 85

8-Chloro-1-cyclohexyl-N,N-dimethyl-4-oxo-4,5-dihydroimidazo-[1,5-a]quinoxaline-7-carboxamide

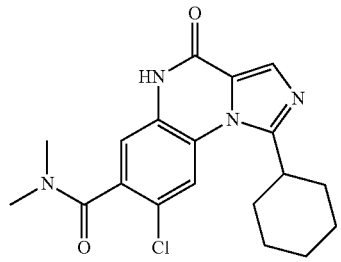 [SMILES: CN(C)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-d$_6$, δ): 1.2-1.4 (1H, m), 1.4-1.6 (2H, m), 1.6-1.9 (3H, m), 1.86 (2H, br d, J=13.1 Hz), 2.09 (2H, br d, J=13.1 Hz), 2.83 (3H, s), 3.03 (3H, s), 3.3-3.5 (1H, m), 7.21 (1H, s), 7.81 (1H, s), 7.89 (1H, s), 11.56 (1H, br s).

MS (m/z): 374 (M$^+$+2), 372 (M$^+$).

Example 86

1-[(8-Chloro-1-cyclohexyl-4-oxo-4,5-dihydroimidazo[1,5-a]-quinoxalin-7-yl)carbonyl]-4-(2-hydroxyethyl)piperazine

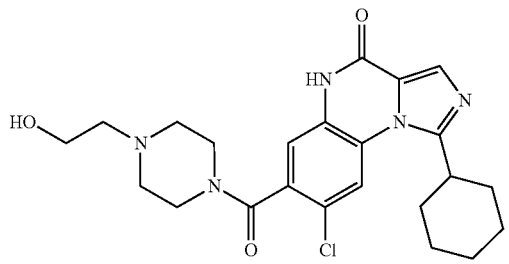

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

1H-NMR (DMSO-d$_6$, δ): 1.2-1.4 (1H, m), 1.4-1.9 (5H, m), 1.86 (2H, br d, J=12.7 Hz), 2.09 (2H, br d, J=12.7 Hz), 2.3-2.5 (4H, m), 3.1-3.3 (2H, m), 3.3-3.6 (3H, m), 3.66 (2H, br s), 4.4-4.5 (1H, m), 7.22 (1H, s), 7.81 (1H, s), 7.88 (1H, s), 11.53 (1H, br s).

MS (m/z): 457 (M$^+$).

Example 87

4-[(8-Chloro-1-cyclohexyl-4-oxo-4,5-dihydroimidazo[1,5-a]-quinoxalin-7-yl)carbonyl]morpholine

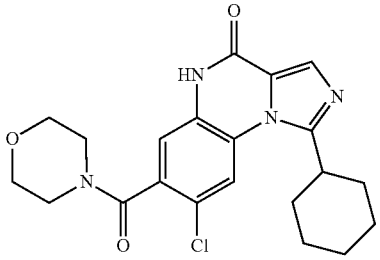 [SMILES: O=C(c1cc2[nH]c(=O)c3cnc(C4CCCCC4)n3c2cc1Cl)N1CCOCC1]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-d$_6$, δ): 1.2-1.4 (1H, m), 1.4-1.9 (5H, m), 1.86 (2H, br d, J=12.7 Hz), 2.09 (2H, br d, J=11.9 Hz), 3.1-3.3 (2H, m), 3.3-3.5 (1H, m), 3.4-3.8 (6H, m), 7.24 (1H, s), 7.81 (1H, s), 7.89 (1H, s), 11.56 (1H, br s).

MS (m/z): 416 (M$^+$+2), 414 (M$^+$).

Example 88

8-Chloro-1-cyclohexyl-N-ethyl-N-methyl-4-oxo-4,5-dihydroimidazo[1,5-]quinoxaline-7-carboxamide

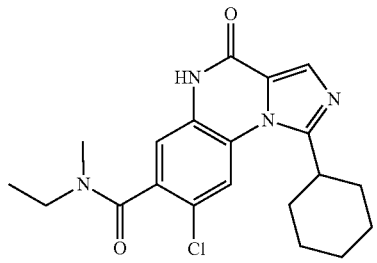 [SMILES: CCN(C)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-d$_6$, δ): 1.05 (1.4H, t, J=7.1 Hz), 1.16 (1.6H, t, J=7.1 Hz), 1.2-1.4 (1H, m), 1.4-1.6 (2H, m), 1.6-2.0 (5H, m), 2.09 (2H, br d, J=13.1 Hz), 2.81 (1.5H, s), 3.01 (1.5H, s), 3.1-3.2 (1H, m), 3.3-3.7 (2H, m), 7.21 (0.5H, s), 7.23 (0.5H, s), 7.81 (1H, s), 7.88 (0.5H, s), 7.89 (0.5H, s), 11.54 (1H, br s).

MS (m/z): 388 (M$^+$+2), 386 (M$^+$).

Example 89

8-Chloro-1-cyclohexyl-N-(2-hydroxyethyl)-N-methyl-4-oxo-4,5-dihydroimidazo[1,5-a]quinoxaline-7-carboxamide

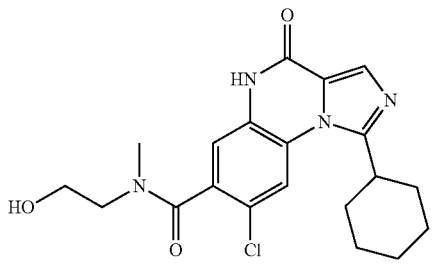 [SMILES: CN(CCO)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.2-1.4 (1H, m), 1.4-1.6 (2H, m), 1.6-2.0 (5H, m), 2.09 (2H, br d, J=12.3 Hz), 2.88 (1.4H, s), 3.04 (1.6H, s), 3.1-3.3 (1H, m), 3.3-3.7 (4H, m), 4.6-4.9 (1H, m), 7.22 (0.5H, s), 7.26 (0.5H, s), 7.81 (0.5H, s), 7.81 (0.5H, s), 7.87 (0.6H, s), 7.89 (0.4H, s), 11.54 (0.5H, br s), 11.56 (0.5H, br s).

MS (m/z): 404 (M$^+$+2), 402 (M$^+$).

Example 90

1-[(8-Chloro-1-cyclohexyl-4-oxo-4,5-dihydroimidazo[1,5-a]-quinoxalin-7-yl)carbonyl]pyrrolidine

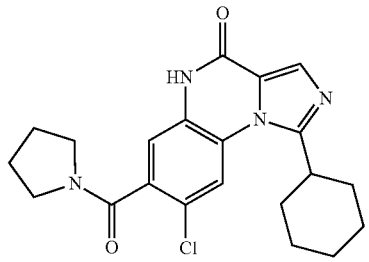 [SMILES: O=C(c1cc2[nH]c(=O)c3cnc(C4CCCCC4)n3c2cc1Cl)N1CCCC1]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.2-1.4 (1H, m), 1.4-1.6 (2H, m), 1.6-2.0 (9H, m), 2.09 (2H, br d, J=12.7 Hz), 3.1-3.3 (2H, m), 3.3-3.6 (3H, m), 7.24 (1H, s), 7.81 (1H, s), 7.89 (1H, s), 11.56 (1H, br s).

MS (m/z): 400 (M$^+$+2), 398 (M$^+$).

Example 91

8-Chloro-1-cyclohexyl-N-(2-methoxyethyl)-N-methyl-4-oxo-4,5-dihydroimidazo[1,5-a]quinoxaline-7-carboxamide

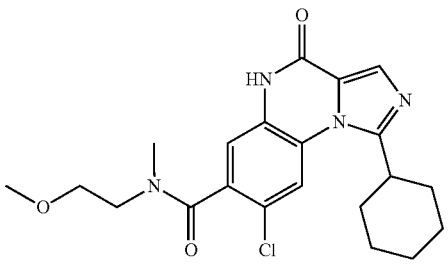 [SMILES: COCCN(C)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.2-1.4 (1H, m), 1.4-1.6 (2H, m), 1.6-2.0 (5H, m), 2.09 (2H, br d, J=12.3 Hz), 2.86 (1.5H, s), 3.03 (1.5H, s), 3.1-3.7 (8H, m), 7.22 (0.5H, s), 7.25 (0.5H, s), 7.81 (0.5H, s), 7.81 (0.5H, s), 7.87 (0.5H, s), 7.89 (0.5H, s), 11.53 (0.5H, br s), 11.57 (0.5H, br s).

MS (m/z): 418 (M$^+$+2), 416 (M$^+$).

Example 92

1-[(8-Chloro-1-cyclohexyl-4-oxo-4,5-dihydroimidazo[1,5-a]-quinoxalin-7-yl)carbonyl]-4-methylpiperazine

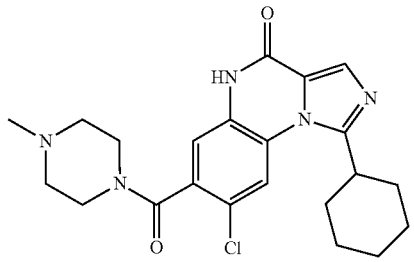 [SMILES: CN1CCN(C(=O)c2cc3[nH]c(=O)c4cnc(C5CCCCC5)n4c3cc2Cl)CC1]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.2-1.4 (1H, m), 1.4-1.9 (5H, m), 1.87 (2H, br d, J=12.3 Hz), 2.09 (2H, br d, J=11.9 Hz), 2.74 (2H, br s), 3.3-3.7 (3H, m), 7.31 (1H, s), 7.82 (1H, s), 7.90 (1H, s), 11.67 (1H, br s).

MS (m/z): 429 (M$^+$+2), 427 (M$^+$).

Example 93

1-[(8-Chloro-1-cyclohexyl-4-oxo-4,5-dihydroimidazo[1,5-a]-quinoxalin-7-yl)carbonyl]-4-hydroxypiperidine

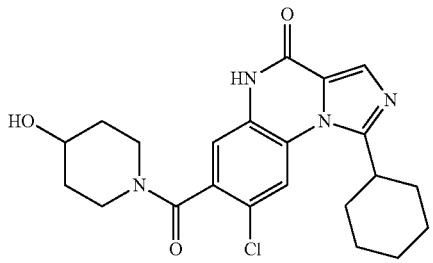 [SMILES: O=C(c1cc2[nH]c(=O)c3cnc(C4CCCCC4)n3c2cc1Cl)N1CCC(O)CC1]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.2-2.0 (12H, m), 2.09 (2H, br d, J=11.6 Hz), 3.0-3.2 (1H, m), 3.2-3.5 (3H, m), 3.76 (1H, br s), 4.06 (1H, br s), 4.7-4.9 (1H, m), 7.19 (0.5H, s), 7.24 (0.5H, s), 7.81 (1H, s), 7.88 (1H, s), 11.50 (0.5H, br s), 11.53 (0.5H, br s).

MS (m/z): 430 (M$^+$+2), 428 (M$^+$).

Example 94

1-[(8-Chloro-1-cyclohexyl-4-oxo-4,5-dihydroimidazo[1,5-a]-quinoxalin-7-yl)carbonyl]-4-(2-hydroxyethyl)piperidine

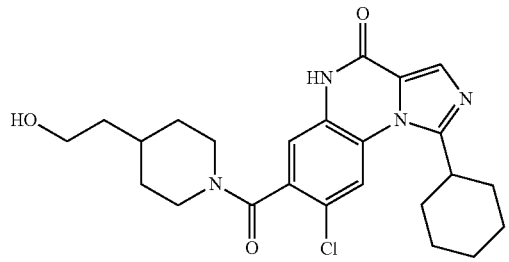

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 0.9-2.0 (13H, m), 2.09 (2H, br d, J=12.7 Hz), 2.7-2.9 (1H, m), 2.9-3.2 (1H, m), 3.3-3.6 (3H, m), 4.3-4.4 (1H, m), 4.4-4.6 (1H, m), 7.16 (0.5H, s), 7.25 (0.5H, s), 7.81 (1H, s), 7.88 (1H, s), 11.46 (0.5H, br s), 11.54 (0.5H, br s).

MS (m/z): 458 (M$^+$+2), 456 (M$^+$).

Example 95

1-Acetyl-4-[(8-chloro-1-cyclohexyl-4-oxo-4,5-dihydroimidazo-[1,5-a]quinoxalin-7-yl)carbonyl]piperazine

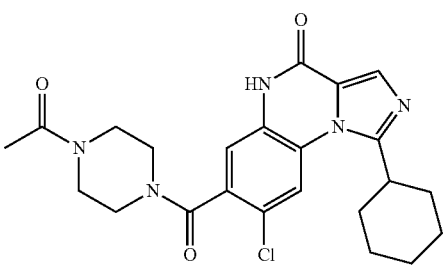 [SMILES: CC(=O)N1CCN(C(=O)c2cc3[nH]c(=O)c4cnc(C5CCCCC5)n4c3cc2Cl)CC1]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.2-1.4 (1H, m), 1.4-1.9 (5H, m), 1.87 (2H, br d, J=12.7 Hz), 2.00 (1.4H, s), 2.06 (1.6H, s), 2.09 (2H, br d, J=13.9 Hz), 3.1-3.4 (2H, m), 3.3-3.8 (7H, m), 7.25 (1H, d, J=2.7 Hz), 7.82 (1H, s), 7.90 (1H, s), 11.57 (1H, br s).

MS (m/z): 457 (M$^+$+2), 455 (M$^+$).

Example 96

8-Chloro-1-cyclohexyl-N,N-diethyl-4-oxo-4,5-dihydroimidazo-[1,5-a]quinoxaline-7-carboxamide

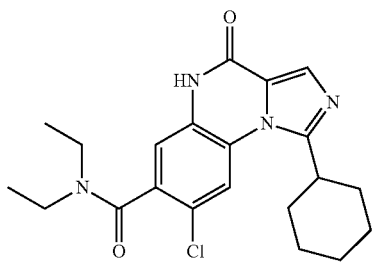 [SMILES: CCN(CC)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-$d_6$, δ): 1.03 (3H, t, J=7.1 Hz), 1.18 (3H, t, J=6.9 Hz), 1.2-1.4 (1H, m), 1.4-1.9 (5H, m), 1.86 (2H, br d, J=13.1 Hz), 2.09 (2H, br d, J=12.3 Hz), 3.0-3.8 (5H, m), 7.23 (1H, s), 7.81 (1H, s), 7.89 (1H, s), 11.50 (1H, br s).

MS (m/z): 402 (M$^+$+2), 400 (M$^+$).

Example 97

8-Chloro-1-cyclohexyl-N-methyl-4-oxo-N-propyl-4,5-dihydroimidazo[1,5-a]quinoxaline-7-carboxamide

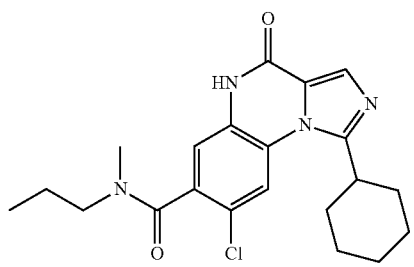 [SMILES: CCCN(C)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-d$_6$, δ): 0.72 (1.3H, t, J=7.3 Hz), 0.94 (1.7H, t, J=7.3 Hz), 1.2-1.4 (1H, m), 1.4-1.9 (9H, m), 2.09 (2H, br d, J=12.3 Hz), 2.81 (1.6H, s), 3.00 (1.4H, s), 3.0-3.6 (3H, m), 7.21 (0.5H, s), 7.22 (0.5H, s), 7.81 (1H, s), 7.88 (0.5H, s), 7.89 (0.5H, s), 11.51 (1H, br s).

MS (m/z): 402 (M$^+$+2), 400 (M$^+$).

Example 98

1-[(8-Chloro-1-cyclohexyl-4-oxo-4,5-dihydroimidazo[1,5-a]-quinoxalin-7-yl)carbonyl]piperidine

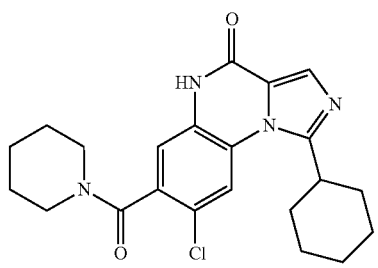 [SMILES: O=C(c1cc2[nH]c(=O)c3cnc(C4CCCCC4)n3c2cc1Cl)N1CCCCC1]

The title compound was obtained from 8-chloro-1-cyclohexyl-4-oxo-4,5-dihydroimidazo[1,5-a]quinoxaline-7-carboxyic acid as synthesized in above Example 84, in the manner similar to Example 59.

$^1$H-NMR (DMSO-d$_6$, δ): 1.2-1.9 (12H, m), 1.86 (2H, br d, J=12.7 Hz), 2.09 (2H, br d, J=12.3 Hz), 3.17 (2H, br s), 3.3-3.5 (1H, m), 3.5-3.8 (2H, m), 7.21 (1H, s), 7.81 (1H, s), 7.88 (1H, s), 11.52 (1H, br s).

MS (m/z): 414 (M$^+$+2), 412 (M$^+$).

Example 99

1-Cyclohexyl-N,N-dimethyl-4-oxo-4,5-dihydroimidazo[1,5-a]-quinoxaline-7-sulfonamide

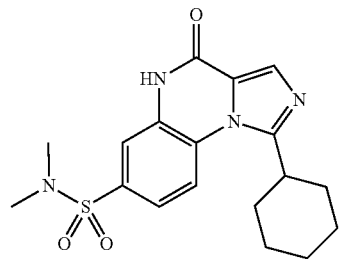 [SMILES: CN(C)S(=O)(=O)c1ccc2c(c1)[nH]c(=O)c1cnc(C3CCCCC3)n12]

The title compound was obtained from 3-amino-4-(2-cyclohexyl-1H-imidazol-1-yl)-N,N-dimethylbenzenesulfonamide as synthesized in Production Example 38, by the operations similar to Example 4.

$^1$H-NMR (DMSO-d$_6$, δ): 1.2-1.4 (1H, m), 1.4-1.9 (5H, m), 1.83 (2H, br d, J=12.7 Hz), 2.08 (2H, br d, J=13.1 Hz), 2.68 (6H, s), 3.4-3.6 (1H, m), 7.64 (1H, dd, J=2.1, 8.7 Hz), 7.73 (1H, d, J=2.3 Hz), 7.84 (1H, s), 8.15 (1H, d, J=8.9 Hz), 11.52 (1H, br s).

MS (m/z): 374 (M$^+$).

Example 100

1-[(1-Cyclohexyl-4-oxo-4,5-dihydroimidazo[1,5-a]quinoxalin-7-yl)sulfonyl]-4-methylpiperazine

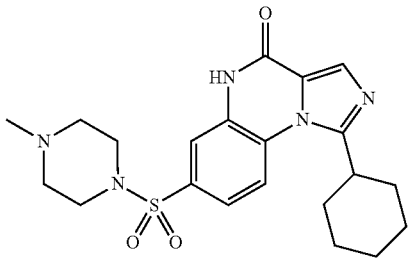 [SMILES: CN1CCN(S(=O)(=O)c2ccc3c(c2)[nH]c(=O)c2cnc(C4CCCCC4)n23)CC1]

The title compound was obtained from 1-[3-amino-4-(2-cyclohexyl-1H-imidazol-1-yl)benzenesulfonyl]-4-methylpiperazine as synthesized in Production Example 41, by the operations similar to Example 4.

$^1$H-NMR (DMSO-d$_6$, δ): 1.2-1.4 (1H, m), 1.4-1.9 (7H, m), 2.08 (2H, br d, J=11.9 Hz), 2.15 (3H, s), 2.3-2.5 (4H, m), 2.96 (4H, br s), 3.4-3.6 (1H, m), 7.62 (1H, dd, J=1.9, 8.9 Hz), 7.72 (1H, d, J=2.3 Hz), 7.84 (1H, s), 8.14 (1H, d, J=8.9 Hz), 11.52 (1H, br s).

MS (m/z): 429 (M$^+$).

Example 101

1-Cyclohexyl-N-(2-dimethylaminoethyl)-N-methyl-4-oxo-4,5-dihydroimidazo[1,5-a]quinoxaline-7-sulfonamide

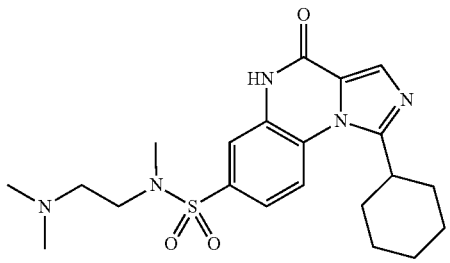 [SMILES: CN(C)CCN(C)S(=O)(=O)c1ccc2c(c1)[nH]c(=O)c1cnc(C3CCCCC3)n12]

The title compound was synthesized from 3-amino-4-(2-cyclohexyl-1H-imidazol-1-yl)-N-(2-dimethylaminoethyl)-N-methylbenzenesulfonamide as synthesized in Production Example 43, by the operations similar to Example 4.

$^1$H-NMR (DMSO-$d_6$, δ): 1.2-1.4 (1H, m), 1.4-1.9 (5H, m), 1.83 (2H, br d, J=12.7 Hz), 2.08 (2H, br d, J=12.3 Hz), 2.15 (6H, s), 2.40 (2H, t, J=6.7 Hz), 2.76 (3H, s), 3.10 (2H, t, J=6.7 Hz), 3.4-3.6 (1H, m), 7.67 (1H, dd, J=1.9, 8.9 Hz), 7.76 (1H, d, J=1.9 Hz), 7.83 (1H, s), 8.13 (1H, d, J=8.9 Hz), 11.50 (1H, br s).

MS (m/z): 430 (M$^+$-1).

Example 102

Ethyl 1-cyclohexyl-4-oxo-4,5-dihydroimidazo[1,5-a]-quinoxaline-8-carboxyate

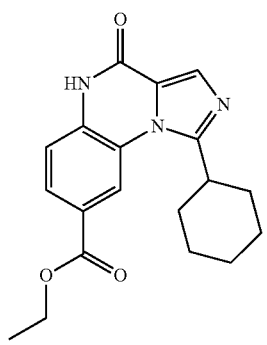 [SMILES: CCOC(=O)c1ccc2[nH]c(=O)c3cnc(C4CCCCC4)n3c2c1]

The title compound was obtained from ethyl 4-amino-3-(2-cyclohexyl-1H-imidazol-1-yl)benzoate as synthesized in Production Example 46, by the operations similar to Example 4.

$^1$H-NMR (DMSO-$d_6$, δ): 1.2-1.5 (1H, m), 1.37 (3H, t, J=7.1 Hz), 1.4-1.9 (5H, m), 1.90 (2H, br d, J=13.1 Hz), 2.12 (2H, br d, J=12.3 Hz), 3.2-3.4 (1H, m), 4.36 (2H, q, J=7.1 Hz), 7.41 (1H, d, J=8.5 Hz), 7.82 (1H, s), 7.94 (1H, dd, J=1.5, 8.5 Hz), 8.51 (1H, d, J=1.2 Hz), 11.69 (1H, br s).

MS (m/z): 339 (M$^+$).

Example 103

1-Cyclohexyl-4-oxo-4,5-dihydroimidazo[1,5-a]quinoxaline-8-carboxyic acid

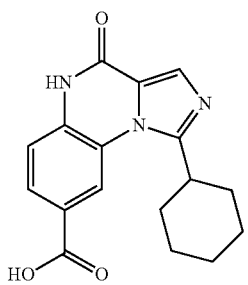 [SMILES: O=C(O)c1ccc2[nH]c(=O)c3cnc(C4CCCCC4)n3c2c1]

The title compound was obtained from ethyl 1-cyclohexyl-4-oxo-4,5-dihydroimidazo[1,5-a]quinoxaline-8-carboxyate as synthesized in above Example 102, by the operations similar to Example 58.

$^1$H-NMR (DMSO-$d_6$, δ): 1.2-1.5 (1H, m), 1.4-1.9 (5H, m), 1.89 (2H, br d, J=12.7 Hz), 2.12 (2H, br d, J=12.7 Hz), 3.2-3.5 (1H, m), 7.40 (1H, d, J=8.5 Hz), 7.81 (1H, s), 7.93 (1H, dd, J=1.5, 8.5 Hz), 8.53 (1H, br s), 11.67 (1H, br s), 13.10 (1H, br s).

MS (m/z): 311 (M$^+$).

Example 104

1-Cyclohexyl-N,N-dimethyl-4-oxo-4,5-dihydroimidazo[1,5-a]-quinoxaline-8-carboxamide

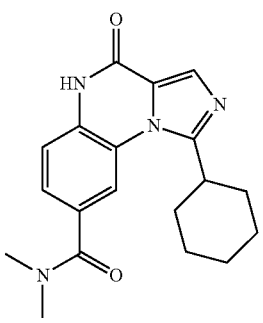 [SMILES: CN(C)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.2-1.4 (1H, m), 1.4-1.9 (7H, m), 2.09 (2H, br d, J=12.7 Hz), 3.03 (6H, s), 3.3-3.5 (1H, m), 7.37 (1H, d, J=8.5 Hz), 7.49 (1H, dd, J=1.5, 8.5 Hz), 7.80 (1H, s), 7.96 (1H, br s), 11.52 (1H, br s).

MS (m/z): 338 (M$^+$).

Example 105

1-Cyclohexyl-N-(2-methoxyethyl)-N-methyl-4-oxo-4,5-dihydroimidazo[1,5-a]quinoxaline-8-carboxamide

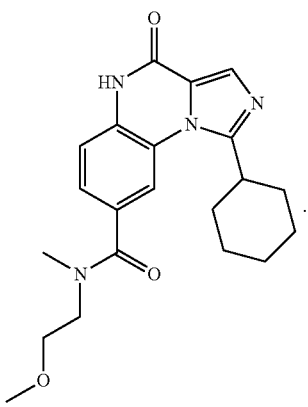 [SMILES: COCCN(C)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.2-2.0 (8H, m), 2.09 (2H, br d, J=11.9 Hz), 3.03 (3H, s), 3.1-3.7 (8H, m), 7.37 (1H, d, J=8.5 Hz), 7.46 (1H, dd, J=1.5, 8.5 Hz), 7.80 (1H, s), 7.89 (1H, br s), 11.52 (1H, br s).

MS (m/z): 382 (M$^+$).

Example 106

4-[(1-Cyclohexyl-4-oxo-4,5-dihydroimidazo[1,5-a]quinoxalin-8-yl)carbonyl]morpholine

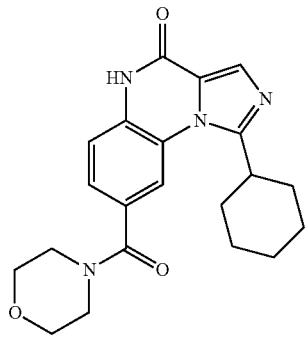 [SMILES: O=C(c1ccc2[nH]c(=O)c3cnc(C4CCCCC4)n3c2c1)N1CCOCC1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.2-1.4 (1H, m), 1.4-2.0 (7H, m), 2.09 (2H, br d, J=13.1 Hz), 3.3-3.8 (9H, m), 7.39 (1H, d, J=8.5 Hz), 7.47 (1H, dd, J=1.3, 8.3 Hz), 7.80 (1H, s), 7.92 (1H, br s), 11.53 (1H, br s).

MS (m/z): 380 (M$^+$).

Example 107

1-Cyclohexyl-N-methyl-4-oxo-4,5-dihydroimidazo[1,5-a]-quinoxaline-8-carboxamide

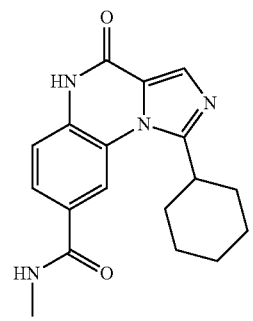 [SMILES: CNC(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.2-1.5 (1H, m), 1.4-1.9 (5H, m), 1.87 (2H, br d, J=12.7 Hz), 2.11 (2H, br d, J=12.7 Hz), 2.84 (3H, d, J=4.6 Hz), 3.4-3.6 (1H, m), 7.34 (1H, d, J=8.5 Hz), 7.80 (1H, s), 7.85 (1H, dd, J=1.2, 8.5 Hz), 8.49 (1H, br s), 8.4-8.7 (1H, m), 11.55 (1H, br s).

MS (m/z): 324 (M$^+$).

Example 108

1-Cyclohexyl-N-(2-methoxyethyl)-4-oxo-4,5-dihydroimidazo-[1,5-a]quinoxaline-8-carboxamide

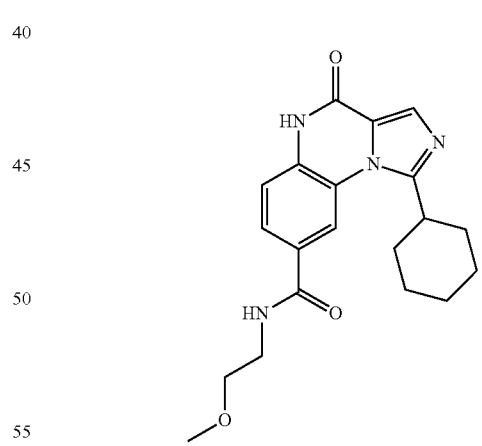

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.2-1.5 (1H, m), 1.4-1.9 (5H, m), 1.87 (2H, br d, J=12.7 Hz), 2.11 (2H, br d, J=12.3 Hz), 3.29 (3H, s), 3.4-3.6 (5H, m), 7.35 (1H, d, J=8.5 Hz), 7.80 (1H, s), 7.88 (1H, dd, J=1.5, 8.5 Hz), 8.47 (1H, br s), 8.6-8.7 (1H, m), 11.56 (1H, br s).

MS (m/z): 368 (M$^+$).

Example 109

1-[(1-Cyclohexyl-4-oxo-4,5-dihydroimidazo[1,5-a]quinoxalin-8-yl)carbonyl]-4-methylpiperazine

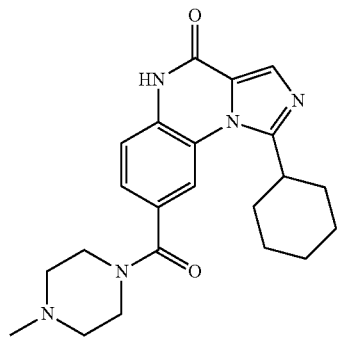 [SMILES: CN1CCN(C(=O)c2ccc3[nH]c(=O)c4cnc(C5CCCCC5)n4c3c2)CC1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-d$_6$, δ): 1.2-1.4 (1H, m), 1.4-1.9 (5H, m), 1.86 (2H, br d, J=13.1 Hz), 2.10 (2H, br d, J=12.7 Hz), 2.22 (3H, s), 2.35 (4H, br s), 3.2-3.7 (5H, m), 7.39 (1H, d, J=8.5 Hz), 7.44 (1H, dd, J=1.3, 8.3 Hz), 7.80 (1H, s), 7.88 (1H, br s), 11.53 (1H, br s).

MS (m/z): 393 (M$^+$).

Example 110

1-[(1-Cyclohexyl-4-oxo-4,5-dihydroimidazo[1,5-a]quinoxalin-8-yl)carbonyl]piperidine

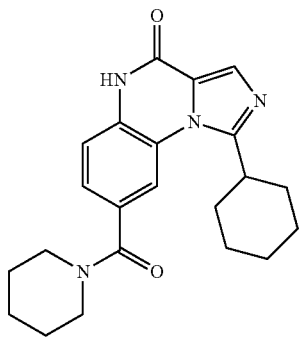 [SMILES: O=C(c1ccc2[nH]c(=O)c3cnc(C4CCCCC4)n3c2c1)N1CCCCC1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-d$_6$, δ): 1.2-1.4 (1H, m), 1.4-1.9 (13H, m), 2.09 (2H, br d, J=12.7 Hz), 3.2-3.7 (5H, m), 7.38 (1H, d, J=8.5 Hz), 7.42 (1H, dd, J=1.3, 8.3 Hz), 7.80 (1H, s), 7.88 (1H, br s), 11.52 (1H, br s).

MS (m/z): 378 (M$^+$).

Example 111

1-[(1-Cyclohexyl-4-oxo-4,5-dihydroimidazo[1,5-a]quinoxalin-8-yl)carbonyl]pyrrolidine

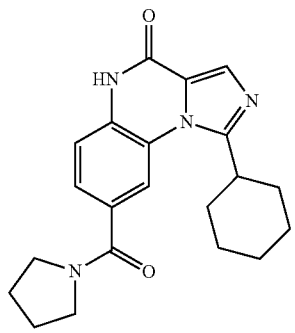 [SMILES: O=C(c1ccc2[nH]c(=O)c3cnc(C4CCCCC4)n3c2c1)N1CCCC1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-d$_6$, δ): 1.2-1.4 (1H, m), 1.4-1.6 (2H, m), 1.6-2.0 (9H, m), 2.09 (2H, br d, J=12.7 Hz), 3.3-3.5 (1H, m), 3.53 (4H, br s), 7.36 (1H, d, J=8.1 Hz), 7.62 (1H, dd, J=1.5, 8.5 Hz), 7.80 (1H, s), 8.12 (1H, br s), 11.53 (1H, br s).

MS (m/z): 364 (M$^+$).

Example 112

1-Cyclohexyl-N,N-diethyl-4-oxo-4,5-dihydroimidazo[1,5-a]-quinoxaline-8-carboxamide

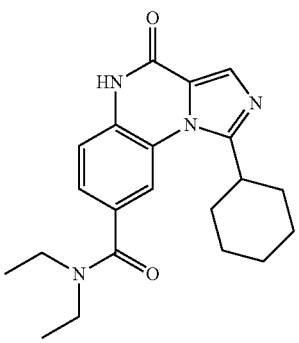 [SMILES: CCN(CC)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-d$_6$, δ): 1.13 (6H, t, J=6.9 Hz), 1.2-1.6 (3H, m), 1.5-2.0 (5H, m), 2.09 (2H, br d, J=12.7 Hz), 3.2-3.6 (5H, m), 7.3-7.5 (2H, m), 7.80 (1H, s), 7.83 (1H, br s), 11.51 (1H, br s).

MS (m/z): 366 (M$^+$).

Example 113

1-Cyclohexyl-N-ethyl-N-methyl-4-oxo-4,5-dihydroimidazo-[1,5-a]quinoxaline-8-carboxamide

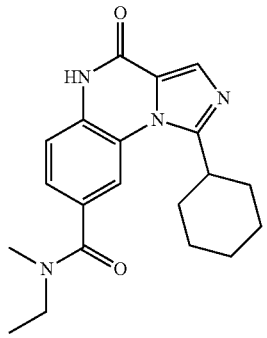 [SMILES: CCN(C)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.14 (3H, t, J=6.9 Hz), 1.2-1.6 (3H, m), 1.5-1.9 (3H, m), 1.85 (2H, br d, J=13.1 Hz), 2.09 (2H, br d, J=12.3 Hz), 2.99 (3H, s), 3.2-3.6 (3H, m), 7.37 (1H, d, J=8.5 Hz), 7.45 (1H, d, J=8.5 Hz), 7.80 (1H, s), 7.90 (1H, s), 11.52 (1H, br s).

MS (m/z): 352 (M$^+$).

Example 114

1-Cyclohexyl-N-methyl-4-oxo-N-propyl-4,5-dihydroimidazo-[1,5-a]quinoxaline-8-carboxamide

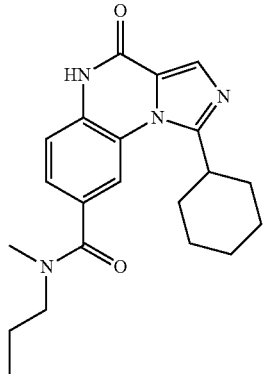 [SMILES: CCCN(C)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 0.87 (3H, br s), 1.2-1.9 (10H, m), 2.09 (2H, br d, J=12.7 Hz), 2.99 (3H, s), 3.2-3.6 (3H, m), 7.37 (1H, d, J=8.5 Hz), 7.44 (1H, d, J=8.1 Hz), 7.80 (1H, s), 7.89 (1H, s), 11.52 (1H, br s).

MS (m/z): 366 (M$^+$).

Example 115

1-[(1-Cyclohexyl-4-oxo-4,5-dihydroimidazo[1,5-a]quinoxalin-8-yl)carbonyl]-4-(2-hydroxyethyl)piperidine

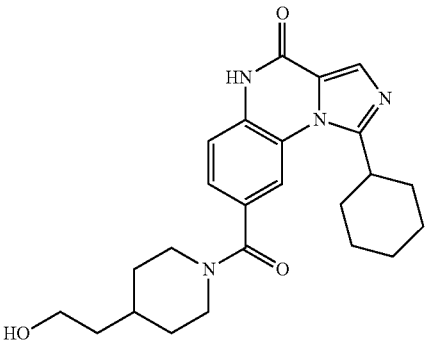 [SMILES: O=C(c1ccc2[nH]c(=O)c3cnc(C4CCCCC4)n3c2c1)N1CCC(CCO)CC1]

The title compound was obtained from 1-cyclohexyl-4-oxo-4,5-dihydroimidazo[1,5-a]quinoxaline-8-carboxyic acid as synthesized in above Example 103, by the operations similar to Example 59.

$^1$H-NMR (DMSO-$d_6$, δ): 1.0-1.2 (2H, m), 1.2-1.6 (5H, m), 1.6-1.9 (6H, m), 1.86 (2H, br d, J=12.7 Hz), 2.09 (2H, br d, J=13.1 Hz), 2.94 (2H, br s), 3.2-3.6 (3H, m), 4.37 (1H, t, J=5.2 Hz), 7.38 (1H, d, J=8.1 Hz), 7.42 (1H, dd, J=1.3, 8.3 Hz), 7.80 (1H, s), 7.86 (1H, br s), 11.52 (1H, br s).

MS (m/z): 422 (M$^+$).

Example 116

1-Cyclohexyl-4-oxo-N-(2-pyridyl)-4,5-dihydroimidazo[1,5-a]-quinoxaline-8-carboxamide

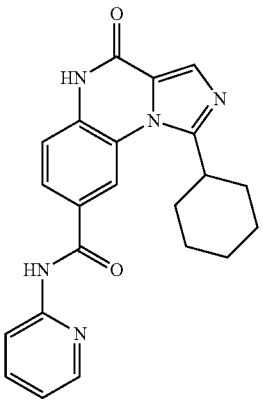 [SMILES: O=C(Nc1ccccn1)c1ccc2[nH]c(=O)c3cnc(C4CCCCC4)n3c2c1]

1-Cyclohexyl-4-oxo-4,5-dihydroimidazo[1,5-a]quinoxaline-8-carboxyic acid as synthesized in above Example 103, 405 mg, 2-aminopyridine 184 mg, 1-hydroxybenzotriazole monohydrate 299 mg, 4-dimethylaminopyridine 31 mg, pyridine 8.5 mL and 1-(3-dimethylaminopropyl)-3-ethylcarbodiimide hydrochloride 375 mg were mixed and stirred for 23 hours. After distilling the solvent off, ethyl acetate and saturated aqueous sodium hydrogencarbonate solution were added to the residue and stirred. The crystals were recovered by filtration and washed successively with water and ethyl acetate. The crystals were heat-suspended in 20 mL of acetone, recovered by filtration and washed with acetone. Drying the crystals, 213 mg of the title compound was obtained.

$^1$H-NMR (DMSO-$d_6$, δ): 1.2-1.4 (1H, m), 1.4-1.9 (5H, m), 1.87 (2H, br d, J=13.1 Hz), 2.15 (2H, br d, J=11.9 Hz), 3.4-3.6

(1H, m), 7.19 (1H, ddd, J=0.8, 5.0, 7.3 Hz), 7.39 (1H, d, J=8.5 Hz), 7.82 (1H, s), 7.87 (1H, dt, J=1.9, 8.5 Hz), 8.15 (1H, dd, J=1.5, 8.5 Hz), 8.21 (1H, d, J=8.5 Hz), 8.4-8.5 (1H, m), 8.56 (1H, br s), 10.91 (1H, br s), 11.64 (1H, br s).
MS (m/z): 266 (M$^+$−121).

Example 117

1-Cyclohexyl-4-oxo-N-(3-pyridyl)-4,5-dihydroimidazo[1,5-a]-quinoxaline-8-carboxamide

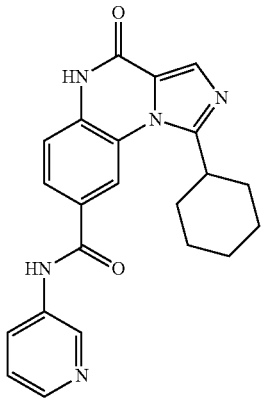 [SMILES: O=C(Nc1cccnc1)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 116.
$^1$H-NMR (DMSO-d$_6$, δ): 1.2-1.4 (1H, m), 1.4-1.6 (2H, m), 1.6-1.9 (3H, m), 1.87 (2H, br d, J=13.1 Hz), 2.15 (2H, br d, J=12.3 Hz), 3.4-3.6 (1H, m), 7.4-7.5 (2H, m), 7.83 (1H, s), 8.06 (1H, dd, J=1.5, 8.5 Hz), 8.23 (1H, ddd, J=1.5, 2.3, 8.5 Hz), 8.34 (1H, dd, J=1.5, 4.6 Hz), 8.53 (1H, br s), 8.93 (1H, d, J=2.3 Hz), 10.56 (1H, br s), 11.65 (1H, br s).
MS (m/z): 387 (M$^+$).

Example 118

1-Cyclohexyl-4-oxo-N-(2-pyridylmethyl)-4,5-dihydroimidazo-[1,5-a]quinoxaline-8-carboxamide

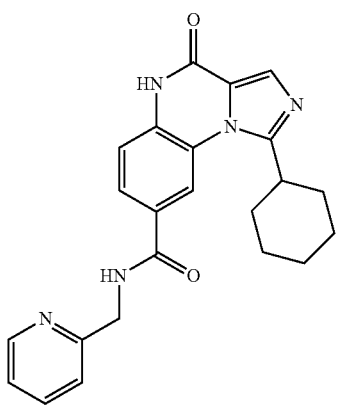 [SMILES: O=C(NCc1ccccn1)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 116.
$^1$H-NMR (DMSO-d$_6$, δ): 1.2-1.4 (1H, m), 1.4-1.9 (5H, m), 1.83 (2H, br d, J=12.7 Hz), 2.11 (2H, br d, J=12.7 Hz), 3.4-3.6 (1H, m), 4.63 (2H, d, J=5.4 Hz), 7.2-7.4 (1H, m), 7.3-7.5 (2H, m), 7.7-7.9 (1H, m), 7.80 (1H, s), 7.96 (1H, dd, J=1.5, 8.5 Hz), 8.5-8.6 (2H, m), 9.1-9.3 (1H, m), 11.58 (1H, br s).
MS (m/z): 401 (M$^+$).

Example 119

1-Cyclohexyl-4-oxo-N-(3-pyridylmethyl)-4,5-dihydroimidazo-[1,5-a]quinoxaline-8-carboxamide

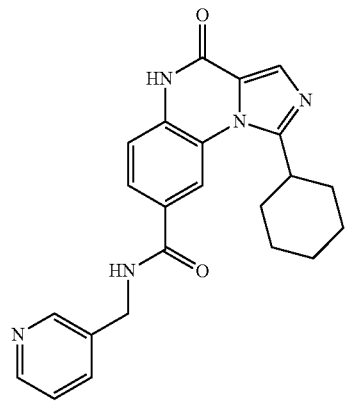 [SMILES: O=C(NCc1cccnc1)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 116.
$^1$H-NMR (DMSO-d$_6$, δ): 1.2-1.4 (1H, m), 1.4-1.6 (2H, m), 1.6-1.9 (3H, m), 1.83 (2H, br d, J=12.7 Hz), 2.10 (2H, br d, J=12.3 Hz), 3.4-3.6 (1H, m), 4.55 (2H, d, J=5.8 Hz), 7.3-7.5 (2H, m), 7.7-7.8 (1H, m), 7.80 (1H, s), 7.92 (1H, dd, J=1.5, 8.5 Hz), 8.4-8.6 (2H, m), 8.59 (1H, d, J=1.5 Hz), 9.1-9.3 (1H, m), 11.57 (1H, br s).
MS (m/z): 401 (M$^+$).

Example 120

1-Cyclohexyl-N-ethyl-N-(2-methoxyethyl)-4-oxo-4,5-dihydroimidazo[1,5-a]quinoxaline-8-carboxamide

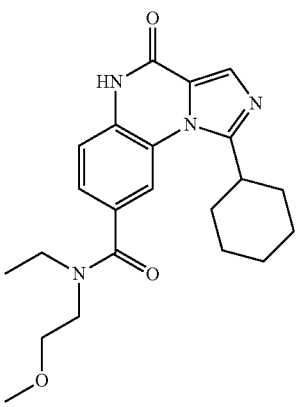 [SMILES: CCN(CCOC)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 59.
$^1$H-NMR (DMSO-d$_6$, δ): 1.11 (3H, br s), 1.2-1.6 (3H, m), 1.6-1.9 (3H, m), 1.85 (2H, br d, J=12.7 Hz), 2.09 (2H, br d, J=12.0 Hz), 3.1-3.7 (10H, m), 7.3-7.5 (2H, m), 7.79 (1H, s), 7.82 (1H, s), 11.50 (1H, br s).
MS (m/z): 396 (M$^+$).

Example 121

1-Cyclohexyl-N-isopropyl-N-(2-methyl)-4-oxo-4,5-dihydroimidazo[1,5-a]quinoxaline-8-carboxamide

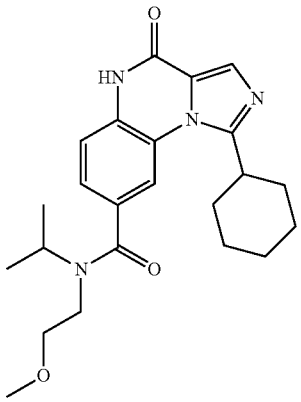 [SMILES: COCCN(C(=O)c1ccc2[nH]c(=O)c3cnc(C4CCCCC4)n3c2c1)C(C)C]

The title compound was obtained from 1-cyclohexyl-4-oxo-4,5-dihydroimidazo[1,5-a]quinoxaline-8-carboxyic acid as synthesized in Example 103, by the operations similar to Example 59.

$^1$H-NMR (DMSO-d$_6$, δ): 1.15 (6H, br d, J=5.8 Hz), 1.2-1.6 (3H, m), 1.6-1.9 (3H, m), 1.85 (2H, br d, J=13.1 Hz), 2.08 (2H, br d, J=12.7 Hz), 3.2-3.4 (4H, m), 3.47 (4H, br s), 3.9-4.2 (1H, m), 7.38 (2H, s), 7.7-7.9 (2H, m), 11.50 (1H, br s).

MS (m/z): 410 (M$^+$).

Example 122

1-Cyclohexyl-N-(2-methoxyethyl)-4-oxo-N-propyl-4,5-dihydroimidazo[1,5-a]quinoxaline-8-carboxamide

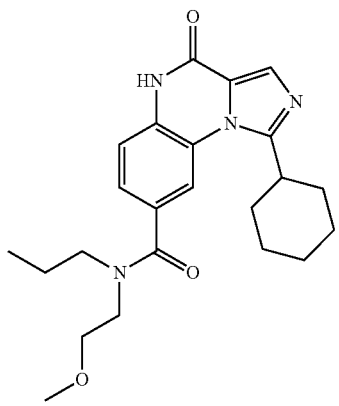 [SMILES: CCCN(CCOC)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 59.

$^1$H-NMR (DMSO-d$_6$, δ): 0.6-1.0 (3H, m), 1.2-1.9 (8H, m), 1.85 (2H, br d, J=13.1 Hz), 2.08 (2H, br d, J=11.9 Hz), 3.1-3.7 (10H, m), 7.3-7.5 (2H, m), 7.7-7.9 (2H, m), 11.50 (1H, br s).

MS (m/z): 410 (M$^+$).

Example 123

1-Cyclohexyl-N-(2-ethoxyethyl)-N-methyl-4-oxo-4,5-dihydroimidazo[1,5-a]quinoxaline-8-carboxamide

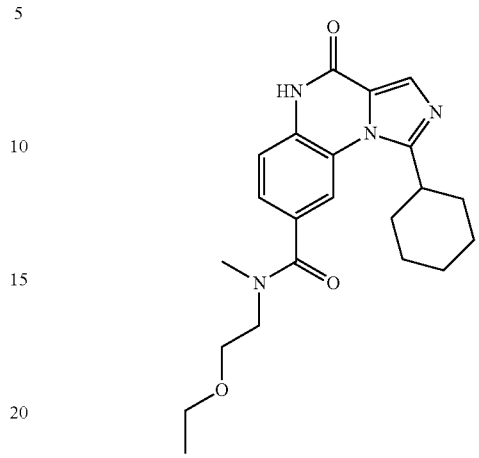

4-Amino-3-(2-cyclohexyl-1H-imidazol-1-yl)-N-(2-ethoxyethyl)-N-methylbenzamide as synthesized in Production Example 50, 2.51 g, 1,1'-carbonyldiimidazole 1.32 g and chlorobenzene 32 mL were mixed, and under nitrogen atmosphere, the temperature outside the reactor was heated to 150° C. for 16 hours. Allowing the reaction liquid to cool off, the solvent was distilled off therefrom. To the residue ethyl acetate and brine were added and the organic layer was separated. The organic layer was washed with saturated brine and dried over magnesium sulfate. After distilling the solvent off, the residue was crystallized from t-butyl methyl ether. Further heat-suspending the crystals in ethyl acetate for purification, 993 mg of the title compound was obtained.

$^1$H-NMR (DMSO-d$_6$, δ): 1.0-1.2 (3H, m), 1.2-1.6 (3H, m), 1.6-1.9 (3H, m), 1.85 (2H, br d, J=13.1 Hz), 2.08 (2H, br d, J=13.1 Hz), 3.04 (3H, s), 3.2-3.7 (7H, m), 7.36 (1H, d, J=8.1 Hz), 7.46 (1H, dd, J=1.5, 8.5 Hz), 7.80 (1H, s), 7.89 (1H, d, J=1.2 Hz), 11.51 (1H, br s).

MS (m/z): 396 (M$^+$).

Example 124

1-Cyclohexyl-N-(3-methoxypropyl)-N-methyl-4-oxo-4,5-dihydroimidazo[15-a]quinoxaline-8-carboxamide

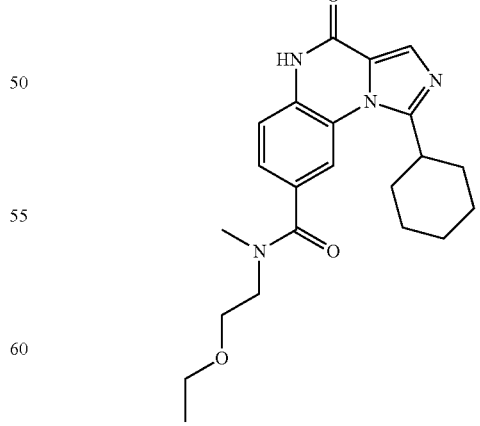

The title compound was obtained from 4-amino-3-(2-cyclohexyl-1H-imidazol-1-yl)-N-(3-methoxypropyl)-N-methyl-benzamide as synthesized in Production Example 54, by the operations similar to Example 123.

¹H-NMR (DMSO-d₆, δ): 1.2-1.6 (3H, m), 1.6-1.9 (7H, m), 2.09 (2H, br d, J=12.3 Hz), 2.99 (3H, s), 3.0-3.6 (8H, m), 7.37 (1H, d, J=8.1 Hz), 7.45 (1H, d, J=8.5 Hz), 7.80 (1H, s), 7.90 (1H, s), 11.51 (1H, br s).
MS (m/z): 396 (M⁺).

Example 125

1-Cyclohexyl-N-methyl-4-oxo-N-(3-pyridylmethyl)-4,5-dihydroimidazo[1,5-a]quinoxaline-8-carboxamide

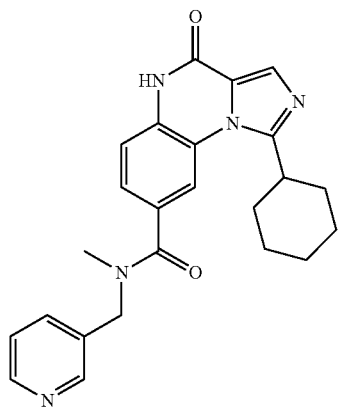 [SMILES: CN(Cc1cccnc1)C(=O)c1ccc2[nH]c(=O)c3cnc(C4CCCCC4)n3c2c1]

The title compound was obtained from 4-amino-3-(2-cyclohexyl-1H-imidazol-1-yl)-N-methyl-N-(3-pyridylmethyl)-benzamide as synthesized in Production Example 58, by the operations similar to Example 123.
¹H-NMR (DMSO-d₆, δ): 1.2-1.5 (3H, m), 1.5-1.9 (5H, m), 2.05 (2H, br d, J=12.7 Hz), 2.97 (3H, s), 3.2-3.4 (1H, m), 4.72 (2H, br s), 7.3-7.5 (2H, m), 7.4-7.6 (1H, m), 7.7-7.9 (1H, m), 7.79 (1H, s), 7.91 (1H, s), 8.4-8.7 (2H, m), 11.53 (1H, br s).
MS (m/z): 415 (M⁺).

Example 126

1-Cyclohexyl-N-methyl-4-oxo-N-(2-pyridylmethyl)-4,5-dihydroimidazo[1,5-a]quinoxaline-8-carboxamide

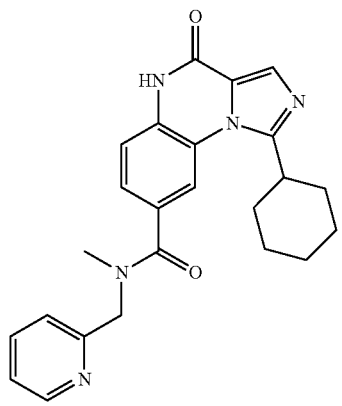 [SMILES: CN(Cc1ccccn1)C(=O)c1ccc2[nH]c(=O)c3cnc(C4CCCCC4)n3c2c1]

The title compound was obtained from 4-amino-3-(2-cyclohexyl-1H-imidazol-1-yl)-N-methyl-N-(2-pyridylmethyl)-benzamide as synthesized in Production Example 62, by the operations similar to Example 123.

¹H-NMR (DMSO-d₆, δ): 1.2-1.6 (3H, m), 1.5-2.0 (5H, m), 2.07 (2H, br d, J=13.1 Hz), 3.03 (3H, br s), 3.2-3.4 (1H, m), 4.6-4.9 (2H, m), 7.2-7.5 (3H, m), 7.5-7.6 (1H, m), 7.7-7.9 (2H, m), 7.95 (1H, s), 8.5-8.6 (1H, m), 11.52 (1H, br s).
MS (m/z): 415 (M⁺).

Example 127

1-Cyclohexyl-N-methyl-4-oxo-N-(4-pyridylmethyl)-4,5-dihydroimidazo[1,5-a]quinoxaline-8-carboxamide

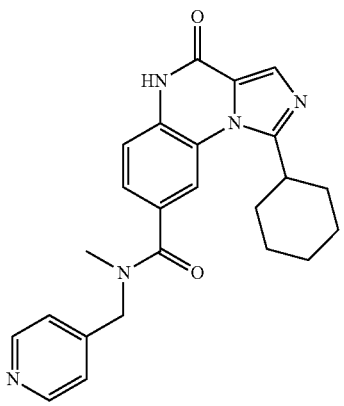 [SMILES: CN(Cc1ccncc1)C(=O)c1ccc2[nH]c(=O)c3cnc(C4CCCCC4)n3c2c1]

The title compound was obtained from 4-amino-3-(2-cyclohexyl-1H-imidazol-1-yl)-N-methyl-N-(4-pyridylmethyl)-benzamide as synthesized in Production Example 66, by the operations similar to Example 123.
¹H-NMR (DMSO-d₆, δ): 1.2-1.6 (3H, m), 1.5-1.9 (5H, m), 2.07 (2H, br d, J=12.7 Hz), 3.00 (3H, s), 3.2-3.5 (1H, m), 4.72 (2H, br s), 7.2-7.7 (4H, m), 7.80 (1H, s), 7.94 (1H, s), 8.56 (2H, d, J=5.8 Hz), 11.53 (1H, br s).
MS (m/z): 415 (M⁺).

Example 128

1-Cyclohexyl-N-methyl-4-oxo-N-[2-(2-pyridyl)ethyl]-4,5-dihydroimidazo[1,5-a]quinoxaline-8-carboxamide

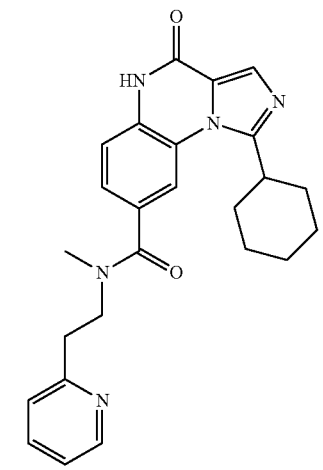 [SMILES: CN(CCc1ccccn1)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 59.

¹H-NMR (DMSO-d₆, δ): 1.2-1.6 (3H, m), 1.5-1.9 (5H, m), 2.07 (2H, br d, J=13.5 Hz), 2.9-3.2 (5H, m), 3.2-3.4 (1H, m), 3.7-3.9 (2H, m), 7.1-7.5 (4H, m), 7.6-8.0 (3H, m), 8.2-8.6 (1H, m), 11.50 (1H, br s).
MS (m/z): 429 (M⁺).

Example 129

1-Cyclohexyl-N-(2-dimethylaminoethyl)-N-methyl-4-oxo-4,5-dihydroimidazo[1,5-a]quinoxaline-8-carboxamide

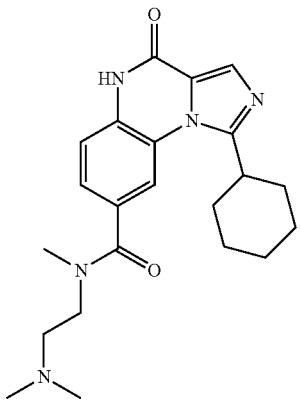 [SMILES: CN(C)CCN(C)C(=O)c1ccc2[nH]c(=O)c3cnc(C4CCCCC4)n3c2c1]

The title compound was obtained from 1-cyclohexyl-4-oxo-4,5-dihydroimidazo[1,5-a]quinoxaline-8-carboxyic acid as synthesized in Example 103, by the operations similar to Example 59.
¹H-NMR (DMSO-d₆, δ): 1.2-1.4 (1H, m), 1.4-1.6 (2H, m), 1.6-1.9 (5H, m), 1.9-2.3 (8H, m), 2.3-2.6 (2H, m), 3.01 (3H, s), 3.2-3.4 (1H, m), 3.4-3.7 (2H, m), 7.37 (1H, d, J=8.1 Hz), 7.44 (1H, dd, J=1.4, 8.3 Hz), 7.80 (1H, s), 7.88 (1H, br s), 11.51 (1H, br s).
MS (m/z): 395 (M⁺).

Example 130

1-Cyclohexyl-8-(1-hydroxy-1-methylethyl)imidazo[1,5-a]-quinoxalin-4 (5H)-one

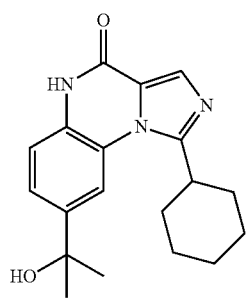 [SMILES: CC(C)(O)c1ccc2[nH]c(=O)c3cnc(C4CCCCC4)n3c2c1]

Ethyl 1-cyclohexyl-4-oxo-4,5-dihydroimidazo[1,5-a]-quinoxaline-8-carboxyate as synthesized in Example 102, 503 mg was suspended in 9 mL of tetrahydrofuran, and into the suspension 1.7 mL of 3M methylmagnesium bromide solution in diethyl ether was dropped, followed by 23 hours' stirring at room temperature under nitrogen atmosphere. The reaction liquid was poured into water, and of which pH was adjusted to 9 with diluted hydrochloric acid and saturated aqueous sodium hydrogencarbonate solution. The precipitated crystals were recovered by filtration and washed with water. The crude product was heat-suspended in acetone and purified. The crude product was alkali-treated and thereafter its pH was adjusted to 10 by addition of diluted hydrochoric acid (i.e. the carboxyic acid was dissolved in water). Thus precipitated crystals were recovered by filtration, washed with water, heat-suspended in 2-propanol and purified. Further recrystallizing the same from N,N-dimethylformamide-water mixed solvent, 133 mg of the title compound was obtained.
¹H-NMR (DMSO-d₆, δ): 1.2-1.4 (1H, m), 1.4-1.6 (2H, m), 1.49 (6H, s), 1.6-2.0 (5H, m), 2.13 (2H, br d, J=12.3 Hz), 3.3-3.5 (1H, m), 5.22 (1H, s), 7.28 (1H, d, J=8.5 Hz), 7.43 (1H, dd, J=1.5, 8.5 Hz), 7.76 (1H, s), 8.14 (1H, br s), 11.28 (1H, br s).
MS (m/z): 325 (M⁺).

Example 131

Ethyl (E)-3-(1-cyclohexyl-4-oxo-4,5-dihydroimidazo[1,5-a]-quinoxalin-7-yl)acrylate

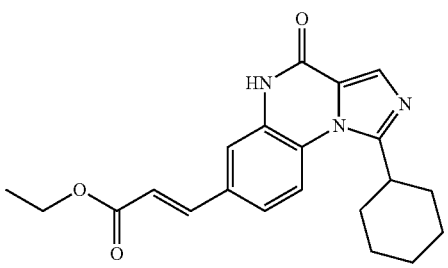 [SMILES: CCOC(=O)/C=C/c1ccc2c(c1)[nH]c(=O)c1cnc(C3CCCCC3)n12]

The title compound was obtained from ethyl (E)-3-[3-amino-4-(2-cyclohexyl-1H-imidazol-1-yl)phenyl]acrylate as synthesized in Production Example 68, by the operations similar to Example 123.
¹H-NMR (DMSO-d₆, δ): 1.2-1.4 (1H, m), 1.28 (3H, t, J=7.1 Hz), 1.4-1.9 (7H, m), 2.08 (2H, br d, J=11.9 Hz), 3.4-3.5 (1H, m), 4.22 (2H, q, J=7.1 Hz), 6.55 (1H, d, J=16.2 Hz), 7.54 (1H, s), 7.6-7.7 (2H, m), 7.79 (1H, s), 7.96 (1H, d, J=8.9 Hz), 11.42 (1H, br s).
MS (m/z): 365 (M⁺).

Example 132

(E)-3-(1-cyclohexyl-4-oxo-4,5-dihydroimidazo[1,5-a]-quinoxalin-7-yl)acrylic acid

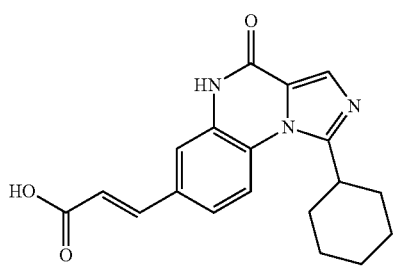 [SMILES: O=C(O)/C=C/c1ccc2c(c1)[nH]c(=O)c1cnc(C3CCCCC3)n12]

The title compound was obtained from ethyl (E)-3-(1-cyclohexyl-4-oxo-4,5-dihydroimidazo[1,5-a]quinoxalin-7-yl)acrylate as synthesized in above Example 131, by the operations similar to Example 58.

$^1$H-NMR (DMSO-d$_6$, δ): 1.2-1.4 (1H, m), 1.4-1.9 (7H, m), 2.08 (2H, br d, J=12.0 Hz), 3.4-3.5 (1H, m), 6.47 (1H, d, J=15.8 Hz), 7.5-7.7 (3H, m), 7.79 (1H, s), 7.96 (1H, d, J=8.5 Hz), 11.42 (1H, br s), 12.56 (1H, br s).

MS (m/z): 337 (M$^+$).

Example 133

7-Acetyl-1-cyclohexyl-8-methoxyimidazo[1,5-a]quinoxalin-4 (5H)-one

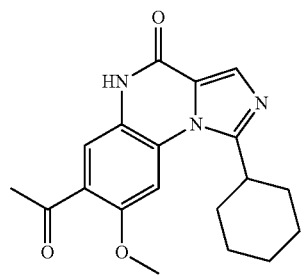 [SMILES: COc1cc2c(cc1C(C)=O)[nH]c(=O)c1cnc(C3CCCCC3)n12]

The title compound was obtained from 1-[5-amino-4-(2-cyclohexyl-1H-imidazol-1-yl)-2-methoxyphenyl]ethanone as synthesized in Production Example 71, by the operations similar to Example 123.

$^1$H-NMR (DMSO-d$_6$, δ): 1.2-1.4 (1H, m), 1.4-1.6 (2H, m), 1.6-1.9 (3H, m), 1.87 (2H, br d, J=13.1 Hz), 2.17 (2H, br d, J=12.7 Hz), 2.59 (3H, s), 3.4-3.6 (1H, m), 4.04 (3H, s), 7.56 (1H, s), 7.64 (1H, s), 7.78 (1H, s), 11.31 (1H, br s).

MS (m/z): 339 (M$^+$).

Example 134

Ethyl 7-chloro-1-cyclohexyl-4-oxo-4,5-dihydroimidazo[1,5-a]-quinoxaline-8-carboxyate

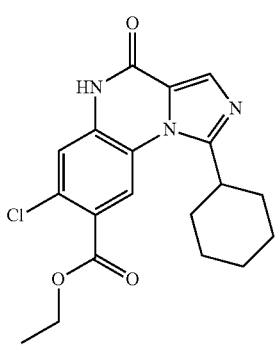 [SMILES: CCOC(=O)c1cc2c(cc1Cl)[nH]c(=O)c1cnc(C3CCCCC3)n12]

The title compound was obtained from ethyl 4-amino-2-chloro-5-(2-cyclohexyl-1H-imidazol-1-yl)benzoate as synthesized in Production Example 74, by the operations similar to Example 123.

$^1$H-NMR (DMSO-d$_6$, δ): 1.2-1.5 (1H, m), 1.37 (3H, t, J=7.1 Hz), 1.4-2.0 (7H, m), 2.10 (2H, br d, J=13.1 Hz), 3.2-3.4 (1H, m), 4.37 (2H, q, J=7.1 Hz), 7.41 (1H, s), 7.83 (1H, s), 8.45 (1H, s), 11.68 (1H, br s).

MS (m/z): 375 (M$^+$+2), 373 (M$^+$).

Example 135

7-Chloro-1-cyclohexyl-4-oxo-4,5-dihydroimidazo[1,5-a]-quinoxaline-8-carboxyic acid

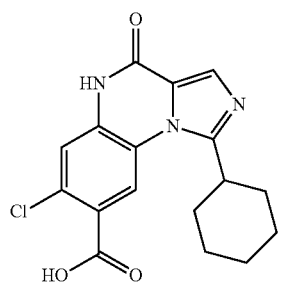 [SMILES: O=C(O)c1cc2c(cc1Cl)[nH]c(=O)c1cnc(C3CCCCC3)n12]

The title compound was obtained from ethyl 7-chloro-1-cyclohexyl-4-oxo-4,5-dihydroimidazo[1,5-a]quinoxaline-8-carboxyate as synthesized in above Example 134, by the operations similar to Example 58.

$^1$H-NMR (DMSO-d$_6$, δ): 1.2-1.4 (1H, m), 1.4-1.9 (5H, m), 1.86 (2H, br d, J=12.7 Hz), 2.10 (2H, br d, J=12.3 Hz), 3.2-3.5 (1H, m), 7.38 (1H, s), 7.81 (1H, s), 8.49 (1H, s), 11.61 (1H, br s).

MS (m/z): 347 (M$^+$+2), 345 (M$^+$).

Example 136

7-Chloro-1-cyclohexyl-N,N-dimethyl-4-oxo-4,5-dihydroimidazo-[1,5-a]quinoxaline-8-carboxamide

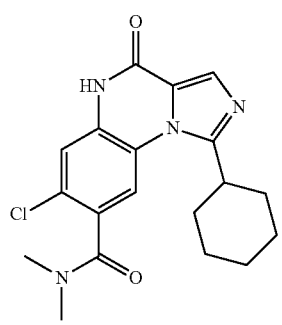 [SMILES: CN(C)C(=O)c1cc2c(cc1Cl)[nH]c(=O)c1cnc(C3CCCCC3)n12]

The title compound was obtained from 7-chloro-1-cyclohexyl-4-oxo-4,5-dihydroimidazo[1,5-a]quinoxaline-8-carboxyic acid as synthesized in above Example 135, by the operations similar to Example 59.

$^1$H-NMR (DMSO-d$_6$, δ): 1.2-1.4 (1H, m), 1.4-1.9 (7H, m), 2.06 (2H, br d, J=12.3 Hz), 2.86 (3H, s), 3.05 (3H, s), 3.3-3.5 (1H, m), 7.40 (1H, s), 7.79 (1H, s), 7.81 (1H, s), 11.53 (1H, br s).

MS (m/z): 374 (M$^+$+2), 372 (M$^+$).

Example 137

7-Chloro-1-cyclohexyl-N-(2-methoxyethyl)-N-methyl-4-oxo-4,5-dihydroimidazo[1,5-a]quinoxaline-8-carboxamide

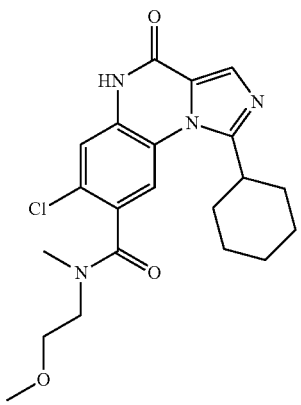 [SMILES: COCCN(C)C(=O)c1cc2c(cc1Cl)[nH]c(=O)c1cnc(C3CCCCC3)n12]

The title compound was obtained from 7-chloro-1-cyclohexyl-4-oxo-4,5-dihydroimidazo[1,5-a]quinoxaline-8-carboxyic acid as synthesized in above Example 135, by the operations similar to Example 59.

$^1$H-NMR (DMSO-$d_6$, δ): 1.2-1.9 (8H, m), 2.06 (2H, br d, J=11.6 Hz), 2.89 (1.7H, s), 3.05 (1.3H, s), 3.18 (1.3H, s), 3.32 (1.7H, s), 3.2-3.9 (5H, m), 7.3-7.5 (1H, m), 7.7-7.8 (1H, m), 7.81 (1H, s), 11.5-11.6 (1H, m).

MS (m/z): 418 (M$^+$+2), 416 (M$^+$).

Example 138

4-[(7-Chloro-1-cyclohexyl-4-oxo-4,5-dihydroimidazo[1,5-a]-quinoxalin-8-yl)carbonyl]morpholine

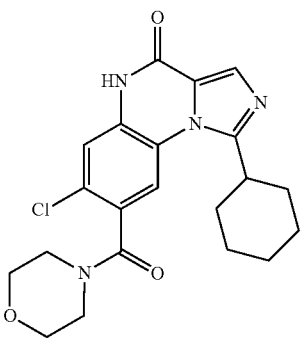 [SMILES: O=C(c1cc2c(cc1Cl)[nH]c(=O)c1cnc(C3CCCCC3)n12)N1CCOCC1]

The title compound was obtained from 7-chloro-1-cyclohexyl-4-oxo-4,5-dihydroimidazo[1,5-a]quinoxaline-8-carboxyic acid as synthesized in above Example 135, by the operations similar to Example 59.

$^1$H-NMR (DMSO-$d_6$, δ): 1.2-1.9 (8H, m), 2.07 (2H, br d, J=10.4 Hz), 3.2-3.8 (9H, m), 7.41 (1H, s), 7.79 (1H, s), 7.81 (1H, s), 11.54 (1H, br s).

MS (m/z): 416 (M$^+$+2), 414 (M$^+$).

Example 139

Ethyl 1-cyclohexyl-3-methyl-4-oxo-4,5-dihydroimidazo[1,5-a]-quinoxaline-8-carboxyate

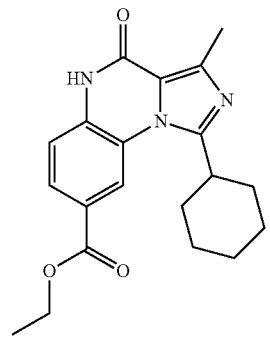 [SMILES: CCOC(=O)c1ccc2[nH]c(=O)c3c(C)nc(C4CCCCC4)n3c2c1]

The title compound was obtained from ethyl 4-amino-3-(2-cyclohexyl-4-methyl-1H-imidazol-1-yl)benzoate as synthesized in Production Example 76, by the operations similar to Example 123.

$^1$H-NMR (DMSO-$d_6$, δ): 1.2-1.4 (1H, m), 1.36 (3H, t, J=7.1 Hz), 1.4-1.6 (2H, m), 1.6-1.9 (3H, m), 1.89 (2H, br d, J=13.1 Hz), 2.09 (2H, br d, J=12.7 Hz), 2.54 (3H, s), 3.2-3.4 (1H, m), 4.35 (2H, q, J=7.2 Hz), 7.35 (1H, d, J=8.5 Hz), 7.89 (1H, dd, J=1.5, 8.5 Hz), 8.43 (1H, br s), 11.46 (1H, br s).

MS (m/z): 353 (M$^+$).

Example 140

1-Cyclohexyl-3-methyl-4-oxo-4,5-dihydroimidazo[1,5-a]-quinoxaline-8-carboxyic acid

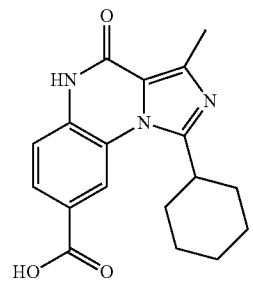 [SMILES: Cc1nc(C2CCCCC2)n2c1c(=O)[nH]c1ccc(C(=O)O)cc12]

The title compound was obtained from ethyl 1-cyclohexyl-3-methyl-4-oxo-4,5-dihydroimidazo[1,5-a]quinoxaline-8-carboxyate as synthesized in above Example 139, by the operations similar to Example 58.

$^1$H-NMR (DMSO-$d_6$, δ): 1.2-1.4 (1H, m), 1.4-1.6 (2H, m), 1.6-1.9 (3H, m), 1.87 (2H, br d, J=13.1 Hz), 2.09 (2H, br d, J=12.3 Hz), 2.54 (3H, s), 3.2-3.4 (1H, m), 7.34 (1H, d, J=8.5 Hz), 7.88 (1H, dd, J=1.5, 8.5 Hz), 8.45 (1H, br s), 11.43 (1H, br s), 13.04 (1H, br s).

MS (m/z): 325 (M$^+$).

Example 141

1-Cyclohexyl-N-(2-methoxyethyl)-N,3-dimethyl-4-oxo-4,5-dihydroimidazo[1,5-a]quinoxaline-8-carboxamide

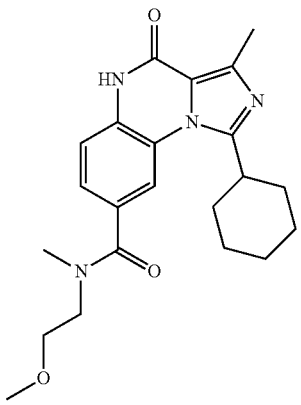 [SMILES: COCCN(C)C(=O)c1ccc2[nH]c(=O)c3c(C)nc(C4CCCCC4)n3c2c1]

The title compound was obtained from 1-cyclohexyl-3-methyl-4-oxo-4,5-dihydroimidazo[1,5-a]quinoxaline-8-carboxyic acid as synthesized in above Example 140, by the operations similar to Example 59.

$^1$H-NMR (DMSO-$d_6$, δ): 1.2-1.6 (3H, m), 1.6-1.9 (3H, m), 1.85 (2H, br d, J=12.7 Hz), 2.06 (2H, br d, J=12.7 Hz), 2.54 (3H, s), 3.03 (3H, s), 3.1-3.4 (4H, m), 3.4-3.8 (4H, m), 7.31 (1H, d, J=8.5 Hz), 7.41 (1H, dd, J=1.2, 8.1 Hz), 7.81 (1H, br s), 11.28 (1H, br s).

MS (m/z): 396 (M$^+$).

Example 142

1-Cyclohexyl-N,O-dimethyl-4-oxo-4,5-dihydroimidazo[1,5-a]-quinoxaline-8-hydroxamic acid

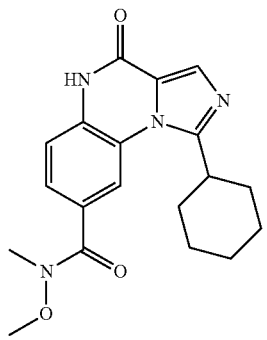

1-Cyclohexyl-4-oxo-4,5-dihydroimidazo[1,5-a]quinoxaline-8-carboxyic acid as synthesized in Example 103, 6.23 g, N,O-dimethylhydroxyamine hydrochloride 2.15 g, 1-(3-dimethylaminopropyl)-3-ethylcarbodiimide hydrochloride 5.75 g, 1-hydroxybenzotriazole monohydrate 3.97 g, acetonitrile 51 mL and N,N-diisopropylethylamine 7.3 mL were mixed and stirred for 24 hours. The reaction liquid was poured in saturated aqueous sodium hydrogencarbonate solution and extracted with tetrahydrofuran and ethyl acetate. The organic layer was washed twice with saturated brine and dried over magnesium sulfate. After distilling the solvent off, the residue was heat-suspended in 200 mL of acetone and purified, to provide 3.36 g of the title compound.

$^1$H-NMR (DMSO-$d_6$, δ): 1.2-1.4 (1H, m), 1.4-1.6 (2H, m), 1.6-2.0 (5H, m), 2.0-2.2 (2H, m), 3.2-3.5 (1H, m), 3.33 (3H, s), 3.58 (3H, s), 7.38 (1H, d, J=8.5 Hz), 7.74 (1H, dd, J=1.5, 8.5 Hz), 7.81 (1H, s), 8.36 (1H, d, J=1.5 Hz), 11.58 (1H, br s).

MS (m/z): 354 (M$^+$).

Example 143

8-Acetyl-1-cyclohexylimidazo[1,5-a]quinoxalin-4(5H)-one

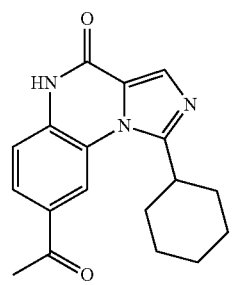 [SMILES: CC(=O)c1ccc2[nH]c(=O)c3cnc(C4CCCCC4)n3c2c1]

To a suspension of 354 mg of 1-cyclohexyl-N,O-dimethyl-4-oxo-4,5-dihydroimidazo[1,5-a]quinoxaline-8-hydroxamic acid as synthesized in above Example 142 in 10 mL of tetrahydrofuran, 1.33 mL of 3M methylmagnesium bromide/tetrahydrofuran solution was added, followed by 3.7 hours' stirring under nitrogen atmosphere and addition of 30 mL of water. The organic layer extracted with ethyl acetate-tetrahydrofuran mixed solvent was washed with water, dried over magnesium sulfate and the solvent therein was distilled off. The crude product was heat-suspended in 10 mL of methanol and purified, to provide 106 mg of the title compound.

$^1$H-NMR (DMSO-$d_6$, δ): 1.2-1.5 (1H, m), 1.4-2.0 (7H, m), 2.13 (2H, br d, J=12.3 Hz), 2.64 (3H, s), 3.3-3.5 (1H, m), 7.41 (1H, d, J=8.5 Hz), 7.82 (1H, s), 8.00 (1H, dd, J=1.5, 8.5 Hz), 8.47 (1H, d, J=1.5 Hz), 11.67 (1H, br s).

MS (m/z): 309 (M$^+$).

Example 144

1-Cyclohexyl-4-oxo-4,5-dihydroimidazo[1,5-a]quinoxaline-7-carbonitrile

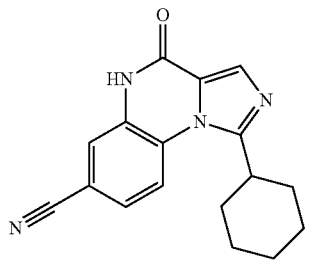 [SMILES: N#Cc1ccc2c(c1)[nH]c(=O)c1cnc(C3CCCCC3)n12]

The title compound was obtained from 3-amino-4-(2-cyclohexyl-1H-imidazol-1-yl)benzonitrile as synthesized in Production Example 78, by the operations similar to Example 4.

$^1$H-NMR (DMSO-$d_6$, δ): 1.2-1.4 (1H, m), 1.5-1.9 (7H, m), 2.0-2.1 (2H, m), 3.3-3.5 (1H, m), 7.64 (1H, d, J=1.9 Hz), 7.72 (1H, dd, J=1.9, 8.9 Hz), 7.83 (1H, s), 8.08 (1H, d, J=8.9 Hz), 11.59 (1H, s).

MS (m/z): 291 (M$^+$−1).

Example 145

7-Bromo-1-cyclohexylimidazo[1,5-a]quinoxalin-4(5H)-one

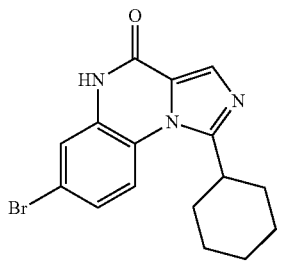 [SMILES: O=c1[nH]c2cc(Br)ccc2n2c(C3CCCCC3)ncc12]

The title compound was obtained from 5-bromo-2-(2-cyclohexyl-1H-imidazol-1-yl)aniline as synthesized in Production Example 80, by the operations similar to Example 4.

¹H-NMR (DMSO-d$_6$, δ): 1.2-1.4 (1H, m), 1.4-1.9 (7H, m), 2.05 (2H, br d, J=12.3 Hz), 3.39 (1H, tt, J=3.1, 10.8 Hz), 7.45 (1H, dd, J=2.3, 8.9 Hz), 7.49 (1H, d, J=2.3 Hz), 7.79 (1H, s), 7.87 (1H, d, J=8.9 Hz), 11.41 (1H, s).

MS (m/z): 346 (M$^+$+1), 344 (M$^+$−1).

Example 146

1-Cyclohexyl-7-(pyrazol-1-yl)imidazo[1,5-a]quinoxalin-4(5H)-one

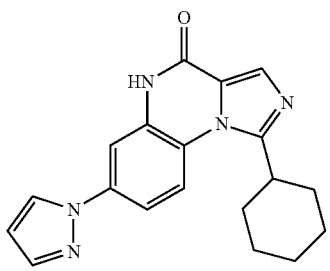 [SMILES: O=c1[nH]c2cc(-n3cccn3)ccc2n2c(C3CCCCC3)ncc12]

7-Bromo-1-cyclohexylimidazo[1,5-a]quinoxalin-4(5H)-one as synthesized in above Example 145, 200 mg, pyrazole 59 mg, potassium carbonate 120 mg, copper iodide 28 mg and N,N-dimethylformamide 4 mL were mixed and stirred for 22 hours at 160° C. The reaction liquid was poured into water, and the precipitated matter was recovered by filtration. The precipitate was mixed with 25% aqueous ammonia and methanol, and heated under stirring. The insoluble matter was recovered by filtration, washed with water and dried by heating under reduced pressure to provide 30 mg of the title compound.

¹H-NMR (DMSO-d$_6$, δ): 1.2-1.4 (1H, m), 1.4-1.9 (7H, m), 2.10 (2H, br d, J=12.0 Hz), 3.46 (1H, tt, J=3.1, 11.0 Hz), 6.60 (1H, t, J=1.9 Hz), 7.73 (1H, dd, J=2.7, 9.2 Hz), 7.79 (1H, s), 7.80 (1H, d, J=1.6 Hz), 7.87 (1H, d, J=2.7 Hz), 8.01 (1H, d, J=9.2 Hz), 8.51 (1H, d, J=2.7 Hz), 11.48 (1H, s).

MS (m/z): 333 (M$^+$).

Example 147

1-Cyclohexyl-7-(3,5-dimethylpyrazol-1-yl)imidazo[1,5-a]-quinoxalin-4(5H)-one

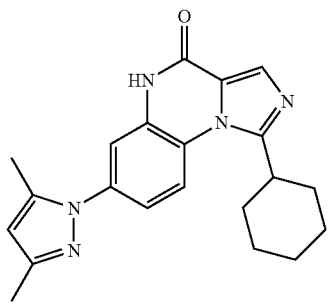 [SMILES: Cc1cc(C)n(-c2ccc3c(c2)[nH]c(=O)c2cnc(C4CCCCC4)n23)n1]

The title compound was obtained from 7-bromo-1-cyclohexylimidazo[1,5-a]quinoxalin-4(5H)-one as synthesized in Example 145, by the operations similar to Example 146.

¹H-NMR (DMSO-d$_6$, δ): 1.2-1.4 (1H, m), 1.4-1.9 (7H, m), 2.0-2.2 (2H, m), 2.20 (3H, s), 2.38 (3H, s), 3.3-3.5 (1H, m), 6.13 (1H, s), 7.45 (1H, dd, J=2.3, 8.9 Hz), 7.53 (1H, d, J=2.3 Hz), 7.80 (1H, s), 8.01 (1H, d, J=9.2 Hz), 11.39 (1H, s).

MS (m/z): 361 (M$^+$).

Example 148

8-Chloro-1-cyclohexyl-N-methyl-4-oxo-N-phenethyl-4,5-dihydroimidazo[1,5-a]quinoxaline-7-carboxamide

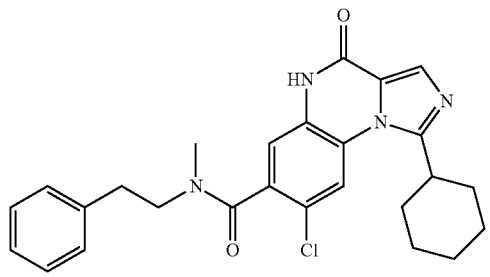 [SMILES: CN(CCc1ccccc1)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in Example 84, by the operations similar to Example 59.

¹H-NMR (DMSO-d$_6$, δ): 1.2-1.4 (1H, m), 1.4-1.9 (7H, m), 2.0-2.2 (2H, m), 2.75 (1.5H, s), 2.7-3.0 (2H, m), 3.04 (1.5H, s), 3.3-3.5 (2H, m), 3.6-3.8 (1H, m), 6.96 (0.5H, s), 7.0-7.1 (1H, m), 7.1-7.4 (4.5H, m), 7.81 (1H, d, J=3.1 Hz), 7.87 (1H, d, J=2.0 Hz), 11.43 (0.5H, s), 11.57 (0.5H, s).

MS (m/z): 462 (M$^+$).

Example 149

8-Chloro-N,1-dicyclohexyl-N-methyl-4-oxo-4,5-dihydroimidazo-[1,5-a]quinoxaline-7-carboxamide

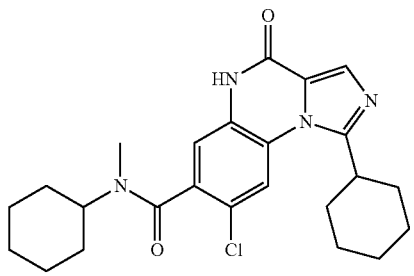 [SMILES: CN(C(=O)c1cc2[nH]c(=O)c3cnc(C4CCCCC4)n3c2cc1Cl)C1CCCCC1]

The title compound was obtained from 8-chloro-1-cyclohexyl-4-oxo-4,5-dihydroimidazo[1,5-a]quinoxaline-7-carboxyic acid as synthesized in Example 84, by the operations similar to Example 59.

$^1$H-NMR (DMSO-d$_6$, δ): 0.9-2.2 (20H, m), 2.69 (1.5H, s), 2.92 (1.5H, s), 3.3-3.5 (1H, m), 4.3-4.5 (1H, m), 7.20 (1H, s), 7.81 (0.5H, s), 7.82 (0.5H, s), 7.88 (0.5H, s), 7.90 (0.5H, s), 11.49 (1H, s).

MS (m/z): 440 (M$^+$).

Example 150

8-Chloro-1-cyclohexyl-N-methyl-4-oxo-N-[2-(2-pyridyl)ethyl]-4,5-dihydroimidazo[1,5-a]quinoxaline-7-carboxamide

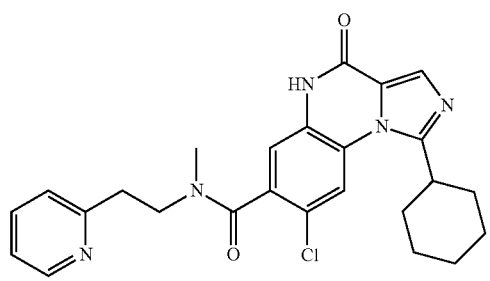 [SMILES: CN(CCc1ccccn1)C(=O)c1cc2[nH]c(=O)c3cnc(C4CCCCC4)n3c2cc1Cl]

The title compound was obtained from 8-chloro-1-cyclohexyl-4-oxo-4,5-dihydroimidazo[1,5-a]quinoxaline-7-carboxyic acid as synthesized in Example 84, by the operations similar to Example 59.

$^1$H-NMR (DMSO-d$_6$, δ): 1.2-1.4 (1H, m), 1.4-2.0 (7H, m), 2.08 (2H, br d, J=12.8 Hz), 2.76 (1.5H, s), 2.96 (1H, t, J=7.3 Hz), 3.02 (1.5H, s), 3.08 (1H, t, J=7.3 Hz), 3.3-3.5 (1H, m), 3.55 (1H, t, J=7.1 Hz), 3.86 (1H, br s), 6.95 (0.5H, s), 7.1-7.3 (2H, m), 7.36 (0.5H, d, J=7.7 Hz), 7.66 (0.5H, dt, J=1.9, 7.7 Hz), 7.75 (0.5H, dt, J=1.9, 7.7 Hz), 7.81 (1H, d, J=2.7 Hz), 7.86 (1H, d, J=1.9 Hz), 8.3-8.4 (0.5H, m), 8.5-8.6 (0.5H, m), 11.47 (0.5H, s), 11.58 (0.5H, s).

MS (m/z): 463 (M$^+$).

Example 151

1-[(1-Cyclohexyl-4-oxo-4,5-dihydroimidazo[1,5-a]quinoxalin-7-yl)carbonyl]-3,5-dimethylpyrazole

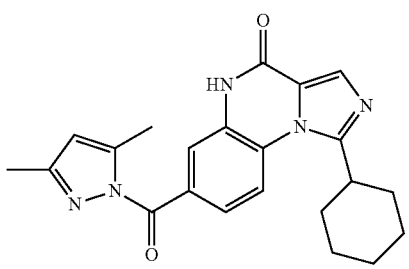 [SMILES: Cc1cc(C)n(C(=O)c2ccc3c(c2)[nH]c(=O)c2cnc(C4CCCCC4)n23)n1]

The title compound was obtained from 1-cyclohexyl-4-oxo-4,5-dihydroimidazo[1,5-a]quinoxaline-7-carboxyic acid as synthesized in Example 58, by the operations similar to Example 33.

$^1$H-NMR (DMSO-d$_6$, δ): 1.2-1.4 (1H, m), 1.5-1.9 (7H, m), 2.09 (2H, br d, J=12.3 Hz), 2.20 (3H, s), 2.58 (3H, s), 3.4-3.6 (1H, m), 6.33 (1H, s), 7.82 (1H, s), 7.84 (1H, dd, J=1.9, 8.9 Hz), 7.94 (1H, d, J=1.9 Hz), 8.07 (1H, d, J=8.9 Hz), 11.51 (1H, s).

MS (m/z): 388 (M$^+$-1).

Example 152

1-Cyclohexyl-7-(3-methyl-[1,2,4]-oxadiazol-5-yl)imidazo-[1,5-a]quinoxalin-4 (5H)-one

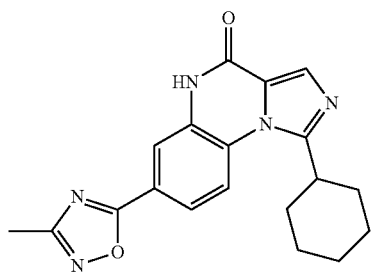 [SMILES: Cc1noc(-c2ccc3c(c2)[nH]c(=O)c2cnc(C4CCCCC4)n23)n1]

1-Cyclohexyl-4-oxo-4,5-dihydroimidazo[1,5-a]quinoxaline-7-carboxyic acid as synthesized in Example 58, 300 mg, N,N-dimethylacetamide 5 mL and 1,1'-carbonyldiimidazole 266 mg were mixed and stirred for 30 minutes at room temperature. To the reaction liquid 143 mg of N-hydroxyacetamidine was added, followed by 12 hours' stirring at 110° C. After returning it to the room temperature, water was added thereto and the precipitated matter was recovered by filtration. Drying the precipitate by heating under reduced pressure, 210 mg of the title compound was obtained.

$^1$H-NMR (DMSO-d$_6$, δ): 1.2-1.4 (1H, m), 1.5-1.9 (7H, m), 2.09 (2H, br d, J=13.0 Hz), 2.43 (3H, s), 3.4-3.6 (1H, m), 7.81 (1H, s), 7.94 (1H, dd, J=1.5, 8.9 Hz), 8.00 (1H, d, J=1.9 Hz), 8.11 (1H, d, J=8.9 Hz), 11.58 (1H, s).

MS (m/z): 348 (M$^+$-1).

Example 153

8-Chloro-1-cyclohexyl-7-(3-methyl-[1,2,4]-oxadiazol-5-yl)-imidazo[1,5-a]quinoxalin-4 (5H)-one

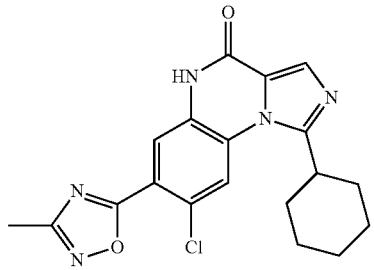

The title compound was obtained from 8-chloro-1-cyclohexyl-4-oxo-4,5-dihydroimidazo[1,5-a]quinoxaline-7-carboxyic acid as synthesized in Example 84, by the operations similar to Example 152.

$^1$H-NMR (DMSO-$d_6$, δ): 1.2-1.4 (1H, m), 1.5-2.0 (7H, m), 2.11 (2H, br d, J=12.0 Hz), 2.47 (3H, s), 3.4-3.5 (1H, m), 7.83 (1H, s), 8.02 (1H, s), 8.05 (1H, s), 11.65 (1H, s).

MS (m/z): 383 (M$^+$).

Example 154

Methyl (E)-3-(1-cyclohexyl-4-oxo-4,5-dihydroimidazo[1,5-a]-quinoxalin-8-yl)acrylate

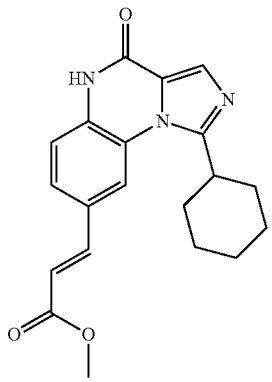 [SMILES: COC(=O)/C=C/c1ccc2[nH]c(=O)c3cnc(C4CCCCC4)n3c2c1]

The title compound was obtained from methyl (E)-3-[4-amino-3-(2-cyclohexy-1H-imidazol-1-yl)phenyl]acrylate as synthesized in Production Example 82, by the operations similar to Example 123.

$^1$H-NMR (DMSO-$d_6$, δ): 1.2-1.4 (1H, m), 1.5-2.0 (7H, m), 2.0-2.2 (2H, m), 3.5-3.7 (1H, m), 3.78 (3H, s), 6.59 (1H, d, J=15.8 Hz), 7.35 (1H, d, J=8.5 Hz), 7.7-7.9 (3H, m), 8.11 (1H, s), 11.56 (1H, s).

MS (m/z): 351 (M$^+$).

Example 155

(E)-3-(1-cyclohexyl-4-oxo-4,5-dihydroimidazo[1,5-a]quinoxalin-8-yl)acrylic acid

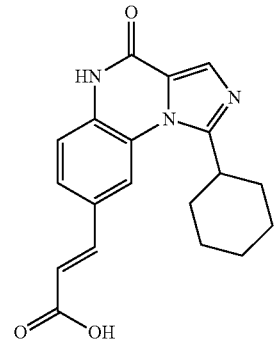 [SMILES: O=C(O)/C=C/c1ccc2[nH]c(=O)c3cnc(C4CCCCC4)n3c2c1]

The title compound was obtained from methyl (E)-3-(1-cyclohexyl-4-oxo-4,5-dihydroimidazo[1,5-a]quinoxalin-8-yl)-acrylate as synthesized in above Example 154, by the operations similar to Example 58.

$^1$H-NMR (DMSO-$d_6$, δ): 1.2-1.4 (1H, m), 1.5-1.9 (7H, m), 2.0-2.2 (2H, m), 3.5-3.7 (1H, m), 6.48 (1H, d, J=15.8 Hz), 7.35 (1H, d, J=8.5 Hz), 7.70 (1H, d, J=15.8 Hz), 7.75 (1H, d, J=8.5 Hz), 7.79 (1H, s), 8.08 (1H, s), 11.54 (1H, s), 12.45 (1H, s).

MS (m/z): 337 (M$^+$).

Example 156

(E)-3-(1-cyclohexyl-4-oxo-4,5-dihydroimidazo[1,5-a]quinoxalin-8-yl)-N,N-dimethylacrylamide

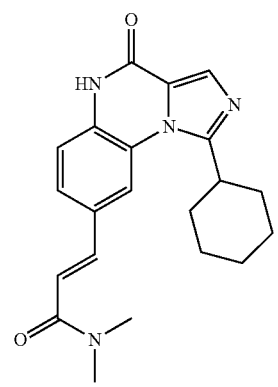 [SMILES: CN(C)C(=O)/C=C/c1ccc2[nH]c(=O)c3cnc(C4CCCCC4)n3c2c1]

The title compound was obtained from (E)-3-(1-cyclohexyl-4-oxo-4,5-dihydroimidazo[1,5-a]quinoxalin-8-yl) acrylic acid as synthesized in above Example 155, by the operations similar to Example 33.

$^1$H-NMR (DMSO-$d_6$, δ): 1.2-1.4 (1H, m), 1.4-2.0 (7H, m), 2.0-2.2 (2H, m), 2.95 (3H, s), 3.18 (3H, s), 3.5-3.7 (1H, m), 7.15 (1H, d, J=15.0 Hz), 7.34 (1H, d, J=8.5 Hz), 7.58 (1H, d, J=15.4 Hz), 7.7-7.8 (2H, m), 8.07 (1H, s), 11.48 (1H, s).

MS (m/z): 364 (M$^+$).

Example 157

(E)-3-(1-cyclohexyl-4-oxo-4,5-dihydroimidazo[1,5-a]quinoxalin-8-yl)-N-methylacrylamide

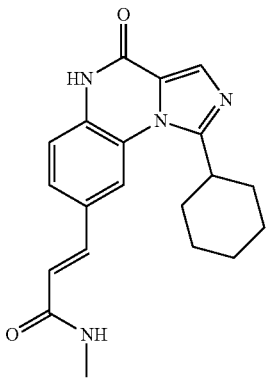 [SMILES: CNC(=O)/C=C/c1ccc2[nH]c(=O)c3cnc(C4CCCCC4)n3c2c1]

The title compound was obtained from (E)-3-(1-cyclohexyl-4-oxo-4,5-dihydroimidazo[1,5-a]quinoxalin-8-yl)acrylic acid as synthesized in above Example 155, by the operations similar to Example 33.

$^1$H-NMR (DMSO-d$_6$, δ): 1.2-1.4 (1H, m), 1.4-2.0 (7H, m), 2.0-2.2 (2H, m), 2.73 (3H, d, J=4.6 Hz), 3.5-3.7 (1H, m), 6.57 (1H, d, J=15.8 Hz), 7.35 (1H, d, J=8.5 Hz), 7.52 (1H, d, J=15.8 Hz), 7.61 (1H, dd, J=1.2, 8.5 Hz), 7.79 (1H, s), 8.01 (1H, br s), 8.09 (1H, q, J=4.4 Hz), 11.50 (1H, s).

MS (m/z): 350 (M$^+$).

Example 158

Methyl 3-(1-cyclohexyl-4-oxo-4,5-dihydroimidazo[1,5-a]-quinoxalin-8-yl)propanoate

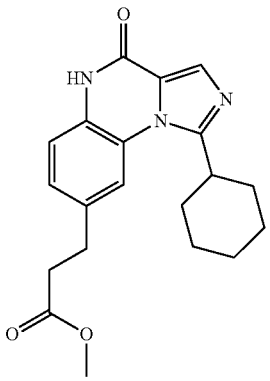 [SMILES: COC(=O)CCc1ccc2[nH]c(=O)c3cnc(C4CCCCC4)n3c2c1]

Methyl (E)-3-(1-cyclohexyl-4-oxo-4,5-dihydroimidazo-[1,5-a]quinoxalin-8-yl)acrylate as synthesized in Example 154, 2.0 g was dissolved in 100 mL of acetic acid, and to the solution 10% Pd/C 200 mg was added in nitrogen atmosphere. After substituting the atmosphere with hydrogen, the reaction liquid was stirred at 25° C. for 2 days. The reaction liquid was filtered through Celite and from the filtrate the solvent was distilled off to provide 1.48 g of the title compound.

$^1$H-NMR (DMSO-d$_6$, δ): 1.2-1.4 (1H, m), 1.5-1.9 (7H, m), 2.0-2.2 (2H, m), 2.71 (2H, t, J=7.3 Hz), 2.96 (2H, t, J=7.3 Hz), 3.4-3.6 (1H, m), 3.58 (3H, s), 7.25 (2H, s), 7.75 (1H, s), 7.77 (1H, s), 11.29 (1H, s).

MS (m/z): 353 (M$^+$).

Example 159

3-(1-Cyclohexyl-4-oxo-4,5-dihydroimidazo[1,5-a]quinoxalin-8-yl)propanoic acid

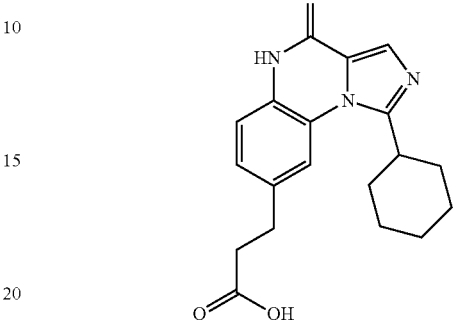

The title compound was obtained from methyl 3-(1-cyclohexyl-4-oxo-4,5-dihydroimidazo[1,5-a]quinoxalin-8-yl)propanoate as synthesized in above Example 158, by the operations similar to Example 58.

$^1$H-NMR (DMSO-d$_6$, δ): 1.2-1.4 (1H, m), 1.4-2.0 (7H, m), 2.0-2.2 (2H, m), 2.61 (2H, t, J=7.3 Hz), 2.93 (2H, t, J=7.3 Hz), 3.3-3.6 (1H, m), 7.25 (2H, s), 7.75 (1H, s), 7.78 (1H, s), 11.28 (1H, s), 12.17 (1H, s).

MS (m/z): 339 (M$^+$).

Example 160

3-(1-Cyclohexyl-4-oxo-4,5-dihydroimidazo[1,5-a]quinoxalin-8-yl)-N,N-dimethylpropionamide

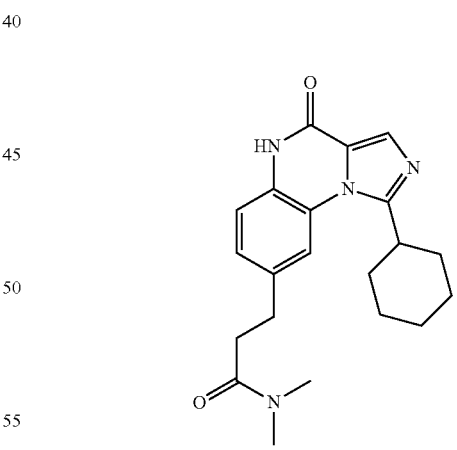

The title compound was obtained from 3-(1-cyclohexyl-4-oxo-4,5-dihydroimidazo[1,5-a]quinoxalin-8-yl)propanoic acid as synthesized in above Example 159, by the operations similar to Example 33.

$^1$H-NMR (DMSO-d$_6$, δ): 1.2-1.4 (1H, m), 1.4-2.0 (7H, m), 2.0-2.2 (2H, m), 2.66 (2H, t, J=7.3 Hz), 2.82 (3H, s), 2.92 (2H, t, J=7.3 Hz), 2.93 (3H, s), 3.4-3.6 (1H, m), 7.25 (2H, s), 7.75 (1H, s), 7.83 (1H, s), 11.26 (1H, s).

MS (m/z): 366 (M$^+$).

Example 161

1-[3-(1-Cyclohexyl-4-oxo-4,5-dihydroimidazo[1,5-a]quinoxalin-8-yl)propanoyl]-4-methylpiperazine

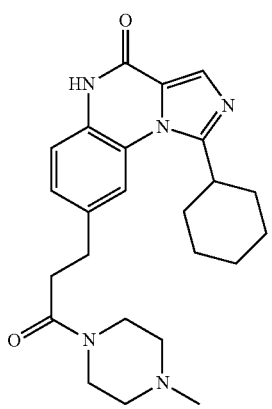 [SMILES: CN1CCN(C(=O)CCc2ccc3[nH]c(=O)c4cnc(C5CCCCC5)n4c3c2)CC1]

The title compound was obtained from 3-(1-cyclohexyl-4-oxo-4,5-dihydroimidazo[1,5-a]quinoxalin-8-yl)propanoic acid as synthesized in above Example 159, by the operations similar to Example 33.

$^1$H-NMR (DMSO-$d_6$, δ): 1.2-1.4 (1H, m), 1.4-2.0 (7H, m), 2.0-2.2 (9H, m), 2.67 (2H, t, J=7.3 Hz), 2.93 (2H, t, J=7.3 Hz), 3.3-3.6 (5H, m), 7.25 (2H, s), 7.75 (1H, s), 7.80 (1H, s), 11.26 (1H, s).

MS (m/z): 421 (M$^+$).

Example 162

Methyl 1-cyclopentyl-4-oxo-4,5-dihydroimidazo[1,5-a]-quinoxaline-8-carboxyate

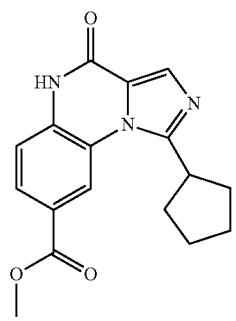 [SMILES: COC(=O)c1ccc2[nH]c(=O)c3cnc(C4CCCC4)n3c2c1]

The title compound was obtained from methyl 4-amino-3-(2-cyclopentyl-1H-imidazol-1-yl)benzoate as synthesized in Production Example 84, by the operations similar to Example 123.

$^1$H-NMR (DMSO-$d_6$, δ): 1.6-1.9 (4H, m), 2.0-2.3 (4H, m), 3.84 (1H, quin, J=7.0 Hz), 3.89 (3H, s), 7.40 (1H, d, J=8.5 Hz), 7.80 (1H, s), 7.92 (1H, dd, J=1.5, 8.5 Hz), 8.64 (1H, d, J=1.6 Hz), 11.69 (1H, s).

MS (m/z): 310 (M$^+$−1).

Example 163

1-Cyclopentyl-4-oxo-4,5-dihydroimidazo[1,5-a]quinoxaline-8-carboxyic acid

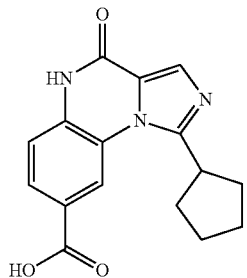 [SMILES: O=C(O)c1ccc2[nH]c(=O)c3cnc(C4CCCC4)n3c2c1]

The title compound was obtained from methyl 1-cyclopentyl-4-oxo-4,5-dihydroimidazo[1,5-a]quinooxaline-8-carboxyate as synthesized in above Example 162, by the operations similar to Example 58.

$^1$H-NMR (DMSO-$d_6$, δ): 1.6-1.9 (4H, m), 2.0-2.3 (4H, m), 3.88 (1H, quin, J=7.2 Hz), 7.40 (1H, d, J=8.1 Hz), 7.80 (1H, s), 7.93 (1H, dd, J=1.6, 8.5 Hz), 8.67 (1H, d, J=1.2 Hz), 11.66 (1H, s), 13.10 (1H, s).

MS (m/z): 296 (M$^+$−1).

Example 164

1-Cyclopentyl-N-(2-methoxyethyl)-4-oxo-4,5-dihydroimidazo-[1,5-a]quinoxaline-8-carboxamide

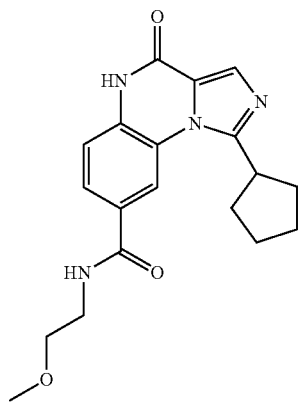 [SMILES: COCCNC(=O)c1ccc2[nH]c(=O)c3cnc(C4CCCC4)n3c2c1]

The title compound was obtained from 1-cyclopentyl-4-oxo-4,5-dihydroimidazo[1,5-a]quinoxaline-8-carboxyic acid as synthesized in above Example 163, by the operations similar to Example 33.

$^1$H-NMR (DMSO-$d_6$, δ): 1.6-1.9 (4H, m), 2.0-2.3 (4H, m), 3.29 (3H, s), 3.4-3.6 (4H, m), 3.98 (1H, quin, J=7.7 Hz), 7.35 (1H, d, J=8.1 Hz), 7.79 (1H, s), 7.87 (1H, dd, J=1.6, 8.5 Hz), 8.58 (1H, d, J=1.1 Hz), 8.63 (1H, br t, J=5.0 Hz), 11.55 (1H, s).

MS (m/z): 354 (M$^+$).

Example 165

1-Cyclopentyl-N-methyl-4-oxo-4,5-dihydroimidazo[1,5-a]-quinoxaline-8-carboxamide

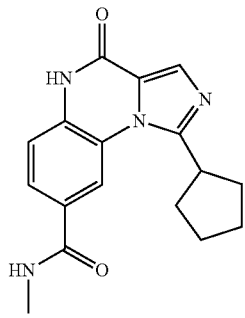 [SMILES: CNC(=O)c1ccc2[nH]c(=O)c3cnc(C4CCCC4)n3c2c1]

The title compound was obtained from 1-cyclopentyl-4-oxo-4,5-dihydroimidazo[1,5-a]quinoxaline-8-carboxyic acid as synthesized in Example 163, by the operations similar to Example 33.

$^1$H-NMR (DMSO-d$_6$, δ): 1.6-1.9 (4H, m), 2.0-2.3 (4H, m), 2.83 (3H, d, J=4.6 Hz), 3.96 (1H, quin, J=7.7 Hz), 7.35 (1H, d, J=8.5 Hz), 7.79 (1H, s), 7.84 (1H, dd, J=1.6, 8.5 Hz), 8.53 (1H, q, J=4.2 Hz), 8.58 (1H, d, J=1.2 Hz), 11.55 (1H, s).

MS (m/z): 310 (M$^+$).

Example 166

1-Cyclopentyl-N-(2-methoxyethyl)-N-methyl-4-oxo-4,5-dihydroimidazo[1,5-a]quinoxaline-8-carboxamide

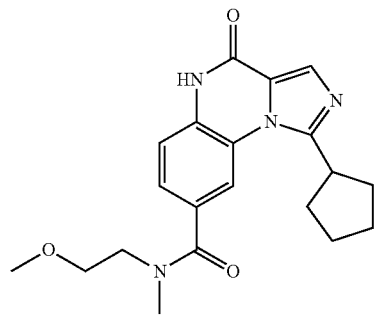 [SMILES: COCCN(C)C(=O)c1ccc2[nH]c(=O)c3cnc(C4CCCC4)n3c2c1]

The title compound was obtained from 1-cyclopentyl-4-oxo-4,5-dihydroimidazo[1,5-a]quinoxaline-8-carboxyic acid as synthesized in Example 163, by the operations similar to Example 33.

$^1$H-NMR (DMSO-d$_6$, δ): 1.6-1.9 (4H, m), 2.0-2.2 (4H, m), 3.02 (3H, s), 3.1-3.4 (5H, m), 3.4-3.8 (2H, m), 3.87 (1H, quin, J=6.9 Hz), 7.36 (1H, d, J=8.5 Hz), 7.43 (1H, dd, J=1.2, 8.1 Hz), 7.78 (1H, s), 8.05 (1H, d, J=1.2 Hz), 11.50 (1H, s).

MS (m/z): 368 (M$^+$).

Example 167

1-Cyclopentyl-N,N-dimethyl-4-oxo-4,5-dihydroimidazo[1,5-a]-quinoxaline-8-carboxamide

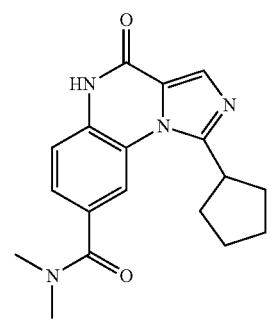 [SMILES: CN(C)C(=O)c1ccc2[nH]c(=O)c3cnc(C4CCCC4)n3c2c1]

The title compound was obtained from 1-cyclopentyl-4-oxo-4,5-dihydroimidazo[1,5-a]quinoxaline-8-carboxyic acid as synthesized in Example 163, by the operations similar to Example 33.

$^1$H-NMR (DMSO-d$_6$, δ): 1.6-1.9 (4H, m), 2.0-2.2 (4H, m), 3.01 (6H, s), 3.91 (1H, quin, J=7.1 Hz), 7.36 (1H, d, J=8.5 Hz), 7.46 (1H, dd, J=1.5, 8.5 Hz), 7.78 (1H, s), 8.10 (1H, br s), 11.51 (1H, s).

MS (m/z): 324 (M$^+$).

Example 168

1-[(1-Cyclopentyl-4-oxo-4,5-dihydroimidazo[1,5-a]quinoxalin-8-yl)carbonyl]-4-(2-hydroxyethyl)piperidine

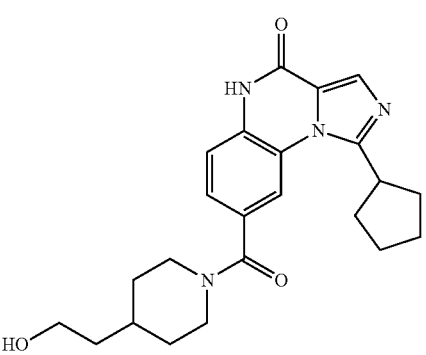 [SMILES: O=C(c1ccc2[nH]c(=O)c3cnc(C4CCCC4)n3c2c1)N1CCC(CCO)CC1]

The title compound was obtained from 1-cyclopentyl-4-oxo-4,5-dihydroimidazo[1,5-a]quinoxaline-8-carboxyic acid as synthesized in Example 163, by the operations similar to Example 33.

$^1$H-NMR (DMSO-d$_6$, δ): 1.0-1.2 (2H, m), 1.3-1.5 (2H, m), 1.6-1.9 (8H, m), 2.0-2.2 (4H, m), 2.8-3.1 (3H, m), 3.46 (2H, q, J=6.0 Hz), 3.88 (1H, quin, J=7.3 Hz), 4.37 (1H, t, J=5.4 Hz), 7.37 (1H, d, J=8.5 Hz), 7.42 (1H, dd, J=1.2, 8.5 Hz), 7.78 (1H, s), 8.04 (1H, d, J=1.2 Hz), 11.42 (1H, s).

MS (m/z): 407 (M$^+$–1).

Example 169

1-[(1-Cyclopentyl-4-oxo-4,5-dihydroimidazo[1,5-a]quinoxalin-8-yl)carbonyl]-3,5-dimethylpyrazole

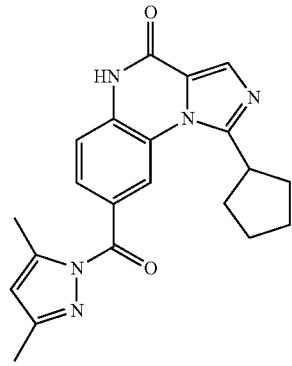 [SMILES: Cc1cc(C)n(C(=O)c2ccc3[nH]c(=O)c4cnc(C5CCCC5)n4c3c2)n1]

The title compound was obtained from 1-cyclopentyl-4-oxo-4,5-dihydroimidazo[1,5-a]quinoxaline-8-carboxyic acid as synthesized in Example 163, by the operations similar to Example 33.

$^1$H-NMR (DMSO-$d_6$, δ): 1.5-1.7 (2H, m), 1.7-1.9 (2H, m), 2.0-2.2 (4H, m), 2.20 (3H, s), 2.58 (3H, s), 3.83 (1H, quin, J=7.3 Hz), 6.32 (1H, s), 7.43 (1H, d, J=8.5 Hz), 7.81 (1H, s), 7.98 (1H, dd, J=1.6, 8.5 Hz), 8.87 (1H, d, J=1.6 Hz), 11.69 (1H, s).

MS (m/z): 375 (M$^+$).

Example 170

Ethyl 4-oxo-1-(1-propylbutyl)-4,5-dihydroimidazo[1,5-a]-quinoxaline-8-carboxyate

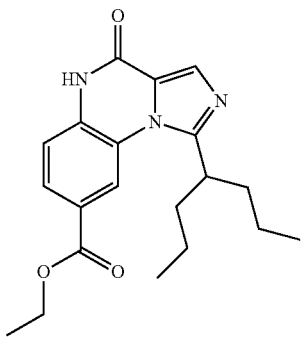 [SMILES: CCCC(CCC)c1ncc2c(=O)[nH]c3ccc(C(=O)OCC)cc3n12]

The title compound was obtained from ethyl 4-amino-3-[2-(1-propylbutyl)-1H-imidazol-1-yl]benzoate as synthesized in Production Example 87, by the operations similar to Example 123.

$^1$H-NMR (DMSO-$d_6$, δ): 0.87 (6H, t, J=7.3 Hz), 1.2-1.5 (4H, m), 1.35 (3H, t, J=6.9 Hz), 1.6-1.8 (2H, m), 1.9-2.1 (2H, m), 3.4-3.6 (1H, m), 4.36 (2H, q, J=7.1 Hz), 7.43 (1H, d, J=8.5 Hz), 7.87 (1H, s), 7.95 (1H, dd, J=1.5, 8.5 Hz), 8.56 (1H, d, J=1.2 Hz), 11.70 (1H, br s).

MS (m/z): 355 (M$^+$).

Example 171

4-Oxo-1-(1-propylbutyl)-4,5-dihydroimidazo[1,5-a]quinoxaline-8-carboxyic acid

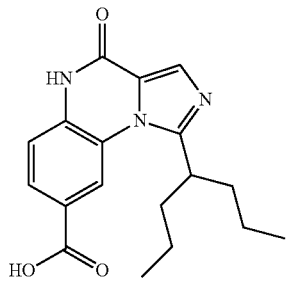 [SMILES: CCCC(CCC)c1ncc2c(=O)[nH]c3ccc(C(=O)O)cc3n12]

The title compound was synthesized from ethyl 4-oxo-1-(1-propylbutyl)-4,5-dihydroimidazo[1,5-a]quinoxaline-8-carboxyate as synthesized in above Example 170, by the operations similar to Example 58.

$^1$H-NMR (DMSO-$d_6$, δ): 0.7-0.9 (6H, m), 1.2-1.5 (4H, m), 1.6-1.8 (2H, m), 1.9-2.1 (2H, m), 3.4-3.6 (1H, m), 7.41 (1H, d, J=8.5 Hz), 7.87 (1H, s), 7.94 (1H, dd, J=1.5, 8.5 Hz), 8.58 (1H, d, J=1.2 Hz), 11.67 (1H, br s), 13.12 (1H, br s).

MS (m/z): 327 (M$^+$).

Example 172

N-(2-methoxyethyl)-N-methyl-4-oxo-1-(1-propylbutyl)-4,5-dihydroimidazo[1,5-a]quinoxaline-8-carboxamide

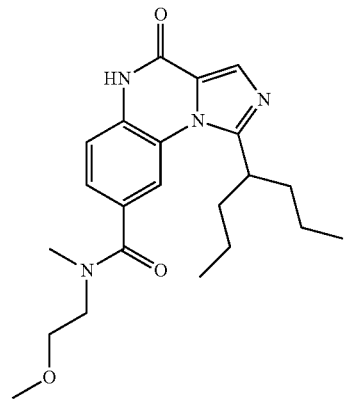 [SMILES: CCCC(CCC)c1ncc2c(=O)[nH]c3ccc(C(=O)N(C)CCOC)cc3n12]

The title compound was obtained from 4-oxo-1-(1-propylbutyl)-4,5-dihydroimidazo[1,5-a]quinoxaline-8-carboxyic acid as synthesized in above Example 171, by the operations similar to Example 59.

$^1$H-NMR (DMSO-$d_6$, δ): 0.84 (6H, t, J=7.3 Hz), 1.2-1.4 (4H, m), 1.6-1.8 (2H, m), 1.8-2.0 (2H, m), 3.01 (3H, s), 3.1-3.8 (8H, m), 7.37 (1H, d, J=8.5 Hz), 7.44 (1H, d, J=9.2 Hz), 7.85 (1H, s), 7.98 (1H, s), 11.51 (1H, br s).

MS (m/z): 398 (M$^+$).

Example 173

1-(Tetrahydropyran-4-yl)-7-trifluoromethlimidazo[1,5-a]-quinoxalin-4 (5H)-one

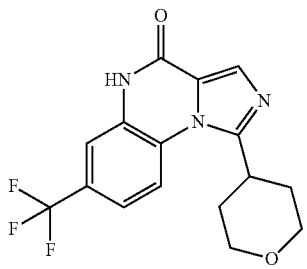 [SMILES: O=c1[nH]c2cc(C(F)(F)F)ccc2n2c(C3CCOCC3)ncc12]

The title compound was obtained from 2-[2-(tetrahydropyran-4-yl)-1H-imidazol-1-yl]-5-trifluoromethylaniline as synthesized in Production Example 90, by the operations similar to Example 123.

$^1$H-NMR (DMSO-d$_6$, δ): 1.8-2.1 (4H, m), 3.64 (2H, dt, J=2.7, 11.2 Hz), 3.7-3.9 (1H, m), 3.9-4.0 (2H, m), 7.61 (1H, dd, J=1.5, 8.9 Hz), 7.64 (1H, d, J=1.5 Hz), 7.86 (1H, s), 8.20 (1H, d, J=8.9 Hz), 11.59 (1H, br s).

MS (m/z): 337 (M$^+$).

Example 174

Ethyl 3-(7-fluoro-4-oxo-4,5-dihydroimidazo[1,5-a]quinoxalin-1-yl)propanoate

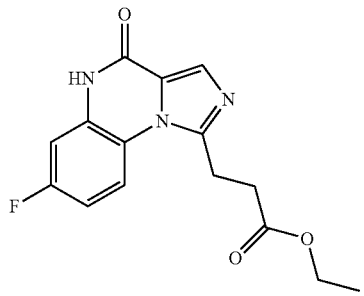 [SMILES: CCOC(=O)CCc1ncc2c(=O)[nH]c3cc(F)ccc3n12]

Ethyl 3-[1-(2-amino-4-fluorophenyl)-1H-imidazol-2-yl]-propanoate as synthesized in Production Example 92, 94 mg, 1,1'-carbonyldiimidazole 83 mg and 1,2-dichlorobenzene 1 mL were mixed and heated under reflux for 0.5 hour. Further 1 mL of 1,2-dichlorobenzene was added and the heating under reflux was continued for further 3 hours. Allowing the reaction liquid to cool off, the precipitate was recovered by filtration, and washed with diethyl ether and ethyl acetate, by the order stated. The resulting crystals were dissolved in a liquid mixture of tetrahydrofuran and methanol, and the insoluble matter was separated by filtration. Distilling the solvent off under reduced pressure, 70 mg of the title compound was obtained.

$^1$H-NMR (DMSO-d$_6$, δ): 1.19 (3H, t, J=7.1 Hz), 3.00 (2H, t, J=6.7 Hz), 3.49 (2H, t, J=6.7 Hz), 4.08 (2H, q, J=7.1 Hz), 7.0-7.2 (2H, m), 7.80 (1H, s), 8.0-8.2 (1H, m), 11.45 (1H, br s).

MS (m/z): 303 (M$^+$), 230 (base).

Example 175

3-(7-Fluoro-4-oxo-4,5-dihydroimidazo[1,5-a]quinoxalin-1-yl)-propanoic acid

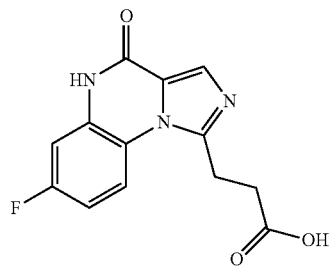 [SMILES: O=C(O)CCc1ncc2c(=O)[nH]c3cc(F)ccc3n12]

The title compound was obtained from ethyl 3-(7-fluoro-4-oxo-4,5-dihydroimidaizo[1,5-a]quinoxalin-1-yl)propanoate as synthesized in above Example 174, by the operations similar to Example 58.

$^1$H-NMR (DMSO-d$_6$, δ): 2.91 (2H, t, J=6.7 Hz), 3.45 (2H, t, J=6.7 Hz), 7.0-7.2 (2H, m), 7.77 (1H, s), 8.0-8.1 (1H, m), 11.45 (1H, br s), 12.21 (1H, br s).

MS (m/z): 275 (M$^+$), 230 (base).

Example 176

Ethyl 3-(7-chloro-4-oxo-4,5-dihydroimidazo[1,5-a]quinoxalin-1-yl)propanoate

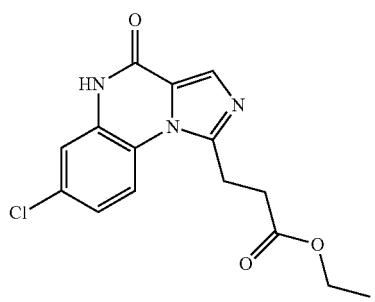 [SMILES: CCOC(=O)CCc1ncc2c(=O)[nH]c3cc(Cl)ccc3n12]

4-Chloro-1-fluoro-2-nitrobenzene 1.04 g, ethyl 3-(1H-imidazol-2-yl) propanoate 1.00 g, potassium carbonate 1.64 g and N,N-dimethylacetamide 20 mL were mixed and heated in nitrogen atmosphere at 100° C. for 12 hours. The reaction liquid was diluted with ethyl acetate, and water was added to induce phase separation. The organic layer was washed with saturated brine, dried over sodium sulfate and removed of the solvent by distillation. Thus obtained compound was dissolved in 10 mL of acetic acid and 10 mL of water and to which 6.00 g of 85% sodium hydrosulfite was added, followed by 2 hours' heating under reflux. The reaction liquid was cooled with ice and neutralized with saturated aqueous sodium hydrogencarbonate solution. Extracting the same with ethyl acetate, the extract was washed with saturated brine, dried over sodium sulfate and removed of the solvent by distillation. The resulting compound was mixed with 1.4 g of 1,1'-carbonyldiimidazole and 20 mL of 1,2-dichlorobenzene and heated under reflux for 5 hours in nitrogen atmosphere. The solvent was distilled off and methanol was added, followed by an overnight's stirring. The precipitated crystals were recovered by filtration, washed with methanol and dried in flowing air to provide 530 mg of the title compound.

¹H-NMR (DMSO-d₆, δ): 1.19 (3H, t, J=7.1 Hz), 2.96 (2H, t, J=6.5 Hz), 3.48 (2H, t, J=6.7 Hz), 4.08 (2H, q, J=7.3 Hz), 7.30 (1H, dd, J=2.3, 8.8 Hz), 7.35 (1H, d, J=2.3 Hz), 7.78 (1H, s), 8.05 (1H, d, J=8.8 Hz), 11.45 (1H, s).

MS (m/z): 321 (M⁺+2), 319 (M⁺).

Example 177

3-(7-Chloro-4-oxo-4,5-dihydroimidazol[1,5-a]quinoxalin-1-yl)-propanoic acid

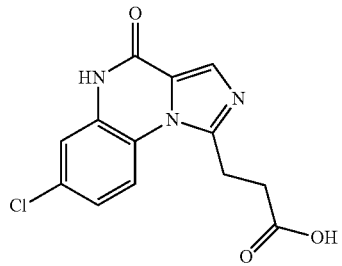 [SMILES: O=C(O)CCc1ncc2c(=O)[nH]c3cc(Cl)ccc3n12]

The title compound was obtained from ethyl 3-(7-chloro-4-oxo-4,5-dihydroimidazo[1,5-a]quinoxalin-1-yl)propanoate as synthesized in above Example 176, by the operations similar to Example 58.

¹H-NMR (DMSO-d₆, δ): 2.90 (2H, t, J=6.6 Hz), 3.44 (2H, t, J=6.6 Hz), 7.30 (1H, dd, J=2.7, 8.9 Hz), 7.35 (1H, d, J=2.7 Hz), 7.78 (1H, s), 8.05 (1H, d, J=8.9 Hz), 11.45 (1H, s), 12.21 (1H, br s).

MS (m/z): 293 (M⁺+2), 291 (M⁺), 248, 246.

Example 178

7-Chloro-1-(3-hydroxypropyl)imidazo[1,5-a]quinoxalin-4 (5H)-one

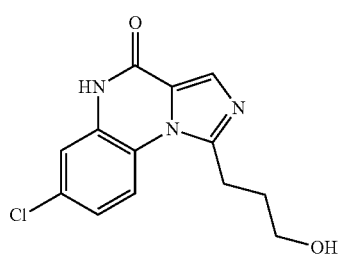 [SMILES: O=c1[nH]c2cc(Cl)ccc2n2c(CCCO)ncc12]

Fifty (50) mg of ethyl 3-(7-chloro-4-oxo-4,5-dihydroimidazo-[1,5-a]quinoxalin-1-yl)propanoate as synthesized in Example 176 was dissolved in 5 mL of tetrahydrofuran, and to the solution 8.9 mg of lithium aluminum hydride was added under cooling with ice. After minutes' stirring, the residual lithium aluminum hydride was quenched with ice pieces, and the reaction liquid was extracted with ethyl acetate. The extract was washed with saturated aqueous ammonium chloride solution, saturated aqueous sodium hydrogencarbonate solution, and with saturated brine by the order stated, and dried over anhydrous sodium sulfate. Distilling the solvent off from the product, 38 mg of the title compound was obtained.

¹H-NMR (DMSO-d₆, δ): 2.02 (2H, quin, J=7.3 Hz), 3.2-3.4 (2H, m), 3.59 (2H, t, J=6.2 Hz), 4.62 (1H, s), 7.29 (1H, dd, J=2.3, 8.9 Hz), 7.35 (1H, d, J=2.3 Hz), 7.79 (1H, s), 7.99 (1H, d, J=8.9 Hz), 11.43 (1H, s).

MS (m/z): 279 (M⁺+2), 277 (M⁺).

Example 179

Ethyl 3-(7-bromo-4-oxo-4,5-dihydroimidazo[1,5-a]quinoxalin-1-yl)propanoate

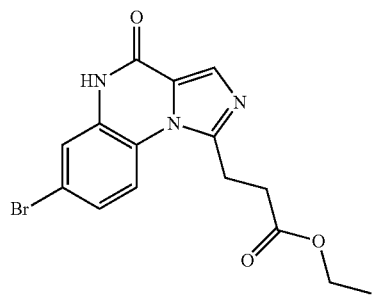

A mixture of 4-bromo-1-fluoro-2-nitrobenzene 324 mg, ethyl 3-(1H-imidazol-2-yl)propanoate 248 mg, potassium carbonate 407 mg and N,N-dimethylacetamide 10 mL was heated at 100° C. for 12 hours in nitrogen atmosphere. The reaction liquid was diluted with ethyl acetate and water was added thereto to induce phase separation. The organic layer was washed with saturated brine and dried over sodium sulfate, from which then the solvent was distilled off. Thus obtained oily substance was dissolved in a liquid mixture of 10 mL of acetic acid and 10 mL of water, and to the solution 1.51 g of 85% sodium hydrosulfite was added, followed by 2 hours' heating under reflux. The reaction liquid was cooled with ice and neutralized with saturated aqueous sodium hydrogencarbonate solution. Extracting the same with ethyl acetate, the extract was washed with saturated brine, dried over sodium sulfate, and from which the solvent was distilled off. To the resulting oily substance, 358 mg of 1,1'-carbonyldiimidazole and 20 mL of 1,2-dichlorobenzene were added, followed by 5 hours' heating under reflux in nitrogen atmosphere. The solvent was distilled off, and to the residue methanol was added and stirred overnight. Thus precipitated crystals were recovered by filtration, washed with methanol and dried in flowing air to provide 112 mg of the title compound.

¹H-NMR (DMSO-d₆, δ): 1.18 (3H, t, J=7.3 Hz), 2.96 (2H, t, J=6.5 Hz), 3.48 (2H, t, J=6.5 Hz), 4.08 (2H, q, J=7.3 Hz), 7.41 (1H, dd, J=2.3, 8.8 Hz), 7.49 (1H, d, J=2.3 Hz), 7.78 (1H, s), 7.98 (1H, d, J=8.8 Hz), 11.44 (1H, s).

MS (m/z): 365 (M⁺+2), 363 (M⁺).

Example 180

3-(7-Bromo-4-oxo-4,5-dihydroimidazo[1,5-a]quinoxalin-1-yl)propanoic acid

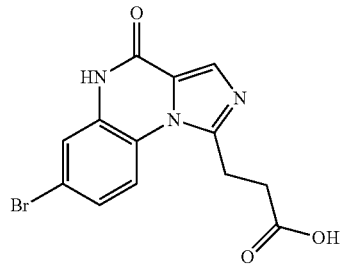

The title compound was obtained from ethyl 3-(7-bromo-4-oxo-4,5-dihydroimidazo[1,5-a]quinoxalin-1-yl)propanoate as synthesized in Example 179, in the manner similar to Example 58.

$^1$H-NMR (DMSO-d$_6$, δ): 2.90 (2H, t, J=6.6 Hz), 3.44 (2H, t, J=6.6 Hz), 7.42 (1H, dd, J=2.3, 9.1 Hz), 7.49 (1H, d, J=2.3 Hz), 7.78 (1H, s), 7.99 (1H, d, J=9.1 Hz), 11.43 (1H, s), 12.22 (1H, br s).

MS (m/z): 337 (M$^+$+2), 335 (M$^+$).

Example 181

Ethyl 3-(7-methyl-4-oxo-4,5-dihydroimidazo[1,5-a]quinoxalin-1-yl)propanoate

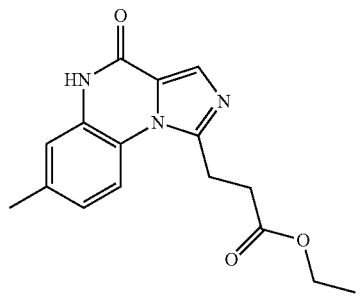 [SMILES: CCOC(=O)CCc1ncc2c(=O)[nH]c3cc(C)ccc3n12]

The title compound was obtained from ethyl 3-[1-(2-amino-4-methylphenyl)-1H-imidazol-2-yl]propanoate as synthesized in Production Example 94, in the manner similar to Example 123.

Example 182

3-(7-Methyl-4-oxo-4,5-dihydroimidazo[1,5-a]quinoxalin-1-yl)propanoic acid

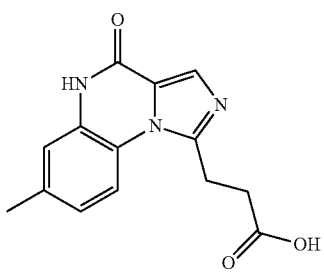 [SMILES: Cc1ccc2c(c1)[nH]c(=O)c1cnc(CCC(=O)O)n12]

Ethyl 3-[1-(2-amino-4-methylphenyl)-1H-imidazol-2-yl]propanoate as synthesized in above Example 181, 160 mg, 1,1'-carbonyldiimidazole 143 mg and 1,2-dichlorobenzene 6 mL were mixed and heated under reflux for 1.5 hours. The reaction liquid was allowed to cool off, and the precipitate was recovered by filtration and washed with ethyl acetate. After being dried under reduced pressure, the product was mixed with 3 mL of ethanol and 3.0 mL of 1N aqueous sodium hydroxide solution and heated under reflux for 20 minutes. Cooling the reaction liquid off, 3.0 mL of 1N hydrochloric acid was added. The precipitated crystals were recovered by filtration, washed with water and dried in flowing air under heating to provide 82 mg of the title compound.

$^1$H-NMR (DMSO-d$_6$, δ): 2.35 (3H, s), 2.90 (2H, t, J=6.7 Hz), 3.45 (2H, t, J=6.7 Hz), 7.08 (1H, dd, J=1.2, 8.5 Hz), 7.13 (1H, d, J=1.2 Hz), 7.74 (1H, s), 7.93 (1H, d, J=8.5 Hz), 11.29 (1H, br s), 12.20 (1H, br s).

MS (m/z): 271 (M$^+$), 226 (base).

Example 183

Ethyl 3-(7-acetyl-4-oxo-4,5-dihydroimidazo[1,5-a]quinoxalin-1-yl)propanoate

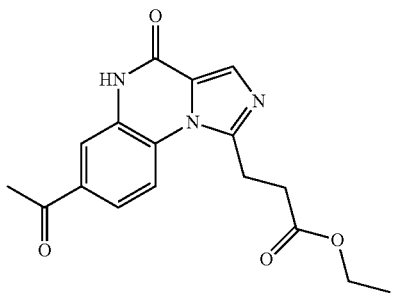 [SMILES: CCOC(=O)CCc1ncc2c(=O)[nH]c3cc(C(C)=O)ccc3n12]

The title compound was obtained from ethyl 3-[1-(4-acetyl-2-aminophenyl)-1H-imidazol-2-yl]propanoate as synthesized in Production Example 96, in the manner similar to Example 4.

$^1$H-NMR (DMSO-d$_6$, δ): 1.19 (3H, t, J=7.1 Hz), 2.61 (3H, s), 2.98 (2H, t, J=6.7 Hz), 3.53 (2H, t, J=6.7 Hz), 4.09 (2H, q, J=7.1 Hz), 7.79 (1H, s), 7.84 (1H, dd, J=1.9, 8.9 Hz), 7.89 (1H, d, J=1.9 Hz), 8.15 (1H, d, J=8.9 Hz), 11.49 (1H, br s).

MS (m/z): 327 (M$^+$), 254 (base).

Example 184

Ethyl 3-(7-ethyl-4-oxo-4,5-dihydroimidazo[1,5-a]quinoxalin-1-yl)propanoate

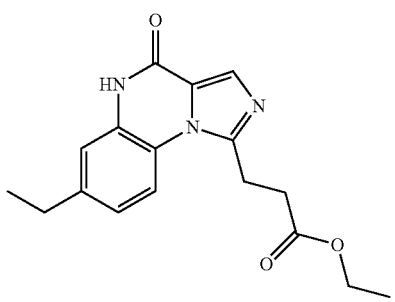 [SMILES: CCOC(=O)CCc1ncc2c(=O)[nH]c3cc(CC)ccc3n12]

A mixture of ethyl 3-(7-acetyl-4-oxo-4,5-dihydroimidazo[1,5-a]-quinoxalin-1-yl)propanoate as synthesized in above Example 183, 131 mg, Pearlman's catalyst 100 mg and acetic acid 5 mL was stirred in hydrogen atmosphere at room temperature for 43 hours. Then 75 mg of Pearlman's catalyst was added and the reaction liquid was mildly heated. Twenty-two hours later, the reaction liquid was filtered through Celite, and 30 mL of water was added to the filtrate. The precipitate was recovered by filtration, washed with water and dried in flowing air under heating to provide 65 mg of the title compound.

$^1$H-NMR (DMSO-d$_6$, δ): 1.19 (3H, t, J=7.1 Hz), 1.21 (3H, t, J=7.7 Hz), 2.66 (2H, q, J=7.7 Hz), 2.96 (2H, t, J=6.6 Hz), 3.50 (2H, t, J=6.6 Hz), 4.08 (2H, q, J=7.1 Hz), 7.12 (1H, dd, J=1.9, 8.5 Hz), 7.18 (1H, d, J=1.9 Hz), 7.74 (1H, s), 7.96 (1H, d, J=8.5 Hz), 11.29 (1H, br s).

MS (m/z): 313 (M$^+$), 240 (base).

Example 185

3-(7-Ethyl-4-oxo-4,5-dihydroimidazo[1,5-a]quinoxalin-1-yl)-propanoic acid

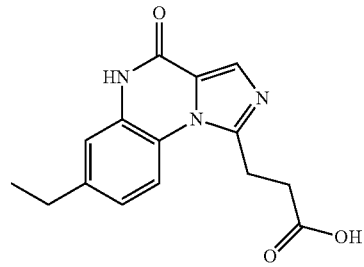 [SMILES: CCc1ccc2c(c1)[nH]c(=O)c1cnc(CCC(=O)O)n12]

To a mixture of ethyl 3-(7-ethyl-4-oxo-4,5-dihydroimidazo-[1,5-a]-quinoxalin-1-yl)propanoate as synthesized in above Example 184, 50 mg and ethanol 3 mL, 1N sodium hydroxide solution 1.2 mL was added and heated under reflux for 2 hours. The reaction liquid was allowed to cool off, and to which 1N hydrochloric acid 1.2 mL was added. The precipitated crystals were recovered by filtration, washed with water and dried in flowing air to provide 37 mg of the title compound.

$^1$H-NMR (DMSO-$d_6$, δ): 1.21 (3H, t, J=7.5 Hz), 2.66 (2H, q, J=7.5 Hz), 2.91 (2H, t, J=6.7 Hz), 3.46 (2H, t, J=6.7 Hz), 7.12 (1H, dd, J=1.9, 8.9 Hz), 7.18 (1H, d, J=1.9 Hz), 7.74 (1H, s), 7.96 (1H, d, J=8.9 Hz), 11.29 (1H, br s), 12.20 (1H, br s).

MS (m/z): 285 (M$^+$), 240 (base).

Example 186

Ethyl 3-(4-oxo-7-trifluoromethyl-4,5-dihydroimidazo[1,5-a]-quinoxalin-1-yl)propanoate

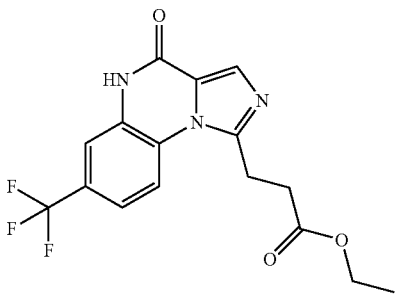 [SMILES: CCOC(=O)CCc1ncc2c(=O)[nH]c3cc(C(F)(F)F)ccc3n12]

The title compound was obtained from ethyl 3-[1-(2-amino-4-trifluoromethylphenyl)-1H-imidazol-2-yl]propanoate as synthesized in Production Example 98, in the manner similar to Example 4.

$^1$H-NMR (DMSO-$d_6$, δ): 1.19 (3H, t, J=7.1 Hz), 2.99 (2H, t, J=6.7 Hz), 3.53 (2H, t, J=6.7 Hz), 4.09 (2H, q, J=7.1 Hz), 7.59 (1H, dd, J=1.5, 8.9 Hz), 7.65 (1H, d, J=1.9 Hz), 7.82 (1H, s), 8.25 (1H, d, J=8.9 Hz), 11.58 (1H, br s).

MS (m/z): 353 (M$^+$), 280 (base).

Example 187

3-(4-Oxo-7-trifluoromethyl-4,5-dihydroimidazo[1,5-a]-quinoxalin-1-yl)propanoic acid

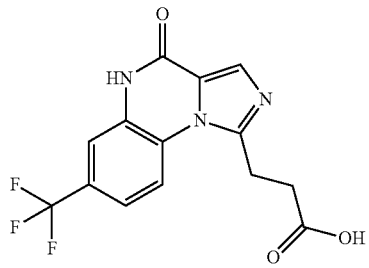 [SMILES: O=C(O)CCc1ncc2c(=O)[nH]c3cc(C(F)(F)F)ccc3n12]

The title compound was obtained from ethyl 3-(4-oxo-7-trifluoromethyl-4,5-dihydroimidazo[1,5-a]quinoxalin-1-yl)propanoate as synthesized in above Example 186, in the manner similar to Example 58.

$^1$H-NMR (DMSO-$d_6$, δ): 2.93 (2H, t, J=6.7 Hz), 3.50 (2H, t, J=6.7 Hz), 7.60 (1H, dd, J=1.5, 8.9 Hz), 7.65 (1H, d, J=1.5 Hz), 7.82 (1H, s), 8.25 (1H, d, J=8.9 Hz), 11.57 (1H, br s), 12.24 (1H, br s).

MS (m/z): 325 (M$^+$), 280 (base).

Example 188

Ethyl (E)-3-(4-oxo-7-trifluoromethyl-4,5-dihydropyrrolo[1,2-a]-quinoxalin-1-yl)acrylate

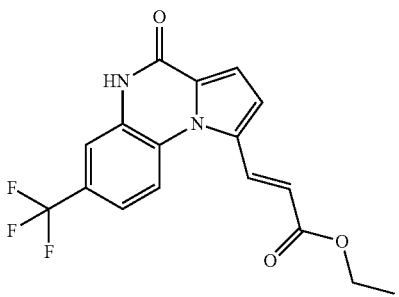 [SMILES: CCOC(=O)/C=C/c1ccc2c(=O)[nH]c3cc(C(F)(F)F)ccc3n12]

A mixture of 1-fluoro-2-nitro-4-trifluoromethylbenzene 523 mg, ethyl 5-[(E)-2-ethoxycarbonylvinyl]-1H-pyrrole-2-carboxyate 593 mg, potassium carbonate 864 mg and dimethylsulfoxide 10 mL was heated at 100° C. for 3.5 hours. After cooling off the reaction liquid, 100 mL of diethyl ether was added, followed by filtration. To the filtrate 100 mL of water was added to separate the organic layer. The aqueous layer was extracted twice with 50 mL of diethyl ether, and the extract was combined with the organic layer, followed by washing three times with 20 mL of water and once with 20 mL of saturated brine by the order stated. After drying the same over magnesium sulfate, the solvent was distilled off under reduced pressure, leaving 965 mg of a brown, viscous substance. This was dissolved in a liquid mixture of 12 mL of acetic acid and 5 mL of water, and to the solution 1.31 g of sodium hyposulfite was added, followed by heating under reflux for 30 minutes. After cooling off the reaction liquid, 50 mL of water was added and the precipitated crystals were recovered by filtration. The crystals were washed with water and diethyl ether, and dried under heating to provide 600 mg of the title compound.

¹H-NMR (DMSO-d₆, δ): 1.30 (3H, t, J=7.2 Hz), 4.25 (2H, q, J=7.2 Hz), 6.64 (1H, d, J=15.8 Hz), 7.1-7.3 (2H, m), 7.6-7.7 (2H, m), 7.93 (1H, d, J=8.1 Hz), 8.07 (1H, d, J=15.8 Hz), 11.67 (1H, br s).

MS (m/z): 350 (M⁺), 277 (base).

Example 189

(E)-3-(4-oxo-7-trifluoromethyl-4,5-dihydropyrrolo[1,2-a]-quinoxalin-1-yl)acrylic acid

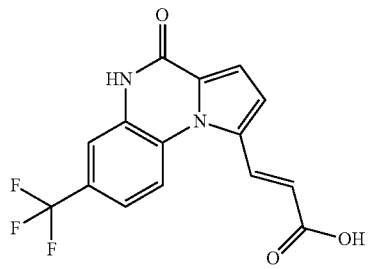 [SMILES: O=C(O)/C=C/c1ccc2c(=O)[nH]c3cc(C(F)(F)F)ccc3n12]

The title compound was obtained from ethyl (E)-3-(4-oxo-7-trifluoromethyl-4,5-dihydropyrrolo[1,2-a]quinoxalin-1-yl)acrylate as synthesized in above Example 188, in the manner similar to Example 58.

¹H-NMR (DMSO-d₆, δ): 6.55 (1H, d, J=15.4 Hz), 7.1-7.3 (2H, m), 7.6-7.7 (2H, m), 7.95 (1H, d, J=9.6 Hz), 8.02 (1H, d, J=15.4 Hz), 11.66 (1H, br s), 12.65 (1H, br s).

MS (m/z): 322 (M⁺), 277 (base).

Example 190

Ethyl 3-(4-oxo-7-trifluoromethyl-4,5-dihydropyrrolo[1,2-a]-quinoxalin-1-yl)propanoate

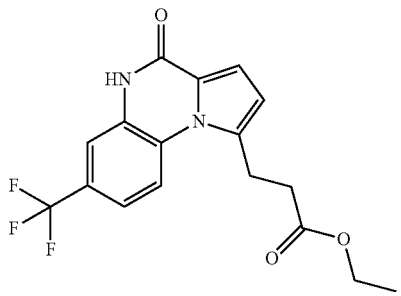 [SMILES: CCOC(=O)CCc1ccc2c(=O)[nH]c3cc(C(F)(F)F)ccc3n12]

Ethyl (E)-3-(4-oxo-7-trifluoromethyl-4,5-dihydropyrrolo[1,2-a]-quinoxalin-1-yl)acrylate as synthesized in Example 188, 182 mg, 5% palladium carbon 80 mg and acetic acid 6 mL were mixed and stirred under hydrogen atmosphere at room temperature for 16 hours. Filtering the reaction liquid through Celite, 50 mL of water was added to the filtrate and the precipitated crystals were recovered by filtration. The crystals were washed successively with water and diethyl ether, and dried in flowing air under heating to provide 120 mg of the title compound.

¹H-NMR (DMSO-d₆, δ): 1.20 (3H, t, J=7.1 Hz), 2.85 (2H, t, J=7.3 Hz), 3.49 (2H, t, J=7.3 Hz), 4.11 (2H, q, J=7.1 Hz), 6.52 (1H, d, J=4.0 Hz), 7.09 (1H, d, J=4.0 Hz), 7.53 (1H, dd, J=1.9, 8.9 Hz), 7.63 (1H, d, J=1.9 Hz), 8.21 (1H, d, J=8.9 Hz), 11.45 (1H, br s).

MS (m/z): 352 (M⁺), 265 (base).

Example 191

3-(4-Oxo-7-trifluoromethyl-4,5-dihydropyrrolo[1,2-a]-quinoxalin-1-yl)propanoic acid

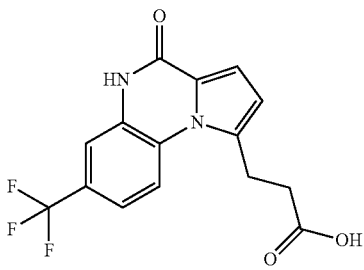 [SMILES: O=C(O)CCc1ccc2c(=O)[nH]c3cc(C(F)(F)F)ccc3n12]

The title compound was obtained from ethyl 3-(4-oxo-7-trifluoromethyl-4,5-dihydropyrrolo[1,2-a]quinoxalin-1-yl)propanoate as synthesized in above Example 190, by the operations similar to Example 58.

¹H-NMR (DMSO-d₆, δ): 2.77 (2H, t, J=7.3 Hz), 3.45 (2H, t, J=7.3 Hz), 6.53 (1H, d, J=4.0 Hz), 7.09 (1H, d, J=4.0 Hz), 7.53 (1H, dd, J=1.7, 8.9 Hz), 7.63 (1H, d, J=1.7 Hz), 8.21 (1H, d, J=8.9 Hz), 11.45 (1H, br s), 12.37 (1H, br s).

MS (m/z): 324 (M⁺), 265 (base).

Example 192

Ethyl (E)-3-(3-methyl-4-oxo-7-trifluoromethyl-4,5-dihydropyrrolo[1,2-a]quinoxalin-1-yl)acrylate

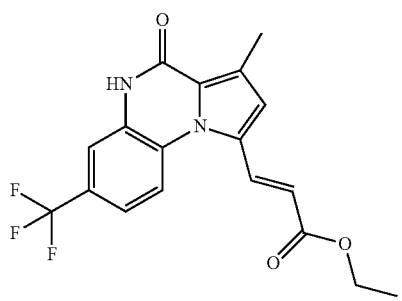 [SMILES: CCOC(=O)/C=C/c1cc(C)c2c(=O)[nH]c3cc(C(F)(F)F)ccc3n12]

The title compound was obtained from ethyl 5-[(E)-2-ethoxycarbonylvinyl]-3-methyl-1H-pyrrole-2-carboxyate as synthesized in Production Example 99, by the operations similar to Example 188.

¹H-NMR (DMSO-d₆, δ): 1.29 (3H, t, J=7.1 Hz), 2.48 (3H, s), 4.24 (2H, q, J=7.1 Hz), 6.56 (1H, d, J=15.6 Hz), 7.04 (1H, s), 7.5-7.7 (2H, m), 7.80 (1H, d, J=8.5 Hz), 7.99 (1H, d, J=15.6 Hz), 11.44 (1H, br s).

MS (m/z): 364 (M⁺), 291 (base).

Example 193

Ethyl 3-(3-methyl-4-oxo-7-trifluoromethyl-4,5-dihydropyrrolo-[1,2-a]quinoxalin-1-yl)propanoate

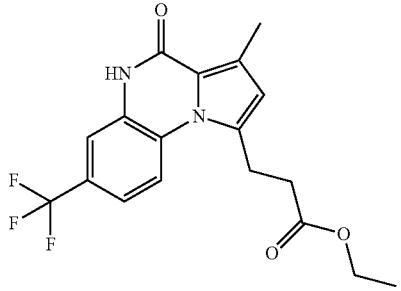 [SMILES: CCOC(=O)CCc1cc(C)c2c(=O)[nH]c3cc(C(F)(F)F)ccc3n12]

The title compound was obtained from ethyl (E)-3-(3-methyl-4-oxo-7-trifluoromethyl-4,5-dihydropyrrolo[1,2-a]quinoxalin-1-yl)-acrylate as synthesized in above Example 192, by the operations similar to Example 190.

$^1$H-NMR (DMSO-d$_6$, δ): 1.19 (3H, t, J=7.1 Hz), 2.46 (3H, s), 2.80 (2H, t, J=7.3 Hz), 3.41 (2H, t, J=7.3 Hz), 4.10 (2H, q, J=7.1 Hz), 6.35 (1H, s), 7.47 (1H, dd, J=1.7, 8.9 Hz), 7.56 (1H, d, J=1.7 Hz), 8.09 (1H, d, J=8.9 Hz), 11.19 (1H, br s).

MS (m/z): 366 (M$^+$), 279 (base).

Example 194

3-(3-Methyl-4-oxo-7-trifluoromethyl-4,5-dihydropyrrolo-[1,2-a]quinoxalin-1-yl)propanoic acid

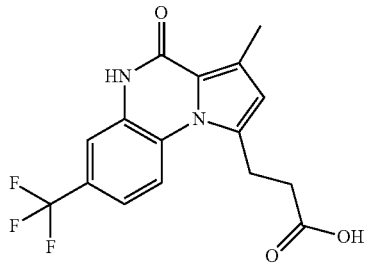 [SMILES: Cc1cc(CCC(=O)O)n2c1c(=O)[nH]c1cc(C(F)(F)F)ccc12]

The title compound was obtained from ethyl 3-(3-methyl-4-oxo-7-trifluoromethyl-4,5-dihydropyrrolo[1,2-a]quinoxalin-1-yl)-propanoate as synthesized in above Example 193, by the operations similar to Example 58.

$^1$H-NMR (DMSO-d$_6$, δ): 2.46 (3H, s), 2.73 (2H, t, J=7.3 Hz), 3.37 (2H, t, J=7.3 Hz), 6.36 (1H, s), 7.47 (1H, dd, J=1.7, 8.9 Hz), 7.56 (1H, d, J=1.7 Hz), 8.11 (1H, d, J=8.9 Hz), 11.18 (1H, br s).

MS (m/z): 338 (M$^+$), 279 (base).

Example 195

Ethyl (E)-3-(2-methyl-4-oxo-7-trifluoromethyl-4,5-dihydropyrrolo[1,2-a]quinoxalin-1-yl)acrylate

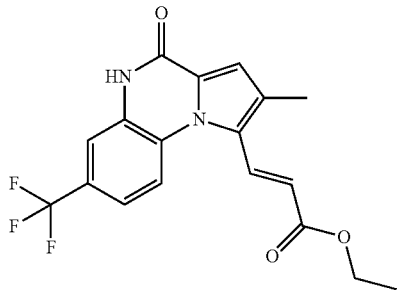 [SMILES: CCOC(=O)/C=C/c1c(C)cc2c(=O)[nH]c3cc(C(F)(F)F)ccc3n12]

The title compound was obtained from 5-[(E)-2-ethoxycarbonylvinyl]-4-methyl-1H-pyrrole-2-carboxyate as synthesized in Production Example 100, by the operations similar to Example 188.

$^1$H-NMR (DMSO-d$_6$, δ): 1.31 (3H, t, J=7.1 Hz), 2.30 (3H, s), 4.26 (2H, q, J=7.1 Hz), 6.34 (1H, d, J=16.0 Hz), 7.09 (1H, s), 7.5-7.6 (1H, m), 7.63 (1H, d, J=1.9 Hz), 7.88 (1H, d, J=8.5 Hz), 7.94 (1H, d, J=16.0 Hz), 11.64 (1H, br s).

MS (m/z): 364 (M$^+$), 291 (base).

Example 196

Ethyl 3-(2-methyl-4-oxo-7-trifluoromethyl-4,5-dihydropyrrolo-[1,2-a]quinoxalin-1-yl)propanoate

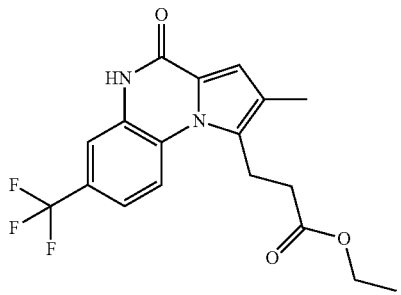 [SMILES: CCOC(=O)CCc1c(C)cc2c(=O)[nH]c3cc(C(F)(F)F)ccc3n12]

The title compound was obtained from ethyl (E)-3-(2-methyl-4-oxo-7-trifluoromethyl-4,5-dihydropyrrolo[1,2-a]quinoxalin-1-yl)-acrylate as synthesized in above Example 195, by the operations similar to Example 190.

$^1$H-NMR (DMSO-d$_6$, δ): 1.15 (3H, t, J=7.1 Hz), 2.18 (3H, s), 2.65 (2H, t, J=7.5 Hz), 3.45 (2H, t, J=7.5 Hz), 4.05 (2H, q, J=7.1 Hz), 6.97 (1H, s), 7.50 (1H, dd, J=1.7, 8.9 Hz), 7.61 (1H, d, J=1.7 Hz), 8.11 (1H, d, J=8.9 Hz), 11.41 (1H, br s).

MS (m/z): 366 (M$^+$), 279 (base).

Example 197

3-(2-methyl-4-oxo-7-trifluoromethyl-4,5-dihydropyrrolo-[1,2-a]quinoxalin-1-yl)propanoic acid

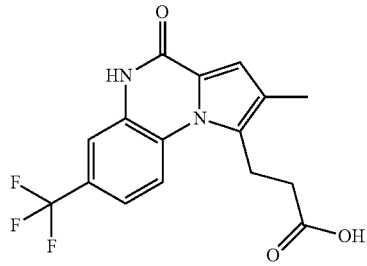 [SMILES: Cc1cc2c(=O)[nH]c3cc(C(F)(F)F)ccc3n2c1CCC(=O)O]

The title compound was synthesized from ethyl 3-(2-methyl-4-oxo-7-trifluoromethyl-4,5-dihydropyrrolo[1,2-a]quinoxalin-1-yl)-propanoate as synthesized in above Example 196, by the operations similar to Example 58.

$^1$H-NMR (DMSO-$d_6$, δ): 2.19 (3H, s), 2.57 (2H, t, J=7.7 Hz), 3.42 (2H, t, J=7.7 Hz), 6.97 (1H, s), 7.4-7.6 (1H, m), 7.61 (1H, d, J=1.9 Hz), 8.10 (1H, d, J=8.9 Hz), 11.40 (1H, br s), 12.32 (1H, br s).

MS (m/z): 338 (M$^+$), 279 (base).

Example 198

Ethyl (E)-3-(2,3-dimethyl-4-oxo-7-trifluoromethyl-4,5-dihydropyrrolo[1,2-a]quinoxalin-1-yl)acrylate

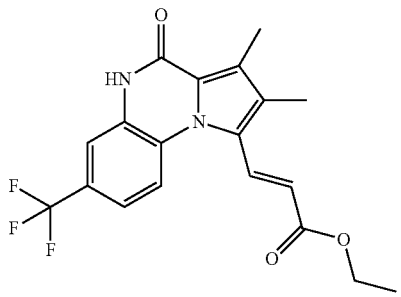 [SMILES: CCOC(=O)/C=C/c1c(C)c(C)c2c(=O)[nH]c3cc(C(F)(F)F)ccc3n12]

The title compound was synthesized from ethyl 5-[(E)-2-ethoxycarbonylvinyl]-3,4-dimethyl-1H-pyrrole-2-carboxyate as synthesized in Production Example 101, by the operations similar to Example 188.

$^1$H-NMR (DMSO-$d_6$, δ): 1.31 (3H, t, J=7.1 Hz), 2.16 (3H, s), 2.45 (3H, s), 4.25 (2H, q, J=7.1 Hz), 6.30 (1H, d, J=15.8 Hz), 7.4-7.6 (2H, m), 7.77 (1H, d, J=8.9 Hz), 7.86 (1H, d, J=15.8 Hz), 11.40 (1H, br s).

MS (m/z): 378 (M$^+$), 305 (base).

Example 199

Ethyl 3-(2,3-dimethyl-4-oxo-7-trifluoromethyl-4,5-dihydropyrrolo[1,2-a]quinoxalin-1-yl)propanoate

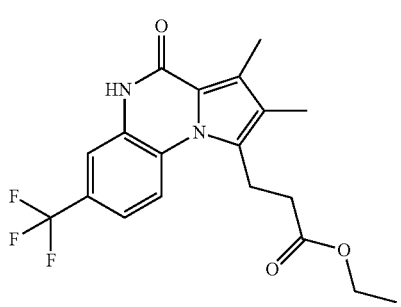 [SMILES: CCOC(=O)CCc1c(C)c(C)c2c(=O)[nH]c3cc(C(F)(F)F)ccc3n12]

The title compound was obtained from ethyl (E)-3-(2,3-dimethyl-4-oxo-7-trifluoromethyl-4,5-dihydropyrrolo[1,2-a]-quinoxalin-1-yl)acrylate as synthesized in above Example 198, by the operations similar to Example 190.

$^1$H-NMR (DMSO-$d_6$, δ): 1.15 (3H, t, J=7.1 Hz), 2.06 (3H, s), 2.42 (3H, s), 2.62 (2H, t, J=7.5 Hz), 3.43 (2H, t, J=7.5 Hz), 4.05 (2H, q, J=7.1 Hz), 7.44 (1H, dd, J=1.7, 8.9 Hz), 7.55 (1H, d, J=1.7 Hz), 8.02 (1H, d, J=8.9 Hz), 11.17 (1H, br s).

MS (m/z): 380 (M$^+$), 293 (base).

Example 200

3-(2,3-Dimethyl-4-oxo-7-trifluoromethyl-4,5-dihydropyrrolo-[1,2-a]quinoxalin-1-yl)propanoic acid

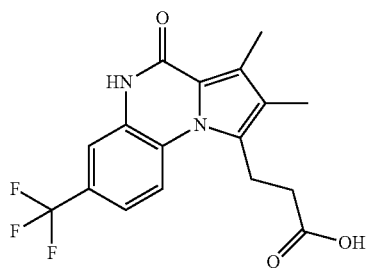 [SMILES: Cc1c(C)c2c(=O)[nH]c3cc(C(F)(F)F)ccc3n2c1CCC(=O)O]

The title compound was obtained from ethyl 3-(2,3-dimethyl-4-oxo-7-trifluoromethyl-4,5-dihydropyrrolo[1,2-a]quinoxalin-1-yl)-propanoate as synthesized in above Example 199, by the operations similar to Example 58.

$^1$H-NMR (DMSO-$d_6$, δ): 2.07 (3H, s), 2.43 (3H, s), 2.5-2.6 (2H, m), 3.3-3.5 (2H, m), 7.44 (1H, dd, J=1.9, 8.9 Hz), 7.55 (1H, d, J=1.9 Hz), 8.02 (1H, d, J=8.9 Hz), 11.16 (1H, br s), 12.33 (1H, br s).

MS (m/z): 352 (M$^+$), 293 (base).

Example 201

Ethyl 2-methyl-3-(4-oxo-7-trifluoromethyl-4,5-dihydropyrrolo-[1,2-a]quinoxalin-1-yl)propanoate

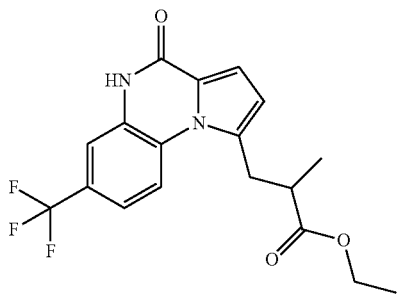 [SMILES: CCOC(=O)C(C)Cc1ccc2c(=O)[nH]c3cc(C(F)(F)F)ccc3n12]

Methyl 5-formyl-1H-pyrrole-2-carboxyate 3.06 g, (carbethoxyethylidene)triphenylphosphorane 7.97 g and acetonitrile 100 mL were mixed and heated under reflux for 16 hours. The solvent was distilled off from the reaction mixture under reduced pressure and the residue was recrystallized from ethyl acetate to provide 770 mg of white crystals. The crystals 712 mg, 1-fluoro-2-nitro-4-trifluoromethylbenzene 690 mg, potassium carbonate, 1.04 g and dimethylsulfoxide 12 mL were mixed and heated at 100° C. for 3 hours. After cooling the reaction liquid off, water was added thereto, followed by extraction with diethyl ether, washed with saturated brine, dried over magnesium sulfate, and removed of the solvent by distillation under reduced pressure to provide 1.21 g of brown solid. With 938 mg of the solid, 12 mL of acetic acid and 6 mL of water were mixed, to the mixture 1.15 g of sodium hyposulfite was added and heated under reflux. After 2.5 hours' heating, 383 mg of sodium hyposulfite was added and the heating under reflux was continued for additional 2.5 hours. The reaction liquid was cooled off, to which 10 mL of water was added and the precipitated crystals were recovered by filtration and washed with water. The crystals were dried in flowing air under heating and subjected to silica gel chromatography (hexane:ethyl acetate=3:1) to provide 270 mg of pale yellow solid. A mixture of 180 mg of this solid, 50 mg of 5% palladium carbon and 6 mL of acetic acid was stirred in hydrogen atmosphere for 7 hours at room temperature and then heated to 30° C. After 14 hours' stirring, the reaction liquid was filtered through Celite. To the filtrate 30 mL of water was added and extracted with 40 mL of diethyl ether. The extract was washed three times with 40 mL of saturated sodium hydrogencarbonate and then once with 10 mL of saturated brine, and dried over magnesium sulfate. After distilling off the solvent under reduced pressure, the residue was crystallized from diethyl ether and recovered by filtration. The crystals were washed with diethyl ether and dried under reduced pressure to provide 40 mg of the title compound.

$^1$H-NMR (DMSO-$d_6$, δ): 1.12 (3H, t, J=7.1 Hz), 1.24 (3H, d, J=6.6 Hz), 2.9-3.0 (1H, m), 3.2-3.4 (1H, m), 3.4-3.6 (1H, m), 4.03 (2H, q, J=7.1 Hz), 6.50 (1H, d, J=4.0 Hz), 7.08 (1H, d, J=4.0 Hz), 7.53 (1H, dd, J=1.9, 8.9 Hz), 7.63 (1H, d, J=1.9 Hz), 8.21 (1H, d, J=8.9 Hz), 11.46 (1H, br s).

MS (m/z): 366 (M$^+$), 265 (base).

Example 202

2-Methyl-3-(4-oxo-7-trifluoromethyl-4,5-dihydropyrrolo[1,2-a]-quinoxalin-1-yl)propanoic acid

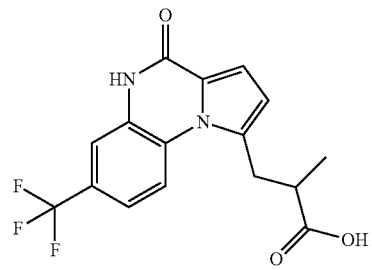 [SMILES: CC(Cc1ccc2c(=O)[nH]c3cc(C(F)(F)F)ccc3n12)C(=O)O]

The title compound was synthesized from ethyl 2-methyl-3-(4-oxo-7-trifluoromethyl-4,5-dihydropyrrolo[1,2-a]-quinoxalin-1-yl)propanoate as synthesized in above Example 201, by the operations similar to Example 58.

$^1$H-NMR (DMSO-$d_6$, δ): 1.23 (3H, d, J=6.9 Hz), 2.8-3.0 (1H, m), 3.2-3.4 (1H, m), 3.4-3.6 (1H, m), 6.52 (1H, d, J=3.9 Hz), 7.09 (1H, d, J=3.9 Hz), 7.53 (1H, dd, J=1.9, 8.9 Hz), 7.63 (1H, d, J=1.9 Hz), 8.20 (1H, d, J=8.9 Hz), 11.46 (1H, br s), 12.38 (1H, br s).

MS (m/z): 338 (M$^+$), 265 (base).

Example 203

Ethyl 3-(7-ethyl-4-oxo-4,5-dihydropyrrolo[1,2-a]quinoxalin-1-yl)propanoate

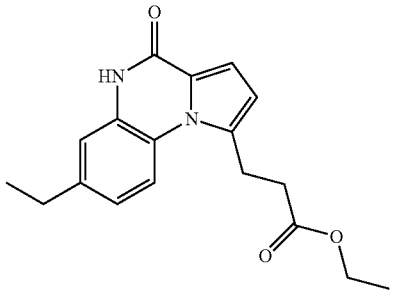 [SMILES: CCOC(=O)CCc1ccc2c(=O)[nH]c3cc(CC)ccc3n12]

4-Ethyl-2-nitroaniline 1.00 g, ethyl 6-(1,3-dioxolan-2-yl)-4-oxohexanoate 1.38 g, p-toluenesulfonic acid monohydride 114 mg and toluene 150 mL were mixed and heated under reflux for 70 hours with Dean-Stark device, and thereafter the solvent was distilled off under reduced pressure. The residue was subjected to silica gel chromatography (chloroform) to provide 1.29 g of a brown, viscous substance, to which 20 mL of acetic acid and 8 mL of water were added, followed by addition of 2.35 g of sodium hyposulfite and 3 hours' heating under reflux. The reaction liquid was allowed to cool off, to which 50 g of ice was added and it was made weakly alkaline with 25% aqueous ammonia, and extracted with ethyl acetate. The organic layer was washed with 20 mL of saturated brine, dried over anhydrous magnesium sulfate and from which the solvent was distilled off under reduced pressure. The residue was purified on silica gel chromatography (hexane:ethyl acetate=1:1) to provide 471 mg of a brown, viscous substance. It was mixed with 178 mg of triphosgene and 10 mL of toluene, and heated under reflux for 14.5 hours. Cooling the reaction liquid off, the precipitate was recovered by filtration, washed with ethyl acetate and dried under reduced pressure to provide 277 mg of the title compound.

$^1$H-NMR (DMSO-d$_6$, δ): 1.1-1.3 (6H, m), 2.65 (2H, q, J=7.5 Hz), 2.82 (2H, t, J=7.3 Hz), 3.45 (2H, t, J=7.3 Hz), 4.10 (2H, q, J=7.2 Hz), 6.42 (1H, d, J=4.2 Hz), 6.98 (1H, d, J=4.2 Hz), 7.06 (1H, dd, J=1.9, 8.9 Hz), 7.16 (1H, d, J=1.9 Hz), 7.93 (1H, d, J=8.9 Hz), 11.14 (1H, br s).

MS (m/z): 312 (M$^+$), 225 (base).

Example 204

3-(7-Ethyl-4-oxo-4,5-dihydropyrrolo[1,2-a]quinoxalin-1-yl)-propanoic acid

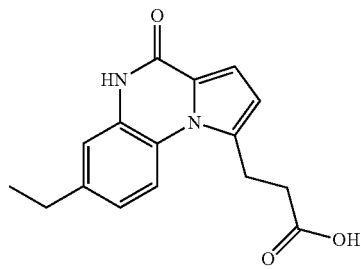 [SMILES: CCc1ccc2c(c1)[nH]c(=O)c1ccc(CCC(=O)O)n12]

The title compound was obtained from ethyl 3-(7-ethyl-4-oxo-4,5-dihydropyrrolo[1,2-a]quinoxalin-1-yl)propanoate as synthesized in above Example 203, by the operations similar to Example 58.

$^1$H-NMR (DMSO-d$_6$, δ): 1.21 (3H, t, J=7.5 Hz), 2.64 (2H, q, J=7.5 Hz), 2.75 (2H, t, J=7.3 Hz), 3.42 (2H, t, J=7.3 Hz), 6.43 (1H, d, J=3.9 Hz), 6.99 (1H, d, J=3.9 Hz), 7.06 (1H, dd, J=1.9, 8.5 Hz), 7.16 (1H, d, J=1.9 Hz), 7.93 (1H, d, J=8.5 Hz), 11.14 (1H, br s), 12.34 (1H, br s).

MS (m/z): 284 (M$^+$), 225 (base).

Example 205

Ethyl 3-(7-methyl-4-oxo-4,5-dihydropyrrolo[1,2-a]quinoxalin-1-yl)propanoate

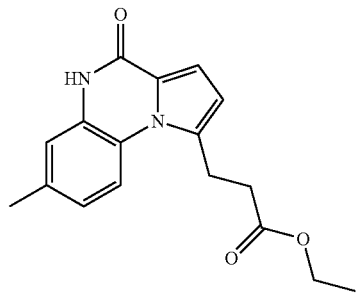 [SMILES: CCOC(=O)CCc1ccc2c(=O)[nH]c3cc(C)ccc3n12]

The title compound was obtained by similar operations to Example 203.

$^1$H-NMR (DMSO-d$_6$, δ): 1.19 (3H, t, J=7.1 Hz), 2.34 (3H, s), 2.82 (2H, t, J=7.3 Hz), 3.45 (2H, t, J=7.3 Hz), 4.10 (2H, q, J=7.1 Hz), 6.42 (1H, d, J=4.0 Hz), 6.98 (1H, d, J=4.0 Hz), 7.02 (1H, dd, J=1.5, 8.7 Hz), 7.12 (1H, d, J=1.5 Hz), 7.90 (1H, d, J=8.7 Hz), 11.15 (1H, br s).

MS (m/z): 298 (M$^+$), 211 (base).

Example 206

3-(7-Methyl-4-oxo-4,5-dihydropyrrolo[1,2-a]quinoxalin-1-yl)-propanoic acid

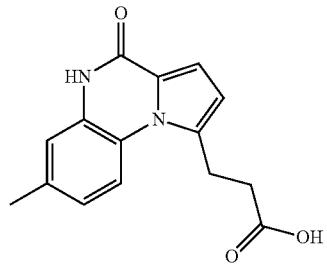 [SMILES: Cc1ccc2c(c1)[nH]c(=O)c1ccc(CCC(=O)O)n12]

The title compound was obtained from ethyl 3-(7-methyl-4-oxo-4,5-dihydropyrrolo[1,2-a]quinoxalin-1-yl)propanoate as synthesized in above Example 205, by the operations similar to Example 58.

$^1$H-NMR (DMSO-d$_6$, δ): 2.34 (3H, s), 2.75 (2H, t, J=7.3 Hz), 3.41 (2H, t, J=7.3 Hz), 6.43 (1H, d, J=4.0 Hz), 6.99 (1H, d, J=4.0 Hz), 7.02 (1H, dd, J=1.5, 8.5 Hz), 7.12 (1H, d, J=1.5 Hz), 7.90 (1H, d, J=8.5 Hz), 11.14 (1H, br s), 12.33 (1H, br s).

MS (m/z): 270 (M$^+$), 211 (base).

Example 207

Ethyl 3-(4-oxo-7-propyl-4,5-dihydropyrrolo[1,2-a]quinoxalin 1-yl)propanoate

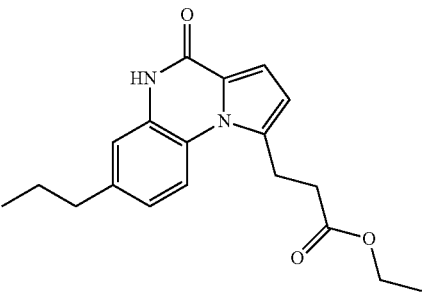 [SMILES: CCCc1ccc2c(c1)[nH]c(=O)c1ccc(CCC(=O)OCC)n12]

The title compound was obtained by similar operations to Example 203.

$^1$H-NMR (DMSO-d$_6$, δ): 0.92 (3H, t, J=7.3 Hz), 1.19 (3H, t, J=7.2 Hz), 1.62 (2H, sextet, J=7.3 Hz), 2.59 (2H, t, J=7.3 Hz), 2.82 (2H, t, J=7.3 Hz), 3.46 (2H, t, J=7.3 Hz), 4.10 (2H, q, J=7.2 Hz), 6.42 (1H, d, J=4.0 Hz), 6.98 (1H, d, J=4.0 Hz), 7.04 (1H, dd, J=1.5, 8.5 Hz), 7.13 (1H, d, J=1.5 Hz), 7.92 (1H, d, J=8.5 Hz), 11.14 (1H, br s).

MS (m/z): 326 (M$^+$), 239 (base).

Example 208

3-(4-Oxo-7-propyl-4,5-dihydropyrrolo[1,2-a]quinoxalin-1-yl)propanoic acid

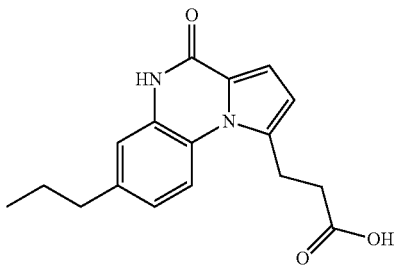

The title compound was obtained from ethyl 3-(4-oxo-7-propyl-4,5-dihydropyrrolo[1,2-a]quinoxalin-1-yl)propanoate as synthesized in Example 207, by the operations similar to Example 58.

$^1$H-NMR (DMSO-$d_6$, δ): 0.92 (3H, t, J=7.3 Hz), 1.62 (2H, sex, J=7.3 Hz), 2.59 (2H, t, J=7.3 Hz), 2.75 (2H, t, J=7.3 Hz), 3.42 (2H, t, J=7.3 Hz), 6.44 (1H, d, J=3.9 Hz), 6.99 (1H, d, J=3.9 Hz), 7.04 (1H, dd, J=1.9, 8.5 Hz), 7.13 (1H, d, J=1.9 Hz), 7.93 (1H, d, J=8.5 Hz), 11.13 (1H, br s), 12.33 (1H, br s).

MS (m/z): 298 (M$^+$), 239 (base).

Example 209

Ethyl 3-(7-butyl-4-oxo-4,5-dihydropyrrolo[1,2-a]quinoxalin-1-yl)propanoate

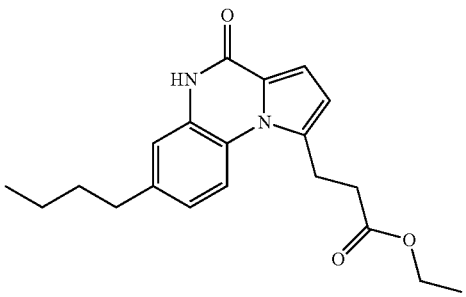 [SMILES: CCCCc1ccc2c(c1)[nH]c(=O)c1ccc(CCC(=O)OCC)n12]

The title compound was obtained by similar operations to Example 203.

$^1$H-NMR (DMSO-$d_6$, δ): 0.92 (3H, t, J=7.3 Hz), 1.19 (3H, t, J=6.9 Hz), 1.34 (2H, sex, J=7.3 Hz), 1.5-1.7 (2H, m), 2.61 (2H, t, J=7.3 Hz), 2.82 (2H, t, J=7.3 Hz), 3.45 (2H, t, J=7.3 Hz), 4.10 (2H, q, J=6.9 Hz), 6.42 (1H, d, J=4.0 Hz), 6.98 (1H, d, J=4.0 Hz), 7.04 (1H, dd, J=1.8, 8.5 Hz), 7.14 (1H, d, J=1.8 Hz), 7.92 (1H, d, J=8.5 Hz), 11.13 (1H, br s).

MS (m/z): 340 (M$^+$), 253 (base).

Example 210

3-(7-Butyl-4-oxo-4,5-dihydropyrrolo[1,2-a]quinoxalin-1-yl)-propanoic acid

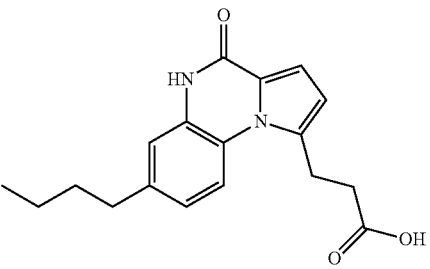

The title compound was obtained from ethyl 3-(7-butyl-4-oxo-4,5-dihydropyrrolo[1,2-a]quinoxalin-1-yl)propanoate as synthesized in above Example 209, by the operations similar to Example 58.

$^1$H-NMR (DMSO-$d_6$, δ): 0.92 (3H, t, J=7.3 Hz), 1.34 (2H, sex, J=7.3 Hz), 1.5-1.7 (2H, m), 2.61 (2H, t, J=7.3 Hz), 2.75 (2H, t, J=7.3 Hz), 3.42 (2H, t, J=7.3 Hz), 6.43 (1H, d, J=4.0 Hz), 6.99 (1H, d, J=4.0 Hz), 7.04 (1H, dd, J=1.7, 8.9 Hz), 7.14 (1H, d, J=1.7 Hz), 7.92 (1H, d, J=8.9 Hz), 11.12 (1H, br s), 12.34 (1H, br s).

MS (m/z): 312 (M$^+$), 253 (base).

Example 211

Ethyl 3-(7,8-dimethyl-4-oxo-4,5-dihydropyrrolo[1,2-a]-quinoxalin-1-yl)propanoate

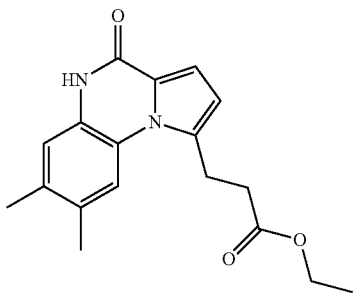 [SMILES: CCOC(=O)CCc1ccc2c(=O)[nH]c3cc(C)c(C)cc3n12]

The title compound was obtained by similar operations to Example 203.

$^1$H-NMR (DMSO-$d_6$, δ): 1.19 (3H, t, J=7.1 Hz), 2.24 (3H, s), 2.30 (3H, s), 2.81 (2H, t, J=7.3 Hz), 3.47 (2H, t, J=7.3 Hz), 4.11 (2H, q, J=7.1 Hz), 6.41 (1H, d, J=3.9 Hz), 6.96 (1H, d, J=3.9 Hz), 7.08 (1H, s), 7.77 (1H, s), 11.06 (1H, br s).

MS (m/z): 312 (M$^+$), 225 (base).

Example 212

3-(7,8-Dimethyl-4-oxo-4,5-dihydropyrrolo[1,2-a]quinoxalin-1-yl)propanoic acid

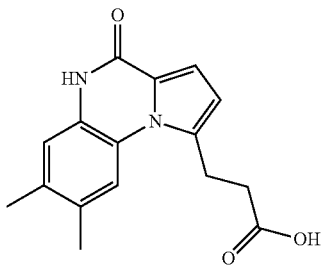 [SMILES: Cc1cc2[nH]c(=O)c3ccc(CCC(=O)O)n3c2cc1C]

The title compound was obtained from ethyl 3-(7,8-dimethyl-4-oxo-4,5-dihydropyrrolo[1,2-a]quinoxalin-1-yl)propanoate as synthesized in above Example 211, by the operations similar to Example 58.

$^1$H-NMR (DMSO-d$_6$, δ): 2.24 (3H, s), 2.30 (3H, s), 2.74 (2H, t, J=7.3 Hz), 3.45 (2H, t, J=7.3 Hz), 6.42 (1H, d, J=3.9 Hz), 6.96 (1H, d, J=3.9 Hz), 7.08 (1H, s), 7.79 (1H, s), 11.05 (1H, br s), 12.36 (1H, br s).

MS (m/z): 284 (M$^+$), 225 (base).

Example 213

Ethyl 3-(7-methoxy-4-oxo-4,5-dihydropyrrolo[1,2-a]quinoxalin 1-yl)propanoate

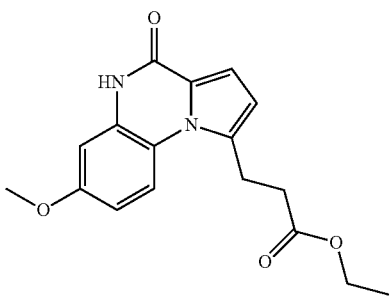

The title compound was obtained by similar operations to Example 203.

$^1$H-NMR (DMSO-d$_6$, δ): 1.20 (3H, t, J=6.9 Hz), 2.82 (2H, t, J=7.3 Hz), 3.43 (2H, t, J=7.3 Hz), 3.79 (3H, s), 4.10 (2H, q, J=6.9 Hz), 6.40 (1H, d, J=3.9 Hz), 6.80 (1H, dd, J=2.9, 9.2 Hz), 6.88 (1H, d, J=2.9 Hz), 6.97 (1H, d, J=3.9 Hz), 7.93 (1H, d, J=9.2 Hz), 11.11 (1H, br s).

MS (m/z): 314 (M$^+$), 227 (base).

Example 214

3-(7-Methoxy-4-oxo-4,5-dihydropyrrolo[1,2-a]quinoxalin-1-yl)-propanoic acid

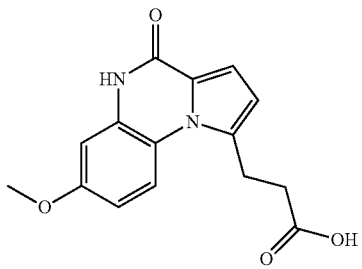

The title compound was obtained from ethyl 3-(7-methoxy-4-oxo-4,5-dihydropyrrolo[1,2-a]quinoxalin-1-yl)propanoate as synthesized in above Example 213, by the operations similar to Example 58.

$^1$H-NMR (DMSO-d$_6$, δ): 2.75 (2H, t, J=7.3 Hz), 3.39 (2H, t, J=7.3 Hz), 3.79 (3H, s), 6.41 (1H, d, J=4.1 Hz), 6.81 (1H, dd, J=2.7, 9.2 Hz), 6.88 (1H, d, J=2.7 Hz), 6.97 (1H, d, J=4.1 Hz), 7.94 (1H, d, J=9.2 Hz), 11.10 (1H, br s), 12.34 (1H, br s).

MS (m/z): 286 (M$^+$), 227 (base).

Example 215

Ethyl 3-(7-ethoxy-4-oxo-4,5-dihydropyrrolo[1,2-a]quinoxalin-1-yl)propanoate

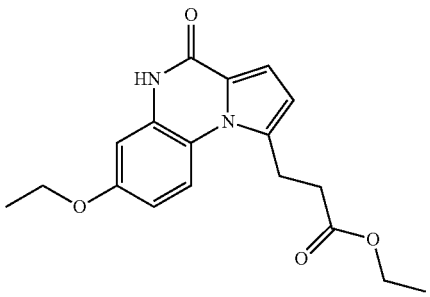 [SMILES: CCOC(=O)CCc1ccc2c(=O)[nH]c3cc(OCC)ccc3n12]

The title compound was obtained by similar operations to Example 203.

$^1$H-NMR (DMSO-d$_6$, δ): 1.20 (3H, t, J=6.9 Hz), 1.35 (3H, t, J=6.9 Hz), 2.82 (2H, t, J=7.3 Hz), 3.43 (2H, t, J=7.3 Hz), 4.05 (2H, q, J=6.9 Hz), 4.10 (2H, q, J=6.9 Hz), 6.40 (1H, d, J=4.0 Hz), 6.79 (1H, dd, J=2.9, 9.2 Hz), 6.86 (1H, d, J=2.9 Hz), 6.97 (1H, d, J=4.0 Hz), 7.92 (1H, d, J=9.2 Hz), 11.10 (1H, br s).

MS (m/z): 328 (M$^+$), 241 (base).

Example 216

3-(7-Ethoxy-4-oxo-4,5-dihydropyrrolo[1,2-a]quinoxalin-1-yl)-propanoic acid

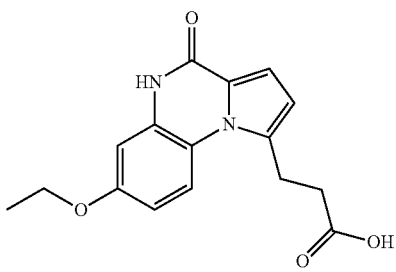

The title compound was obtained from ethyl 3-(7-ethoxy-4-oxo-4,5-dihydropyrrolo[1,2-a]quinoxalin-1-yl)propanoate as synthesized in above Example 215, by the operations similar to Example 58.

$^1$H-NMR (DMSO-d$_6$, δ): 1.36 (3H, t, J=6.9 Hz), 2.75 (2H, t, J=7.3 Hz), 3.39 (2H, t, J=7.3 Hz), 4.05 (2H, q, J=6.9 Hz), 6.40 (1H, d, J=3.9 Hz), 6.79 (1H, dd, J=2.9, 9.2 Hz), 6.86 (1H, d, J=2.9 Hz), 6.97 (1H, d, J=3.9 Hz), 7.92 (1H, d, J=9.2 Hz), 11.10 (1H, br s), 12.33 (1H, br s).

MS (m/z): 300 (M$^+$), 241 (base).

Example 217

3-Chloro-9-cyclohexylimidazo[1,5-a]pyrido[3,2-e]pyrazin-6 (5H)-one

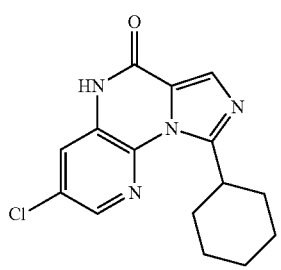 [SMILES: O=c1[nH]c2cc(Cl)cnc2n2c(C3CCCCC3)ncc12]

3-Amino-5-chloro-2-(2-cyclohexyl-1H-imidazol-1-yl)pyridine as synthesized in Production Example 103, 838 mg, 1,1'-carbonyldi-imidazole 983 mg and 1,2-chlorobenzene 25 mL were mixed and heated under reflux for 15 hours. Cooling the reaction liquid off, the precipitate was recovered by filtration and washed with methanol. The resulting crystals were dissolved in a liquid mixture of 2N hydrochloric acid and methanol, and the insoluble matter was separated by filtration. The filtrate was made weakly alkaline with saturated aqueous sodium hydrogencarbonate solution, and the precipitate was recovered by filtration. Drying the same in flowing air under heating, 620 mg of the title compound was obtained.

$^1$H-NMR (DMSO-d$_6$, δ): 1.2-1.7 (5H, m), 1.6-2.1 (5H, m), 3.9-4.1 (1H, m), 7.66 (1H, d, J=2.3 Hz), 7.79 (1H, s), 8.30 (1H, d, J=2.3 Hz), 11.47 (1H, br s).

MS (m/z): 304 (M$^+$+2), 302 (M$^+$), 234 (base).

Production Example 1

3-(1H-imidazol-2-yl)-2-methylpyridine

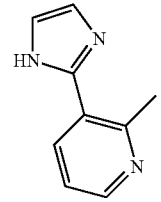

2-Methyl-3-pyridinecarbonitrile 1.05 g, ethylenediamine 5 mL and sulfur 71 mg were mixed, and stirred at 120° C. for 24 hours. Cooling it off to room temperature, toluene and water were added to effect phase separation. The aqueous layer was dried to solid under reduced pressure. Thus obtained crude product was mixed with potassium permanganate/silicon dioxide (carried at a ratio of 2.81 g:3.57 g) 6.38 g and acetonitrile 10 mL at room temperature, and stirred (inducing a rapid exothermic reaction). After the exotherm subsided and the reaction liquid was restored to room temperature, the liquid was diluted with 20 mL of ethanol and filtered through Celite. The solvent was distilled off and the residue was recrystallized from ethyl acetate/methanol (10:1) to provide 1.03 g of the title compound.

$^1$H-NMR (DMSO-d$_6$, δ): 2.73 (3H, s), 7.1-7.3 (3H, m), 7.95 (1H, dd, J=1.9, 7.7 Hz), 8.44 (1H, dd, J=1.9, 5.0 Hz).

MS (m/z): 159 (M$^+$).

Production Example 2

2-(3-Thienyl)-1H-imidazole

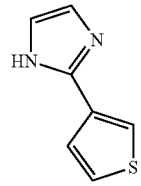

To 11.96 g of thiophene-3-carbaldehyde, 142 mL of ethanol was added, and into which 25 mL of 40% glyoxal solution and 53 mL of 25% aqueous ammonia were successively dropped under cooling with ice, followed by an overnight's stirring at room temperature. After distilling the solvent off, water was added to the residue, followed by extraction with a mixed solvent of tetrahydrofuran and tert-butyl methyl ether. The organic layer was washed with water and extracted with diluted hydrochloric acid. The aqueous layer was rendered alkaline with aqueous sodium hydroxide solution. Extracting the same with ethyl acetate, the organic layer was washed with water and dried over magnesium sulfate. Distilling the solvent off, 1.50 g of the title compound was obtained.

$^1$H-NMR (CDCl$_3$, δ): 7.10 (2H, br s), 7.37 (1H, dd, J=2.7, 5.0 Hz), 7.50 (1H, dd, J=1.4, 5.2 Hz), 7.64 (1H, dd, J=1.2, 3.1 Hz).

MS (m/z): 150 (M$^+$).

Production Example 3

N,N-dimethyl-3-nitro-4-[2-(3-thienyl)-1H-imidazol-1-yl]-benzamide

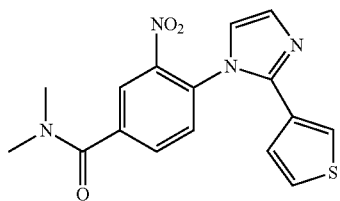 [SMILES: CN(C)C(=O)c1ccc(-n2ccnc2-c2ccsc2)c([N+](=O)[O-])c1]

4-Fluoro-N,N-dimethyl-3-nitrobenzamide 1.06 g, 2-(3-thienyl)-1H-imidazole as synthesized in above Production Example 2, 747 mg, potassium carbonate 1.37 g and N,N-dimethylacetamide 10 mL were mixed, and its outside temperature was heated to 100° C. for 6.5 hours. The reaction liquid was poured into brine and extracted with ethyl acetate. The organic layer was washed with saturated brine and dried over magnesium sulfate. Distilling the solvent off, 1.30 g of the title compound was obtained.

$^1$H-NMR (CDCl$_3$, δ): 2.9-3.3 (6H, m), 7.0-7.1 (2H, m), 7.09 (1H, dd, J=1.2, 5.0 Hz), 7.2-7.3 (2H, m), 7.52 (1H, d, J=7.7 Hz), 7.78 (1H, dd, J=1.9, 8.1 Hz), 8.07 (1H, d, J=1.9 Hz).

MS (m/z): 342 (M$^+$).

Production Example 4

3-Amino-N,N-dimethyl-4-[2-(3-thienyl)-1H-imidazol-1-yl]-benzamide

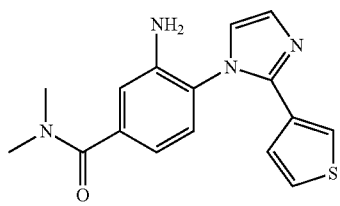 [SMILES: CN(C)C(=O)c1ccc(-n2ccnc2-c2ccsc2)c(N)c1]

To 1.60 g of N,N-dimethyl-3-nitro-4-[2-(3-thienyl)-1H-imidazol-1-yl]benzamide, 5.8 mL of acetic acid and 5.8 mL of water were added, and dissolved under heating. To the solution 3.25 g of 85% sodium hyposulfite was added little by little, followed by 3.3 hours' heating under reflux. The reaction liquid was cooled with ice, to which ethyl acetate was added, and then 25% aqueous ammonia was added little by little to render the same weakly alkaline. Tetrahydrofuran was added and whereby separated organic layer was recovered, which was washed with brine and dried over magnesium sulfate. Distilling the solvent off, 769 mg of the title compound was obtained.

$^1$H-NMR (CDCl$_3$, δ): 2.8-3.3 (6H, m), 3.72 (2H, br s), 6.82 (1H, dd, J=1.7, 7.9 Hz), 6.90 (1H, d, J=1.9 Hz), 6.97 (1H, d, J=1.2 Hz), 7.0-7.3 (4H, m), 7.34 (1H, dd, J=1.2, 5.4 Hz).

MS (m/z): 312 (M$^+$).

Production Example 5

4-[2-(3-Chlorophenyl)-1H-imidazol-1-yl]-N,N-dimethyl-3-nitrobenzamide

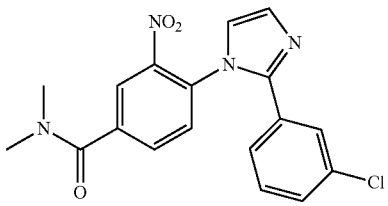 [SMILES: CN(C)C(=O)c1ccc(-n2ccnc2-c2cccc(Cl)c2)c([N+](=O)[O-])c1]

The title compound was obtained by the operations similar to Production Example 3.

MS (m/z): 372 (M$^+$+2), 370 (M$^+$).

Production Example 6

3-Amino-4-[2-(3-chlorophenyl)-1H-imidazol-1-yl]-N,N-dimethylbenzamide

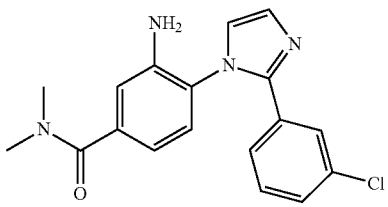

The title compound was obtained from 4-[2-(3-chlorophenyl)-1H-imidazol-1-yl]-N,N-dimethyl-3-nitrobenzamide as synthesized in above Production Example 5, by the operations similar to Production Example 4.

MS (m/z): 342 (M$^+$+2), 340 (M$^+$).

Production Example 7

1-(4-Chloro-2-nitrophenyl)-2-isopropyl-1H-imidazole

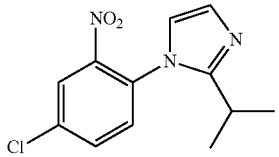 [SMILES: CC(C)c1nccn1-c1ccc(Cl)cc1[N+](=O)[O-]]

A mixture of 4-chloro-1-fluoro-2-nitrobenzene 1.01 g, 2-isopropylimidazole 634 mg, N,N-diisopropylethylamine, 1.46 mL and acetonitrile 12 mL was heated under reflux for 15 hours. The solvent was distilled off and water was added to the residue which was then rendred acidic with diluted hydrochloric acid. After washing the same with diethyl ether, the aqueous layer was rendered alkaline with aqueous sodium hydroxide solution and extracted twice with chloroform. The organic layer was washed with water, dried over magnesium sulfate, and removed of the solvent by distillation to provide 0.98 g of the title compound.

¹H-NMR (CDCl₃, δ): 1.22 (6H, d, J=6.9 Hz), 2.5-2.8 (1H, m), 6.81 (1H, d, J=1.2 Hz), 7.09 (1H, d, J=1.5 Hz), 7.39 (1H, d, J=8.5 Hz), 7.71 (1H, dd, J=2.3, 8.5 Hz), 8.05 (1H, d, J=2.7 Hz).
MS (m/z): 267 (M⁺+2), 265 (M⁺).

Production Example 8

5-Chloro-2-(2-isopropyl-1H-imidazol-1-yl)aniline

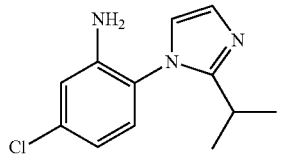

A mixture of 1-(4-chloro-2-nitrophenyl)-2-isopropyl-1H-imidazole as synthesized in above Production Example 7, 0.98 g, tin (II) chloride dihydrate 4.16 g and ethanol 8.8 mL was heated under reflux for 2.7 hours. Neutralizing the reaction liquid with 2N aqueous sodium hydroxide solution under cooling with ice, chloroform was added to the reaction liquid and filtered through Celite. The Celite was washed with chloroform, transferred into a separating funnel and extracted twice with chloroform. The organic layer was washed with water, dried over magnesium sulfate and removed of the solvent by distillation, to provide 0.72 g of the title compound.

¹H-NMR (CDCl₃, δ): 1.21 (6H, d, J=4.2 Hz), 2.6-2.9 (1H, m), 3.63 (2H, br s), 6.7-6.9 (3H, m), 6.99 (1H, d, J=8.5 Hz), 7.12 (1H, d, J=1.5 Hz).
MS (m/z): 237 (M⁺+2), 235 (M⁺).

Production Example 9

Ethyl 4-(2-isopropyl-1H-imidazol-1-yl)-3-nitrobenzoate

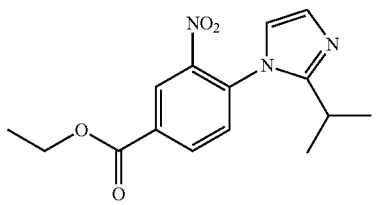

A mixture of ethyl 4-fluoro-3-nitrobenzoate 4.26 g, 2-isopropylimidazole 2.20 g, N,N-diisopropylethylamine 5.2 mL and acetonitrile 40 mL was heated under reflux for 24 hours. After distilling the solvent off, water was added to the residue and extracted with ethyl acetate. The organic layer was washed with brine, dried over magnesium sulfate and removed of the solvent by distillation, to provide 4.95 g of the title compound.

¹H-NMR (CDCl₃, δ): 1.23 (6H, d, J=6.9 Hz), 1.44 (3H, t, J=7.1 Hz), 2.6-2.8 (1H, m), 4.47 (2H, q, J=7.2 Hz), 6.85 (1H, d, J=1.5 Hz), 7.13 (1H, d, J=1.5 Hz), 7.53 (1H, d, J=8.5 Hz), 8.39 (1H, dd, J=1.7, 8.3 Hz), 8.67 (1H, d, J=1.9 Hz).
MS (m/z): 303 (M⁺).

Production Example 10

Ethyl 3-amino-4-(2-isopropyl-1H imidazol-1-yl)benzoate

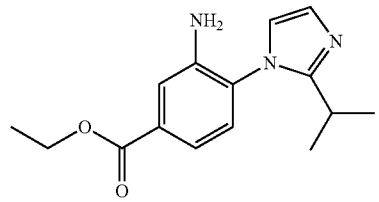 [SMILES: CCOC(=O)c1ccc(-n2ccnc2C(C)C)c([N+](=O)[O-])c1]

A mixture of ethyl 4-(2-isopropyl-1H-imidazol-1-yl)-3-nitrobenzoate as synthesized in above Production Example 9, 4.94 g, methanol 150 mL and 10% palladium carbon 500 mg was stirred for 16 hours in hydrogen atmosphere. After removing the insoluble matter by filtration, the solvent was distilled off to provide 4.12 g of the title compound.

¹H-NMR (CDCl₃, δ): 1.22 (6H, t, J=6.7 Hz), 1.39 (3H, t, J=7.1 Hz), 2.7-2.9 (1H, m), 3.70 (2H, br s), 4.38 (2H, q, J=7.1 Hz), 6.85 (1H, d, J=1.5 Hz), 7.0-7.2 (2H, m), 7.4-7.6 (2H, m).
MS (m/z): 273 (M⁺).

Production Example 11

4-[2-(1-Ethylpropyl)-1H-imidazol-1-yl]-N,N-dimethyl-3-nitrobenzamide

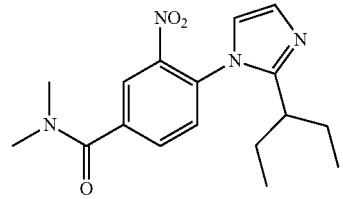 [SMILES: CCC(CC)c1nccn1-c1ccc(C(=O)N(C)C)cc1[N+](=O)[O-]]

The title compound was obtained by carrying out the operations similar to Production Example 3.

¹H-NMR (CDCl₃, δ): 0.76 (6H, t, J=7.3 Hz), 1.4-1.9 (4H, m), 2.1-2.3 (1H, m), 3.0-3.3 (6H, m), 6.90 (1H, d, J=1.5 Hz), 7.16 (1H, d, J=1.5 Hz), 7.44 (1H, d, J=8.1 Hz), 7.79 (1H, dd, J=1.9, 8.1 Hz), 8.10 (1H, d, J=1.9 Hz).
MS (m/z): 330 (M⁺).

Production Example 12

3-Amino-4-[2-(1-ethylpropyl)-1H-imidazol-1-yl]-N,N-dimethylbenzamide

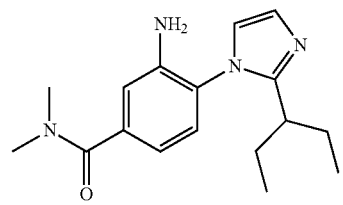

The title compound was obtained from 4-[2-(1-ethylpropyl)-1H-imidazol-1-yl]-N,N-dimethyl-3-nitrobenzamide as synthesized in above Production Example 11, by the operations similar to Production Example 4.

¹H-NMR (CDCl₃, δ): 0.6-1.0 (6H, m), 1.5-1.9 (4H, m), 2.3-2.5 (1H, m), 2.9-3.3 (6H, m), 3.66 (2H, br s), 6.80 (1H, dd, J=1.7, 7.9 Hz), 6.8-7.1 (2H, m), 7.06 (1H, d, J=7.7 Hz), 7.19 (1H, d, J=1.2 Hz).
MS (m/z): 300 (M⁺).

Production Example 13

2-Chloro-4-[2-(1-ethylpropyl)-1H-imidazol-1-yl]-N,N-dimethyl-5-nitrobenzamide

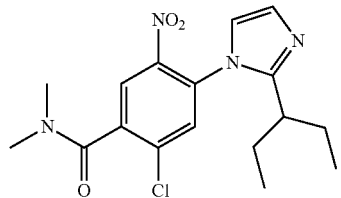 [SMILES: CCC(CC)c1nccn1-c1cc(Cl)c(C(=O)N(C)C)cc1[N+](=O)[O-]]

The title compound was obtained by the operations similar to Production Example 3.

$^1$H-NMR (CDCl$_3$, δ): 0.77 (6H, t, J=7.3 Hz), 1.5-1.9 (4H, m), 2.1-2.3 (1H, m), 2.98 (3H, s), 3.19 (3H, s), 6.89 (1H, d, J=1.5 Hz), 7.17 (1H, d, J=1.5 Hz), 7.46 (1H, s), 8.04 (1H, s).

MS (m/z): 366 (M$^+$+2), 364 (M$^+$).

Production Example 14

5-Amino-2-chloro-4-[2-(1-ethylpropyl)-1H-imidazol-1-yl]-N,N-dimethylbenzamide

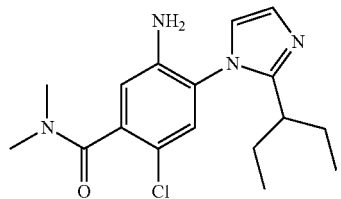

The title compound was obtained from 2-chloro-4-[2-(1-ethylpropyl)-1H-imidazol-1-yl]-N,N-dimethyl-5-nitrobenzamide as synthesized in above Production Example 13, by the operations similar to Production Example 4.

$^1$H-NMR (CDCl$_3$, δ): 0.6-0.9 (6H, m), 1.5-1.9 (4H, m), 2.3-2.5 (1H, m), 2.95 (3H, s), 3.14 (3H, s), 3.69 (2H, br s), 6.74 (1H, s), 6.7-7.0 (1H, m), 7.09 (1H, s), 7.19 (1H, d, J=1.2 Hz).

MS (m/z): 336 (M$^+$+2), 334 (M$^+$).

Production Example 15

Ethyl 4-[2-(1-ethylpropyl)-1H-imidazol-1-yl]-3-nitrobenzoate

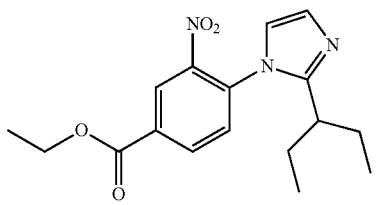

Ethyl 4-fluoro-3-nitrobenzoate 9.16 g, 2-(1-ethylpropyl)-1H-imidazole 5.94 g, N,N-diisopropylethylamine 11.2 mL and acetonitrile 86 mL were mixed and heated under reflux for 15 hours in nitrogen atmosphere. From the reaction liquid the solvent was distilled off, and the residue was dissolved in ethyl acetate and rendered weakly alkaline with saturated aqueous sodium hydrogencarbonate solution. The organic layer was separated, washed with water and dried over magnesium sulfate. Distilling the solvent off, 13.16 g of the title compound was obtained.

$^1$H-NMR (CDCl$_3$, δ): 0.75 (6H, t, J=7.3 Hz), 1.44 (3H, t, J=7.1 Hz), 1.5-1.8 (4H, m), 2.1-2.3 (1H, m), 4.47 (2H, q, J=7.1 Hz), 6.91 (1H, d, J=1.5 Hz), 7.18 (1H, d, J=1.2 Hz), 7.48 (1H, d, J=8.1 Hz), 8.37 (1H, dd, J=1.9, 8.1 Hz), 8.67 (1H, d, J=1.9 Hz).

MS (m/z): 331 (M$^+$).

Production Example 16

Ethyl 3-amino-4-[2-(1-ethylpropyl)-1H-imidazol-1-yl]benzoate

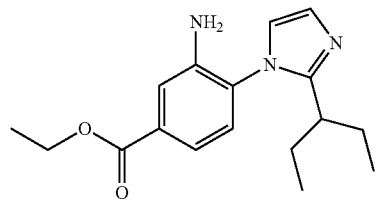 [SMILES: CCOC(=O)c1ccc(-n2ccnc2C(CC)CC)c([N+](=O)[O-])c1]

The title compound was obtained from ethyl 4-[2-(1-ethylpropyl)-1H-imidazol-1-yl]-3-nitrobenzoate as synthesized in above Production Example 15, by the operations similar to Production Example 4.

$^1$H-NMR (CDCl$_3$, δ): 0.6-0.9 (6H, m), 1.40 (3H, t, J=7.1 Hz), 1.5-1.8 (4H, m), 2.2-2.4 (1H, m), 3.70 (2H, br s), 4.38 (2H, q, J=7.2 Hz), 6.87 (1H, d, J=1.5 Hz), 7.10 (1H, d, J=8.1 Hz), 7.20 (1H, s), 7.47 (1H, dd, J=1.9, 8.1 Hz), 7.51 (1H, d, J=1.9 Hz).

MS (m/z): 301 (M$^+$).

Production Example 17

Ethyl 2-chloro-4-[2-(1-ethylpropyl)-1H-imidazol-1-yl]-5-nitrobenzoate

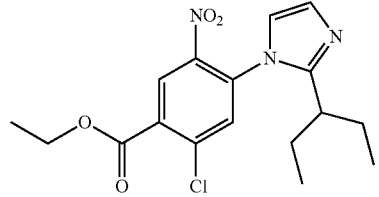 [SMILES: CCOC(=O)c1cc([N+](=O)[O-])c(-n2ccnc2C(CC)CC)cc1Cl]

The title compound was obtained by the operations similar to Production Example 3.

$^1$H-NMR (CDCl$_3$, δ): 0.76 (6H, t, J=7.3 Hz), 1.45 (3H, t, J=7.3 Hz), 1.5-1.8 (4H, m), 2.1-2.3 (1H, m), 4.48 (2H, q, J=7.3 Hz), 6.89 (1H, d, J=1.5 Hz), 7.17 (1H, d, J=11.2 Hz), 7.51 (1H, s), 8.55 (1H, s).

MS (m/z): 365 (M$^+$).

Production Example 18

Ethyl 5-amino-2-chloro-4-[2-(1-ethylpropyl)-1H-imidazol-1-yl]-benzoate

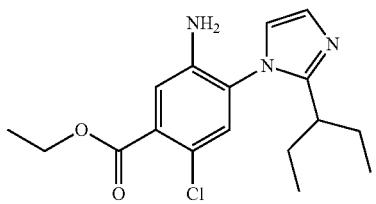

The title compound was obtained from ethyl 2-chloro-4-[2-(1-ethylpropyl)-1H-imidazol-1-yl]-5-nitrobenzoate as synthesized in above Production Example 17, by the operations similar to Production Example 4.

$^1$H-NMR (CDCl$_3$, δ): 0.72 (6H, t, J=7.3 Hz), 1.32 (3H, t, J=7.3 Hz), 1.4-1.8 (4H, m), 2.2-2.4 (1H, m), 4.33 (2H, q, J=7.0 Hz), 5.25 (2H, s), 7.08 (1H, d, J=1.1 Hz), 7.11 (1H, d, J=1.5 Hz), 7.13 (1H, s), 7.27 (1H, s).

MS (m/z): 335 (M$^+$).

Production Example 19

Methyl 4-[2-(1-ethylpropyl)-1H-imidazol-1-yl]-2-methoxy-5-nitrobenzoate

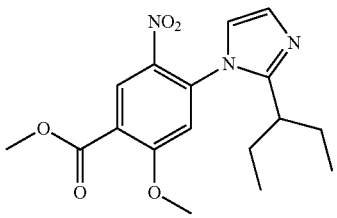

The title compound was obtained by the operations similar to Production Example 3.

$^1$H-NMR (CDCl$_3$, δ): 0.75 (6H, t, J=7.3 Hz), 1.5-1.9 (4H, m), 2.1-2.3 (1H, m), 3.96 (3H, s), 3.98 (3H, s), 6.88 (1H, s), 6.91 (1H, d, J=1.5 Hz), 7.18 (1H, d, J=1.5 Hz), 8.64 (1H, s).

MS (m/z): 347 (M$^+$).

Production Example 20

Methyl 5-amino-4-[2-(1-ethylpropyl)-1H-imidazol-1-yl]-2-methoxybenzoate

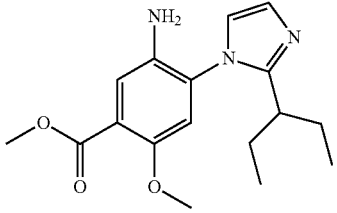 [SMILES: CCC(CC)c1nccn1-c1cc(OC)c(C(=O)OC)cc1[N+](=O)[O-]]

The title compound was obtained from methyl 4-[2-(1-ethylpropyl)-1H-imidazol-1-yl]-2-methoxy-5-nitrobenzoate as synthesized in above Production Example 19, by the operations similar to Production Example 4.

$^1$H-NMR (CDCl$_3$, δ): 0.7-0.9 (6H, m), 1.5-1.9 (4H, m), 2.2-2.5 (1H, m), 3.40 (2H, br s), 3.79 (3H, s), 3.92 (3H, s), 6.69 (1H, s), 6.88 (1H, d, J=1.5 Hz), 7.19 (1H, d, J=1.6 Hz), 7.27 (1H, s).

MS (m/z): 317 (M$^+$).

Production Example 21

Ethyl 3-[2-(1-ethylpropyl)-1H-imidazol-1-yl]-4-nitrobenzoate

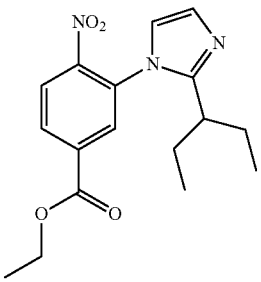 [SMILES: CCOC(=O)c1ccc([N+](=O)[O-])c(-n2ccnc2C(CC)CC)c1]

The title compound was obtained by the operations similar to Production Example 3.

$^1$H-NMR (CDCl$_3$, δ): 0.77 (6H, t, J=7.3 Hz), 1.42 (3H, t, J=7.3 Hz), 1.5-1.9 (4H, m), 2.1-2.3 (1H, m), 4.44 (2H, q, J=7.3 Hz), 6.92 (1H, d, J=1.1 Hz), 7.17 (1H, d, J=1.5 Hz), 8.0-8.1 (2H, m), 8.28 (1H, dd, J=1.5, 8.5 Hz).

MS (m/z): 331 (M$^+$).

Production Example 22

Ethyl 4-amino-3-[2-(1-ethylpropyl)-1H-imidazol-1-yl]benzoate

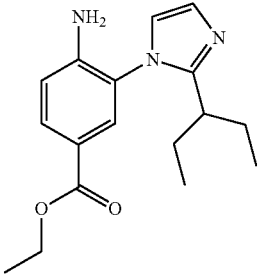

The title compound was obtained from ethyl 3-[2-(1-ethylpropyl)-1H-imidazol-1-yl]-4-nitrobenzoate as synthesized in above Production Example 21, by the operations similar to Production Example 4.

$^1$H-NMR (CDCl$_3$, δ): 0.74 (3H, t, J=7.3 Hz), 0.82 (3H, t, J=7.3 Hz), 1.34 (3H, t, J=7.1 Hz), 1.5-1.8 (4H, m), 2.2-2.4 (1H, m), 4.02 (2H, br s), 4.32 (2H, q, J=6.9 Hz), 6.79 (1H, d, J=8.5 Hz), 6.87 (1H, d, J=1.2 Hz), 7.19 (1H, d, J=1.2 Hz), 7.77 (1H, d, J=1.9 Hz), 7.92 (1H, dd, J=1.9, 8.5 Hz).

MS (m/z): 301 (M$^+$).

Production Example 23

4-(2-Cyclohexyl-1H-imidazol-1-yl)-N,N-dimethyl-3-nitrobenzamide

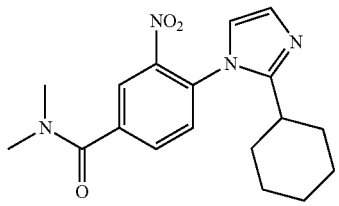

The title compound was obtained by the operations similar to Production Example 3.

$^1$H-NMR (CDCl$_3$, δ): 1.0-1.4 (3H, m), 1.4-1.9 (7H, m), 2.2-2.4 (1H, m), 2.9-3.3 (6H, m), 6.82 (1H, d, J=1.5 Hz), 7.11 (1H, d, J=1.2 Hz), 7.47 (1H, d, J=8.1 Hz), 7.79 (1H, dd, J=1.9, 8.1 Hz), 8.10 (1H, d, J=1.9 Hz).
MS (m/z): 342 (M$^+$).

Production Example 4

3-Amino-4-(2-cyclohexyl-1H-imidazol-1-yl)-N,N-dimethylbenzamide

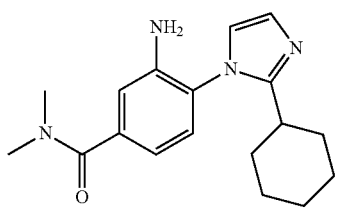 [SMILES: CN(C)C(=O)c1ccc(-n2ccnc2C2CCCCC2)c(N)c1]

The title compound was obtained from 4-(2-cyclohexyl-1H-imidazol-1-yl)-N,N-dimethyl-3-nitrobenzamide as synthesized in above Production Example 23, by the operations similar to Production Example 4.

$^1$H-NMR (CDCl$_3$, δ): 1.0-1.4 (3H, m), 1.4-2.0 (7H, m), 2.3-2.5 (1H, m), 2.9-3.3 (6H, m), 3.64 (2H, m), 6.7-7.0 (2H, m), 6.87 (1H, d, J=1.9 Hz), 7.07 (1H, d, J=8.1 Hz), 7.14 (1H, d, J=1.2 Hz).
MS (m/z): 312 (M$^+$).

Production Example 25

Ethyl 4-(2-cyclohexyl-1H-imidazol 1-yl)-3-nitrobenzoate

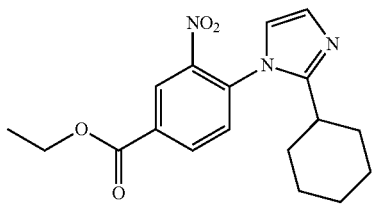

The title compound was obtained by the operations similar to Production Example 15.

$^1$H-NMR (CDCl$_3$, δ): 1.0-1.4 (3H, m), 1.45 (3H, t, J=7.1 Hz), 1.5-1.9 (7H, m), 2.2-2.4 (1H, m), 4.48 (2H, q, J=7.2 Hz), 6.83 (1H, d, J=1.2 Hz), 7.12 (1H, d, J=1.2 Hz), 7.51 (1H, d, J=8.1 Hz), 8.39 (1H, dd, J=1.9, 8.5 Hz), 8.66 (1H, d, J=1.9 Hz).
MS (m/z): 343 (M$^+$).

Production Example 26

Ethyl 3-amino-4-(2-cyclohexyl-1H-imidazol-1-yl)benzoate

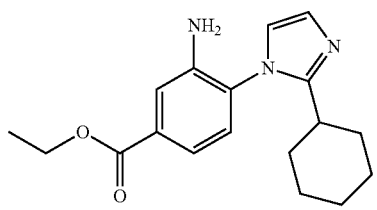 [SMILES: CCOC(=O)c1ccc(-n2ccnc2C2CCCCC2)c(N)c1]

The title compound was obtained from ethyl 4-(2-cyclohexyl-1H-imidazol-1-yl)-3-nitrobenzoate as synthesized in above Production Example 25, by the operations similar to Production Example 4.

$^1$H-NMR (CDCl$_3$, δ): 1.0-1.4 (3H, m), 1.40 (3H, t, J=7.1 Hz), 1.5-2.0 (7H, m), 2.3-2.5 (1H, m), 3.68 (2H, br s), 4.39 (2H, q, J=7.2 Hz), 6.84 (1H, d, J=1.2 Hz), 7.0-7.2 (2H, m), 7.4-7.6 (2H, m).
MS (m/z): 313 (M$^+$).

Production Example 27

Methyl 4-(2-cyclohexyl-1H-imidazol-1-yl)-2-methoxy-5-nitrobenzoate

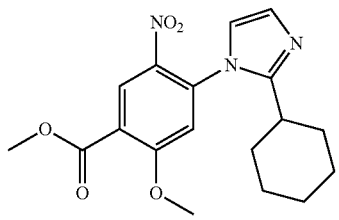 [SMILES: COC(=O)c1cc([N+](=O)[O-])c(-n2ccnc2C2CCCCC2)cc1OC]

A mixture of methyl 4-fluoro-2-methoxy-5-nitrobenzoate 8.57 g, 2-cyclohexylimidazole 5.61 g, potassium carbonate 10.34 g and N,N-dimethylacetamide 75 mL was heated at 100° C. for 5 hours in nitrogen atmosphere. The reaction liquid was diluted with ethyl acetate, poured in water and the organic layer was separated. The organic layer was washed with brine, dried over magnesium sulfate and removed of the solvent by distillation to provide 13.52 g of the title compound.

$^1$H-NMR (CDCl$_3$, δ): 1.0-1.4 (3H, m), 1.5-1.9 (7H, m), 2.2-2.4 (1H, m), 3.97 (3H, s), 4.00 (3H, s), 6.84 (1H, d, J=1.5 Hz), 6.91 (1H, s), 7.13 (1H, d, J=1.2 Hz), 8.66 (1H, s).
MS (m/z): 359 (M$^+$).

Production Example 28

Methyl 5-amino-4-(2-cyclohexyl-1H-imidazol-1-yl)-2-methoxybenzoate

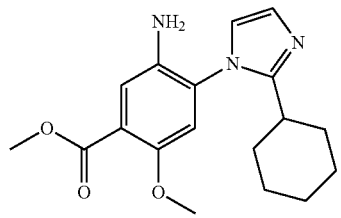

To 13.51 g of methyl 4-(2-cyclohexyl-1H-imidazol-1-yl)-2-methoxy-5-nitrobenzoate as synthesized in above Production Example 27, acetic acid 55 mL and water 55 mL were added and heated to form a solution, to which 22.59 g of 87% sodium hyposulfite was added little by little, followed by heating under reflux for 3.2 hours. The reaction liquid was cooled with ice, to which ethyl acetate and tetrahydrofuran were added, and it was rendered weakly alkaline by addition of 25% aqueous ammonia little by little. The organic layer was separated, washed with saturated brine, dried over magnesium sulfate and removed of the solvent by distillation to provide 9.13 g of the title compound.

$^1$H-NMR (CDCl$_3$, δ): 1.0-1.4 (3H, m), 1.5-1.9 (7H, m), 2.3-2.5 (1H, m), 3.37 (2H, br s), 3.81 (3H, s), 3.92 (3H, s), 6.72 (1H, s), 6.86 (1H, d, J=1.5 Hz), 7.15 (1H, d, J=1.2 Hz), 7.29 (1H, s).

MS (m/z): 329 (M$^+$).

Production Example 29

Methyl 4-(2-cyclohexyl-4-methyl-1H-imidazol-1-yl)-2-methoxy-5-nitrobenzoate

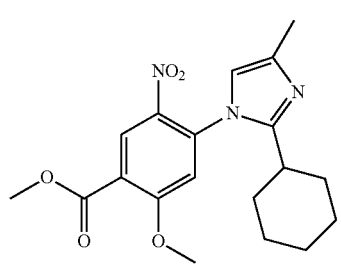 [SMILES: COC(=O)c1cc(N)c(-n2cc(C)nc2C2CCCCC2)cc1OC]

The title compound was obtained by the operations similar to Production Example 3.

$^1$H-NMR (CDCl$_3$, δ): 1.0-1.4 (3H, m), 1.5-1.9 (7H, m), 2.1-2.3 (1H, m), 2.25 (3H, d, J=1.2 Hz), 3.96 (3H, s), 3.99 (3H, s), 6.54 (1H, d, J=0.8 Hz), 6.89 (1H, s), 8.62 (1H, s).

MS (m/z): 373 (M$^+$).

Production Example 30

Methyl 5-amino-4-(2-cyclohexyl-4-methyl-1H-imidazol-1-yl)-2-methoxybenzoate

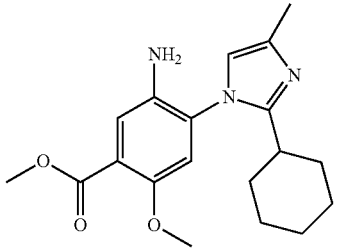

The title compound was obtained from methyl 4-(2-cyclohexyl-4-methyl-1H-imidazol-1-yl)-2-methoxy-5-nitrobenzoate as synthesized in above Production Example 29, by the operations similar to Production Example 4.

$^1$H-NMR (CDCl$_3$, δ): 1.0-1.4 (3H, m), 1.5-1.9 (7H, m), 2.26 (3H, s), 2.3-2.5 (1H, m), 3.39 (2H, br s), 3.80 (3H, s), 3.91 (3H, s), 6.55 (1H, s), 6.70 (1H, s), 7.27 (1H, s).

MS (m/z): 343 (M$^+$).

Production Example 31

Ethyl 2-ethoxy-4-fluorobenzoate

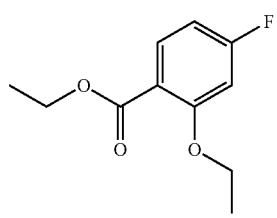

To a liquid mixture of 4-fluoro-2-hydroxybenzoic acid 5.00 g, toluene 32 mL and potassium carbonate 13.29 g, diethyl sulfate 12.6 mL was dropped, followed by an hour's stirring at room temperature and further addition of 25 mL of toluene. After 16 hours' heating under reflux, the reaction liquid was allowed to cool off, to which tert-butyl methyl ether was added and the whole liquid was poured in ice water. The organic layer was extracted, washed with saturated brine and dried over magnesium sulfate. Distilling the solvent off, 6.52 g of the title compound was obtained.

$^1$H-NMR (CDCl$_3$, δ): 1.37 (3H, t, J=7.1 Hz), 1.47 (3H, t, J=6.9 Hz), 4.08 (2H, q, J=6.9 Hz), 4.33 (2H, q, J=7.1 Hz), 6.6-6.7 (2H, m), 7.7-7.9 (1H, m).

MS (m/z): 212 (M$^+$).

Production Example 32

Ethyl 2-ethoxy-4-fluoro-5-nitrobenzoate

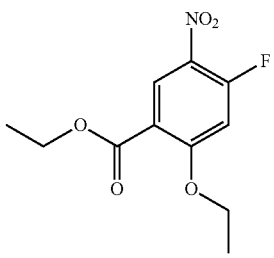 [SMILES: CCOC(=O)c1cc([N+](=O)[O-])c(F)cc1OCC]

In nitrogen atmosphere, to ethyl 2-ethoxy-4-fluorobenzoate as synthesized in above Production Example 31, 6.51 g, conc. sulfuric acid 34 mL was added under cooling with ice. Potassium nitrate 3.26 g was further added little by little, under cooling with salt-ice, followed by stirring for 3.4 hours under cooling with ice. The reaction liquid was poured in ice water, and the precipitated crystals were recovered by filtration and washed with water. Recrystallizing the crystals from tert-butyl methyl ether-hexane mixed solvent, 4.49 g of the title compound was obtained.

$^1$H-NMR (CDCl$_3$, δ): 1.39 (3H, t, J=7.1 Hz), 1.52 (3H, t, J=6.9 Hz), 4.18 (2H, q, J=6.9 Hz), 4.37 (2H, q, J=7.1 Hz), 6.78 (1H, d, J=12.7 Hz), 8.66 (1H, d, J=8.9 Hz).

MS (m/z): 257 (M$^+$).

Production Example 33

Ethyl 4-(2-cyclohexyl-1H-imidazol-1-yl)-2-ethoxy-5-nitrobenzoate

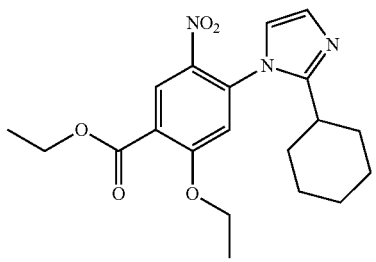 [SMILES: CCOC(=O)c1cc([N+](=O)[O-])c(-n2ccnc2C2CCCCC2)cc1OCC]

The title compound was obtained from ethyl 2-ethoxy-4-fluoro-5-nitrobenzoate as synthesized in above Production Example 32, by the operations similar to Production Example 3.

$^1$H-NMR (CDCl$_3$, δ): 1.0-1.4 (3H, m), 1.43 (3H, t, J=7.1 Hz), 1.52 (3H, t, J=6.9 Hz), 1.4-1.9 (7H, m), 2.2-2.4 (1H, m), 4.19 (2H, q, J=6.9 Hz), 4.43 (2H, q, J=7.2 Hz), 6.82 (1H, d, J=1.2 Hz), 6.88 (1H, s), 7.12 (1H, d, J=1.2 Hz), 8.63 (1H, s).

MS (m/z): 387 (M$^+$).

Production Example 34

Ethyl 5-amino-4-(2-cyclohexyl-1H-imidazol-1-yl)-2-ethoxybenzoate

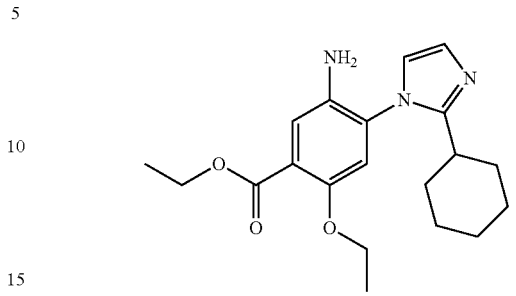

The title compound was obtained from ethyl 4-(2-cyclohexyl-1H-imidazol-1-yl)-2-ethoxy-5-nitrobenzoate as synthesized in above Production Example 33, by the operations similar to Production Example 4.

$^1$H-NMR (CDCl$_3$, δ): 1.0-1.9 (16H, m), 2.3-2.6 (1H, m), 3.36 (2H, br s), 3.99 (2H, q, J=6.9 Hz), 4.38 (2H, q, J=7.1 Hz), 6.71 (1H, s), 6.84 (1H, d, J=1.2 Hz), 7.14 (1H, d, J=1.5 Hz), 7.26 (1H, s).

MS (m/z): 357 (M$^+$).

Production Example 35

Ethyl 2-chloro-4-(2-cyclohexyl-1H-imidazol-1-yl)-5-nitrobenzoate

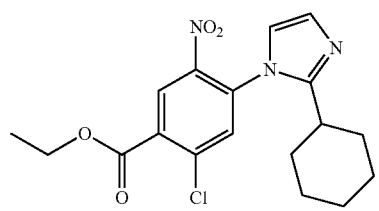 [SMILES: CCOC(=O)c1cc([N+](=O)[O-])c(-n2ccnc2C2CCCCC2)cc1Cl]

The title compound was obtained from ethyl 6-chloro-4-fluoro-3-nitrobenzoate, by the operations similar to Production Example 3.

$^1$H-NMR (CDCl$_3$, δ): 1.0-1.4 (3H, m), 1.46 (3H, t, J=7.1 Hz), 1.5-1.9 (7H, m), 2.2-2.4 (1H, m), 4.49 (2H, q, J=7.2 Hz), 6.82 (1H, d, J=1.5 Hz), 7.12 (1H, d, J=1.5 Hz), 7.54 (1H, s), 8.56 (1H, s).

MS (m/z): 379 (M$^+$+2), 377 (M$^+$).

Production Example 36

Ethyl 5-amino-2-chloro-4-(2-cyclohexyl-1H-imidazol-1-yl)-benzoate

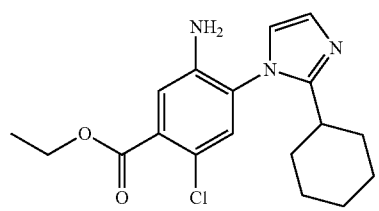

The title compound was obtained from ethyl 2-chloro-4-(2-cyclohexyl-1H-imidazol-1-yl)-5-nitrobenzoate as synthesized in above Production Example 35, by the operations similar to Production Example 4.

$^1$H-NMR (CDCl$_3$, δ): 1.0-1.4 (3H, m), 1.42 (3H, t, J=7.1 Hz), 1.5-1.9 (7H, m), 2.3-2.5 (1H, m), 3.70 (2H, br s), 4.42

(2H, q, J=7.1 Hz), 6.81 (1H, d, J=1.5 Hz), 7.16 (1H, d, J=1.2 Hz), 7.17 (1H, s), 7.26 (1H, s).
MS (m/z): 349 (M⁺+2), 347 (M⁺).

Production Example 37

4-(2-Cyclohexyl-1H-imidazol-1-yl)-N,N-dimethyl-3-nitrobenzenesulfonamide

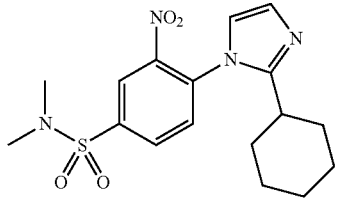

The title compound was obtained by the operations similar to Production Example 3.
¹H-NMR (CDCl₃, δ): 1.0-1.9 (10H, m), 2.2-2.4 (1H, m), 2.88 (6H, s), 6.84 (1H, d, J=1.5 Hz), 7.14 (1H, d, J=1.5 Hz), 7.61 (1H, d, J=8.1 Hz), 8.11 (1H, dd, J=2.1, 8.3 Hz), 8.39 (1H, d, J=1.9 Hz).
MS (m/z): 378 (M⁺).

Production Example 38

3-Amino-4-(2-cyclohexyl-1H-imidazol-1-yl)-N,N-dimethyl-benzenesulfonamide

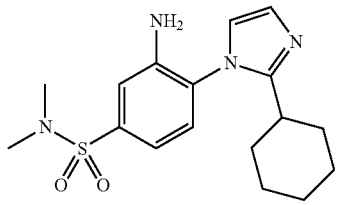 [SMILES: CN(C)S(=O)(=O)c1ccc(-n2ccnc2C2CCCCC2)c([N+](=O)[O-])c1]

The title compound was obtained from 4-(2-cyclohexyl-1H-imidazol-1-yl)-N,N-dimethyl-3-nitrobenzenesulfonamide as synthesized in above Production Example 37, by the operations similar to Production Example 4.
¹H-NMR (CDCl₃, δ): 1.0-1.9 (10H, m), 2.3-2.5 (1H, m), 2.79 (6H, s), 3.85 (2H, br s), 6.86 (1H, d, J=1.5 Hz), 7.1-7.3 (4H, m).
MS (m/z): 348 (M⁺).

Production Example 39

1-(4-Chloro-3-nitrobenzenesulfonyl)-4-methylpiperazine

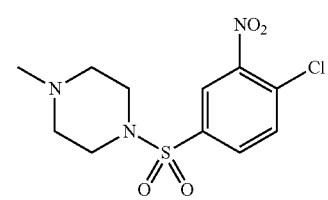 [SMILES: CN1CCN(S(=O)(=O)c2ccc(Cl)c([N+](=O)[O-])c2)CC1]

N-methylpiperazine 3.6 mL, N,N-diisopropylethylamine 5.7 mL and tetrahydrofuran 31 mL were mixed and dropped into a solution of 4-chloro-3-nitrobenzenesulfonyl chloride 8.19 g in tetrahydrofuran 51 mL, under cooling with ice, followed by stirring for 30 minutes under cooling with ice. The stirring was then continued for 17 hours at room temperature. The solvent was distilled off and the residue was poured in water, of which pH was raised to 9 with saturated aqueous sodium hydrogencarbonate solution, followed by extraction with ethyl acetate-tetrahydrofuran mixed solvent. The organic layer was washed with saturated brine, dried over magnesium sulfate, and from which the solvent was distilled off. Recrystallizing the crude product from ethyl acetate-hexane mixed solvent, 4.29 g of the title compound was obtained.
¹H-NMR (CDCl₃, δ): 2.28 (3H, s), 2.4-2.6 (4H, m), 3.10 (4H, br s), 7.73 (1H, d, J=8.5 Hz), 7.86 (1H, dd, J=2.3, 8.5 Hz), 8.22 (1H, d, J=1.9 Hz).
MS (m/z): 321 (M⁺+2), 319 (M⁺).

Production Example 40

1-[4-(2-Cyclohexyl-1H-imidazol-1-yl)-3-nitrobenzenesulfonyl]-4-methylpiperazine

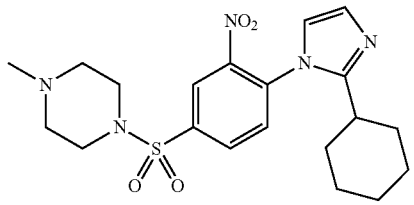 [SMILES: CN1CCN(S(=O)(=O)c2ccc(-n3ccnc3C3CCCCC3)c([N+](=O)[O-])c2)CC1]

The title compound was obtained from 1-(4-chloro-3-nitrobenzenesulfonyl)-4-methylpiperazine as synthesized in above Production Example 39, by the operations similar to Production Example 3.
¹H-NMR (CDCl₃, δ): 1.0-1.9 (10H, m), 2.2-2.4 (1H, m), 2.31 (3H, s), 2.4-2.7 (4H, m), 3.19 (4H, br s), 6.81 (1H, d, J=1.5 Hz), 7.13 (1H, d, J=1.2 Hz), 7.60 (1H, d, J=8.5 Hz), 8.08 (1H, dd, J=1.9, 8.1 Hz), 8.36 (1H, d, J=1.9 Hz).
MS (m/z): 433 (M⁺).

Production Example 41

1-[3-Amino-4-(2-cyclohexyl-1H-imidazol-1-yl)benzenesulfonyl]-4-methylpiperazine

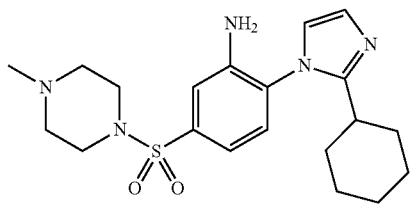 [SMILES: CN1CCN(S(=O)(=O)c2ccc(-n3ccnc3C3CCCCC3)c(N)c2)CC1]

The title compound was obtained from 1-[4-(2-cyclohexyl-1H-imidazol-1-yl)-3-nitrobenzenesulfonyl]-4-methylpiperazine as synthesized in above Production Example 40, by the operations similar to Production Example 4.
¹H-NMR (CDCl₃, δ): 1.1-1.9 (10H, m), 2.2-2.5 (1H, m), 2.30 (3H, s), 2.4-2.7 (4H, m), 3.13 (4H, br s), 3.83 (2H, br s), 6.81 (1H, d, J=1.2 Hz), 7.1-7.3 (4H, m).
MS (m/z): 403 (M⁺).

Production Example 42

4-(2-Cyclohexyl-1H-imidazol-1-yl)-N-(2-dimethylaminoethyl)-N-methyl-3-nitrobenzenesulfonamide

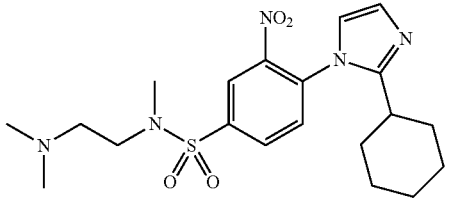

The title compound was obtained by the operations similar to Production Example 3.

$^1$H-NMR (CDCl$_3$, δ): 1.0-1.9 (10H, m), 2.1-2.4 (1H, m), 2.22 (6H, s), 2.49 (2H, t, J=6.4 Hz), 2.95 (3H, s), 3.36 (2H, t, J=6.4 Hz), 6.82 (1H, d, J=1.2 Hz), 7.13 (1H, d, J=1.5 Hz), 7.56 (1H, d, J=8.5 Hz), 8.17 (1H, dd, J=1.9, 8.1 Hz), 8.58 (1H, d, J=1.9 Hz).

MS (m/z): 434 (M$^+$−1).

Production Example 43

3-Amino-4-(2-cyclohexyl-1H-imidazol-1-yl)-N-(2-dimethyl-aminoethyl)-N-methylbenzenesulfonamide

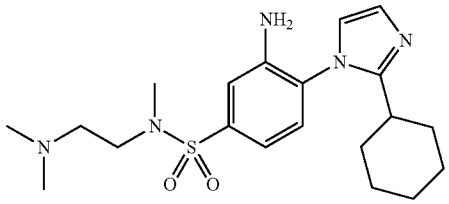 [SMILES: CN(C)CCN(C)S(=O)(=O)c1ccc(-n2ccnc2C2CCCCC2)c([N+](=O)[O-])c1]

The title compound was obtained from 4-(2-cyclohexyl-1H-imidazol-1-yl)-N-(2-dimethylaminoethyl)-N-methyl-3-nitrobenzene-sulfonamide as synthesized in above Production Example 42, by the operations similar to Production Example 4.

$^1$H-NMR (CDCl$_3$, δ): 1.0-1.9 (10H, m), 2.1-2.4 (1H, m), 2.26 (6H, s), 2.51 (2H, t, J=7.1 Hz), 2.87 (3H, s), 3.19 (2H, t, J=7.1 Hz), 3.83 (2H, br s), 6.84 (1H, d, J=1.5 Hz), 7.1-7.3 (4H, m).

MS (m/z): 404 (M$^+$−1).

Production Example 44

Ethyl 3-fluoro-4-nitrobenzoate

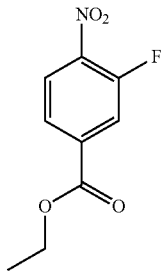

To the liquid mixture of 3-fluoro-4-nitrobenzoic acid 9.71 g and ethanol 35 mL, conc. sulfuric acid 1.6 mL was added, followed by 16 hours' heating under reflux. After distilling the solvent off, water and tert-butyl methyl ether were added to the residue. The organic layer was extracted, washed with water and dried over magnesium sulfate. Distilling the solvent off, 7.40 g of the title compound was obtained.

$^1$H-NMR (CDCl$_3$, δ): 1.42 (3H, t, J=7.1 Hz), 4.43 (2H, q, J=7.2 Hz), 7.9-8.0 (2H, m), 8.0-8.2 (1H, m).

MS (m/z): 213 (M$^+$).

Production Example 45

Ethyl 3-(2-cyclohexyl-1H-imidazol-1-yl)-4-nitrobenzoate

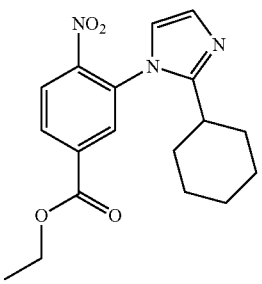 [SMILES: CCOC(=O)c1ccc([N+](=O)[O-])c(-n2ccnc2C2CCCCC2)c1]

The title compound was obtained from ethyl 3-fluoro-4-nitrobenzoate as synthesized in above Production Example 44, by the operations similar to Production Example 3.

$^1$H-NMR (CDCl$_3$, δ): 1.0-1.4 (3H, m), 1.43 (3H, t, J=7.1 Hz), 1.5-1.9 (7H, m), 2.2-2.4 (1H, m), 4.46 (2H, q, J=7.1 Hz), 6.85 (1H, d, J=1.5 Hz), 7.12 (1H, d, J=1.5 Hz), 8.0-8.2 (2H, m), 8.30 (1H, dd, J=1.5, 8.5 Hz).

MS (m/z): 343 (M$^+$).

Production Example 46

Ethyl 4-amino-3-(2-cyclohexyl-1H-imidazol-1-yl)benzoate

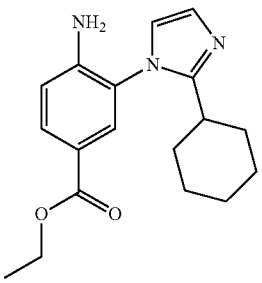

The title compound was obtained from ethyl 3-(2-cyclohexyl-1H-imidazol-1-yl)-4-nitrobenzoate as synthesized in above Production Example 45, by the operations similar to Production Example 4.

$^1$H-NMR (CDCl$_3$, δ): 1.0-1.4 (3H, m), 1.36 (3H, t, J=7.1 Hz), 1.5-2.0 (7H, m), 2.3-2.5 (1H, m), 3.96 (2H, br s), 4.2-4.5 (2H, m), 6.7-6.9 (2H, m), 7.14 (1H, d, J=1.2 Hz), 7.78 (1H, d, J=1.9 Hz), 7.94 (1H, dd, J=2.1, 8.7 Hz).

MS (m/z): 313 (M$^+$).

Production Example 47

N-(2-ethoxyethyl)-3-fluoro-4-nitrobenzamide

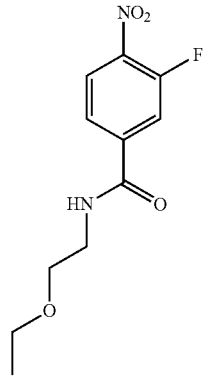 [SMILES: CCOCCNC(=O)c1ccc([N+](=O)[O-])c(F)c1]

3-Fluoro-4-nitrobenzoic acid 5.55 g, 2-ethoxyethylamine 3.15 mL, N,N-diisopropylethylamine 5.23 mL, 1-(3-dimethylaminopropyl)-3-ethyl carbodiimide hydrochloride 8.63 g, 1-hydroxybenzotriazole monohydrate 5.96 g and acetonitrile 77 mL were mixed and stirred for 19 hours. The reaction liquid was poured in diluted hydrochloric acid and extracted with ethyl acetate. The extract was washed with saturated brine, saturated aqueous sodium hydrogencarbonate solution and saturated brine, by the order stated, and dried over magnesium sulfate. Distilling the solvent off, 6.86 g of the title compound was obtained.

$^1$H-NMR (CDCl$_3$, δ): 1.22 (3H, t, J=6.9 Hz), 3.4-3.8 (6H, m), 6.57 (1H, br s), 7.65 (1H, dd, J=0.8, 8.5 Hz), 7.73 (1H, dd, J=1.9, 11.2 Hz), 8.12 (1H, dd, J=7.3, 8.5 Hz).

MS (m/z): 257 (M$^+$+1).

Production Example 48

3-(2-Cyclohexyl-1H-imidaol-1-yl)-N-(2-ethoxyethyl)-4-nitrobenzamide

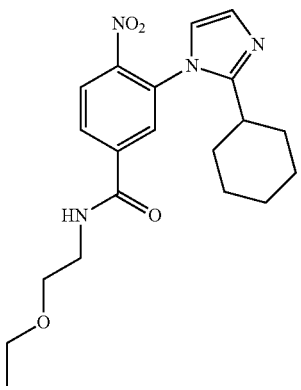 [SMILES: CCOCCNC(=O)c1ccc([N+](=O)[O-])c(-n2ccnc2C2CCCCC2)c1]

The title compound was obtained from N-(2-ethoxyethyl)-3-fluoro-4-nitrobenzamide as synthesized in above Production Example 47, by the operations similar to Production Example 3.

$^1$H-NMR (CDCl$_3$, δ): 1.0-1.4 (3H, m), 1.21 (3H, t, J=6.9 Hz), 1.5-1.9 (7H, m), 2.2-2.4 (1H, m), 3.55 (2H, q, J=6.9 Hz), 3.6-3.8 (4H, m), 6.75 (1H, br s), 6.84 (1H, d, J=1.5 Hz), 7.11 (1H, d, J=1.2 Hz), 7.85 (1H, d, J=1.9 Hz), 8.02 (1H, dd, J=1.9, 8.5 Hz), 8.09 (1H, d, J=8.5 Hz).

MS (m/z): 386 (M$^+$).

Production Example 49

3-(2-Cyclohexyl-1H-imidazol-1-yl)-N-(2-ethoxyethyl)-N-methyl-4-nitrobenzamide

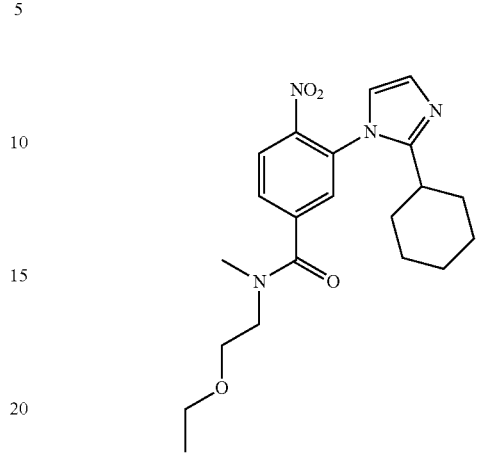

To the solution of 3-(2-cyclohexyl-1H-imidaol-1-yl)-N-(2-ethoxyethyl)-4-nitrobenzamide as synthesized in above Production Example 48, 3.86 g in N,N-dimethylacetamide 32 mL, sodium hydride (formed by washing 60% sodium hydride, oiliness 600 mg with hexane) was added under cooling with ice. Then methyl iodide 1.55 mL was added and the ice bath was removed. After 1.8 hours' stirring, sodium hydride (formed by washing 60% sodium hydride, oiliness 200 mg with hexane) was added, followed by 5 hours' stirring. The reaction liquid was poured in water and extracted with ethyl acetate. The organic layer was washed with saturated brine and dried over magnesium sulfate. Distilling the solvent off, 3.35 g of the title compound was obtained.

$^1$H-NMR (CDCl$_3$, δ): 1.0-1.4 (6H, m), 1.5-1.9 (7H, m), 2.2-2.4 (1H, m), 2.9-3.2 (3H, m), 3.3-3.9 (6H, m), 6.83 (1H, d, J=1.2 Hz), 7.09 (1H, s), 7.4-7.9 (2H, m), 8.0-8.2 (1H, m).

MS (m/z): 400 (M$^+$).

Production Example 50

4-Amino-3-(2-cyclohexyl-1H-imidazol-1-yl)-N-(2-ethoxyethyl)-N-methylbenzamide

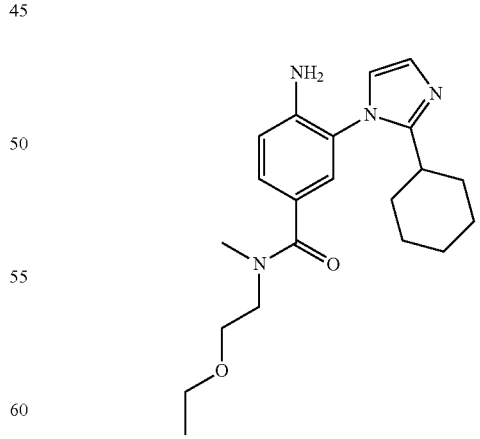

The title compound was obtained from 3-(2-cyclohexyl-1H-imidazol-1-yl)-N-(2-ethoxyethyl)-N-methyl-4-nitrobenzamide as synthesized in above Production Example 49, by the operations similar to Production Example 4.

$^1$H-NMR (CDCl$_3$, δ): 1.0-1.4 (6H, m), 1.5-1.9 (7H, m), 2.3-2.5 (1H, m), 3.0-3.2 (3H, m), 3.3-3.8 (8H, m), 6.81 (1H, d, J=8.1 Hz), 6.83 (1H, d, J=1.5 Hz), 7.13 (1H, d, J=1.5 Hz), 7.1-7.4 (1H, m), 7.42 (1H, dd, J=1.9, 8.5 Hz).

MS (m/z): 370 (M+).

Production Example 51

3-Fluoro-N-(3-methoxypropyl)-4-nitrobenzamide

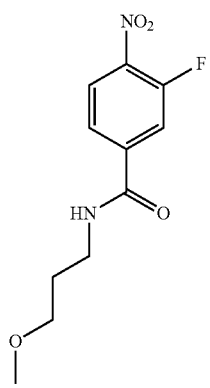 [SMILES: COCCCNC(=O)c1ccc([N+](=O)[O-])c(F)c1]

The title compound was obtained by the operations similar to Production Example 47.

$^1$H-NMR (CDCl$_3$, δ): 1.8-2.0 (2H, m), 3.40 (3H, s), 3.5-3.7 (4H, m), 7.23 (1H, br s), 7.61 (1H, d, J=8.5 Hz), 7.69 (1H, dd, J=1.6, 11.2 Hz), 8.10 (1H, dd, J=6.9, 8.1 Hz).

MS (m/z): 256 (M+).

Production Example 52

3-(2-Cyclohexyl-1H-imidazol-1-yl)-N-(3-methoxypropyl)-4-nitrobenzamide

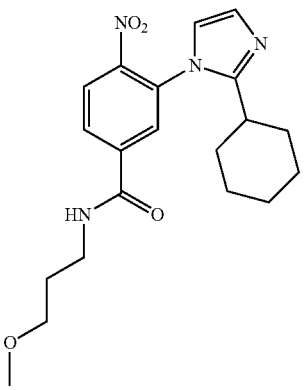 [SMILES: COCCCNC(=O)c1ccc([N+](=O)[O-])c(-n2ccnc2C2CCCCC2)c1]

The title compound was obtained from 3-fluoro-N-(3-methoxypropyl)-4-nitrobenzamide as synthesized in above Production Example 51, by the operations similar to Production Example 3.

$^1$H-NMR (CDCl$_3$, δ): 1.0-1.4 (3H, m), 1.5-1.8 (7H, m), 1.8-2.0 (2H, m), 2.2-2.4 (1H, m), 3.37 (3H, s), 3.5-3.7 (4H, m), 6.84 (1H, d, J=1.2 Hz), 7.11 (1H, d, J=1.2 Hz), 7.38 (1H, br s), 7.82 (1H, d, J=1.5 Hz), 7.97 (1H, dd, J=1.5, 8.5 Hz), 8.09 (1H, d, J=8.5 Hz).

MS (m/z): 386 (M+).

Production Example 53

3-(2-Cyclohexyl-1H-imidazol-1-yl)-N-(3-methoxypropyl)-N-methyl-4-nitrobenzamide

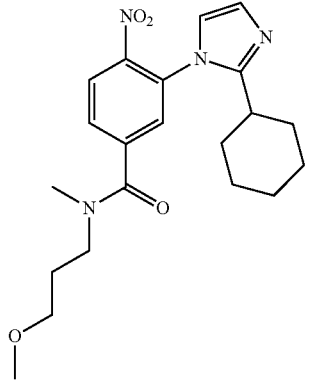 [SMILES: COCCCN(C)C(=O)c1ccc([N+](=O)[O-])c(-n2ccnc2C2CCCCC2)c1]

The title compound was obtained from 3-(2-cyclohexyl-1H-imidazol-1-yl)-N-(3-methoxypropyl)-4-nitrobenzamide as synthesized in above Production Example 52, by the operations similar to Production Example 49.

$^1$H-NMR (CDCl$_3$, δ): 1.0-1.4 (3H, m), 1.5-2.0 (9H, m), 2.2-2.4 (1H, m), 2.8-3.8 (10H, m), 6.84 (1H, s), 7.10 (1H, d, J=1.5 Hz), 7.44 (1H, s), 7.67 (1H, d, J=8.1 Hz), 8.08 (1H, d, J=8.5 Hz).

MS (m/z): 400 (M+).

Production Example 54

4-Amino-3-(2-cyclohexyl-1H-imidazol-1-yl)-N-(3-methoxy-propyl)-N-methylbenzamide

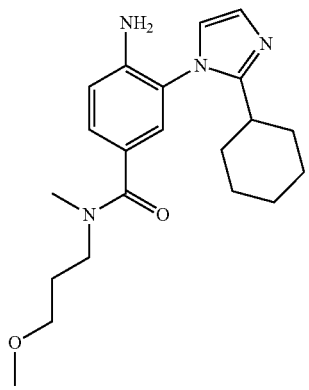

The title compound was obtained from 3-(2-cyclohexyl-1H-imidazol-1-yl)-N-(3-methoxypropyl)-N-methyl-4-nitrobenzamide as synthesized in above Production Example 53, by the operations similar to Production Example 4.

$^1$H-NMR (CDCl$_3$, δ): 1.0-1.3 (3H, m), 1.5-2.0 (9H, m), 2.3-2.5 (1H, m), 3.04 (3H, s), 3.1-3.7 (7H, m), 3.74 (2H, br s), 6.81 (1H, d, J=8.5 Hz), 6.83 (1H, d, J=1.5 Hz), 7.13 (1H, d, J=1.2 Hz), 7.18 (1H, d, J=1.9 Hz), 7.38 (1H, dd, J=1.9, 8.5 Hz).

MS (m/z): 370 (M+).

Production Example 55

3-Fluoro-4-nitro-N-(3-pyridylmethyl)benzamide

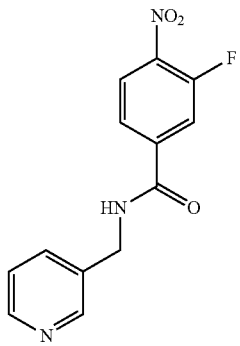 [SMILES: O=C(NCc1cccnc1)c1ccc([N+](=O)[O-])c(F)c1]

3-Fluoro-4-nitrobenzoic acid 2.78 g, 3-pyridylmethylamine 1.55 mL, N,N-diisopropylethylamine 2.61 mL, 1-(3-dimethylaminopropyl)-3-ethylcarbodiimide hydrochloride 4.31 g, 1-hydroxybenzotriazole monohydrate 2.98 g and acetonitrile 39 mL were mixed and stirred for 20 hours. The reaction liquid was poured in saturated aqueous sodium hydrogencarbonate solution and extracted with ethyl acetate. The organic layer was washed with saturated aqueous sodium hydrogencarbonate solution and saturated brine by the order stated, and dried over magnesium sulfate. Distilling the solvent off, 4.09 g of the title compound was obtained.

$^1$H-NMR (CDCl$_3$, δ): 4.67 (2H, d, J=5.8 Hz), 6.69 (1H, br s), 7.2-7.4 (1H, m), 7.6-7.9 (3H, m), 8.12 (1H, t, J=7.7 Hz), 8.57 (1H, d, J=3.5 Hz), 8.60 (1H, s).

MS (m/z): 275 (M$^+$).

Production Example 56

3-(2-Cyclohexyl-1H-imidazol-1-yl)-4-nitro-N-(3-pyridylmethyl)benzamide

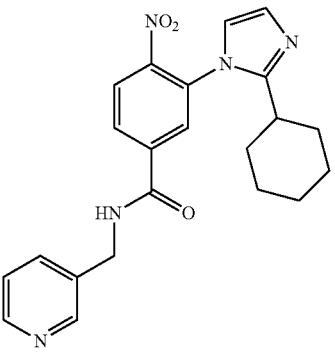 [SMILES: O=C(NCc1cccnc1)c1ccc([N+](=O)[O-])c(-n2ccnc2C2CCCCC2)c1]

The title compound was obtained from 3-fluoro-4-nitro-N-(3-pyridylmethyl)benzamide as synthesized in above Production Example 55, by the operations similar to Production Example 2.

$^1$H-NMR (CDCl$_3$, δ): 0.9-1.2 (3H, m), 1.3-1.8 (7H, m), 2.1-2.3 (1H, m), 4.71 (2H, br s), 6.79 (1H, d, J=1.2 Hz), 6.97 (1H, d, J=1.6 Hz), 7.2-7.4 (1H, m), 7.7-7.8 (1H, m), 7.94 (1H, d, J=1.9 Hz), 8.12 (1H, d, J=8.5 Hz), 8.29 (1H, dd, J=1.9, 8.5 Hz), 8.50 (1H, dd, J=1.5, 5.0 Hz), 8.57 (1H, d, J=1.9 Hz), 8.5-8.7 (1H, m).

MS (m/z): 405 (M$^+$).

Production Example 57

3-(2-Cyclohexyl-1H-imidazol-1-yl)-N-methyl-4-nitro-N-(3-pyridylmethyl)benzamide

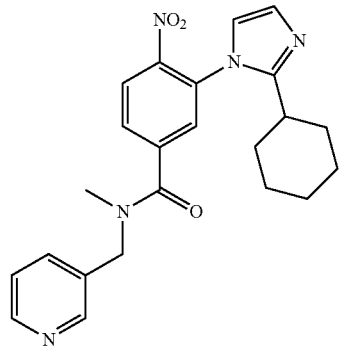

The title compound was obtained from 3-(2-cyclohexyl-1H-imidazol-1-yl)-4-nitro-N-(3-pyridylmethyl)benzamide as synthesized in above Production Example 56, by the operations similar to Production Example 49.

MS (m/z): 419 (M$^+$).

Production Example 58

4-Amino-3-(2-cyclohexyl-1H-imidazol-1-yl)-N-methyl-N-(3-pyridylmethyl)benzamide

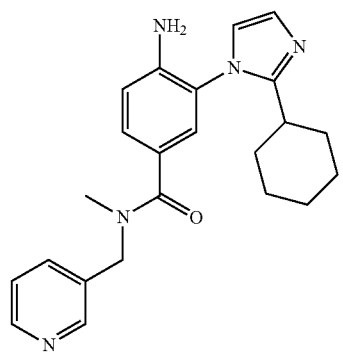 [SMILES: CN(Cc1cccnc1)C(=O)c1ccc([N+](=O)[O-])c(-n2ccnc2C2CCCCC2)c1]

The title compound was obtained from 3-(2-cyclohexyl-1H-imidazol-1-yl)-N-methyl-4-nitro-N-(3-pyridylmethyl)benzamide as synthesized in above Production Example 57, by the operations similar to Production Example 4.

$^1$H-NMR (CDCl$_3$, δ): 1.0-1.4 (3H, m), 1.5-2.0 (7H, m), 2.3-2.5 (1H, m), 2.99 (3H, s), 3.79 (2H, br s), 4.6-4.8 (2H, m), 6.7-6.9 (2H, m), 7.13 (1H, d, J=1.2 Hz), 7.2-7.4 (2H, m), 7.43 (1H, dd, J=1.9, 8.5 Hz), 7.5-7.8 (1H, m), 8.4-8.7 (2H, m).

MS (m/z): 389 (M$^+$).

Production Example 59

3-Fluoro-4-nitro-N-(2-pyridylmethyl)benzamide

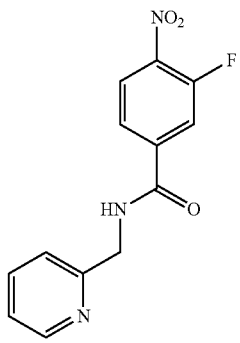 [SMILES: O=C(NCc1ccccn1)c1ccc([N+](=O)[O-])c(F)c1]

The title compound was obtained by the operations similar to Production Example 55.

¹H-NMR (CDCl₃, δ): 4.76 (2H, d, J=4.2 Hz), 7.2-7.4 (2H, m), 7.6-8.0 (4H, m), 8.14 (1H, t, J=7.3, 8.5 Hz), 8.57 (1H, d, J=5.0 Hz).

MS (m/z): 275 (M⁺).

Production Example 60

3-(2-Cyclohexyl-1H-imidazol-1-yl)-4-nitro-N-(2-pyridylmethyl)benzamide

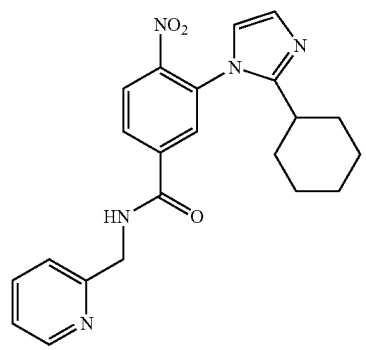 [SMILES: O=C(NCc1ccccn1)c1ccc([N+](=O)[O-])c(-n2ccnc2C2CCCCC2)c1]

The title compound was obtained from 3-fluoro-4-nitro-N-(2-pyridylmethyl)benzamide as synthesized in above Production Example 59, by the operations similar to Production Example 3.

¹H-NMR (CDCl₃, δ): 1.0-1.4 (3H, m), 1.5-1.9 (7H, m), 2.2-2.4 (1H, m), 4.78 (2H, d, J=4.2 Hz), 6.86 (1H, d, J=1.5 Hz), 7.12 (1H, d, J=1.5 Hz), 7.2-7.4 (1H, m), 7.32 (1H, d, J=7.7 Hz), 7.72 (1H, dt, J=1.5, 7.7 Hz), 7.94 (1H, d, J=1.5 Hz), 8.03 (1H, br s), 8.0-8.2 (2H, m), 8.56 (1H, d, J=4.2 Hz).

MS (m/z): 405 (M⁺).

Production Example 61

3-(2-Cyclohexyl-1H-imidazol-1-yl)-N-methyl-4-nitro-N-(2-pyridylmethyl)benzamide

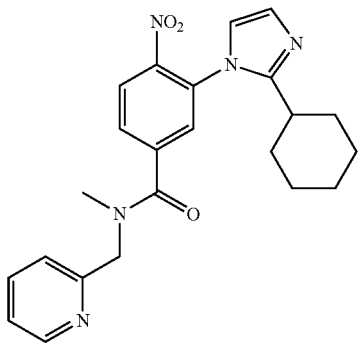 [SMILES: CN(Cc1ccccn1)C(=O)c1ccc([N+](=O)[O-])c(-n2ccnc2C2CCCCC2)c1]

The title compound was obtained from 3-(2-cyclohexyl-1H-imidazol-1-yl)-4-nitro-N-(2-pyridylmethyl)benzamide as synthesized in above Production Example 60, by the operations similar to Production Example 49.

MS (m/z): 419 (M⁺).

Production Example 62

4-Amino-3-(2-cyclohexyl-1H-imidazol-1-yl)-N-methyl-N-(2-pyridylmethyl)benzamide

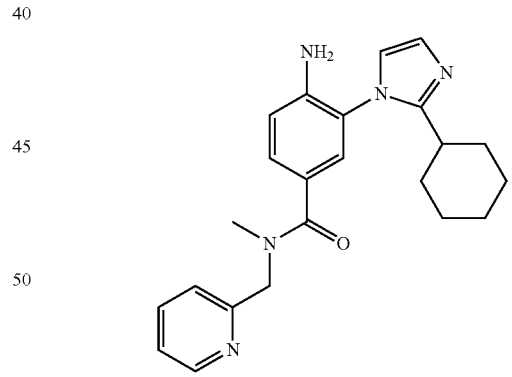

The title compound was obtained from 3-(2-cyclohexyl-1H-imidazol-1-yl)-N-methyl-4-nitro-N-(2-pyridylmethyl)benzamide as synthesized in above Production Example 61, by the operations similar to Production Example 4.

¹H-NMR (CDCl₃, δ): 0.9-1.4 (3H, m), 1.4-2.0 (7H, m), 2.2-2.5 (1H, m), 3.06 (3H, s), 3.76 (2H, br s), 4.4-5.0 (2H, m), 6.7-6.9 (2H, m), 7.0-7.4 (4H, m), 7.46 (1H, dd, J=1.7, 8.3 Hz), 7.68 (1H, dt, J=1.9, 7.7 Hz), 8.5-8.7 (1H, m).

MS (m/z): 389 (M⁺).

Production Example 63

3-Fluoro-4-nitro-N-(4-pyridylmethyl)benzamide

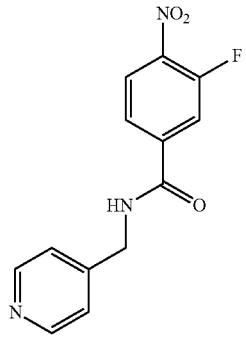 [SMILES: O=C(NCc1ccncc1)c1ccc([N+](=O)[O-])c(F)c1]

The title compound was obtained by the operations similar to Production Example 55.

$^1$H-NMR (CDCl$_3$, δ): 4.68 (2H, d, J=6.2 Hz), 6.56 (1H, br s), 7.2-7.3 (2H, m), 7.69 (1H, dd, J=1.2, 8.1 Hz), 7.77 (1H, dd, J=1.5, 10.8 Hz), 8.14 (1H, t, J=7.3, 8.5 Hz), 8.60 (2H, dd, J=1.5, 4.6 Hz).

MS (m/z): 275 (M$^+$).

Production Example 64

3-(2-Cyclohexyl-1H-imidazol-1-yl)-4-nitro-N-(4-pyridylmethyl)benzamide

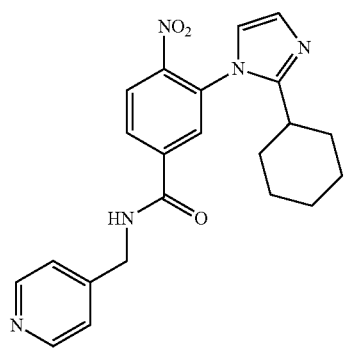 [SMILES: O=C(NCc1ccncc1)c1ccc([N+](=O)[O-])c(-n2ccnc2C2CCCCC2)c1]

The title compound was obtained from 3-fluoro-4-nitro-N-(4-pyridylmethyl)benzamide as synthesized in above Production Example 63, by the operations similar to Production Example 3.

$^1$H-NMR (CDCl$_3$, δ): 0.9-1.2 (3H, m), 1.3-1.8 (7H, m), 2.1-2.3 (1H, m), 4.72 (2H, br s), 6.80 (1H, d, J=1.5 Hz), 6.96 (1H, d, J=1.5 Hz), 7.2-7.4 (2H, m), 7.91 (1H, d, J=1.9 Hz), 8.13 (1H, d, J=8.5 Hz), 8.31 (1H, dd, J=1.9, 8.5 Hz), 8.56 (2H, dd, J=1.5, 4.2 Hz), 8.6-8.8 (1H, m).

MS (m/z): 405 (M$^+$).

Production Example 65

3-(2-Cyclohexyl-1H-imidazol-1-yl)-N-methyl-4-nitro-N-(4-pyridylmethyl)benzamide

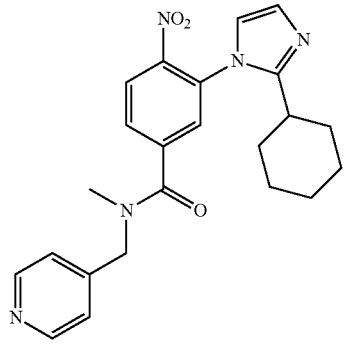 [SMILES: CN(Cc1ccncc1)C(=O)c1ccc([N+](=O)[O-])c(-n2ccnc2C2CCCCC2)c1]

The title compound was obtained from 3-(2-cyclohexyl-1H-imidazol-1-yl)-4-nitro-N-(4-pyridylmethyl)benzamide as synthesized in above Production Example 64, by the operations similar to Production Example 49.

MS (m/z): 419 (M$^+$).

Production Example 66

4-Amino-3-(2-cyclohexyl-1H-imidazol-1-yl)-N-methyl-N-(4-pyridylmethyl)benzamide

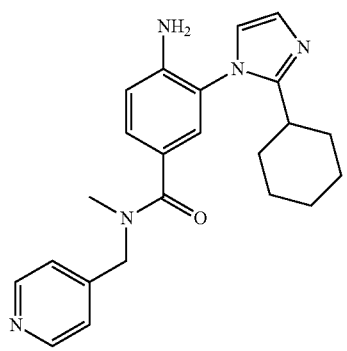 [SMILES: CN(Cc1ccncc1)C(=O)c1ccc(N)c(-n2ccnc2C2CCCCC2)c1]

The title compound was obtained from 3-(2-cyclohexyl-1H-imidazol-1-yl)-N-methyl-4-nitro-N-(4-pyridylmethyl)benzamide as synthesized in above Production Example 65, by the operations similar to Production Example 4.

$^1$H-NMR (CDCl$_3$, δ): 1.0-1.4 (3H, m), 1.5-2.0 (7H, m), 2.3-2.5 (1H, m), 3.02 (3H, s), 3.7-4.0 (2H, m), 4.5-4.8 (2H, m), 6.7-7.0 (3H, m), 7.0-7.5 (4H, m), 8.5-8.7 (2H, m).

MS (m/z): 389 (M$^+$).

Production Example 67

Ethyl (E)-3-[4-(2-cyclohexyl-1H-imidazol-1-yl)-3-nitrophenyl]-acrylate

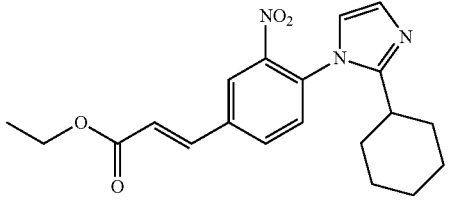 [SMILES: CCOC(=O)/C=C/c1ccc(-n2ccnc2C2CCCCC2)c([N+](=O)[O-])c1]

The title compound was obtained by the operations similar to Production Example 3.
$^1$H-NMR (CDCl$_3$, δ): 1.0-1.9 (10H, m), 1.36 (3H, t, J=7.3 Hz), 2.2-2.4 (1H, m), 4.31 (2H, q, J=7.1 Hz), 6.59 (1H, d, J=15.8 Hz), 6.82 (1H, d, J=1.2 Hz), 7.11 (1H, d, J=1.5 Hz), 7.45 (1H, d, J=8.1 Hz), 7.72 (1H, d, J=16.2 Hz), 7.84 (1H, dd, J=1.9, 8.5 Hz), 8.16 (1H, d, J=1.9 Hz).
MS (m/z): 369 (M$^+$).

Production Example 68

Ethyl (E)-3-[3-amino-4-(2-cyclohexyl-1H-imidazol-1-yl)phenyl]-acrylate

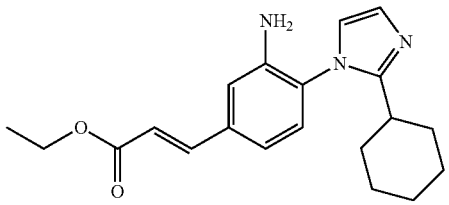

The title compound was obtained from ethyl (E)-3-[4-(2-cyclohexyl-1H-imidazol-1-yl)-3-nitrophenyl]acrylate as synthesized in above Production Example 67, by the operations similar to Production Example 4.
$^1$H-NMR (CDCl$_3$, δ): 1.1-1.9 (10H, m), 1.34 (3H, t, J=7.1 Hz), 2.3-2.5 (1H, m), 3.63 (2H, br s), 4.28 (2H, q, J=7.2 Hz), 6.42 (1H, d, J=15.8 Hz), 6.84 (1H, d, J=1.5 Hz), 6.9-7.0 (2H, m), 7.07 (1H, d, J=8.1 Hz), 7.14 (1H, d, J=1.2 Hz), 7.62 (1H, d, J=15.8 Hz).
MS (m/z): 339 (M$^+$).

Production Example 69

1-(4-Fluoro-2-methoxy-5-nitrophenyl)ethanone

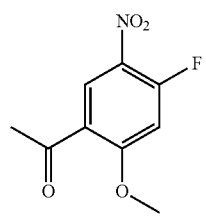

In nitrogen atmosphere, conc. sulfuric acid 36 mL was added to 1-(4-fluoro-2-methoxyphenyl)ethanone 5.50 g, followed by heating to homogeneity. Cooling the same with salt-ice, potassium nitrate 3.47 g was added little by little, followed by an hour's stirring. The reaction liquid was poured in ice water, and the precipitated crystals were recovered by filtration and washed with water. Drying the crystals, 6.47 g of the title compound was obtained.

$^1$H-NMR (CDCl$_3$, δ): 2.61 (3H, s), 4.03 (3H, s), 6.83 (1H, d, J=12.3 Hz), 8.61 (1H, d, J=8.5 Hz).
MS (m/z): 213 (M$^+$).

Production Example 70

1-[4-(2-Cyclohexyl-1H-imidazol-1-yl)-2-methoxy-5-nitrophenyl]ethanone

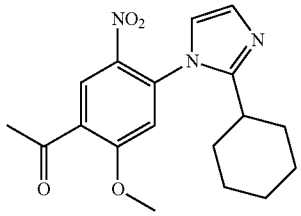 [SMILES: COc1cc(-n2ccnc2C2CCCCC2)c([N+](=O)[O-])cc1C(C)=O]

The title compound was obtained from 1-(4-fluoro-2-methoxy-5-nitrophenyl)ethanone as synthesized in above Production Example 69, by the operations similar to Production Example 3.
$^1$H-NMR (CDCl$_3$, δ): 1.0-1.4 (3H, m), 1.5-1.9 (7H, m), 2.2-2.4 (1H, m), 2.69 (3H, s), 4.03 (3H, s), 6.84 (1H, d, J=1.5 Hz), 6.93 (1H, s), 7.13 (1H, d, J=1.5 Hz), 8.56 (1H, s).
MS (m/z): 343 (M$^+$).

Production Example 71

1-[5-Amino-4-(2-cyclohexyl-1H-imidazol-1-yl)-2-methoxy-phenyl]ethane

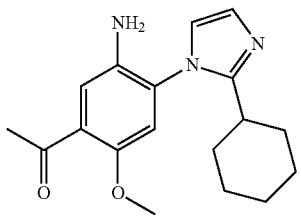 [SMILES: COc1cc(-n2ccnc2C2CCCCC2)c(N)cc1C(C)=O]

The title compound was obtained from 1-[4-(2-cyclohexyl-1H-imidazol-1-yl)-2-methoxy-5-nitrophenyl]ethanone as synthesized in above Production Example 70, by the operations similar to Production Example 4.
$^1$H-NMR (CDCl$_3$, δ): 1.1-1.4 (3H, m), 1.5-1.9 (7H, m), 2.3-2.5 (1H, m), 2.64 (3H, s), 3.36 (2H, br s), 3.82 (3H, s), 6.71 (1H, s), 6.85 (1H, d, J=1.2 Hz), 7.15 (1H, d, J=1.5 Hz), 7.22 (1H, s).
MS (m/z): 313 (M$^+$).

Production Example 72

Ethyl 2-chloro-5-fluoro-4-nitrobenzoate

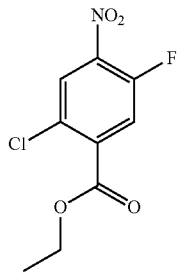 [SMILES: CCOC(=O)c1cc(F)c([N+](=O)[O-])cc1Cl]

The title compound was obtained by the operations similar to Production Example 44.

¹H-NMR (CDCl₃, δ): 1.42 (3H, t, J=7.1 Hz), 4.45 (2H, q, J=7.2 Hz), 7.75 (1H, d, J=10.4 Hz), 8.15 (1H, d, J=6.2 Hz).
MS (m/z): 249 (M⁺+2), 247 (M⁺).

Production Example 73

Ethyl 2-chloro-5-(2-cyclohexyl-1H-imidazol-1-yl)-4-nitrobenzoate

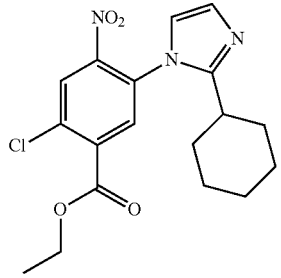 [SMILES: CCOC(=O)c1cc(-n2ccnc2C2CCCCC2)c([N+](=O)[O-])cc1Cl]

The title compound was obtained from ethyl 2-chloro-5-fluoro-4-nitrobenzoate as synthesized in above Production Example 72, by the operations similar to Production Example 3.
MS (m/z): 379 (M⁺+2), 377 (M⁺).

Production Example 74

Ethyl 4-amino-2-chloro-5-(2-cyclohexyl-1H-imidazol-1-yl)-benzoate

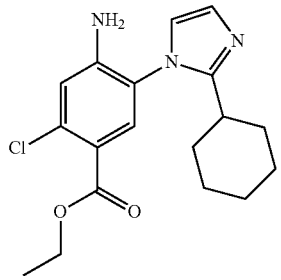 [SMILES: CCOC(=O)c1cc(-n2ccnc2C2CCCCC2)c(N)cc1Cl]

The title compound was obtained from ethyl 2-chloro-5-(2-cyclohexyl-1H-imidazol-1-yl)-4-nitrobenzoate as synthesized in above Production Example 73, by the operations similar to Production Example 4.
MS (m/z): 349 (M⁺+2), 347 (M⁺).

Production Example 75

Ethyl 3-(2-cyclohexyl-4-methyl-1H-imidazol-1-yl)-4-nitrobenzoate

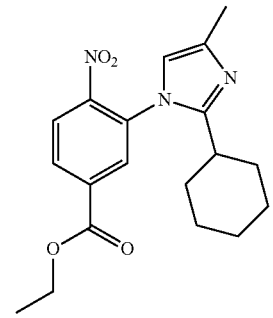 [SMILES: CCOC(=O)c1ccc([N+](=O)[O-])c(-n2cc(C)nc2C2CCCCC2)c1]

The title compound was obtained by the operations similar to Production Example 3.
¹H-NMR (CDCl₃, δ): 1.0-1.4 (3H, m), 1.42 (3H, t, J=7.3 Hz), 1.5-1.9 (7H, m), 2.1-2.3 (1H, m), 2.24 (3H, d, J=1.2 Hz), 4.45 (2H, q, J=7.2 Hz), 6.55 (1H, d, J=0.8 Hz), 8.02 (1H, d, J=8.5 Hz), 8.05 (1H, d, J=1.5 Hz), 8.27 (1H, dd, J=1.5, 8.5 Hz).
MS (m/z): 357 (M⁺).

Production Example 76

Ethyl 4-amino-3-(2-cyclohexyl-4-methyl-1H-imidazol-1-yl)-benzoate

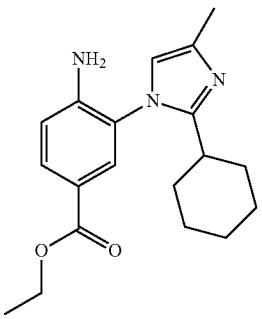

The title compound was obtained from ethyl 3-(2-cyclohexyl-4-methyl-1H-imidazol-1-yl)-4-nitrobenzoate as synthesized in above Production Example 75, by the operations similar to Production Example 4.
¹H-NMR (CDCl₃, δ): 1.0-1.3 (3H, m), 1.36 (3H, t, J=7.1 Hz), 1.5-1.9 (7H, m), 2.2-2.4 (1H, m), 3.99 (2H, br s), 4.2-4.5 (2H, m), 6.53 (1H, d, J=1.2 Hz), 6.79 (1H, d, J=8.5 Hz), 7.76 (1H, d, J=1.9 Hz), 7.93 (1H, dd, J=1.9, 8.5 Hz).
MS (m/z): 327 (M⁺).

Production Example 77

4-(2-Cyclohexyl-1H-imidazol-1-yl)-3-nitrobenzonitrile

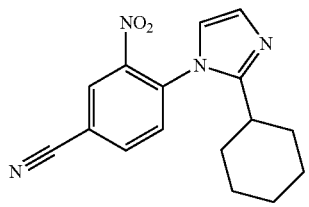 [SMILES: N#Cc1ccc(-n2ccnc2C2CCCCC2)c([N+](=O)[O-])c1]

The title compound was obtained by the operations similar to Production Example 3.
¹H-NMR (DMSO-d₆, δ): 1.0-2.0 (10H, m), 2.2-2.4 (1H, m), 6.98 (1H, d, J=1.2 Hz), 7.19 (1H, d, J=1.5 Hz), 7.97 (1H, d, J=8.5 Hz), 8.39 (1H, dd, J=1.9, 8.1 Hz), 8.80 (1H, d, J=1.9 Hz).
MS (m/z): 296 (M⁺).

Production Example 78

3-Amino-4-(2-cyclohexyl-1H-imidazol-1-yl)benzonitrile

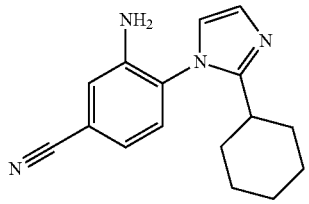 [SMILES: N#Cc1ccc(-n2ccnc2C2CCCCC2)c(N)c1]

The title compound was obtained from 4-(2-cyclohexyl-1H-imidazol-1-yl)-3-nitrobenzonitrile as synthesized in above Production Example 77, by the operations similar to Production Example 4.

$^1$H-NMR (DMSO-$d_6$, δ): 1.0-2.0 (10H, m), 2.2-2.4 (1H, m), 5.30 (2H, br s), 6.9-7.1 (3H, m), 7.1-7.2 (2H, m).

MS (m/z): 266 (M$^+$).

Production Example 79

1-(4-Bromo-2-nitrophenyl)-2-cyclohexyl-1H-imidazole

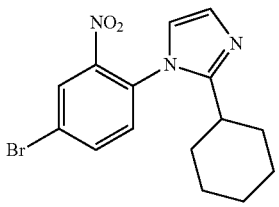

The title compound was obtained by the operations similar to Production Example 3.

$^1$H-NMR (CDCl$_3$, δ): 1.0-2.0 (10H, m), 2.27 (1H, tt, J=3.5, 11.6 Hz), 6.79 (1H, d, J=1.6 Hz), 7.09 (1H, d, J=1.5 Hz), 7.30 (1H, d, J=8.1 Hz), 7.86 (1H, dd, J=2.3, 8.5 Hz), 8.18 (1H, d, J=2.3 Hz).

MS (m/z): 352 (M$^+$+3), 350 (M$^+$+1).

Production Example 80

5-Bromo-2-(2-cyclohexyl-1H-imidazol-1-yl)aniline

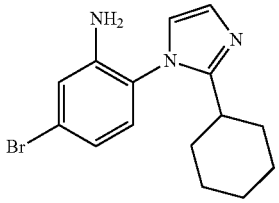

The title compound was obtained from 1-(4-bromo-2-nitrophenyl)-2-cyclohexyl-1H-imidazole as synthesized in above Production Example 79, by the operations similar to Production Example 4.

$^1$H-NMR (DMSO-$d_6$, δ): 1.0-1.3 (2H, m), 1.4-1.8 (8H, m), 2.33 (1H, tt, J=3.1, 11.6 Hz), 5.12 (2H, s), 6.76 (1H, dd, J=2.3, 8.1 Hz), 6.94 (1H, d, J=8.1 Hz), 6.99 (2H, br s), 7.04 (1H, d, J=2.3 Hz).

MS (m/z): 321 (M$^+$+2), 319 (M$^+$).

Production Example 81

Methyl (E)-3-[3-(2-cyclohexyl-1H-imidazol-1-yl)-4-nitrophenyl]acrylate

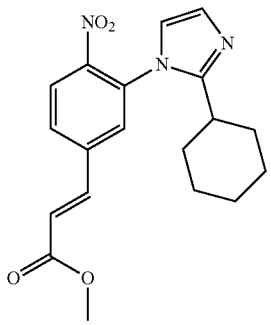

The title compound was obtained by the operations similar to Production Example 3.

$^1$H-NMR (CDCl$_3$, δ): 0.9-1.3 (3H, m), 1.5-1.9 (7H, m), 2.2-2.4 (1H, m), 3.82 (3H, s), 6.57 (1H, d, J=16.2 Hz), 6.84 (1H, d, J=1.6 Hz), 7.12 (1H, d, J=1.5 Hz), 7.51 (1H, d, J=2.0 Hz), 7.69 (1H, d, J=16.1 Hz), 7.76 (1H, dd, J=1.9, 8.5 Hz), 8.09 (1H, d, J=8.5 Hz).

MS (m/z): 355 (M$^+$).

Production Example 82

Methyl (E)-3-[4-amino-3-(2-cyclohexyl-1H-imidazol-1-yl)-phenyl]acrylate

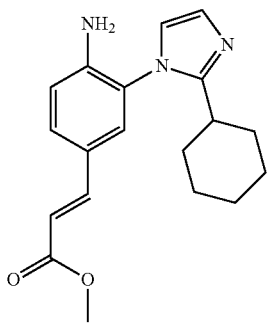 [SMILES: COC(=O)/C=C/c1ccc([N+](=O)[O-])c(-n2ccnc2C2CCCCC2)c1]

The title compound was obtained from methyl (E)-3-[3-(2-cyclohexyl-1H-imidazol-1-yl)-4-nitrophenyl]acrylate as synthesized in above Production Example 81, by the operations similar to Production Example 4.

$^1$H-NMR (CDCl$_3$, δ): 1.0-1.3 (3H, m), 1.5-1.9 (7H, m), 2.3-2.5 (1H, m), 3.78 (3H, s), 3.84 (2H, s), 6.26 (1H, d, J=15.8 Hz), 6.81 (1H, d, J=8.5 Hz), 6.84 (1H, d, J=1.6 Hz), 7.15 (1H, d, J=1.2 Hz), 7.24 (1H, d, J=1.9 Hz), 7.45 (1H, dd, J=1.9, 8.5 Hz), 7.58 (1H, d, J=15.8 Hz).

MS (m/z): 325 (M$^+$).

Production Example 83

Methyl 3-(2-cyclopentyl-1H-imidazol-1-yl)-4-nitrobenzoate

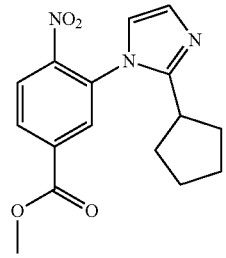 [SMILES: COC(=O)c1ccc([N+](=O)[O-])c(-n2ccnc2C2CCCC2)c1]

The title compound was obtained by the operations similar to Production Example 3.

$^1$H-NMR (CDCl$_3$, δ): 1.3-2.0 (8H, m), 2.70 (1H, quin, J=8.2 Hz), 3.94 (3H, s), 6.88 (1H, d, J=1.6 Hz), 7.11 (1H, d, J=1.2 Hz), 8.07 (1H, d, J=8.5 Hz), 8.10 (1H, d, J=1.9 Hz), 8.29 (1H, dd, J=1.9, 8.5 Hz).

MS (m/z): 315 (M$^+$).

Production Example 84

Methyl 4-amino-3-(2-cyclopentyl-1H-imidazol-1-yl)benzoate

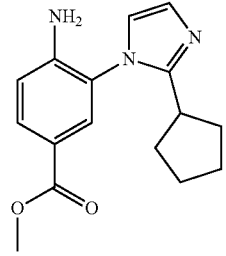

The title compound was obtained from methyl 3-(2-cyclopentyl-1H-imidazol-1-yl)-4-nitrobenzoate as synthesized in above Production Example 83, by the operations similar to Production Example 4.

$^1$H-NMR (CDCl$_3$, δ): 1.4-1.6 (2H, m), 1.6-1.9 (6H, m), 2.80 (1H, quin, J=8.3 Hz), 3.86 (3H, s), 4.01 (2H, br s), 6.80 (1H, d, J=8.8 Hz), 6.86 (1H, d, J=1.6 Hz), 7.13 (1H, d, J=1.2 Hz), 7.79 (1H, d, J=1.9 Hz), 7.93 (1H, dd, J=1.9, 8.5 Hz).

MS (m/z): 285 (M$^+$).

Production Example 85

2-(1-Propylbutyl)imidazole

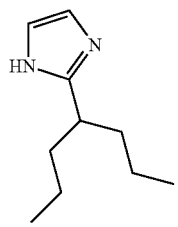

The title compound was obtained by the operations similar to Production Example 2.

$^1$H-NMR (CDCl$_3$, δ): 0.85 (6H, t, J=7.3 Hz), 1.1-1.4 (4H, m), 1.5-1.8 (4H, m), 2.7-2.9 (1H, m), 6.95 (2H, s).

MS (m/z): 166 (M$^+$).

Production Example 86

Ethyl 4-nitro-3-[2-(1-propylbutyl)-1H-imidazol-1-yl]benzoate

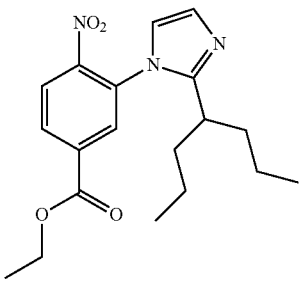 [SMILES: CCCC(CCC)c1nccn1-c1cc(C(=O)OCC)ccc1[N+](=O)[O-]]

The title compound was obtained from 2-(1-propylbutyl)-imidazole as synthesized in above Production Example 85, by the operations similar to Production Example 3.

$^1$H-NMR (CDCl$_3$, δ): 0.77 (6H, t, J=7.1 Hz), 1.0-1.3 (4H, m), 1.41 (3H, t, J=7.1 Hz), 1.4-1.9 (4H, m), 2.3-2.5 (1H, m), 4.45 (2H, q, J=6.7 Hz), 6.90 (1H, d, J=1.2 Hz), 7.15 (1H, d, J=1.5 Hz), 8.05 (1H, d, J=1.9 Hz), 8.06 (1H, d, J=8.5 Hz), 8.28 (1H, dd, J=1.5, 8.5 Hz).

MS (m/z): 359 (M$^+$).

Production Example 87

Ethyl 4-amino-3-[2-(1-propylbutyl)-1H-imidazol-1-yl]benzoate

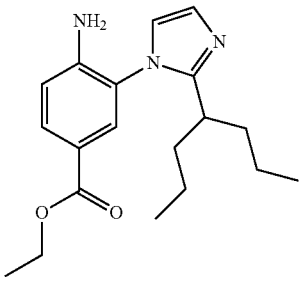

The title compound was obtained from ethyl 4-nitro-3-[2-(1-propylbutyl)-1H-imidazol-1-yl]benzoate as synthesized in above Production Example 86, by the operations similar to Production Example 4.

$^1$H-NMR (CDCl$_3$, δ): 0.75 (3H, t, J=7.3 Hz), 0.81 (3H, t, J=7.3 Hz), 1.0-1.4 (4H, m), 1.35 (3H, t, J=7.1 Hz), 1.4-1.6 (2H, m), 1.6-1.8 (2H, m), 2.4-2.6 (1H, m), 4.00 (2H, br s), 4.2-4.4 (2H, m), 6.80 (1H, d, J=8.9 Hz), 6.87 (1H, d, J=1.2 Hz), 7.19 (1H, d, J=1.2 Hz), 7.77 (1H, d, J=1.9 Hz), 7.93 (1H, dd, J=1.9, 8.5 Hz).

MS (m/z): 329 (M$^+$).

Production Example 88

2-(Tetrahydropyran-4-yl)imidazole

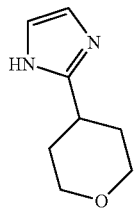 [SMILES: c1c[nH]c(C2CCOCC2)n1]

The title compound was obtained by the operations similar to Production Example 2.

¹H-NMR (CDCl₃, δ): 1.8-2.1 (4H, m), 2.9-3.1 (1H, m), 3.52 (2H, dt, J=2.7, 11.6 Hz), 4.05 (2H, ddd, J=2.3, 4.2, 11.6 Hz), 6.98 (2H, s).
MS (m/z): 152 (M⁺).

Production Example 89

1-(2-Nitro-4-trifluoromethylphenyl)-2-(tetrahydropyran-4-yl)-1H-imidazole

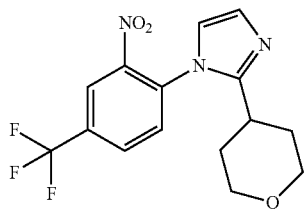

The title compound was obtained from 2-(tetrahydropyran-4-yl)imidazole as synthesized in above Production Example 88, by the operations similar to Production Example 3.

¹H-NMR (CDCl₃, δ): 1.5-1.7 (2H, m), 1.9-2.2 (2H, m), 2.5-2.7 (1H, m), 3.31 (2H, dt, J=2.2, 11.8 Hz), 3.99 (2H, ddd, J=2.0, 4.2, 11.6 Hz), 6.86 (1H, d, J=1.5 Hz), 7.16 (1H, d, J=1.2 Hz), 7.62 (1H, d, J=8.1 Hz), 8.03 (1H, dd, J=1.9, 8.5 Hz), 8.33 (1H, d, J=1.9 Hz).
MS (m/z): 341 (M⁺).

Production Example 90

2-[2-(Tetrahydropyran-4-yl)-1H-imidazol-1-yl]-5-trifluoromethylaniline

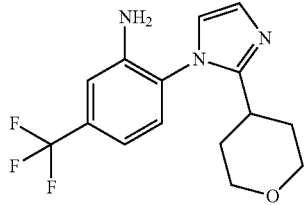 [SMILES: Nc1cc(C(F)(F)F)ccc1-n1ccnc1C1CCOCC1]

The title compound was obtained from 1-(2-nitro-4-trifluoromethylphenyl)-2-(tetrahydropyran-4-yl)-1H-imidazole as synthesized in above Production Example 89, by the operations similar to Production Example 4.

¹H-NMR (CDCl₃, δ): 1.5-1.8 (2H, m), 1.9-2.1 (2H, m), 2.6-2.8 (1H, m), 3.34 (2H, ddt, J=2.3, 3.5, 11.9 Hz), 3.78 (2H, br s), 3.9-4.1 (2H, m), 6.87 (1H, d, J=1.2 Hz), 7.0-7.1 (2H, m), 7.1-7.3 (2H, m).
MS (m/z): 311 (M⁺).

Production Example 91

Ethyl 3-[1-(4-fluoro-2-nitrophenyl)-1H-imidazol-2-yl]-propanoate

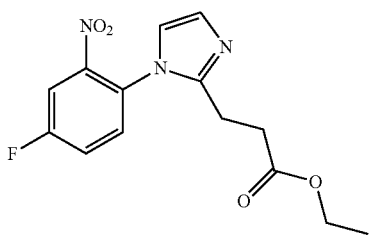

1,4-Difluoro-2-nitrobenzene 239 mg, ethyl 3-(1H-imidazol-2-yl)propanoate 252 mg, potassium carbonate 415 mg and N,N-dimethylacetamide 10 mL were heated at 100° C. for 64 hours. The reaction liquid was diluted with ethyl acetate and filtered. The filtrate was condensed under reduced pressure and subjected to silica gel chromatography (ethyl acetate) to provide 220 mg of the title compound.

¹H-NMR (CDCl₃, δ): 1.21 (3H, t, J=7.3 Hz), 2.6-3.0 (4H, m), 4.08 (2H, q, J=7.3 Hz), 6.86 (1H, d, J=1.5 Hz), 7.08 (1H, d, J=1.5 Hz), 7.4-7.6 (2H, m), 7.80 (1H, dd, J=2.9, 7.5 Hz).
MS (m/z): 308 (M⁺+1), 187 (base).

Production Example 92

Ethyl 3-[1-(2-amino-4-fluorophenyl)-1H-imidazol-2-yl]-propanoate

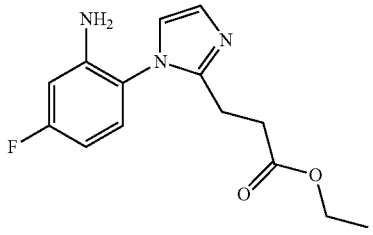 [SMILES: CCOC(=O)CCc1nccn1-c1ccc(F)cc1[N+](=O)[O-]]

Ethyl 3-[1-(4-fluoro-2-nitrophenyl)-1H-imidazol-2-yl]-propanoate as synthesized in above Production Example 91, 210 mg was dissolved in 1 mL of acetic acid and 1 mL of water, to which 533 mg of 85% sodium hyposulfite was added, followed by 2.5 hours' heating under reflux. The reaction liquid was allowed to cool off and rendered weakly alkaline with saturated aqueous sodium hydrogencarbonate solution, which was extracted with ethyl acetate. The extract was washed with saturated brine and dried over sodium sulfate. Distilling the solvent off under reduced pressure, 100 mg of the title compound was obtained.

¹H-NMR (CDCl₃, δ): 1.21 (3H, t, J=7.1 Hz), 2.7-3.0 (4H, m), 3.82 (2H, br s), 4.07 (2H, q, J=7.1 Hz), 6.4-6.6 (2H, m), 6.87 (1H, d, J=1.2 Hz), 7.03 (1H, dd, J=5.8, 8.5 Hz), 7.10 (1H, d, J=1.2 Hz).
MS (m/z): 277 (M⁺), 204 (base).

Production Example 93

Ethyl 3-[1-(4-methyl-2-nitrophenyl)-1H-imidazol-2-yl]-propanoate

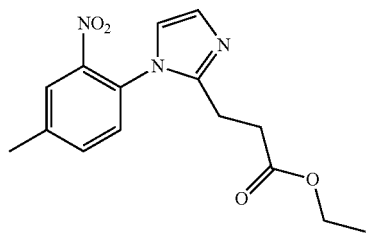 [SMILES: CCOC(=O)CCc1nccn1-c1ccc(C)cc1[N+](=O)[O-]]

1-Fluoro-4-methyl-2-nitrobenzene 239 mg, ethyl 3-(1H-imidazol-2-yl)propanoate 252 mg, potassium carbonate 415 mg and N,N-dimethylacetamide 10 mL were stirred at 100° C. for 11.5 hours, and then at 130° C., for 6 hours. The reaction liquid was diluted with diethyl ether, washed with water and saturated brine by the order stated, and dried over magnesium sulfate. Distilling the solvent off under reduced pressure, the residue was subjected to silica gel chromatography (ethyl acetate) to provide 422 mg of the title compound.

$^1$H-NMR (CDCl$_3$, δ): 1.21 (3H, t, J=7.2 Hz), 2.53 (3H, s), 2.6-3.0 (4H, m), 4.08 (2H, q, J=7.2 Hz), 6.86 (1H, d, J=1.5 Hz), 7.07 (1H, d, J=1.5 Hz), 7.36 (1H, d, J=7.8 Hz), 7.5-7.6 (1H, m), 7.8-7.9 (1H, m).

MS (m/z): 304 (M$^+$+1), 183 (base).

Production Example 94

Ethyl 3-[1-(2-amino-4-methylphenyl)-1H-imidazol-2-yl]-propanoate

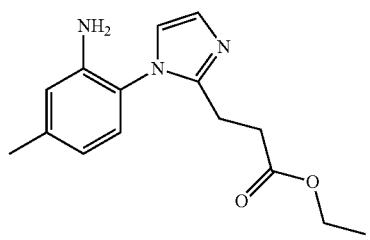 [SMILES: CCOC(=O)CCc1nccn1-c1ccc(C)cc1N]

The title compound was obtained from ethyl 3-[1-(4-methyl-2-nitrophenyl)-1H-imidazol-2-yl]propanoate as synthesized in above Production Example 93, by the operations similar to Production Example 92.

$^1$H-NMR (CDCl$_3$, δ): 1.21 (3H, t, J=7.1 Hz), 2.31 (3H, s), 2.6-3.0 (4H, m), 3.60 (2H, br s), 4.09 (2H, q, J=7.1 Hz), 6.5-6.7 (2H, m), 6.88 (1H, d, J=1.2 Hz), 6.94 (1H, d, J=8.1 Hz), 7.09 (1H, d, J=1.2 Hz).

MS (m/z): 273 (M$^+$), 200 (base).

Production Example 95

Ethyl 3-[1-(4-acetyl-2-nitrophenyl)-1H-imidazol-2-yl]-propanoate

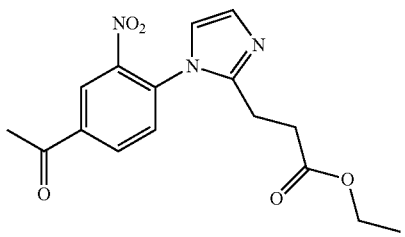 [SMILES: CCOC(=O)CCc1nccn1-c1ccc(C(C)=O)cc1[N+](=O)[O-]]

A mixture of 4'-fluoro-3'-nitroacetophenone 2.04 g, ethyl 3-(1H-imidazol-2-yl)propanoate 1.87 g, potassium carbonate 3.07 g and N,N-dimethylacetamide 28 mL was heated at 100° C. for 16.5 hours. The reaction liquid was allowed to cool off and to which 60 mL of diethyl ether was added, followed by filtration. Adding 100 mL of water to the filtrate, the organic layer was separated. The aqueous layer was extracted with 100 mL of diethyl ether. The extract was combined with the organic layer, washed twice with 20 mL of water and once with 10 mL of saturated brine by the order stated, and dried over magnesium sulfate. Distilling the solvent off under reduced pressure, 2.54 g of the title compound was obtained.

$^1$H-NMR (CDCl$_3$, δ): 1.21 (3H, t, J=7.1 Hz), 2.6-3.0 (7H, m), 4.08 (2H, q, J=7.1 Hz), 6.89 (1H, d, J=1.5 Hz), 7.11 (1H, d, J=1.5 Hz), 7.66 (1H, d, J=8.3 Hz), 8.30 (1H, dd, J=1.9, 8.3 Hz), 8.57 (1H, d, J=1.9 Hz).

MS (m/z): 332 (M$^+$+1), 211 (base).

Production Example 96

Ethyl 3-[1-(4-acetyl-2-aminophenyl)-1H-imidazol-2-yl]-propanoate

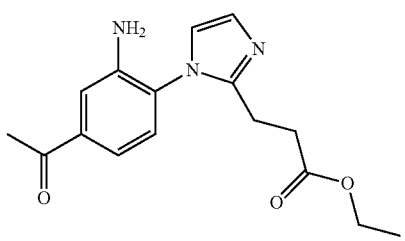 [SMILES: CCOC(=O)CCc1nccn1-c1ccc(C(C)=O)cc1N]

The title compound was obtained from ethyl 3-[1-(4-acetyl-2-nitrophenyl)-1H-imidazol-2-yl]propanoate as synthesized in above Production Example 95, by the operations similar to Production Example 4.

$^1$H-NMR (CDCl$_3$, δ): 1.21 (3H, t, J=7.2 Hz), 2.60 (3H, s), 2.7-3.0 (4H, m), 3.89 (2H, br s), 4.09 (2H, q, J=7.2 Hz), 6.91 (1H, d, J=1.5 Hz), 7.13 (1H, d, J=1.5 Hz), 7.17 (1H, d, J=8.1 Hz), 7.36 (1H, dd, J=1.5, 8.1 Hz), 7.41 (1H, d, J=1.5 Hz).

MS (m/z): 301 (M$^+$), 228 (base).

Production Example 97

Ethyl 3-[1-(2-nitro-4-trifluoromethylphenyl)-1H-imidazol-2-yl]propanoate

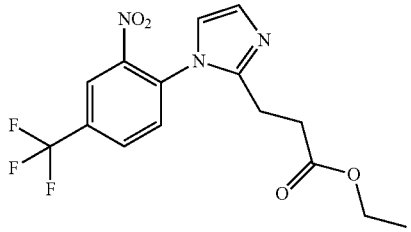 [SMILES: CCOC(=O)CCc1nccn1-c1ccc(C(F)(F)F)cc1[N+](=O)[O-]]

The title compound was obtained from 2-fluoro-5-trifluoro-nitrobenzene, in the manner similar to Production Example 3.

$^1$H-NMR (CDCl$_3$, δ): 1.21 (3H, t, J=7.2 Hz), 2.73 (2H, t, J=7.1 Hz), 2.8-3.0 (2H, m), 4.08 (2H, q, J=7.2 Hz), 6.89 (1H, d, J=1.2 Hz), 7.12 (1H, d, J=11.2 Hz), 7.73 (1H, d, J=8.5 Hz), 8.02 (1H, dd, J=1.9, 8.5 Hz), 8.32 (1H, d, J=1.9 Hz).

MS (m/z): 357 (M$^+$), 81 (base).

Production Example 98

Ethyl 3-[1-(2-amino-4-trifluoromethylphenyl)-1H-imidazol-2-yl]propanoate

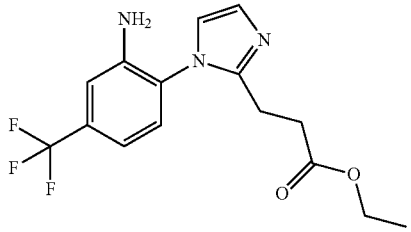

The title compound was obtained from ethyl 3-[1-(2-nitro-4-trifluoromethylphenyl)-1H-imidazol-2-yl]propanoate as synthesized in above Production Example 97, in the manner similar to Production Example 4.

$^1$H-NMR (CDCl$_3$, δ): 1.22 (3H, t, J=7.3 Hz), 2.7-3.0 (4H, m), 3.97 (2H, br s), 4.08 (2H, q, J=7.3 Hz), 6.90 (1H, d, J=1.5 Hz), 7.0-7.1 (2H, m), 7.13 (1H, d, J=1.5 Hz), 7.19 (1H, d, J=7.7 Hz).

MS (m/z): 327 (M$^+$), 254 (base).

Production Example 99

Ethyl 5-[(E)-2-ethoxycarbonylvinyl]-3-methyl-1H-pyrrole-2-carboxyate

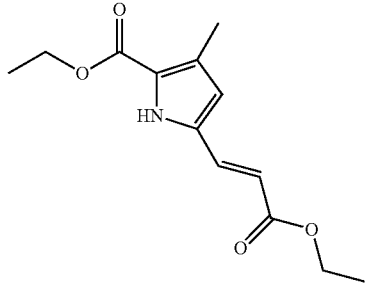 [SMILES: CCOC(=O)/C=C/c1cc(C)c(C(=O)OCC)[nH]1]

Ethyl 5-formyl-3-methyl-1H-pyrrole-2-carboxyate 470 mg, monoethyl malonate 378 mg, piperidine 0.05 mL and pyridine 6 mL were mixed and stirred at 100° C. for 38 hours. Ice water was added to the reaction liquid and the precipitate was recovered by filtration. The precipitate was washed with water and dried in flowing air under heating to provide 311 mg of the title compound.

$^1$H-NMR (CDCl$_3$, δ): 1.31 (3H, t, J=7.1 Hz), 1.37 (3H, t, J=7.1 Hz), 2.32 (3H, s), 4.24 (2H, q, J=7.1 Hz), 4.36 (2H, q, J=7.1 Hz), 6.20 (1H, d, J=16.0 Hz), 6.36 (1H, d, J=2.7 Hz), 7.45 (1H, d, J=16.0 Hz), 9.27 (1H, br s).

MS (m/z): 251 (M$^+$), 159 (base).

Production Example 100

Ethyl 5-[(E)-2-ethoxycarbonylvinyl]-4-methyl-1H-pyrrole-2-carboxyate

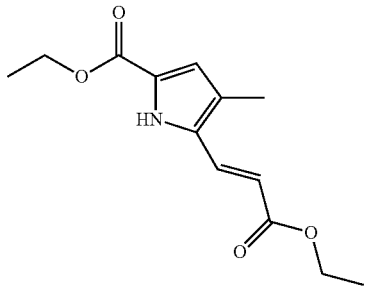 [SMILES: CCOC(=O)/C=C/c1[nH]c(C(=O)OCC)cc1C]

The title compound was obtained by the operations similar to Production Example 99.

$^1$H-NMR (CDCl$_3$, δ): 1.32 (3H, t, J=7.1 Hz), 1.36 (3H, t, J=7.1 Hz), 2.20 (3H, s), 4.25 (2H, q, J=7.1 Hz), 4.34 (2H, q, J=7.1 Hz), 6.14 (1H, d, J=16.0 Hz), 6.72 (1H, d, J=1.9 Hz), 7.58 (1H, d, J=16.0 Hz), 9.29 (1H, br s).

MS (m/z): 251 (M$^+$), 160 base).

Production Example 101

Ethyl 5-[(E)-2-ethoxycarbonylvinyl]-3,4-dimethyl-1H-pyrrole-2-carboxyate

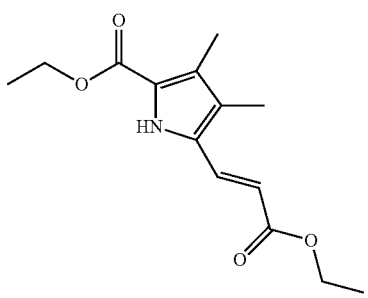 [SMILES: CCOC(=O)/C=C/c1[nH]c(C(=O)OCC)c(C)c1C]

The title compound was obtained by the operations similar to Production Example 99.

$^1$H-NMR (CDCl$_3$, δ): 1.32 (3H, t, J=7.1 Hz), 1.37 (3H, t, J=7.1 Hz), 2.10 (3H, s), 2.25 (3H, s), 4.24 (2H, q, J=7.1 Hz), 4.34 (2H, q, J=7.1 Hz), 6.09 (1H, d, J=16.2 Hz), 7.57 (1H, d, J=16.2 Hz), 8.91 (1H, br s).

MS (m/z): 265 (M$^+$, base).

Production Example 102

5-Chloro-2-(2-cyclohexyl-1H-imidazol-1-yl)-3-nitropyridine

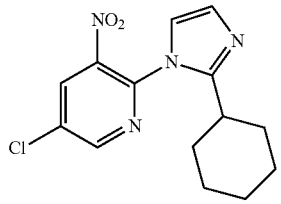 [SMILES: O=[N+]([O-])c1cc(Cl)cnc1-n1ccnc1C1CCCCC1]

2,5-Dichloro-3-nitropyridine 1.00 g, 2-cyclohexylimidazole 1.56 g, sodium iodide 500 mg and N,N-dimethylformamide 25 mL were mixed and stirred at 160° C. for 15.5 hours. The reaction liquid was poured in ice water and extracted with diethyl ether. The organic layer was washed successively with water and saturated brine, and dried over anhydrous magnesium sulfate. Distilling the solvent off under reduced pressure, the residue was subjected to silica gel chromatography (hexane:ethyl acetate=2:1) to provide 1.08 g of the title compound.

$^1$H-NMR (CDCl$_3$, δ): 1.1-1.4 (3H, m), 1.5-1.9 (7H, m), 2.4-2.6 (1H, m), 6.84 (1H, d, J=1.5 Hz), 7.09 (1H, d, J=1.5 Hz), 8.37 (1H, d, J=2.3 Hz), 8.77 (1H, d, J=2.3 Hz).

MS (m/z): 308 (M$^+$+2), 306 (M$^+$), 55 (base).

Production Example 103

3-Amino-5-chloro-2-(2-cyclohexyl-1H-imidazol-1-yl)pyridine

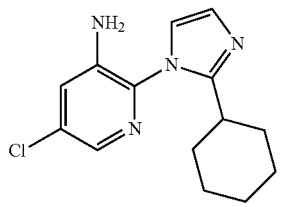 [SMILES: Nc1cc(Cl)cnc1-n1ccnc1C1CCCCC1]

The title compound was obtained from 5-chloro-2-(2-cyclohexyl-1H-imidazol-1-yl)-3-nitropyridine as synthesized in above Production Example 102, by the operations similar to Production Example 4.

$^1$H-NMR (CDCl$_3$, δ): 1.1-1.3 (3H, m), 1.5-1.9 (7H, m), 2.4-2.6 (1H, m), 3.77 (2H, br s), 6.93 (1H, d, J=1.4 Hz), 7.13 (1H, d, J=1.4 Hz), 7.16 (1H, d, J=2.3 Hz), 7.92 (1H, d, J=2.3 Hz).

MS (m/z): 278 (M$^+$+2), 276 (M$^+$), 135 (base).

Formulation Example 1

| Tablet: | |
|---|---|
| | mg/tablet |
| Active ingredient | 5.0 |
| Starch | 10.0 |
| Lactose | 73.0 |
| Carboxymethyl cellulose calcium | 10.0 |
| Talc | 1.0 |
| Magnesium stearate | 1.0 |
| | 100.0 |

The active ingredient was pulverized to the particle size not greater than 70 μm, to which starch, lactose and carboxymethyl cellulose calcium were added and mixed thoroughly. Ten (10) % starch paste was added to the above powdery mixture, mixed and stirred to form granules. After drying, their particle size was dressed to around 1000 μm, with which talc and magnesium stearate were mixed and tabletted.

The invention claimed is:

1. A compound of the formula (I)

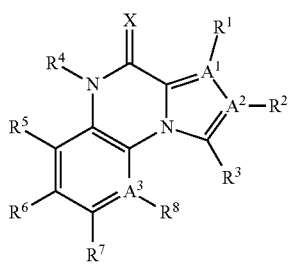

wherein,
$R^1$ independently is
hydrogen; halogen;
$C_{1-6}$ alkyl or $C_{1-6}$ alkoxy each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, $C_{1-6}$ alkanoyl, amino, amido, carbamoyl, oxo, carbocyclic group or heterocyclic group;
acyl which is optionally substituted with hydroxy, $C_{1-6}$ alkyl, $C_{2-6}$ alkenyl, $C_{2-6}$ alkynyl, $C_{1-6}$ haloalkyl having 1-9 halogen atoms, $C_{1-6}$ alkoxy, $C_{1-6}$ haloalkoxy having 1-9 halogen atoms, amino, carbocyclic group or heterocyclic group;
amino which is optionally substituted with 1-2 substituents selected from $C_{1-6}$ alkyl, $C_{2-6}$ alkenyl, $C_{2-6}$ alkynyl, alkanoyl, carbocyclic group and heterocyclic group;
hydroxy; or
pyrimidinyl which is optionally substituted with halogen, $C_{1-6}$ alkyl, $C_{1-6}$ alkoxy, $C_{1-6}$ haloalkoxy having 1-9 halogen atoms, nitro or amino,
$R^2$ is absent,
$R^3$ is
$C_{1-9}$ alkyl which is substituted with carboxy; or $C_{2-9}$ alkenyl which may be substituted with carboxy; or
$C_{5-7}$ cycloalkyl,
$R^4$ is
hydrogen; hydroxy;
$C_{1-6}$ alkyl which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl or oxo; or
amino which is optionally substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group,
$R^5$ and $R^8$ each independently are
hydrogen; halogen;
$C_{1-6}$ alkyl, $C_{2-6}$ alkenyl or $C_{1-6}$ alkoxy each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl or oxo;
cyano; or nitro,
$R^6$ is hydrogen,
$R^7$ is
hydrogen; halogen;
$C_{1-6}$ alkyl, $C_{2-6}$ alkenyl, $C_{2-6}$ alkynyl or $C_{1-6}$ alkoxy each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (wherein the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group or heterocyclic group (wherein the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl);
cyano;
amino which is optionally substituted with 1-2 substituents selected from $C_{1-6}$ alkyl, $C_{2-6}$ alkenyl, $C_{2-6}$ alkynyl (wherein the $C_{1-6}$ alkyl, $C_{2-6}$ alkenyl and $C_{2-6}$ alkynyl may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, $C_{1-6}$ alkanoyl, amino, amido, carbamoyl, oxo, carbocyclic group and heterocyclic group), alkanoyl, carbocyclic group and heterocyclic group (wherein the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{16}$ alkoxycarbonyl, amino, amido or carbamoyl);
COR$^9$; or SO$_2$R$^9$,
R$^9$ is
hydrogen; hydroxy;
$C_{1-6}$ alkyl, $C_{2-6}$ alkenyl, $C_{2-6}$ alkynyl or $C_{1-6}$ alkoxy, each of which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (wherein the amino may further be substituted with 1-2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, oxo, carbocyclic group or heterocyclic group (wherein the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl);
amino which may be substituted with 1-2 substituents selected from $C_{1-6}$ alkyl, $C_{2-6}$ alkenyl, $C_{2-6}$ alkynyl, $C_{1-6}$ alkoxy (wherein the $C_{1-6}$ alkyl, $C_{2-6}$ alkenyl, $C_{2-6}$ alkynyl and $C_{1-6}$ alkoxy may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, oxo, carbocyclic group or heterocyclic group), $C_{1-6}$ haloalkyl having 1-9 halogen atoms, alkanoyl, carbocyclic group and heterocyclic group (wherein the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl); or
aziridin-1-yl, azetidin-1-yl, pyrrolidin-1-yl, piperidin-1-yl, piperazin-1-yl, morpholin-1-yl or pyrazol-1-yl, each of which may be substituted with 1 2 substituents selected from hydroxy, halogen, $C_{1-6}$ alkyl, $C_{2-6}$ alkenyl, $C_{2-6}$ alkynyl, $C_{1-6}$ alkoxy (wherein the $C_{1-6}$ alkyl, $C_{2-6}$ alkenyl, $C_{2-6}$ alkynyl and $C_{1-6}$ alkoxy may further be substituted with, independently of each other, hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl, oxo, carbocyclic group or heterocyclic group), $C_{1-6}$ haloalkoxy having 1-9 halogen atoms, carboxy, $C_{1-6}$ alkoxycarbonyl, alkanoyl, amino (wherein the amino may further be substituted with 1 2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group and heterocyclic group (here the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl),
X is S or O,
A$^1$ is C, A$^2$ is N and A$^3$ is C, or a pharmaceutically acceptable salt thereof.

2. A compound according to claim 1,
in which R$^4$ is hydrogen; or
$C_{1-6}$ alkyl which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino, amido, carbamoyl or oxo.

3. A compound according to claim 2, in which R$^4$ is hydrogen or $C_{1-6}$ alkyl.

4. A compound according to claim 1, in which A$^3$ is C and R$^8$ is hydrogen.

5. A compound according to claim 1, in which A$^3$ is C and both R$^5$ and R$^8$ are hydrogen.

6. A compound according to claim 1,
in which R$^7$ is halogen; or
$C_{1-6}$ alkoxy which is optionally substituted with hydroxy, halogen, $C_{1-6}$ alkoxy, $C_{1-6}$ haloalkoxy having 1-9 halogen atoms, carboxy, $C_{1-6}$ alkoxycarbonyl, alkanoyl, amino (wherein the amino may further be substituted with 1 2 substituents selected from $C_{1-6}$ alkyl, $C_{2-6}$ alkenyl, $C_{2-6}$ alkynyl, $C_{1-6}$ haloalkyl having 1-9 halogen atoms, alkanoyl, carbocyclic group and heterocyclic group), amido, carbamoyl, oxo, carbocyclic group or heterocyclic group (wherein the carbocyclic group and heterocyclic group each may further be substituted with hydroxy, halogen, $C_{1-6}$ alkyl, $C_{2-6}$ alkenyl, $C_{2-6}$ alkynyl, $C_{1-6}$ alkoxy, carboxy, $C_{1-6}$ alkoxycarbonyl, amino, amido or carbamoyl).

7. A compound according to claim 1, in which X is O.

8. A pharmaceutical composition comprising a compound of the formula (I) or a pharmaceutically acceptable salt therof according to claim 1 and a pharmaceutically acceptable carrier.

9. A method for modulating phosphodiesterase type-9 activity in a mammal, comprising administering to said mammal a compound according to claim 1, or a pharmaceutically acceptable salt thereof.

10. The compound 1-cyclohexyl-4-oxo-4,5-dihydroimidazo[1,5-a]quinoxaline-8-carboxylic acid or a pharmaceutically acceptable salt thereof.

11. The compound 1-cyclohexyl-N,N-dimethyl-4-oxo-4,5-dihydroimidazo[1,5-a]-quinoxaline-8-carboxamide or a pharmaceutically acceptable salt thereof.

12. The compound 1-cyclohexyl-N-(2-methoxyethyl)-N-methyl-4-oxo-4,5-dihydroimidazo[1,5-a]quinoxaline-8-carboxamide or a pharmaceutically acceptable salt thereof.

13. The compound 1-[(1-cyclohexyl-4-oxo-4,5-dihydroimidazo[1,5-a]quinoxalin-8-yl)carbonyl]-4-(2-hydroxyethyl)piperidine or a pharmaceutically acceptable salt thereof.

14. The compound 1-cyclohexyl-4-oxo-N-(3-pyridylmethyl)-4,5-dihydroimidazo-[1,5-a]quinoxaline-8-carboxamide or a pharmaceutically acceptable salt thereof.

15. The compound 1-cyclohexyl-N-methyl-4-oxo-N-(2-pyridylmethyl)-4,5-dihydroimidazo[1,5-a]quinoxaline-8-carboxamide or a pharmaceutically acceptable salt thereof.

16. The compound 1-cyclopentyl-4-oxo-4,5-dihydroimidazo[1,5-a]quinoxaline-8-carboxylic acid or a pharmaceutically acceptable salt thereof.

* * * * *

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Synthetic construct: hPDE9-5A primer

<400> SEQUENCE: 1
cctagctagc caccatggga tccggctcct cc            32

<210> SEQ ID NO 2
<211> LENGTH: 43
<212> TYPE: DNA
<213> ORGANISM: Artificial Sequence
<220> FEATURE:
<223> OTHER INFORMATION: Synthetic construct: hPDE9-3A primer

<400> SEQUENCE: 2
ttttcctttt gcggccgctt attaggcaca gtctccttca ctg            43

```
<210> SEQ ID NO 3
<211> LENGTH: 24
<212> TYPE: DNA
<213> ORGANISM: Artificial Sequence
<220> FEATURE:
<223> OTHER INFORMATION: Synthetic construct: hPDE5-5' E primer

<400> SEQUENCE: 3
cggaattcca accatggagc gggc                                              24

<210> SEQ ID NO 4
<211> LENGTH: 27
<212> TYPE: DNA
<213> ORGANISM: Artificial Sequence
<220> FEATURE:
<223> OTHER INFORMATION: Synthetic construct: hPDE5-3' primer

<400> SEQUENCE: 4
gctctagatc agttccgctt ggcctgg                                           27
```